United States Patent
Todd et al.

(10) Patent No.: US 11,802,308 B2
(45) Date of Patent: *Oct. 31, 2023

(54) DETECTION OF NUCLEIC ACIDS

(71) Applicant: SPEEDX PTY LTD, Eveleigh (AU)

(72) Inventors: Alison Velyian Todd, Glebe (AU);
Elisa Mokany, Caringbah (AU);
Samantha Walker, Windsor Downs
(AU); Cortny Donald, Farmborough
Heights (AU); Dina Lonergan, Coogee
(AU); Lit Yeen Tan, Winston Hills
(AU)

(73) Assignee: SPEEDX PTY LTD, Eveleigh (AU)

( * ) Notice: Subject to any disclaimer, the term of this patent is extended or adjusted under 35 U.S.C. 154(b) by 295 days.

This patent is subject to a terminal disclaimer.

(21) Appl. No.: 16/912,622

(22) Filed: Jun. 25, 2020

(65) Prior Publication Data

US 2021/0108261 A1    Apr. 15, 2021

Related U.S. Application Data

(63) Continuation of application No. 15/937,657, filed on Mar. 27, 2018, now Pat. No. 10,724,080, which is a continuation of application No. 14/379,178, filed as application No. PCT/AU2013/000149 on Feb. 20, 2013, now Pat. No. 9,963,738.

(30) Foreign Application Priority Data

Feb. 20, 2012 (AU) ................................ 2012900624
May 29, 2012 (AU) ................................ 2012902218

(51) Int. Cl.
*C12Q 1/6858* (2018.01)
*C12Q 1/6818* (2018.01)
*C12Q 1/6853* (2018.01)
*C12Q 1/6848* (2018.01)
*C12N 15/113* (2010.01)

(52) U.S. Cl.
CPC .......... *C12Q 1/6858* (2013.01); *C12N 15/113* (2013.01); *C12Q 1/6818* (2013.01); *C12Q 1/6848* (2013.01); *C12Q 1/6853* (2013.01); *C12N 2310/12* (2013.01)

(58) Field of Classification Search
CPC .. C12Q 1/6858; C12Q 1/6818; C12Q 1/6848; C12Q 1/6853; C12N 15/113; C12N 2310/12
See application file for complete search history.

(56) References Cited

U.S. PATENT DOCUMENTS 9,845,492 B2 * 12/2017 Chun .................. C12Q 1/6816
9,963,738 B2    5/2018 Todd et al.
10,724,080 B2   7/2020 Todd et al.
2004/0121374 A1 6/2004 Iwaki et al.
2007/0231810 A1 10/2007 Todd et al.
2012/0171673 A1 7/2012 Nakamura et al.

FOREIGN PATENT DOCUMENTS

WO    WO 08/040095 A1    4/2008
WO    WO 08/122084 A1    10/2008
WO    WO 11/001496       1/2011
WO    WO 13/123552 A1    8/2013

OTHER PUBLICATIONS

Edelheit et al., "Simple and efficient site-directed mutagenesis using two single-primer reactions in parallel to generate mutants for protein structure-function studies," BMC Biotechnology, 9:61, doi: 10.1186/1472-6750-9-61, 8 pages, (2009).
Kammann et al., "Rapid insertionai mutagenesis of DNA by polymerase chain reaction (PCR)," Nucleic Acids Research, 17(13):5404, (1989).
Liu et al., "An efficient one-step site-directed deletion, insertion, single and multiple-site plasmid mutagenesis protocol," BMC Biotechnology, 8 (91), doi: 10.1186/1472-6750-8-91, 10 pages, (2008).
Mokany et al., "MNAzymes, a Versatile New Class of Nucleic Acid Enzymes That Can Function as Biosensors and Molecular Switches," J Am Chem Soc, 132(3):1051-1059, doi:10.1021/JA9076777, (2010). Published on the Internet on Dec. 28, 2009.
Nakamura et al., "Development of multisample detection system using a tag insertion primer and an electrochemical DNA chip," Analytical Biochemistry, 419:190-195, (2011).
EPO Application No. 13751988.0 (Published as EP2817421), Supplementary Europeanl Search Report and Europeanl Search Opinion dated Dec. 4, 2015.
U.S. Appl. No. 14/379,178, Non-Final Office Action dated Jun. 20, 2017.
U.S. Appl. No. 14/379,178, Notice of Allowance dated Dec. 27, 2017.
U.S. Appl. No. 14/379,178, Requirement for Restriction/Election dated Mar. 6, 2017.
U.S. Appl. No. 15/937,657, Non-Final Office Action dated Nov. 8, 2019.
U.S. Appl. No. 15/937,657, Notice of Allowance dated Mar. 9, 2020.
WIPO Application No. PCT/AU2013/000149, PCT International Preliminary Report on Patentability completed Feb. 19, 2014.
WIPO Application No. PCT/AU2013/000149, PCT International Search Report and Written Opinion of the International Searching Authority dated Apr. 17, 2013.

* cited by examiner

*Primary Examiner* — David C Thomas
(74) *Attorney, Agent, or Firm* — Alston & Bird LLP

(57) ABSTRACT

The present invention provides modified oligonucleotides and methods for their use in the detection of nucleic acids. The oligonucleotides and methods find particular application in amplifying and/or detecting areas of genetic variation in target nucleic acid sequences.

17 Claims, 16 Drawing Sheets
Specification includes a Sequence Listing.

Figure 2
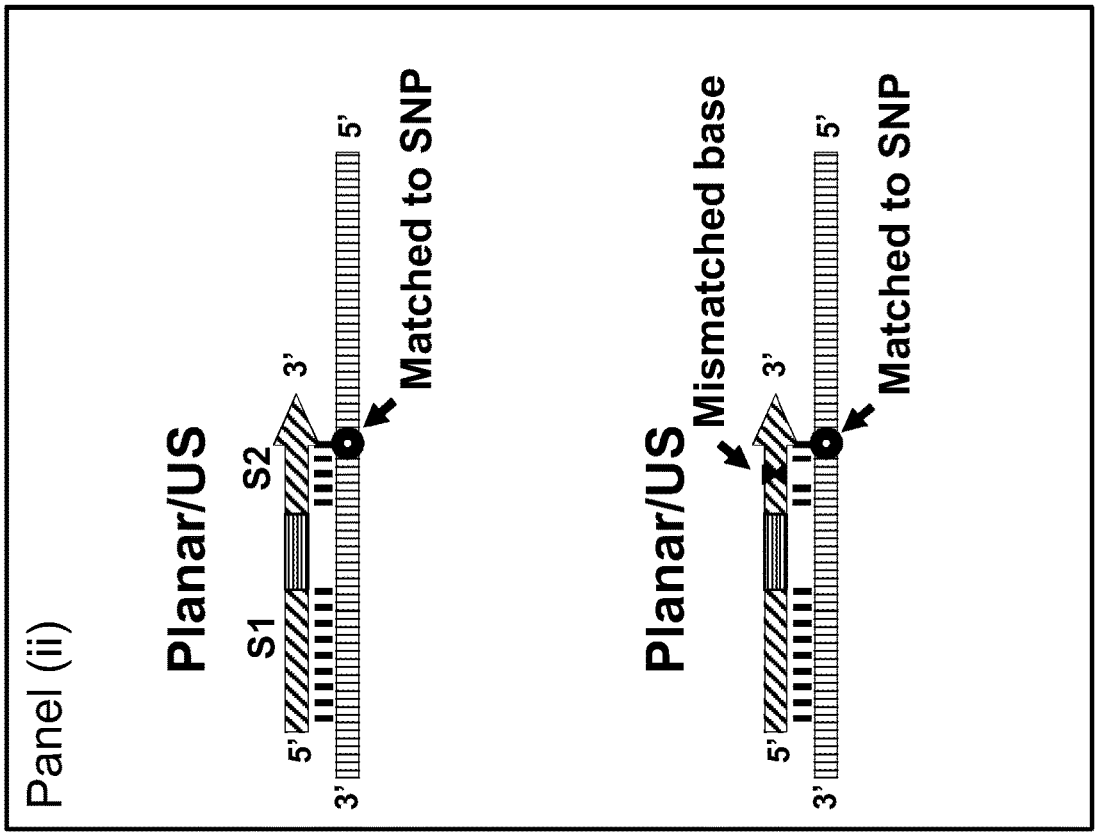
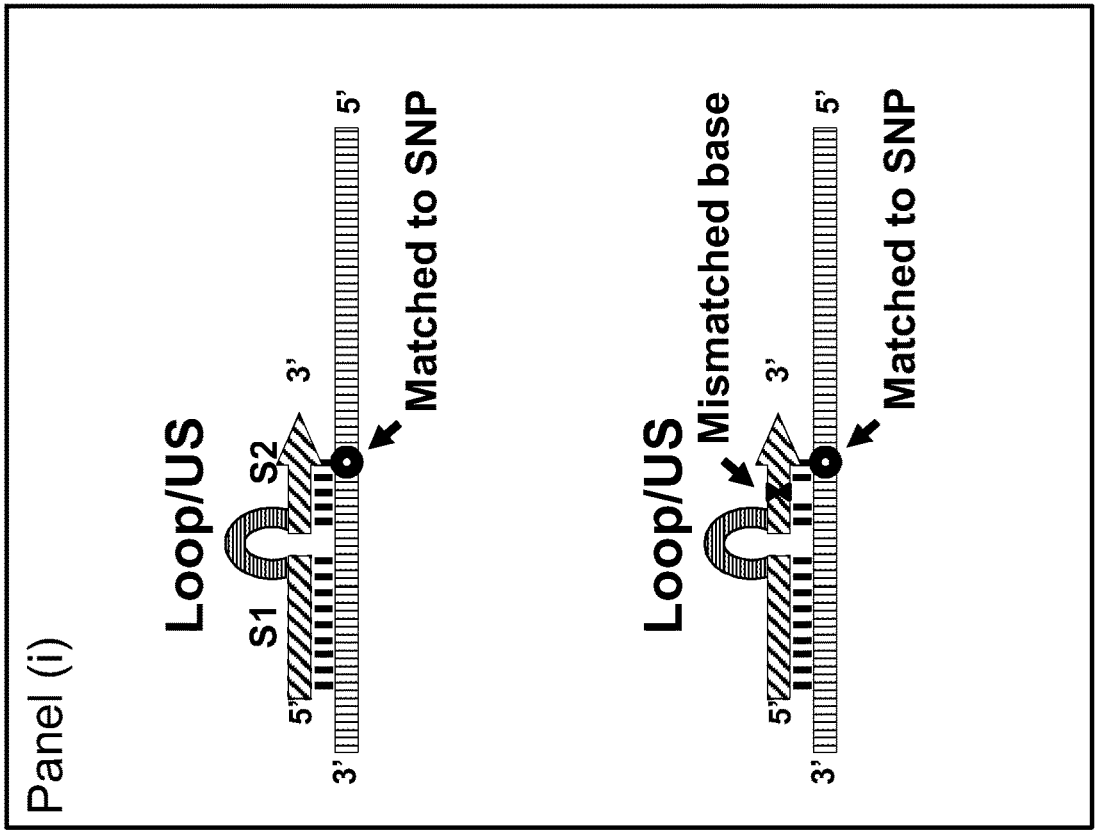

DETECTION OF NUCLEIC ACIDS

CROSS-REFERENCE TO RELATED APPLICATIONS

The present application is a continuation of U.S. Ser. No. 15/937,657 filed Mar. 27, 20189, which is a continuation of U.S. Ser. No. 14/379,178 filed Aug. 15, 2014, which is the US national stage of PCT/AU2013/000149 filed Feb. 20, 2013, which claims the benefit of AU 2012900624 filed Feb. 20, 2012 and AU 2012902218 filed May 29, 2012, the entire contents of all of which are incorporated by cross-reference.

REFERENCE TO A SEQUENCE LISTING

The application includes an electronic sequence listing in a file named 549929SEQLST.TXT, created on Jun. 25, 2020, and containing 54,681 bytes, which is incorporated by reference.

TECHNICAL FIELD

The present invention relates generally to the field of molecular biology. More specifically, the present invention provides modified oligonucleotides and methods for their use in the detection of target nucleic acids. The oligonucleotides and methods find particular application in amplifying and/or detecting areas of genetic variation in target nucleic acid sequences.

BACKGROUND

A variety of inherited and acquired diseases are associated with genetic variations such as point mutations, deletions and insertions. Genetic variations such as single nucleotide polymorphisms may be informative in predicting response to drugs and providing prognostic indications of disease risk and severity. Some genetic variants are directly associated with the presence of disease, while others correlate with disease risk and/or prognosis. There are more than 500 human genetic diseases which result from mutations in single genes. These include cystic fibrosis, muscular dystrophy, al-antitrypsin deficiency, phenylketonuria, sickle cell anaemia or trait, and various other haemoglobinopathies. Furthermore, individuals with increased susceptibility to several common polygenic conditions, such as atherosclerotic heart disease, have been shown to have an association with the inheritance of a particular DNA sequence polymorphism. Cancer is thought to develop due the accumulation of genetic lesions in genes involved in cellular proliferation or differentiation.

The genetic variability within pathogens can play a role in the severity of associated disease and the nature of therapeutic intervention. Examples include (i) mutations associated with drug resistant strains of bacteria such as Tuberculosis; (ii) therapy induced resistance in viruses such as HIV which is associated with specific nucleotides, and (iii) specific sequences in HCV that are predictive of therapeutic response.

Genetic analysis is becoming routine in the clinic for assessing disease risk, diagnosis of disease, predicting a patient's prognosis or response to therapy, and for monitoring a patient's progress. The introduction of such genetic tests depends on the development of simple, inexpensive, and rapid assays for discriminating genetic variations.

Methods of in vitro nucleic acid amplification have widespread applications in genetics and disease diagnosis. Such methods include polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). Each of these target amplification strategies requires the use of oligonucleotide primers. The process of amplification results in the exponential amplification of amplicons which incorporate the oligonucleotide primers at their 5' termini and which contain newly synthesized copies of the sequences located between the primers.

Commonly used methods for detection of small genetic variations involving PCR include High Resolution Melt curve analysis and the use of Molecular Beacons. Melt curve and Molecular Beacons are suitable methods for detection of sequences that represent a large proportion of the population, but they are not suitable for situations where the mutation must be detected in a large background of non-mutated DNA such as for acquired mutations involved in cancer, genotyping rare/emerging viral strains or identification of drug resistant bacteria in a background of drug sensitive bacteria.

As an example, PCR is extremely versatile and many modifications of the basic protocols have been developed. Primers used in PCR may be a perfectly matched to the target sequence or they can contain mismatched and or modified bases. Additional tag sequences at the 5' end of primers can facilitate capture of PCR amplicons and the inclusion of labelled primers can facilitate detection. Other protocols which have introduced non-target related sequence (non-complementary tag sequence) into the 5' portion of oligonucleotide primers have done so to introduce restriction sites for cloning or to tag amplicons for second round of amplification with generic primer which are not related to the original target. While it is known in the art that the 5' half of a given primer can tolerate the insertion of bases that do not hybridize to the initial target, it also well acknowledged that the 3' portion of the primer is far less amenable to the presence of mismatched bases.

This observation led to the development of oligonucleotide primers for Amplification Refractory Mutation System (ARMS) (Newton et al 1989 Nucleic Acids Research 17:2503-2516) also known as Allele Specific PCR (AS-PCR). ARMS primers promote discrimination of small genetic variations such as a single nucleotide polymorphism (SNP). This ability is based on the fact that oligonucleotides with a mismatched 3' residue will not function as efficiently as primers compared to fully matched sequences. Kwok et al. demonstrated that this discrimination was not complete and depended on the DNA bases involved in the mismatch (Kwok, et al. 1990 Nucleic Acids Research 18: 999-10005). Double mismatches between a primer and template, with one mismatch at the 3' end of the primer, provide an increased ability of ARMS primers to effectively discriminate between alleles (Kwok, et al. 1990 Nucleic Acids Research 18: 999-10005). ARMS primers must be well designed with the strength of the 3' mismatch balanced by the strength of the second mismatch. This is also balanced by carefully selecting the annealing temperature of the PCR which has an effect on the efficiency with which mismatched primers anneal to their target. Design of ARMS assays can be difficult and development of reaction conditions, for example temperature, where all primers discriminate effectively is tedious.

Universal bases exhibit the ability to replace the four normal bases without significantly destabilizing neighboring base-pair interactions or disrupting the expected functional biochemical utility of the modified oligonucleotide. It is well known in the art that oligonucleotides that include a universal base will function as a primer for DNA sequencing or PCR. The most commonly used degenerate modified base is deoxyinosine, which serves as a "universal" base, as it is capable of wobble base pairing with all four natural nucleotides, though not with equal affinity (I-C>I-A>I-T~I-G>I-I). As such, inosine has been extensively used in PCR in applications such as amplification of ambiguous sequences which require degeneracy at certain base positions of primers and probes.

WO 2006/092941 describes the use of dual specificity oligonucleotides composed of three different Tm portions to enhance specific amplification from PCR. The dual specificity oligonucleotide (DSO) is composed of 3 regions of sequence. The 5' portion of the DSO is target-specific and has a high Tm. The middle portion of the DSO is a separation portion composed between 2 to 10 "universal" bases which are not any of the standard DNA bases (i.e. not G, A, T or C). The 3' portion of the DSO is target-specific. DSO can tolerate mismatches within the 5' and 3' portions of the oligonucleotides and thus to use DSO as primers to effectively discriminate small genetic variations requires stringent conditions for primer annealing. The universal bases in the middle portion are capable of non-specific base paring with all four conventional DNA bases. As such these DSO primers are capable of binding to the initial target along the entire length of the primer (since the bases are universal as opposed to mismatched), although the temperature may be set such that the universal portion may not be bound during primer annealing. Once copied however, amplicons will contain variant sequence opposite the position of the universal bases and thus the presence of universal bases does not introduce any specific unique sequence into the amplicons generated using DSO primers.

Despite the relatively large number of techniques that have been developed for amplifying, detecting and analysing sequences, there is a substantial need for more rapid, accurate and inexpensive assays for discriminating genetic variations. A need also exists for methods that improve the amplification of sequences that comprise regions of genetic variability in cases where the variability is non-informative and complicates amplification. Further, better methods are required to increase the capacity to analyse more than one target in a multiplex format, particularly when detecting small genetic variations (e.g. single nucleotide polymorphisms—SNPs).

SUMMARY OF THE INVENTION

The present invention meets at least one of the needs mentioned above by providing oligonucleotides capable of introducing unique specific sequences into amplicons. A unique sequence introduced into an amplicon by an oligonucleotide provided herein may be used to provide a greater region of variability in an amplified target polynucleotide that would otherwise comprise only a small genetic variation (e.g. an SNP), thus facilitating easier discrimination. Alternatively, in cases where genetic variability in a target sequence is non-informative and/or makes amplification difficult, oligonucleotides provided herein many may be used to replace those variable regions in amplicons with a unique sequence, thereby improving the efficacy of amplification and detection of related sequences.

The present invention relates at least in part to the following embodiments 1-118:

Embodiment 1. A method for determining the presence or absence of a target polynucleotide in a sample, the method comprising:
  providing a primer oligonucleotide comprising
    a first primer component terminating at the 5' end of the oligonucleotide and capable of hybridising to a first portion of a strand of the target polynucleotide by complementary base pairing, and
    a second primer component terminating at the 3' end of the oligonucleotide and capable of hybridising to a second portion of the target polynucleotide strand by complementary base pairing;
  contacting a sample potentially comprising the target polynucleotide with the primer oligonucleotide under conditions suitable for hybridisation of the first primer component and second primer component with the target polynucleotide strand to thereby form a double-stranded duplex, wherein at least one strand of an intermediate section of the duplex comprises a sequence of at least four nucleotides that remains unhybridised to an opposing strand of the intermediate section due to an absence of a sequence of nucleotides in the opposing strand of the intermediate section sharing base pair complementarity with the sequence of at least four nucleotides;
  contacting the sample with a polymerase enzyme capable of using the target polynucleotide strand as a template to extend the length of the primer oligonucleotide of the duplex and thereby generate an amplicon comprising an internal component intermediate to first and second end components, wherein
    the first end component of the amplicon is capable of hybridising by complementary base pairing to said first portion of the target polynucleotide strand,
    the second end component of the amplicon is capable of hybridising by complementary base pairing to said second portion of the target polynucleotide strand, and
    said hybridising of the first and second end components of the amplicon to the target polynucleotide strand positions the internal component of the amplicon to oppose an intermediate sequence of nucleotides in the target polynucleotide strand located between the first and second portions of the target polynucleotide strand that does not share base pair complementarity with the internal component; and
  detecting whether the amplicon is generated, wherein detection of the amplicon indicates the presence of the target polynucleotide in the sample, and failure to detect the amplicon indicates the absence of the target polynucleotide in the sample.

Embodiment 2. The method according to embodiment 1, wherein said detecting comprises detecting the internal component of the amplicon or a sequence of nucleotides complementary to the internal component of the amplicon.

Embodiment 3. The method according to embodiment 1 or embodiment 2, wherein the melting temperature of the first primer component is greater than the melting temperature of the second primer component upon said hybridising to the target polynucleotide strand by complementary base pairing.

Embodiment 4. The method according to any one of embodiments 1 to 3, wherein the at least one strand of the intermediate section of the double-stranded duplex comprises at least five, at least six, at least seven, or at least 8 nucleotides that remain unhybridised to the opposing strand of the duplex.

Embodiment 5. The method according to any one of embodiments 1 to 4, wherein the primer oligonucleotide comprises a third primer component located between the first primer component and second primer component, wherein the third primer component consists of a sequence of nucleotides that
   does not share base pair complementarity with said intermediate sequence of nucleotides in the target polynucleotide strand, and
   is identical to a sequence of nucleotides in the internal component of the amplicon.

Embodiment 6. The method according to embodiment 5, wherein the third primer component is located partially or completely in the 3' half of the primer oligonucleotide.

Embodiment 7. The method according to embodiment 5 or embodiment 6, wherein the number of nucleotides in the third primer component and intermediate sequence of nucleotides is equal.

Embodiment 8. The method according to embodiment 5 or embodiment 6, wherein the number of nucleotides in the third primer component exceeds the number of nucleotides in said intermediate sequence of nucleotides.

Embodiment 9. The method according to embodiment 5 or embodiment 6, wherein the number of nucleotides in the third primer component is less than the number of nucleotides in said intermediate sequence of nucleotides.

Embodiment 10. The method according to embodiment 9, wherein the number of nucleotides in the third primer component is between 1 and 200 nucleotides, 1 and 150 nucleotides, 1 and 100 nucleotides, 1 and 75 nucleotides, 1 and 50 nucleotides 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides, less than the number of unhybridised nucleotides in the target polynucleotide located between portions of the target polynucleotide hybridised to the first primer component and second primer component.

Embodiment 11. The method according to any one of embodiments 1 to 10, wherein the number of nucleotides in the first primer component exceeds the number of nucleotides in the second primer component.

Embodiment 12. The method according to any one of embodiments 1 to 4, wherein said at least one strand of the intermediate section of the double-stranded duplex is a component of the target polynucleotide strand.

Embodiment 13. The method according to embodiment 12, wherein the component of the target polynucleotide strand consists of said intermediate sequence of nucleotides.

Embodiment 14. The method according to embodiment 12 or embodiment 13, wherein the first primer component and second primer component hybridise by complementary base pairing to separate non-contiguous components of the target polynucleotide strand, thereby juxtaposing the non-contiguous components and creating a loop portion comprising unhybridised nucleotides in the target polynucleotide strand.

Embodiment 15. The method according to any one of embodiments 12 to 14, wherein all nucleotides of the primer oligonucleotide are hybridised to the target oligonucleotide strand by complementary base pairing.

Embodiment 16. The method according to embodiment 14 or embodiment 15, wherein the loop portion of the target polynucleotide comprises between 1 and 200 nucleotides, 1 and 150 nucleotides, 1 and 100 nucleotides, 1 and 75 nucleotides, 1 and 50 nucleotides 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides.

Embodiment 17. The method according to any one of embodiments 1 to 16, wherein said contacting comprises
   contacting a second primer oligonucleotide that shares base pair complementarity with a second target polynucleotide strand that is the complement of said first target polynucleotide strand, and
   using a polymerase enzyme to extend the length of the second primer oligonucleotide using the second target polynucleotide strand as a template and thereby generate a second amplicon.

Embodiment 18. The method according to embodiment 17, wherein said detecting comprises detecting the second amplicon.

Embodiment 19. The method according to any one of embodiments 1 to 17, wherein said method comprises the use of any one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Embodiment 20. The method according to any one of embodiments 1 to 19, wherein
   the target polynucleotide strand comprises a polymorphic region that varies between two or more individual members of a population of the target polynucleotides,
   the first primer component and the second primer component are each capable of hybridising to multiple members of the population by virtue of the first primer component sharing sequence complementarity with a component of the target polynucleotide strand positioned upstream of the polymorphic region and the second primer component sharing sequence complementarity with a component of the target polynucleotide strand positioned downstream of the polymorphic region, and
   the polymorphic region remains unhybridised to the primer oligonucleotide when the first primer component and the second primer component are hybridised to the target polynucleotide.

Embodiment 21. The method according to embodiment 20, wherein the polymorphic region comprises deletion of one or more nucleotides such that the length of the polymorphic region differs between the two or more individual members of said population of the target polynucleotides.

Embodiment 22. The method according to embodiment 20 or embodiment 21, wherein the polymorphic region comprises substitution of one or more nucleotides such that the polymorphic region nucleotide sequence differs between the two or more individual members of said population of the target polynucleotides.

Embodiment 23. The method according to any one of embodiments 1 to 19, wherein
   the target polynucleotide strand comprises a single nucleotide polymorphism (SNP) and/or point mutation;

the amplicon comprises
  (i) a nucleotide complementary to the SNP, and/or
  (ii) a nucleotide complementary to the point mutation; and
the first or second primer component is capable of hybridising to (i) and/or (ii) above by complementary base pairing.

Embodiment 24. The method according to embodiment 23, wherein the second primer component comprises the nucleotide complementary to the SNP, or the nucleotide complementary to the point mutation, located
  at the 3' terminus of the second primer component,
  one, two, three, four, five, or more than five nucleotides upstream of the 3' terminus of the second primer component,
  at the 3' terminus of the second primer component wherein the second primer component also comprises a nucleotide that is non-complementary to the target polynucleotide located two, three, four, five, six, or more than six nucleotides upstream of the 3' terminus, or
  one, two three, four, five, or more than five nucleotides upstream of the 3' terminus of the second primer component, wherein the second primer component also comprises a further nucleotide that is non-complementary to the target polynucleotide, and said further nucleotide is located 3' or 5' of said nucleotide complementary to the SNP or point mutation.

Embodiment 25. The method according to any one of embodiments 1 to 19, wherein
  the target polynucleotide strand comprises a polymorphic region that differs between at least two individual members of a population of the target polynucleotides,
  the polymorphic region comprises deletion of one or more nucleotides such that the the polymorphic region differs between the two or more individual members of said population of the target polynucleotides, and
  the first primer component or the second primer component is capable of hybridising to the polymorphic region in said target polynucleotide strand by complementary base pairing, wherein the polymorphic region is present in the target polynucleotide strand of only a subset of population members.

Embodiment 26. The method according to any one of embodiments 1 to 25, wherein said detecting whether the amplicon is generated comprises measuring a signal provided by a dye that binds to double-stranded DNA and/or an amplicon sequence specific-probe.

Embodiment 27. The method according to embodiment 26, wherein the dye that binds to double-stranded DNA is SYBR Green.

Embodiment 28. The method according to embodiment 26, wherein the sequence-specific probe is a. Molecular Beacon, minor groove binder (MGB) probe, or a TaqMan® Probe.

Embodiment 29. The method according to any one of embodiments 1 to 25, wherein said detecting comprises use of an multi-component nucleic acid enzyme (MNAzyme) comprising at least two or more partzyme component oligonucleotides, wherein at least a first partzyme component and a second partzyme component self-assemble in the presence the amplicon to form a catalytically active MNAzyme, wherein each of the first and second partzyme components comprise a substrate arm portion, a catalytic core portion, and a sensor arm portion;
  wherein upon self-assembly, the sensor arm portion of the first and second partzyme components act as sensor arms of the MNAzyme, the substrate arm portion of the first and second partzyme components act as substrate arms of the MNAzyme, and the catalytic core portion of the first and second partzyme components act as a catalytic core of the MNAzyme;
  and wherein the sensor arms of the MNAzyme hybridise with some or all of the amplicon by complementary base pairing so as to maintain the first and second partzyme components in proximity for association of their respective catalytic core portions to form the catalytic core of the MNAzyme, the catalytic core being capable of modifying at least one substrate, and wherein the substrate arms of the MNAzyme engage a substrate so that the catalytic core of the MNAzyme can modify the substrate and thereby provide a detectable effect.

Embodiment 30. The method according to embodiment 29, wherein a first and/or second sensor arm of said MNAzyme is complementary or substantially complementary to a sequence of nucleotides that comprises or consists of:
  the internal component of the amplicon or a component thereof, or
  a sequence of nucleotides complementary to the internal component of the amplicon or component thereof.

Embodiment 31. The method according to embodiment 30, wherein the first and/or second sensor arm of said MNAzyme is additionally complementary to a sequence of nucleotides in the amplicon that comprises or consists of:
  the first end component and/or the second end component of the amplicon, or a component thereof, or
  a sequence of nucleotides complementary to the first end component and/or the second end component of the amplicon, or component thereof.

Embodiment 32. The method according to embodiment 29, wherein a first and/or second sensor arm of said MNAzyme is complementary or substantially complementary to:
  a sequence of nucleotides in the amplicon that does not comprise or consist of the internal component of the amplicon, or a component thereof, or
  a sequence of nucleotides complementary to a sequence of nucleotides in the amplicon that does not comprise or consist of the internal component of the amplicon or a component thereof.

Embodiment 33. The method according to any one of embodiments 29 to 32, wherein the first and/or second sensor arm of said MNAzyme comprises a nucleotide that is complementary to:
  a single nucleotide polymorphism (SNP), and/or a point mutation present in the target polynucleotide strand, or
  a nucleotide complementary to the SNP, and/or a nucleotide complementary to the point mutation present in the target polynucleotide strand.

Embodiment 34. The method according to any one of embodiments 29 to 33, wherein
  the target polynucleotide strand comprises a polymorphic region that differs between two or more individual members of a population of the target polynucleotides, and
  the first and/or second sensor arm of said MNAzyme is additionally complementary to a sequence of nucleotides in the amplicon that comprises or consists of
    the polymorphic region of a given member of the population, or a component thereof, or a sequence of nucleotides that is complementary to the polymorphic region of a given member of the population, or a component thereof.

Embodiment 35. The method according to embodiment 34, wherein the polymorphic region comprises one or more deletions, insertions and/or substitutions of nucleotides such that the sequence of the polymorphic region varies between the individual members of the population.

Embodiment 36. The method according to embodiment 29, wherein a sensor arm of the MNAzyme comprises or consists of a first sensor arm component, a second sensor arm component, and a third sensor arm component, wherein
the first sensor arm component is capable of hybridising to the amplicon by complementary base pairing;
the second sensor arm component is capable of hybridising to the amplicon by complementary base pairing; and
the third sensor arm component is located between the first sensor arm component and the second sensor arm component and is not capable of hybridising to the amplicon by complementary base pairing when the first sensor arm component and second sensor arm component are hybridised to the amplicon.

Embodiment 37. The method according to embodiment 36, wherein the number of nucleotides in the third sensor arm component is equal to or exceeds the number of unhybridised nucleotides in the amplicon located between portions of the amplicon hybridised to the first sensor arm component and the second sensor arm component.

Embodiment 38. The method according to embodiment 36, wherein the number of nucleotides in the third sensor arm component is less than the number of unhybridised nucleotides in the amplicon located between portions of the amplicon hybridised to the first sensor arm component and the second sensor arm component.

Embodiment 39. The method according to embodiment 38, wherein the number of nucleotides in the third sensor arm component is between 1 and 50 nucleotides, 1 and 40 nucleotides, 1 and 30 nucleotides 1 and 20 nucleotides, 1 and 10 nucleotides, 5 and 50 nucleotides, 5 and 40 nucleotides, 5 and 30 nucleotides 5 and 20 nucleotides, 5 and 10 nucleotides, 10 and 50 nucleotides, 10 and 40 nucleotides, 10 and 30 nucleotides, or 10 and 20 nucleotides, less than the number of unhybridised nucleotides in the amplicon located between portions of the amplicon hybridised to the first sensor arm component and the second sensor arm component.

Embodiment 40. The method according to embodiment 29, wherein the first sensor arm component and second sensor arm component are capable of hybridising to separate non-contiguous components of the amplicon by complementary base pairing, thereby juxtaposing the non-contiguous components and creating a loop portion comprising unhybridised nucleotides in the amplicon.

Embodiment 41. The method according to embodiment 40, wherein the loop portion of the amplicon comprises between 1 and 50 nucleotides, 1 and 40 nucleotides, 1 and 30 nucleotides, 1 and 20 nucleotides, 1 and 10 nucleotides, 1 and 5 nucleotides, 5 and 50 nucleotides, 5 and 40 nucleotides, 5 and 30 nucleotides 5 and 20 nucleotides, 5 and 10 nucleotides, 10 and 50 nucleotides, 10 and 40 nucleotides, 10 and 30 nucleotides, or 10 and 20 nucleotides.

Embodiment 42. The method according to embodiment 40 or embodiment 41, wherein the loop portion of the amplicon comprises said internal component of amplicon.

Embodiment 43. The method according to any one of embodiments 5 to 11, wherein the target polynucleotide strand comprises a polymorphic region that differs between two or more individual members of a population of the target polynucleotides, and:
said providing comprises providing multiple forms of the primer oligonucleotide, wherein different forms of the primer oligonucleotide share base pair complementarity with
different forms of the polymorphic region, or,
a portion of the target polynucleotide strand adjacent or substantially adjacent to one or more forms of the polymorphic region;
said contacting with the primer oligonucleotide comprises contacting a sample potentially comprising one or more members of the target polynucleotide population with said multiple forms of the primer oligonucleotide under the conditions suitable for hybridisation; and
wherein each of the multiple forms of the primer oligonucleotide comprises said third primer component located between the first primer component and second primer component and consisting of a sequence of nucleotides that does not share base pair complementarity with said intermediate sequence of nucleotides in the target polynucleotide strand.

Embodiment 44. The method according to embodiment 43, wherein said detecting comprises using an MNAzyme comprising a first sensor arm component, a second sensor arm component, and a third sensor arm component, wherein
the first sensor arm component is capable of hybridising to the internal component of the amplicon, and optionally to the first end component of the amplicon, by complementary base pairing; and
the second sensor arm component is capable of hybridising to the second end component of the amplicon by complementary base pairing; and
the third sensor arm component is located between the first sensor arm component and the second sensor arm component and is not capable of hybridising to said polymorphic region or a sequence of nucleotides complementary to said polymorphic region by complementary base pairing when the first sensor arm component and second sensor arm component are hybridised to the amplicon.

Embodiment 45. The method according to embodiment 44, wherein
multiple forms of the amplicon comprising the polymorphic region are generated by said contacting of the sample with a polymerase enzyme, wherein the polymorphic region of said each form of the amplicon differs; and
the sensor arm comprises or consists of a first sensor arm component, a second sensor arm component, and a third sensor arm component that is not complementary to a sequence of nucleotides in the amplicon comprising or consisting of the polymorphic region, wherein
the first sensor arm component is capable of hybridising to any said form of the amplicon by complementary base pairing upstream of the polymorphic region,
the second sensor arm component is capable of hybridising to any said form of the amplicon by complementary base pairing downstream of the polymorphic region,
the third sensor arm component is located between the first sensor arm component and the second sensor arm component, and is not capable of hybridising by complementary base pairing to the polymorphic region of any said form of the amplicon.

Embodiment 46. The method according to embodiment 43, wherein
multiple forms of the amplicon comprising the polymorphic region are generated by said contacting of the sample with a polymerase enzyme, wherein the polymorphic region of said forms of the amplicon differ; and
the sensor arm comprises or consists of a first sensor arm component and a second sensor arm component, wherein
the first sensor arm component and second sensor arm component hybridise by complementary base pairing to separate non-contiguous components of any given form of said amplicon, thereby juxtaposing the non-contiguous components and creating a loop portion in the amplicon comprising unhybridised nucleotides, and
the unhybridised nucleotides of the loop portion comprise the polymorphic region of the amplicon.

Embodiment 47. The method according to any one of embodiments 43 to 46, wherein the polymorphic region comprises any one or more of nucleotide insertions, deletions and/or substitutions, such that said two or more individual members of the population of target polynucleotides can differ.

Embodiment 48. The method according to any one of embodiments 1 to 47, wherein the primer oligonucleotide and/or target polynucleotide and/or amplicon comprise or consist of deoxyribonucleotides, ribonucleotides, or a combination thereof.

Embodiment 49. The method according to any one of embodiments 1 to 48, wherein the target polynucleotide and/or amplicon is genomic DNA, complementary DNA (cDNA), or RNA.

Embodiment 50. The method according to any one of embodiments 1 to 29, 32, 36 to 41, 43 or 46 wherein the primer oligonucleotide comprises a sequence of nucleotides that is complementary to a functionally active catalytic nucleic acid.

Embodiment 51. The method according to embodiment 50, wherein said amplicon comprises said functionally active catalytic nucleic acid, and said detecting whether the amplicon is generated comprises detecting catalytic activity of said functionally active catalytic nucleic acid present in the amplicon.

Embodiment 52. The method according to embodiment 50 or embodiment 51, wherein the functionally active catalytic nucleic acid is a DNAzyme or a ribozyme.

Embodiment 53. The method according to embodiment 51 or embodiment 52, wherein said detecting catalytic activity of said functionally active catalytic nucleic acid present in the amplicon comprises contacting the amplicon with a substrate of said functionally active catalytic nucleic acid.

Embodiment 54. An isolated primer or partzyme oligonucleotide comprising
a first component terminating at the 5' end of the oligonucleotide and capable of hybridising to a first portion of a second polynucleotide by complementary base pairing,
a second component terminating at the 3' end of the oligonucleotide and capable of hybridising to a second portion of the second polynucleotide by complementary base pairing, and
a third component located between the first and second components comprising a sequence of at least four nucleotides that do not share base pair complementarity with an opposing sequence of nucleotides in the second polynucleotide when the first and second components are hybridised to the second polynucleotide;
wherein the third component is located partially or completely in the 3' half of the oligonucleotide.

Embodiment 55. The oligonucleotide according to embodiment 54, wherein the third component comprises a sequence of at least four, at least five, at least six, at least seven or at least eight nucleotides do not share base pair complementarity with the opposing sequence of nucleotides in the second polynucleotide.

Embodiment 56. The oligonucleotide according to embodiment 54 or embodiment 55, wherein the number of nucleotides in the first component is:
less than the number of nucleotides in the third component; or
more than the number of nucleotides in the third component.

Embodiment 57. The oligonucleotide according to any one of embodiments 54 to 56, wherein the oligonucleotide comprises DNA, complementary DNA (cDNA), RNA, or any combination thereof.

Embodiment 58. The oligonucleotide according to any one of embodiments 54 to 57, wherein the oligonucleotide is a component of a partzyme sensor arm.

Embodiment 59. Use of the oligonucleotide according to any one of embodiments 54 to 58 in the method according to any one of embodiments 1 to 53.

Embodiment 60. An isolated double stranded nucleic acid duplex comprising the oligonucleotide of any one of embodiments 54 to 58 hybridised to a second polynucleotide by complementary base pairing, wherein
a first component of the oligonucleotide terminates at the 5' end of the oligonucleotide and is hybridised to a first portion of a second polynucleotide by complementary base pairing,
a second component of the oligonucleotide terminates at the 3' end of the oligonucleotide and is hybridised to a second portion of the second polynucleotide by complementary base pairing, and
a third component of the oligonucleotide is located between said first and second components and comprises a sequence of at least two nucleotides that do not share base pair complementarity with an opposing sequence of nucleotides in the second polynucleotide; and
the third component of the oligonucleotide is located partially or completely in the 3' half of the oligonucleotide.

Embodiment 61. The double stranded nucleic acid duplex according to embodiment 60, wherein the number of nucleotides in said third component is equal to the number of unhybridised nucleotides in the second polynucleotide located between portions of the second polynucleotide hybridised to said first and second components.

Embodiment 62. The double stranded nucleic acid duplex according to embodiment 61, wherein the number of nucleotides in said third component exceeds to the number of unhybridised nucleotides in the second polynucleotide located between portions of the second polynucleotide hybridised to said first and second components.

Embodiment 63. The double stranded nucleic acid duplex according to embodiment 61, wherein the number of nucleotides in said third component is less than the number of unhybridised nucleotides in the second polynucleotide located between portions of the second polynucleotide hybridised to said first and second components.

Embodiment 64. The double stranded nucleic acid duplex according to embodiment 61, wherein the number of nucleotides in said third is between between 1 and 200 nucleotides, 1 and 150 nucleotides, 1 and 100 nucleotides, 1 and 75 nucleotides, 1 and 50 nucleotides 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides, less than the number of unhybridised nucleotides in the second polynucleotide located between portions of the second polynucleotide hybridised to said first and second components.

Embodiment 65. The double stranded nucleic acid duplex according to any one of embodiments 60 to 64, wherein the oligonucleotide and/or second polynucleotide is genomic DNA, complementary DNA (cDNA), or RNA.

Embodiment 66. A multi-component nucleic acid enzyme (MNAzyme) comprising a sensor arm that comprises or consists of a first sensor arm component and a second sensor arm component, wherein
  the first sensor arm component and second sensor arm component are capable of hybridising by complementary base pairing to an assembly facilitator polynucleotide to thereby form a double-stranded duplex, wherein at least one strand of an intermediate component of the duplex comprises at least two nucleotides that remain unhybridised to an opposing strand of the duplex.

Embodiment 67. The MNAzyme according to embodiment 66, wherein the sensor arm comprises or consists of a first sensor arm component, a second sensor arm component, and a third sensor arm component located between the first sensor arm component and the second sensor arm component, wherein upon said hybridising of the first sensor arm component and the second sensor arm component to the assembly facilitator polynucleotide, the third sensor arm component is not capable of hybridising to the assembly facilitator polynucleotide due to an absence of base pair complementarity with said assembly facilitator polynucleotide.

Embodiment 68. The MNAzyme according to embodiment 67, wherein the number of nucleotides in the third sensor arm component is equal to or exceeds the number of unhybridised nucleotides in the assembly facilitator polynucleotide located between portions of the assembly facilitator polynucleotide hybridised to the first sensor arm component and the second sensor arm component.

Embodiment 69. The MNAzyme according to embodiment 67, wherein the number of nucleotides in the third sensor arm component is less than the number of unhybridised nucleotides in the assembly facilitator polynucleotide located between portions of the the assembly facilitator polynucleotide hybridised to the first sensor arm component and the second sensor arm component.

Embodiment 70. The MNAzyme according to embodiment 69, wherein the number of nucleotides in the third sensor arm component is between 1 and 200 nucleotides, 1 and 150 nucleotides, 1 and 100 nucleotides, 1 and 75 nucleotides, and 50 nucleotides, 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides, less than the number of unhybridised nucleotides in the assembly facilitator polynucleotide located between portions of the assembly facilitator polynucleotide hybridised to the first sensor arm component and the second sensor arm component.

Embodiment 71. The MNAzyme according to embodiment 66, wherein the first sensor arm component and second sensor arm component are capable of hybridising to separate non-contiguous components of the assembly facilitator polynucleotide by complementary base pairing, thereby juxtaposing the non-contiguous components and creating a loop portion comprising unhybridised nucleotides in the assembly facilitator polynucleotide.

Embodiment 72. The MNAzyme according to embodiment 71, wherein the loop portion of the assembly facilitator polynucleotide comprises between 1 and 50 nucleotides, 1 and 40 nucleotides, 1 and 30 nucleotides, 1 and 20 nucleotides, 1 and 10 nucleotides, 1 and 5 nucleotides, 5 and 50 nucleotides, 5 and 40 nucleotides, 5 and 30 nucleotides 5 and 20 nucleotides, 5 and 10 nucleotides, 10 and 50 nucleotides, 10 and 40 nucleotides, 10 and 30 nucleotides, or 10 and 20 nucleotides.

Embodiment 73. The MNAzyme according to any one of 66 to 72, wherein the assembly facilitator polynucleotide is a target polynucleotide for detection by the MNAzyme.

Embodiment 74. A nucleic acid complex comprising the MNAzyme of any one of embodiments 66 to 73 hybridised to said assembly facilitator polynucleotide by complementary base pairing.

Embodiment 75. Use of the MNAzyme according to any one of embodiments 66 to 73 for detecting the presence or absence of a target polynucleotide in a sample, wherein the polynucleotide target is said assembly facilitator.

Embodiment 76. A method for determining the presence or absence of a target polynucleotide in a sample, the method comprising:
  providing a primer oligonucleotide capable of hybridising to the target polynucleotide by complementary base pairing,
  contacting a sample potentially comprising the target polynucleotide with the primer oligonucleotide under conditions suitable for hybridisation of the primer oligonucleotide with the target polynucleotide by complementary base pairing to thereby form a double-stranded duplex,
  contacting the sample with a polymerase enzyme capable of using the target polynucleotide as a template to extend the length of the primer oligonucleotide of the duplex and thereby generate an amplicon, and
  detecting whether the amplicon is generated using an MNAzyme according embodiment 66, wherein detection of the amplicon indicates the presence of the target polynucleotide in the sample, and failure to detect the amplicon indicates the absence of the target polynucleotide in the sample.

Embodiment 77. The method according to embodiment 76, wherein said first sensor arm component comprises a sequence of nucleotides sharing base pair complementarity with:
  (i) the amplicon or a component thereof, or
  (ii) a sequence of nucleotides complementary to the amplicon or a component thereof;
  and said detecting comprises determining whether said first sensor arm component hybridises by complementary base pairing to either (i) or (ii) above.

Embodiment 78. The method according to embodiment 76, wherein the target polynucleotide comprises a polymorphic region that varies between two or more individual members of a population of the target polynucleotides a series of the primer oligonucleotides are provided each capable of hybridising to at least one said target polynucleotide of the target polynucleotide population by complementary base pairing, wherein each said primer oligonucleotide shares base pair complementarity with a specific form of the polymorphic region present in only some of said members of the target polynucleotide population; and each said primer oligonucleotide comprises an identical tag portion nucleotide sequence that is incorporated into each of a population of said amplicons after said contacting of the the sample with a polymerase enzyme, wherein each said member of the amplicon population comprises a polymorphic region present in only some of said members of the amplicon population; and wherein said detecting comprises determining whether said first sensor arm of the MNAzyme hybridises with said tag portion of members of the amplicon population by complementary base pairing.

Embodiment 79. A method for determining the presence or absence of a target polynucleotide in a sample, wherein the target polynucleotide comprises a polymorphic region that varies between two or more individual members of a population of the target polynucleotides, the method comprising:

providing a primer oligonucleotide capable of hybridising to the target polynucleotide by complementary base pairing, wherein the primer oligonucleotide shares base pair complementarity with a specific form of the polymorphic region present in only some of said members of the population, or, with a portion of the target polynucleotide adjacent or substantially adjacent to the specific form of the polymorphic region;

contacting a sample potentially comprising the target polynucleotide with the primer oligonucleotide under conditions suitable for hybridisation of the primer oligonucleotide with the target polynucleotide by complementary base pairing to thereby form a double-stranded duplex, contacting the sample with a polymerase enzyme capable of using the target polynucleotide as a template to extend the length of the primer oligonucleotide of the duplex and thereby generate an amplicon comprising the specific form of the polymorphic region; and detecting whether the amplicon is generated using an MNAzyme according embodiment 66, wherein detection of the amplicon indicates the presence of the target polynucleotide in the sample, and failure to detect the amplicon indicates the absence of the target polynucleotide in the sample.

Embodiment 80. The method according to any one of embodiments 76 to 79 comprising producing copies of said amplicon using any one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Embodiment 81. The method according to embodiment 79 or 80, wherein said providing comprises providing multiple forms of the primer oligonucleotide, wherein different forms of the primer oligonucleotide share base pair complementarity with different forms of the polymorphic region, or, a portion of the target polynucleotide adjacent or substantially adjacent to one or more forms of the polymorphic region;

said contacting with the primer oligonucleotide comprises contacting a sample potentially comprising one or more members of the target polynucleotide population with the multiple forms of the primer oligonucleotide under said conditions suitable for hybridisation; and said detecting comprises detecting whether multiple forms of the amplicon comprising different polymorphic regions are generated using said MNAyme.

Embodiment 82. The method according to any one of embodiments embodiment 79 to 81, wherein multiple forms of the amplicon are generated by said contacting of the sample with a polymerase enzyme, wherein the polymorphic region of said forms of the amplicon differ; and the sensor arm of the MNAzyme comprises or consists of a first sensor arm component and a second sensor arm component comprising a sequence of nucleotides complementary to different portions of the amplicon, and a third sensor arm component located between the first sensor arm component and the second sensor arm component, wherein the first sensor arm component is capable of hybridising to any said form of the amplicon by complementary base pairing upstream of the polymorphic region, the second sensor arm component is capable of hybridising to any said form of the amplicon by complementary base pairing downstream of the polymorphic region, the third sensor arm component is located between the first sensor arm component and the second sensor arm component, and is not capable of hybridising by complementary base pairing to the polymorphic region of any said form of the amplicon due to an absence of a sequence of nucleotides in the third sensor arm component sharing base pair complementarity with the polymorphic region of any said form of the amplicon.

Embodiment 83. The method according to embodiment 82, wherein the number of nucleotides in the third sensor arm component is equal to or exceeds the number of unhybridised nucleotides in the amplicon comprising the polymorphic region.

Embodiment 84. The method according to embodiment 82, wherein the number of nucleotides in the third sensor arm component is less than the number of unhybridised nucleotides in the amplicon comprising the polymorphic region.

Embodiment 85. The method according to embodiment 84, wherein the number of nucleotides in the third sensor arm component is between 1 and 50 nucleotides, 1 and 40 nucleotides, 1 and 30 nucleotides 1 and 20 nucleotides, 1 and 10 nucleotides, 5 and 50 nucleotides, 5 and 40 nucleotides, 5 and 30 nucleotides 5 and 20 nucleotides, 5 and 10 nucleotides, 10 and 50 nucleotides, 10 and 40 nucleotides, 10 and 30 nucleotides, or 10 and 20 nucleotides, less than the number of unhybridised nucleotides in the assembly facilitator polynucleotide located between portions of the assembly facilitator polynucleotide hybridised to the first sensor arm component and the second sensor arm component.

Embodiment 86. The method according to embodiment 79 or embodiment 80, wherein multiple forms of the amplicon comprising the polymorphic region are generated by said contacting of the sample with a polymerase enzyme, wherein the polymorphic region of said forms of the amplicon differ; and the sensor arm comprises or consists of a first sensor arm component and a second sensor arm component, wherein the first sensor arm component and second sensor arm component hybridise by complementary base pairing to separate non-contiguous components of any given form of said amplicon, thereby juxtaposing the non-contiguous components and creating a loop portion comprising unhybridised nucleotides in the amplicon, and the unhybridised nucleotides in the amplicon comprise the polymorphic region.

Embodiment 87. The method according to embodiment 86, wherein the loop portion comprising unhybridised nucleotides in the target polynucleotide comprises between between 1 and 200 nucleotides, 1 and 150 nucleotides, 1 and 100 nucleotides, 1 and 75 nucleotides, and 50 nucleotides, 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides.

Embodiment 88. The method according to any one of embodiments 81 to 87, further comprising using an enzymatic reaction to provide amplified copies of one or more of the target polynucleotides.

Embodiment 89. The method according to embodiment 88, comprising amplifying one or more of the nascent polynucleotides using a second oligonucleotide that is substantially complementary to a different component of the target polynucleotide than the primer oligonucleotides.

Embodiment 90. The method according to any one of embodiments 78 to 89, wherein the polymorphic region comprises any one or more of nucleotide insertions, deletions and/or substitutions, such that said individual members of the population of target polynucleotides can differ.

Embodiment 91. The method according to any one of embodiments 76 to 90, wherein the primer oligonucleotide and/or target polynucleotide and/or amplicon and/or MNAzyme comprise or consist of deoxyribonucleotides, ribonucleotides, or a combination thereof.

Embodiment 92. The method according to any one of embodiments 76 to 91, wherein the target polynucleotide and/or amplicon is genomic DNA, complementary DNA (cDNA), or RNA.

Embodiment 93. The method according to any one of embodiments 29 to 42 or 76 to 92, wherein said MNAyme is capable of modifying a substrate comprising a detectable portion and a quencher portion, wherein a detectable effect is provided by the cleavage of the substrate by the MNAzyme which separates said detectable and quencher portions, thereby indicating the presence of the target polynucleotide in the sample.

Embodiment 94. The method according to embodiment 93, further comprising amplifying the detectable effect produced upon modification of the substrate by the MNAzyme.

Embodiment 95. The method according to any one of embodiments 29 to 42 or 76 to 93, wherein the target polynucleotide is from a bacterium, virus, fungi/yeast, protist or nematode.

Embodiment 96. The method according to any one of embodiments 29 to 42 or 76 to 93, wherein the target polynucleotide is from an enterovirus.

Embodiment 97. The method according to any one of embodiments 1 to 53 or 76 to 96, wherein the method is performed in vitro or ex vivo.

Embodiment 98. The method according to any one of embodiments 5 to 10, wherein the sample comprises a population of target polynucleotides;

the target polynucleotide strand comprises a polymorphic region that varies between at least two individual members of the population of the target polynucleotides;

said providing comprises providing two forms of the primer oligonucleotide wherein the first or second primer component of a first said form of the primer oligonucleotide shares base pair complementarity with the polymorphic region of the target polynucleotide strand of a first member of the population of target polynucleotides, the first or second primer component of a second said form of the primer oligonucleotide shares base pair complementarity with the polymorphic region of the target polynucleotide strand of a second member of the population of target polynucleotides, the polymorphic region of said first and second members of the population of target polynucleotides differs in nucleotide sequence, and the third component of the first and second forms of the primer oligonucleotide differs in nucleotide sequence;

said contacting of the sample comprises contacting the sample with the first and second forms of the primer oligonucleotide; and said contacting of the sample with the polymerase enzyme generates a population of said amplicons, wherein a first member of said population of amplicons comprises an end component sharing sequence complementarity with said polymorphic region of the first member of the population of target polynucleotides, a second member of said population of amplicons comprises an end component sharing sequence complementarity with said polymorphic region of the second member of the population of target polynucleotides, and the nucleotide sequence of the internal component of said first and second members of said population of amplicons differs.

Embodiment 99. The method according to any one of embodiments 14 to 16, wherein the sample comprises a population of target polynucleotides;

the target polynucleotide strand comprises a polymorphic region that varies between at least two individual members of the population of the target polynucleotides;

said providing comprises providing two forms of the primer oligonucleotides wherein the first or second primer component of a first said form of the primer oligonucleotide shares base pair complementarity with the polymorphic region of the target polynucleotide strand of a first member of the population of target polynucleotides, the first or second primer component of a second said form of the primer oligonucleotide shares base pair complementarity with the polymorphic region of the target polynucleotide strand of a second member of the population of target polynucleotides, the polymorphic region of said first and second members of the population of target polynucleotides differs in nucleotide sequence, the number of nucleotides between said non-contiguous components of the target polynucleotide strand hybridised by the first said form of the primer oligonucleotide differs from the number of nucleotides between said non-contiguous components of the target polynucleotide strand hybridised by the second said form of the primer oligonucleotide, and the nucleotide sequence of the loop portion created by said hybridisation of the first form of the primer oligonucleotide to the target polynucleotide strand differs from the nucleotide sequence of the loop portion created by said hybridisation of the second form of the primer oligonucleotide to the target polynucleotide strand;

said contacting of the sample comprises contacting the sample with the first and second forms of the primer oligonucleotides; and said contacting of the sample with the polymerase enzyme generates a population of said amplicons, wherein a first member of said population of amplicons comprises an end component sharing sequence complementarity with said polymorphic region of the first member of the population of target polynucleotides, a second member of said population of amplicons comprises an end component sharing sequence complementarity with said polymorphic region of the second member of the population of target polynucleotides, and the nucleotide sequence of the internal component of said first and second members of said population of amplicons differs.

Embodiment 100. The method according to embodiment 98 or embodiment 99, wherein the polymorphic region comprises one or more deletions, insertions and/or substitutions of nucleotides such that the sequence of the polymorphic region varies between the first and second members of the target polynucleotide population.

Embodiment 101. The method according to embodiment 100, wherein the polymorphic region comprises a SNP and/or a point mutation.

Embodiment 102. The method according to embodiment 100, wherein the polymorphic region varies in length between the first and second members of the target polynucleotide population.

Embodiment 103. The method according to any one of embodiments 98 to 102, wherein said detecting whether the amplicon is generated comprises measuring a signal provided by a dye that binds to double-stranded DNA and/or an amplicon sequence specific-probe.

Embodiment 104. The method according to embodiment 103, wherein the dye that binds to double-stranded DNA is SYBR Green Embodiment 105. The method according to any one of embodiments 98 to 104, wherein said method comprises the use of any one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Embodiment 106. The method according to any one of embodiments 103 to 105, wherein said detecting comprises monitoring said generating of said first and second members of the population of amplicons using a melting curve analysis.

Embodiment 107. The method according to any one of embodiments 98 to 106, wherein the target polynucleotide and/or amplicon is genomic DNA, complementary DNA (cDNA), or RNA.

Embodiment 108. The use according to embodiment 75, wherein said MNAyme is capable of modifying a substrate comprising a detectable portion and a quencher portion, wherein a detectable effect is provided by the cleavage of the substrate by the MNAzyme which separates said detectable and quencher portions, thereby indicating the presence of the target polynucleotide in the sample.

Embodiment 109. The use according to embodiment 75, further comprising amplifying the detectable effect produced upon modification of the substrate by the MNAzyme.

Embodiment 110. The isolated oligonucleotide according to any one of embodiments 54 to 58, wherein the third component of the oligonucleotide comprises or consists of a nucleotide sequence as defined in any one of SEQ ID NOs: 182, 183, 184, 185, 186, 187, 188, 189, 190, 191, 192, 193, 194, 195 or 196, or a complement of any one of said sequences.

Embodiment 111. A kit comprising the oligonucleotide according to any one of embodiments 54 to 58, 110 or 110.

Embodiment 112. A kit comprising the double stranded nucleic acid duplex according to any one of embodiments 60 to 65.

Embodiment 113. A kit comprising the MNAzyme according to any one of embodiments 66 to 73.

Embodiment 114. A kit comprising the nucleic acid complex according to embodiment 74.

Embodiment 115. The method according to embodiment 36, wherein the first sensor arm component is capable of hybridising to the internal component of the amplicon, and optionally to the first end component of the amplicon, by complementary base pairing; and the second sensor arm component is capable of hybridising to the second end component of the amplicon by complementary base pairing.

Embodiment 116. The method according to embodiment 115, wherein the first sensor arm component is capable of hybridising to the internal component of the amplicon and the first end component of the amplicon, by complementary base pairing; and the second sensor arm component is capable of hybridising to the second end component of the amplicon by complementary base pairing.

Embodiment 117. The method according to embodiment 50, wherein the third component of the primer oligonucleotide comprises a sequence of nucleotides that is complementary to a functionally active catalytic nucleic acid.

The present invention also relates at least in part to the following embodiments 1-33:

Embodiment 1. A method for determining the presence or absence in a sample of a target polynucleotide that is a component of:
(i) a Kirsten rat sarcoma viral oncogene homolog (KRAS) wild-type gene;
(ii) a Kirsten rat sarcoma viral oncogene homolog (KRAS) gene comprising a sequence of nucleotides encoding a G12V or G12S mutation; or
(iii) an enterovirus, the method comprising:
  providing a primer oligonucleotide comprising
    a first primer component terminating at the 5' end of the oligonucleotide and capable of hybridising to a first portion of a strand of the target polynucleotide by complementary base pairing, and
    a second primer component terminating at the 3' end of the oligonucleotide and capable of hybridising to a second portion of the target polynucleotide strand by complementary base pairing;
  contacting a sample potentially comprising the target polynucleotide with the primer oligonucleotide under conditions suitable for hybridisation of the first primer component and second primer component with the target polynucleotide strand to thereby form a double-stranded duplex, wherein at least one strand of an intermediate section of the duplex comprises a sequence of at least four nucleotides that remains unhybridised to an opposing strand of the intermediate section due to an absence of a sequence of nucleotides in the opposing strand of the intermediate section sharing base pair complementarity with the sequence of at least four nucleotides;
  contacting the sample with a polymerase enzyme capable of using the target polynucleotide strand as a template to extend the length of the primer oligonucleotide of the duplex and thereby generate an amplicon comprising an internal component intermediate to first and second end components, wherein
    the first end component of the amplicon is capable of hybridising by complementary base pairing to said first portion of the target polynucleotide strand,
    the second end component of the amplicon is capable of hybridising by complementary base pairing to said second portion of the target polynucleotide strand, and
    said hybridising of the first and second end components of the amplicon to the target polynucleotide strand positions the internal component of the amplicon to oppose an intermediate sequence of nucleotides in the target polynucleotide strand located between the first and second portions of the target polynucleotide strand that does not share base pair complementarity with the internal component; and
  detecting whether the amplicon is generated, wherein detection of the amplicon indicates the presence of the target polynucleotide in the sample, and failure to detect the amplicon indicates the absence of the target polynucleotide in the sample.

Embodiment 2. The method according to embodiment 1, wherein
  the target polynucleotide is a component of a Kirsten rat sarcoma viral oncogene homolog (KRAS) gene comprising a sequence of nucleotides encoding a G12V mutation,
  the primer oligonucleotide comprises a third primer component located between the first primer component and second primer component, wherein
    the third primer component consists of a sequence of nucleotides that does not share base pair complementarity with said intermediate sequence of nucleotides in the target polynucleotide strand, and, is identical to a sequence of nucleotides in the internal component of the amplicon, and
    the primer oligonucleotide comprises or consists of a sequence as defined in any one of SEQ ID NOs: 35, 36, 37, 38, 39, 40, 41, 42, 50, 59, 60, 61, 62, 172, 173, 174, 175, 176, 292, 297, 293, 298, 294, 299, 295, 300, 296, 301, 66, 87, 70, 71, 72, 73, 74, 75, 76, 77, 78, 79 or 99.

Embodiment 3. The method according to embodiment 2, comprising
  contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and
  using a polymerase enzyme to extend the length of the second primer oligonucleotide using the second target polynucleotide strand as a template and thereby generate a second amplicon wherein
    (i) the primer oligonucleotide comprises or consists of a sequence as defined in any one of SEQ ID NOs: 35, 36, 37, 38, 39, 40, 41, 42, 50, 59, 60, 61, 62, 172, 173, 174, 175, 176, 292, 297, 293, 298, 294, 299, 295, 300, 296, or 301, and the second primer oligonucleotide comprises or consists of a sequence as defined in SEQ ID NO: 26;
    (ii) the primer oligonucleotide comprises or consists of a sequence as defined in SEQ ID NO: 66 or 87, and the second primer oligonucleotide comprises or consists of a sequence as defined in SEQ ID NO: 65;
    (iii) the primer oligonucleotide comprises or consists of a sequence as defined in any one of SEQ ID NOs: 70-79 or 99, and the second primer oligonucleotide comprises or consists of a sequence as defined in SEQ ID NO: 69; or
    (iv) the primer oligonucleotide comprises or consists of a sequence as defined in SEQ ID NO: 87, and the second primer oligonucleotide comprises or consists of a sequence as defined in SEQ ID NO: 26 or 171.

Embodiment 4. The method according to embodiment 1, wherein
  the target polynucleotide is a component of a Kirsten rat sarcoma viral oncogene homolog (KRAS) gene comprising a sequence of nucleotides encoding a G12V mutation,
  the first primer component and second primer component hybridise by complementary base pairing to separate non-contiguous components of the target polynucleotide strand, thereby juxtaposing the non-contiguous components and creating a loop portion comprising unhybridised nucleotides in the target polynucleotide strand; and
  the primer oligonucleotide comprises or consists of a sequence as defined in any one of SEQ ID NOs: 177, 178 or 171.

Embodiment 5. The method according to embodiment 4, comprising
  contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and
  using a polymerase enzyme to extend the length of the second primer oligonucleotide using the second target polynucleotide strand as a template and thereby generate a second amplicon wherein:

(i) the primer oligonucleotide comprises or consists of a sequence as defined in SEQ ID NO: 177 or 178, and the second primer oligonucleotide comprises or consists of a sequence as defined in SEQ ID NO: 26; or (ii) the primer oligonucleotide comprises or consists of a sequence as defined in SEQ ID NO: 171, and the second primer oligonucleotide comprises or consists of a sequence as defined in SEQ ID NO: 87.

Embodiment 6. The method according to embodiment 3 or embodiment 5, wherein said detecting whether the amplicon is generated comprises using first and second partzymes, wherein (i) the first partzyme comprises a sequence as defined in any one of SEQ ID NOs: 22, 24, 23, 47, 53, 54, 64, 164, 165, 287, 288, 289, 290, or 291, and the second partzyme comprises a sequence as defined in SEQ ID NO: 18;

(ii) the first partzyme comprises a sequence as defined in any one of SEQ ID NOs: 64, 24, 67, 68 or 88, and the second partzyme comprises a sequence as defined in SEQ ID NO: 63; or (iii) the first partzyme comprises a sequence as defined in SEQ ID NO: 24, and the second partzyme comprises a sequence as defined in SEQ ID NO: 18.

Embodiment 7. The method according to embodiment 1, wherein:

the target polynucleotide is a component of a Kirsten rat sarcoma viral oncogene homolog (KRAS) gene comprising a sequence of nucleotides encoding a G12S mutation, the primer oligonucleotide comprises a third primer component located between the first primer component and second primer component, wherein the third primer component consists of a sequence of nucleotides that does not share base pair complementarity with said intermediate sequence of nucleotides in the target polynucleotide strand, and, is identical to a sequence of nucleotides in the internal component of the amplicon, and the primer oligonucleotide comprises or consists of a sequence as defined in any one of SEQ ID NOs: 166-169.

Embodiment 8. The method according to embodiment 7 comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein (i) the primer oligonucleotide comprises or consists of a sequence as defined in any one of SEQ ID NOs: 166-169, and the second primer oligonucleotide comprises or consists of a sequence as defined in SEQ ID NO: 26; or (ii) the primer oligonucleotide comprises or consists of a sequence as defined in SEQ ID NO: 166, and the second primer oligonucleotide comprises or consists of a sequence as defined in SEQ ID NO: 171.

Embodiment 9. The method according to embodiment 1, wherein:

the target polynucleotide is a component of a Kirsten rat sarcoma viral oncogene homolog (KRAS) gene comprising a sequence of nucleotides encoding a Gin mutation.

the first primer component and second primer component hybridise by complementary base pairing to separate non-contiguous components of the target polynucleotide strand, thereby juxtaposing the non-contiguous components and creating a loop portion comprising unhybridised nucleotides in the target polynucleotide strand; and the primer oligonucleotide comprises or consists of a sequence as defined in SEQ ID NO: 170 or 171.

Embodiment 10. The method according to embodiment 9 comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein (i) the primer oligonucleotide comprises or consists of a sequence as defined in SEQ ID NO: 170, and the second primer oligonucleotide comprises or consists of a sequence as defined in SEQ ID NO: 26 or 171; or (ii) the primer oligonucleotide comprises or consists of a sequence as defined in SEQ ID NO: 171, and the second primer oligonucleotide comprises or consists of a sequence as defined in SEQ ID NO: 166 or 170.

Embodiment 11. The method according to embodiment 8 or embodiment 10, wherein said detecting whether the amplicon is generated comprises using first and second partzymes, wherein the first partzyme comprises a sequence as defined in SEQ ID NO: 161 or 162, and the second partzyme comprises a sequence as defined in SEQ ID NO: 18.

Embodiment 12. The method according to embodiment 1, wherein the target polynucleotide is a component of an enterovirus gene, the primer oligonucleotide comprises a third primer component located between the first primer component and second primer component, wherein the third primer component consists of a sequence of nucleotides that does not share base pair complementarity with said intermediate sequence of nucleotides in the target polynucleotide strand, and, is identical to a sequence of nucleotides in the internal component of the amplicon, and the primer oligonucleotide comprises or consists of a sequence as defined in SEQ ID NO: 317.

Embodiment 13. The method according to embodiment 12 comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein the primer oligonucleotide comprises or consists of a sequence as defined in SEQ ID NO: 317, and the second primer oligonucleotide comprises or consists of a sequence as defined in SEQ ID NO: 318.

Embodiment 14. The method according to embodiment 13, wherein said detecting whether the amplicon is generated comprises using first and second partzymes, wherein the first partzyme comprises a sequence as defined in SEQ ID NO: 314, and the second partzyme comprises a sequence as defined in SEQ ID NO: 315.

Embodiment 15. A method for determining the presence or absence in a sample of a target polynucleotide that is a component of an epidermal growth factor receptor (EGFR) gene and the target polynucleotide comprises a polymorphic region that varies between two or more individual members of a population of the target polynucleotides, the method comprising:

providing a primer oligonucleotide capable of hybridising to the target polynucleotide by complementary base pairing, wherein the primer oligonucleotide shares base pair complementarity with a specific form of the polymorphic region present in only some of said members of the population, or, with a portion of the target polynucleotide adjacent or substantially adjacent to the specific form of the polymorphic region;

contacting a sample potentially comprising the target polynucleotide with the primer oligonucleotide under conditions suitable for hybridisation of the primer oligonucleotide with the target polynucleotide by complementary base pairing to thereby form a double-stranded duplex, contacting the sample with a polymerase enzyme capable of using the target polynucleotide as a template to extend the length of the primer oligonucleotide of the duplex and thereby generate an amplicon comprising the specific form of the polymorphic region; and detecting whether the amplicon is generated using multi-component nucleic acid enzyme (MNAzyme) wherein, a sensor arm of the MNAzyme comprises or consists of a first sensor arm component and a second sensor arm component comprising a sequence of nucleotides complementary to different portions of the amplicon, and a third sensor arm component located between the first sensor arm component and the second sensor arm component, wherein the first sensor arm component is capable of hybridising to any said form of the amplicon by complementary base pairing upstream of the polymorphic region, the second sensor arm component is capable of hybridising to any said form of the amplicon by complementary base pairing downstream of the polymorphic region, the third sensor arm component is located between the first sensor arm component and the second sensor arm component, and is not capable of hybridising by complementary base pairing to the polymorphic region of any said form of the amplicon due to an absence of a sequence of nucleotides in the third sensor arm component sharing base pair complementarity with the polymorphic region of any said form of the amplicon.

Embodiment 16. The method according to embodiment 15, wherein the first sensor arm component of said sensor arm comprises or consists of a sequence as defined in any one of SEQ ID NOs: 120, 127, 128 or 129.

Embodiment 17. The method according to embodiment 16, wherein said MNAzyme comprises a second sensor arm capable of hybridising to any said form of the amplicon by complementary base pairing, and (i) the sensor arm comprises or consists of a sequence as defined in SEQ ID NO: 120, and the second sensor arm comprises or consists of a sequence as defined in SEQ ID NO: 119; or (ii) the sensor arm comprises or consists of a sequence as defined in any one of SEQ ID NOs: 127, 128, or 129, and the second sensor arm comprises or consists of a sequence as defined in SEQ ID NO: 119.

Embodiment 18. The method according to embodiment 17, wherein the sensor arm comprises or consists of a sequence as defined in SEQ ID NO: 128 or 129, and the second sensor arm comprises or consists of a sequence as defined in SEQ ID NO: 119, and the primer oligonucleotide comprises or consists of a sequence as defined in SEQ ID NO: 131.

Embodiment 19. The method according to embodiment 18, comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein the primer oligonucleotide comprises or consists of a sequence as defined in SEQ ID NO: 131, and the second primer oligonucleotide comprises or consists of a sequence as defined in SEQ ID NO: 122.

Embodiment 20. The method according to embodiment 17, comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein the primer oligonucleotide comprises or consists of a sequence as defined in SEQ ID NO: 122, and the second primer oligonucleotide comprises or consists of a sequence as defined in any one of SEQ ID NOs: 123-126 or 130.

Embodiment 21. An isolated primer or partzyme oligonucleotide comprising a first component terminating at the 5' end of the oligo-
nucleotide and capable of hybridising to a first portion
of a second polynucleotide by complementary base
pairing,
a second component terminating at the 3' end of the
oligonucleotide and capable of hybridising to a second
portion of the second polynucleotide by complemen-
tary base pairing, and
a third component located between the first and second
components comprising a sequence of at least four
nucleotides that do not share base pair complementarity
with an opposing sequence of nucleotides in the second
polynucleotide when the first and second components
are hybridised to the second polynucleotide;
wherein
the third component is located partially or com-
pletely in the 3' half of the oligonucleotide, and
the oligonucleotide comprises or consists of a
sequence as defined in any one of SEQ ID NOs:
35, 36, 37, 38, 39, 40, 41, 42, 50, 59, 60, 61, 62,
172, 173, 174, 175, 176, 292, 297, 293, 298, 294,
299, 295, 300, 296, 301, 66, 87, 70, 71, 72, 73, 74,
75, 76, 77, 78, 79, 99, 166-171, 317, 120, 127,
128, 129, or 131.

Embodiment 22. The primer oligonucleotide according to
embodiment 21, wherein the primer oligonucleotide com-
prises or consists of a sequence as defined in any one of SEQ
ID NOs: 35, 36, 37, 38, 39, 40, 41, 42, 50, 59, 60, 61, 62,
172, 173, 174, 175, 176, 292, 297, 293, 298, 294, 299, 295,
300, 296, 301, 66, 87, 70, 71, 72, 73, 74, 75, 76, 77, 78, 79,
99, 166-171, 317 or 131.

Embodiment 23. The partzyme oligonucleotide according
to embodiment 21, wherein the partzyme oligonucleotide
comprises or consists of a sequence as defined in any one of
SEQ ID NOs: 120, 127, 128, or 129.

Embodiment 24. An isolated primer oligonucleotide com-
prising or consisting of a sequence as defined in any one of
SEQ ID NOs: 177, 178, 170, or 171.

Embodiment 25. A kit comprising one or more isolated
oligonucleotides according to any one of embodiments 21 to
24.

Embodiment 26. The kit according to embodiment 25
comprising
(i) a first primer oligonucleotide comprising or consisting
of a sequence as defined in any one of SEQ ID NOs: 35,
36, 37, 38, 39, 40, 41, 42, 50, 59, 60, 61, 62, 172, 173,
174, 175, 176, 292, 297, 293, 298, 294, 299, 295, 300,
296, or 301, and a second primer oligonucleotide
comprising or consisting of a sequence as defined in
SEQ ID NO: 26;
(ii) a first primer oligonucleotide comprising or consisting
of a sequence as defined in any one of SEQ ID NOs: 66
or 87, and a second primer oligonucleotide comprising
or consisting of a sequence as defined in SEQ ID NO:
65;
(iii) a first primer oligonucleotide comprising or consist-
ing of a sequence as defined in any one of SEQ ID NOs:
70-79 or 99, and a second primer oligonucleotide
comprising or consisting of a sequence as defined in
SEQ ID NO: 69;
(iv) a first primer oligonucleotide comprising or consist-
ing of a sequence as defined in SEQ ID NO: 87, and a
second primer oligonucleotide comprising or consist-
ing of a sequence as defined in SEQ ID NO: 26 or 171;
(v) a first primer oligonucleotide comprising or consisting
of a sequence as defined in SEQ ID NO: 177 or 178,
and a second primer oligonucleotide comprising or
consisting of a sequence as defined in SEQ ID NO: 26;
(vi) a first primer oligonucleotide comprising or consist-
ing of a sequence as defined in SEQ ID NO: 171, and
a second primer oligonucleotide comprising or consist-
ing of a sequence as defined in SEQ ID NO: 87;
(vii) a first primer oligonucleotide comprising or consist-
ing of a sequence as defined in any one of SEQ ID NOs:
166-169, and a second primer oligonucleotide compris-
ing or consisting of a sequence as defined in SEQ ID
NO: 26;
(viii) a first primer oligonucleotide comprising or con-
sisting of a sequence as defined in SEQ ID NO: 166,
and a second primer oligonucleotide comprising or
consisting of a sequence as defined in SEQ ID NO: 171;
(ix) a first primer oligonucleotide comprising or consist-
ing of a sequence as defined in SEQ ID NO: 170, and
a second primer oligonucleotide comprising or consist-
ing of a sequence as defined in SEQ ID NO: 26 or 171;
(x) a first primer oligonucleotide comprising or consisting
of a sequence as defined in SEQ ID NO: 171, and a
second primer oligonucleotide comprising or consist-
ing of a sequence as defined in SEQ ID NO: 166 or 170;
(xi) a first primer oligonucleotide comprising or consist-
ing of a sequence as defined in SEQ ID NO: 317, and
a second primer oligonucleotide comprising or consist-
ing of a sequence as defined in SEQ ID NO: 318;
(xii) a first partzyme oligonucleotide comprising a
sequence as defined in any one of SEQ ID NO: 120,
127, 128, or 129, and a second sensor arm partzyme
oligonucleotide comprising a sequence as defined in
SEQ ID NO: 119; or
(xiii) a first primer oligonucleotide comprising or con-
sisting of a sequence as defined in SEQ ID NO: 131,
and a second primer oligonucleotide comprising or
consisting of a sequence as defined in SEQ ID NO: 122.

Embodiment 27. The kit according to embodiment 26,
further comprising:
(i) a first partzyme comprising a sequence as defined in
any one of SEQ ID NOs: 22, 24, 23, 47, 53, 54, 64, 164,
165, 287, 288, 289, 290, or 291, and a second partzyme
comprising a sequence as defined in SEQ ID NO: 18;
(ii) a first partzyme comprising a sequence as defined in
any one of SEQ ID NOs: 64, 24, 67, 68 or 88, and a
second partzyme comprising a sequence as defined in
SEQ ID NO: 63;
(iii) a first partzyme comprising a sequence as defined in
SEQ ID NO: 24, and a second partzyme comprising a
sequence as defined in SEQ ID NO: 18;
(iv) a first partzyme comprising a sequence as defined in
SEQ ID NO: 161 or 162 and a second partzyme
comprising a sequence as defined in SEQ ID NO: 18;
(v) a first partzyme comprising a sequence as defined in
SEQ ID NO: 314 and a second partzyme comprising a
sequence as defined in SEQ ID NO: 315;
(vi) a primer oligonucleotide comprising or consisting of
a sequence as defined in SEQ ID NO: 122, and a second
primer oligonucleotide comprising or consisting of a
sequence as defined in any one of SEQ ID NOs:
123-126 or 130; or
(vii) a first partzyme comprising a sequence as defined in
SEQ ID NO: 128 or 129 and a second partzyme
comprising a sequence as defined in SEQ ID NO: 119.

Embodiment 28. An MNAzyme comprising a partzyme
oligonucleotide according to embodiment 23.

Embodiment 29. The method according to embodiment 1,
wherein the target polynucleotide is a component of a Kirsten rat sarcoma viral oncogene homolog (KRAS) wild-type gene, the primer oligonucleotide comprises a third primer component located between the first primer component and second primer component, wherein the third primer component consists of a sequence of nucleotides that does not share base pair complementarity with said intermediate sequence of nucleotides in the target polynucleotide strand, and, is identical to a sequence of nucleotides in the internal component of the amplicon, and the primer oligonucleotide comprises or consists of a sequence as defined in any one of SEQ ID NOs: 27, 28, 29, 30, 31, 32, 49, 33, 34, 55, 56, 57, 58, 83, 257, 258, 259, 260, 261, 262, 263, 264, 265, 266, 267, 268, 269, 270, 271, 272, 273, 274, 275, 276, 277, 278, 279, 280, 281, 282, 283, 284, 285, or 286.

Embodiment 30. The method according to embodiment 29, comprising contacting the sample with a second primer oligonucleotide that shares base pair complementarity with a second target polynucleotide strand that is the complement of said first target polynucleotide strand, wherein said contacting is under conditions suitable for hybridisation of the second primer oligonucleotide and the second target polynucleotide strand by complementary base pairing, and using a polymerase enzyme to extend the length of the second primer oligonucleotide using the second target polynucleotide strand as a template and thereby generate a second amplicon wherein (i) the primer oligonucleotide comprises or consists of a sequence as defined in any one of SEQ ID NOs: 27, 28, 29, 30, 31, 32, 49, 33, 34, 55, 56, 57, or 58, and the second primer oligonucleotide comprises or consists of a sequence as defined in SEQ ID NO: 26;

(ii) the primer oligonucleotide comprises or consists of a sequence as defined in SEQ ID NO: 83, and the second primer oligonucleotide comprises or consists of a sequence as defined in SEQ ID NO: 69; or (iii) the primer oligonucleotide comprises or consists of a sequence as defined in any one of SEQ ID NOs: 257, 258, 259, 260, 261, 262, 263, 264, 265, 266, 267, 268, 269, 270, 271, 272, 273, 274, 275, 276, 277, 278, 279, 280, 281, 282, 283, 284, 285, or 286, and the second primer oligonucleotide comprises or consists of a sequence as defined in SEQ ID NO: 65.

Embodiment 31. The method according to embodiment 30, wherein said detecting whether the amplicon is generated comprises using first and second partzymes, wherein:

(i) the first partzyme comprises a sequence as defined in any one of SEQ ID NOs: 19-21, 51 or 52, and a second partzyme the second partzyme comprises a sequence as defined in SEQ ID NO: 18;

(ii) the first partzyme comprises a sequence as defined in SEQ ID NO: 80 and the second partzyme comprises a sequence as defined in SEQ ID NO: 63;

(iii) the first partzyme comprises a sequence as defined in any one of SEQ ID NOs: 242-256, and the second partzyme comprises a sequence as defined in SEQ ID NO: 241;

Embodiment 32. An isolated primer oligonucleotide comprising or consisting of a sequence as defined in any one of SEQ ID NOs: 27, 28, 29, 30, 31, 32, 49, 33, 34, 55, 56, 57, 58, 83, 257, 258, 259, 260, 261, 262, 263, 264, 265, 266, 267, 268, 269, 270, 271, 272, 273, 274, 275, 276, 277, 278, 279, 280, 281, 282, 283, 284, 285, or 286.

Embodiment 33. A kit comprising one or more isolated oligonucleotides according to embodiment 32.

The present invention also relates at least in part to the following embodiments 1-40:

Embodiment 1. A method for detecting a target polynucleotide, the method comprising:

providing a first oligonucleotide comprising a first component that is substantially complementary to the target polynucleotide and a second component that is substantially non-complementary to the target polynucleotide;

contacting the target polynucleotide with the first oligonucleotide under conditions suitable for hybridisation of the first oligonucleotide with the target polynucleotide, and amplifying the target polynucleotide using an enzymatic reaction to produce an amplified copy of said target polynucleotide comprising the second component of the first oligonucleotide; and detecting the amplified copy of the target polynucleotide.

Embodiment 2. The method according to embodiment 1, wherein said second component of the first oligonucleotide is located between first and third components of the first oligonucleotide that are substantially complementary to the target polynucleotide.

Embodiment 3. The method according to embodiment 2, wherein the number of nucleotides in the first and third components is less than the number of nucleotides in the second component.

Embodiment 4. The method according to embodiment 2, wherein the number of nucleotides in the first and third components is equal to the number of nucleotides in the second component.

Embodiment 5. The method according to embodiment 2, wherein the number of nucleotides in the first and third components is more than the number of nucleotides in the second component.

Embodiment 6. The method according to any one of embodiments 1 to 3, wherein the second component forms a loop upon binding of the first oligonucleotide to the polynucleotide target.

Embodiment 7. The method according to any one of embodiments 1 to 6, wherein said detecting comprises detecting the second portion of the oligonucleotide in the amplified copy.

Embodiment 8. The method according to any one of embodiments 1 to 6, wherein said detecting comprises detecting a sequence of nucleotides in the amplified copy that is complementary to the second portion of the first oligonucleotide.

Embodiment 9. The method according to any one of embodiments 1 to 8, wherein amplifying the target polynucleotide comprises using a second oligonucleotide that is substantially complementary to a different component of the target polynucleotide than the first oligonucleotide.

Embodiment 10. The method according to any one of embodiments 1 to 9, wherein the enzymatic reaction is any one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Embodiment 11. The method according to any one of embodiments 1 to 10, wherein the enzymatic reaction is a polymerase chain reaction (PCR).

Embodiment 12. The method according to any one of embodiments 1 to 11, wherein said detecting comprises use of an MNAzyme comprising at least two or more partzyme components, wherein at least a first partzyme component and a second partzyme component self-assemble in the presence the amplified copy of the target polynucleotide to form a catalytically active multi-component nucleic acid enzyme (MNAzyme), wherein each of the first and second partzyme components comprise a substrate arm portion, a catalytic core portion, and a sensor arm portion;
  wherein upon self-assembly, the sensor arm portion of the first and second partzyme components act as sensor arms of the MNAzyme, the substrate arm portion of the first and second partzyme components act as substrate arms of the MNAzyme, and the catalytic core portion of the first and second partzyme components act as a catalytic core of the MNAzyme;
  and wherein the sensor arms of the MNAzyme interact with the amplified copy of the target polynucleotide so as to maintain the first and second partzyme components in proximity for association of their respective catalytic core portions to form the catalytic core of the MNAzyme, the catalytic core capable of modifying at least one substrate, and wherein the substrate arms of the MNAzyme engage a substrate so that the catalytic core of the MNAzyme can modify the substrate and thereby provide a detectable effect.

Embodiment 13. The method according to embodiment 12, wherein a first sensor arm of said MNAzyme is substantially complementary to a sequence of nucleotides in the amplified copy comprising:
  (i) the second portion of the first oligonucleotide, or a component thereof; and
  (ii) a portion of the target polynucleotide.

Embodiment 14. The method according to embodiment 12, wherein a first sensor arm of said MNAzyme is substantially complementary to a sequence of nucleotides in the amplified copy comprising:
  (i) a sequence of nucleotides complementary to the second portion of the first oligonucleotide, or a component thereof; and
  (ii) a portion of the target polynucleotide.

Embodiment 15. The method according to any one of embodiments 1 to 14, wherein the target polynucleotide comprises a single nucleotide polymorphism (SNP) or a point mutation.

Embodiment 16. The method according to embodiment 15, wherein the first oligonucleotide comprises a nucleotide positioned 3' to said second component that is complementary to the SNP or point mutation.

Embodiment 17. The method according to embodiment 15 or embodiment 16, wherein the first oligonucleotide comprises a nucleotide 3' to said second component, and said nucleotide is not complementary to the polynucleotide target.

Embodiment 18. The method according to any one of embodiments 2 to 17, wherein:
  the polynucleotide target comprises a polymorphic sequence of nucleotides that varies between individuals of a given species comprising the polynucleotide target;
  the first component of the first oligonucleotide binds to the polynucleotide target 5' of the polymorphic sequence of nucleotides;
  the third component of the first oligonucleotide binds to the polynucleotide target 3' of the polymorphic sequence of nucleotides; and
  the second component of the first oligonucleotide is non-complementary to the polymorphic sequence of nucleotides.

Embodiment 19. The method of any one of embodiments 12 to 18, wherein said substrate comprises a detectable portion and a quencher portion, wherein the detectable effect is provided by the cleavage of the substrate by the MNAzyme which separates said detectable and quencher portions.

Embodiment 20. The method according to any one of embodiments 12 to 19, further comprising amplifying the detectable effect produced upon modification of the substrate by the MNAzyme in a cascade.

Embodiment 21. The method of any one of embodiments 1 to 20, further comprising detecting a second target polynucleotide that differs in sequence from the first target polynucleotide.

Embodiment 22. The method of embodiment 21, comprising:
  providing an additional oligonucleotide comprising a first component that is substantially complementary to the second target polynucleotide and a second component that is substantially non-complementary to the second target oligonucleotide;
  contacting the second target polypeptide with the additional oligonucleotide under conditions suitable for hybridisation of the additional oligonucleotide with the second target polynucleotide, and amplifying the second target polynucleotide using an second enzymatic reaction to produce an amplified copy of said second target polynucleotide comprising the second component of the additional oligonucleotide; and
  detecting the amplified copy of the second target polynucleotide.

Embodiment 23. The method according to embodiment 22, wherein said second component of the additional oligonucleotide is located between first and third components of the first oligonucleotide which are substantially complementary to the target polynucleotide.

Embodiment 24. The method according to embodiment 23, wherein the number of nucleotides in the first and third components of the additional oligonucleotide is:
  (i) less than the number of nucleotides in the second component;
  (ii) equal to the number of nucleotides in the second component; or
  (iii) more than the number of nucleotides in the second component.

Embodiment 25. The method according to any one of embodiments 22 to 24, wherein the second component of the additional oligonucleotide forms a loop upon binding of the additional oligonucleotide to the second polynucleotide target.

Embodiment 26. The method according to any one of embodiments 22 to 25, wherein the second enzymatic reaction is any one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Embodiment 27. The method according to any one of embodiments 21 to 26, wherein the detection of said first and second polynucleotide targets is performed simultaneously.

Embodiment 28. The method according to any one of embodiments 21 to 26, wherein the detection of said first and second polynucleotide targets is performed sequentially.

Embodiment 29. The method according to any one of embodiments 1 to 28, wherein the method is performed in vitro or ex vivo.

Embodiment 30. The method according to any one of embodiments 1 to 29, wherein the first or second target polynucleotide is DNA, RNA or cDNA.

Embodiment 31. An oligonucleotide comprising three components, wherein:
  a first and a third component of the oligonucleotide are substantially complementary to different components of a target polynucleotide; and
  a second component of the oligonucleotide located between the first and third components is non-complementary to the target polypeptide.

Embodiment 32. The oligonucleotide according to embodiment 31, wherein the second component is more than 3, 4, 5, 6, 7, 8, 9 or 10 nucleotides in length.

Embodiment 33. The oligonucleotide according to embodiment 31 or embodiment 32, wherein the first component is more than 3, 4, 5, 6, 7, 8, 9 or 10 nucleotides in length.

Embodiment 34. The oligonucleotide according to any one of embodiments 31 to 33, wherein the third component is more than 3, 4, 5, 6, 7, 8, 9 or 10 nucleotides in length.

Embodiment 35. The oligonucleotide according to any one of embodiments 31 to 33, wherein the number of nucleotides in the first and third components is less than the number of nucleotides in the second component.

Embodiment 36. The oligonucleotide according to any one of embodiments 31 to 33, wherein the number of nucleotides in the first and third components is equal to the number of nucleotides in the second component.

Embodiment 37. The oligonucleotide according to any one of embodiments 31 to 33, wherein the number of nucleotides in the first and third components is more than the number of nucleotides in the second component.

Embodiment 38. The oligonucleotide according to any one of embodiments 31 to 35, wherein the second component forms a loop upon binding of the oligonucleotide to the polynucleotide target.

Embodiment 39. The oligonucleotide of any one of embodiments 31 to 38, wherein the oligonucleotide is DNA, RNA or cDNA.

Embodiment 40. Use of the oligonucleotide according to any one of embodiments 31 to 39 in the method according to any one of embodiments 1 to 30.

BRIEF DESCRIPTION OF THE DRAWINGS

Preferred embodiments of the present invention will now be described, by way of example only, with reference to the accompanying FIGS. 1-16 as set out below.

When PASS primers are combined with MNAzyme qPCR, the MNAzyme may comprise a partzyme that binds to the complement of the unique sequence (cUS) as illustrated, or alternatively the unique sequence, while the other partzyme binds adjacently on the amplified target sequence of interest. Formation of active MNAzymes from partzyme components may result in the cleavage of a universal probe labelled with a fluorophore and quencher, producing a signal that can be monitored in real-time.

FIG. 2: PASS primers designed to discriminate single nucleotide polymorphisms (SNPs) and/or acquired point mutations: PASS primers may be designed to enhance discrimination of single base changes such as SNPs or point mutations. In one embodiment, S2 of either a looped PASS primer (Panel (i)) or a planar PASS primer (Panel (ii)) can be used to target and specifically bind to the SNP or point mutation.

The base matched to the SNP or point mutation in S2 of the PASS primer may be located at the 3' terminus of the primer, or may be placed at other positions within S2 (top of Panels (i) and (ii)). Further, additional bases may be mismatched between S2 and the target of interest to aid in better discrimination of the SNP (bottom of Panels (i) and (ii)).

Figure 3:
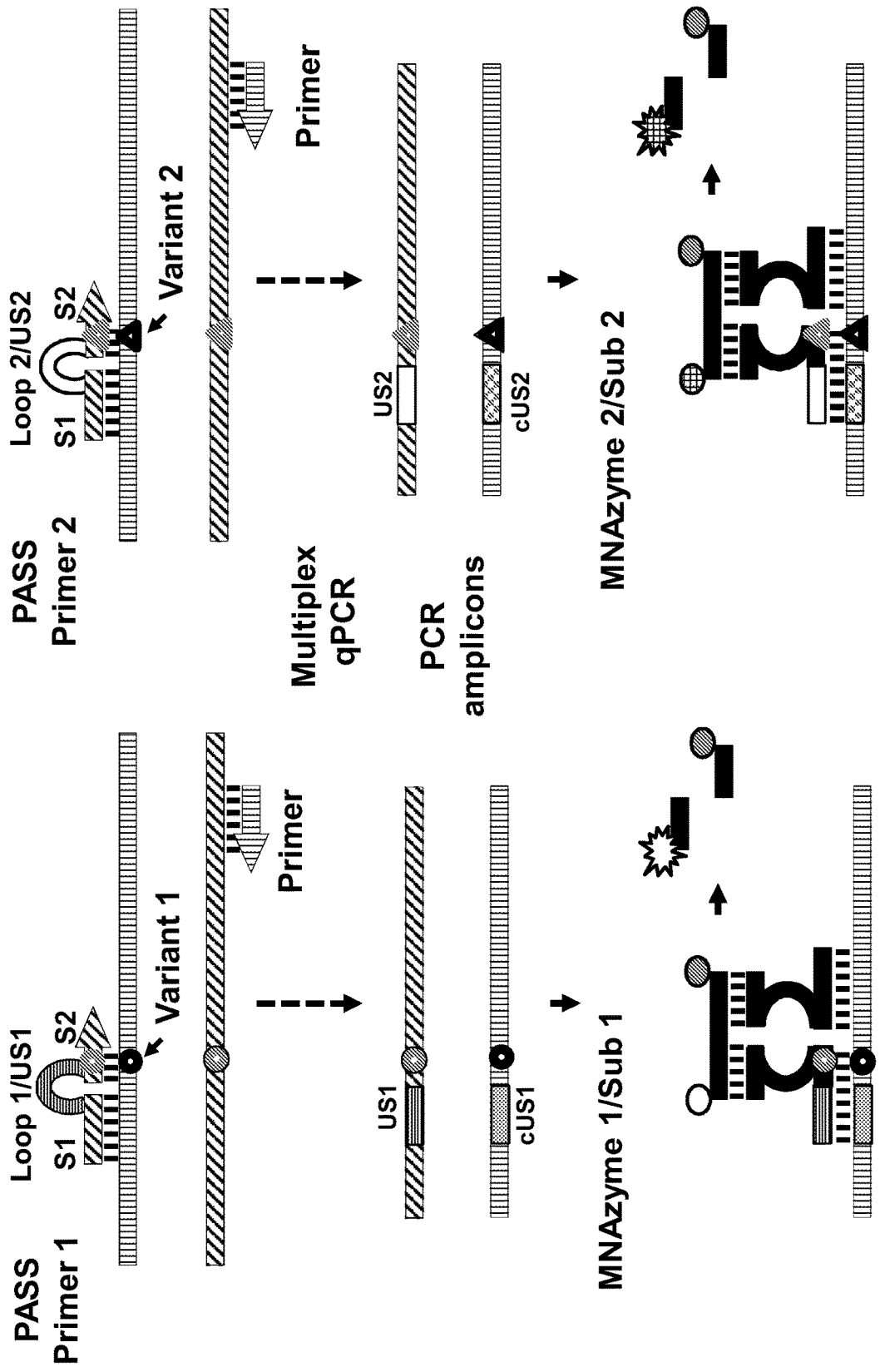

FIG. 3: Using PASS primers to discriminate between single base changes with a multiplex MNAzyme readout: PASS primers can be designed to enhance discrimination between variant sequences, such as SNPs or mutations. This may be performed in multiplex MNAzyme qPCR reactions. Detection of, and discrimination between, two sequences which vary by only a single base is illustrated in this figure with variant 1 denoted by a circle in the left hand panel and variant 2 denoted by a triangle in the right hand panel. S2 of PASS primer 1 is specifically matched to variant 1, and the US of PASS primer 1 is a first non-target unique sequence 1 (US1) in a loop format (Loop 1). S2 of PASS primer 2 is specifically matched to variant 2, and the US of PASS primer 2 is a second non-target unique sequence (US2) in a loop format (Loop 2). Use of these PASS primers result in amplicons for each variant that differ by both the (a) the variant base and (b) the US incorporated via the PASS primer.

Detection of resultant amplicons may be mediated by MNAzymes. By way of example, MNAzyme 1 may be designed to detect variant 1 amplicons by designing a partzyme sensor arm that is comprised of sequence which is specific for both variant 1 and the complement of US1. MNAzyme 1 can be designed to cleave a universal probe 1 (Sub 1) labeled with fluorophore 1 only in the presence of amplicons with variant 1. MNAzyme 2 may be designed to detect variant 2 amplicons by designing a partzyme sensor arm that is comprised of sequence which is specific for both variant 2 and the complement of US2. MNAzyme 2 can be designed to cleave a universal probe 2 (Sub 2) labeled with fluorophore 2 only in the presence of amplicons with variant 2.

In this strategy, real-time detection, discrimination and quantification of both variants 1 and 2 could occur simultaneously in the one reaction tube.

Figure 4:
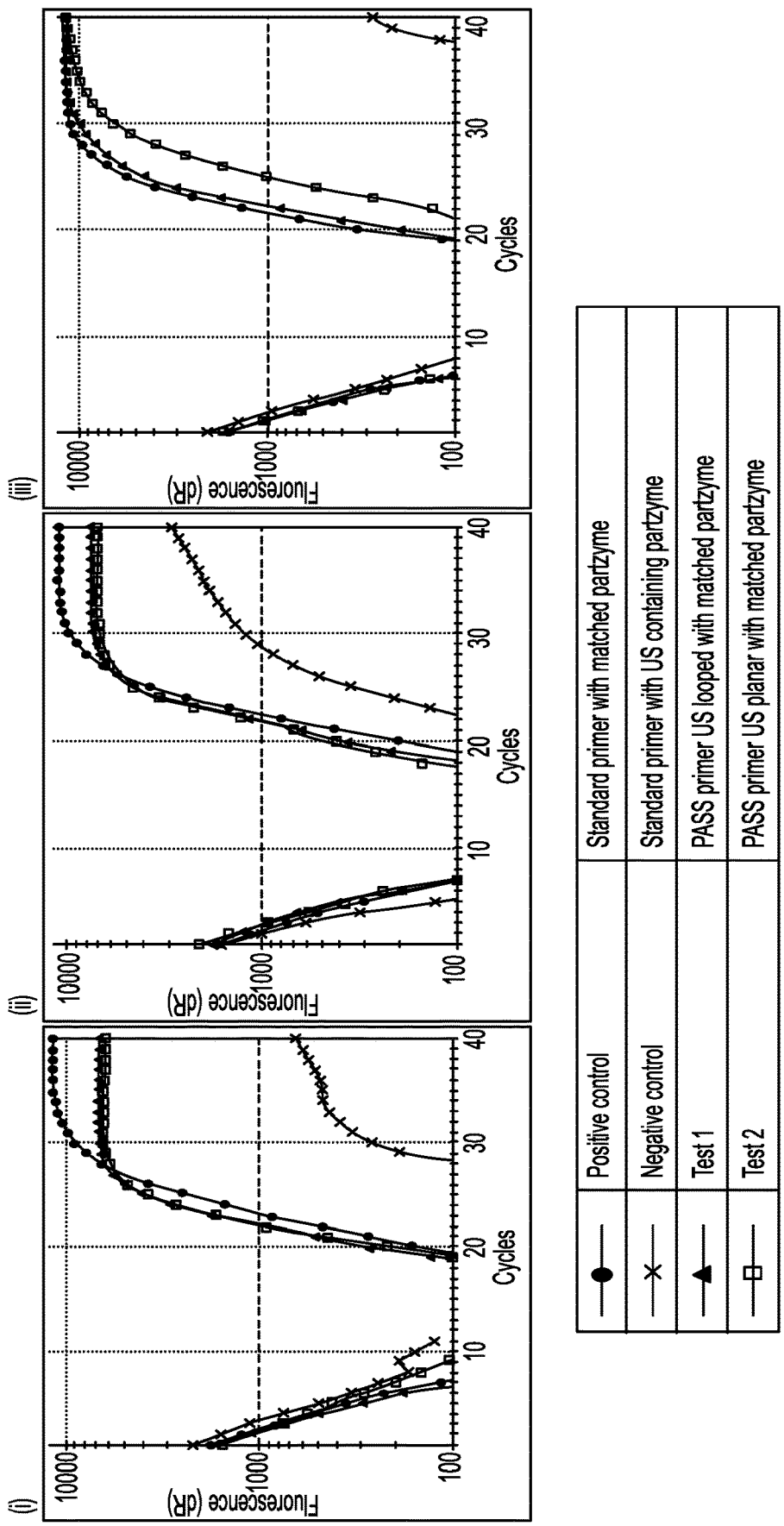

FIG. 4: Combining PASS primers with MNAzyme qPCR: PASS primers were combined in qPCR with an MNAzyme readout. The forward primer, which in this example could also be the PASS primer, was positioned at different positions in relation to the partzyme junction. The 3' end of the forward/PASS primer was located at either (i) 5 bases from the partzyme junction, (ii) 3 bases from the partzyme junction, or (iii) at the partzyme junction In the qPCR reactions, MNAzymes were designed to target each of the 3 scenarios created by the PASS primers (i-iii). For each scenario the PASS primers with a looped US (black triangle—Test 1) or a planar US (white square—Test 2) were compared to a standard (non-PASS) primer with matching MNAzyme (black circle—positive control) or the standard (non-PASS) primer combined with the partzymes designed to detect the US (cross—negative control).

Figure 5:
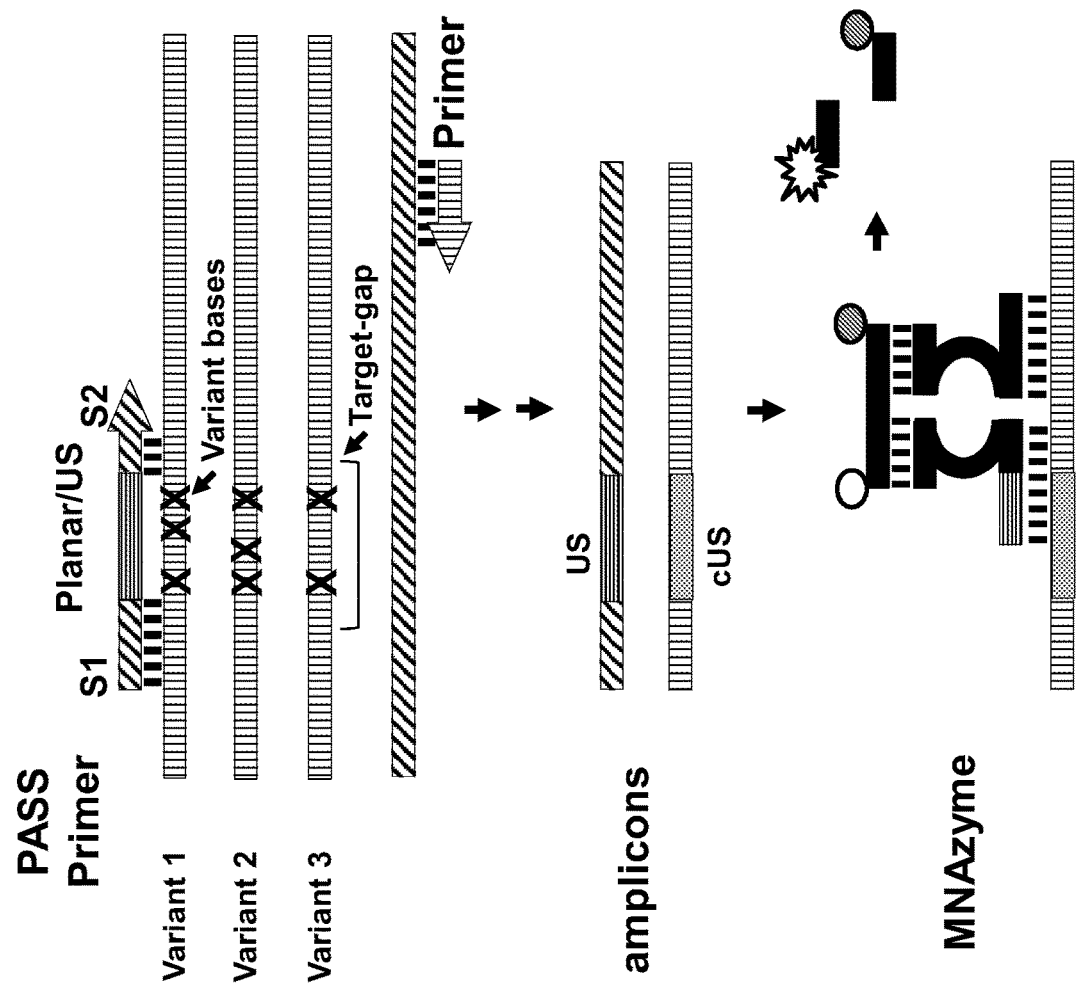

FIG. 5: Using PASS primers to skip highly variable sequence: The US incorporated into amplicons via use of a PASS primer may also be used to skip areas of non-informative genetic variation that exist between conserved sequences to be detected. PASS primers may be designed such that S1 and S2 are complementary to two conserved, non-adjacent sequences of a target. The gap in the target sequence between the areas that hybridize to S1 and S2 (target-gap) would contain differences in sequence between three variants to be detected. The US of the PASS primer may be designed to contain the same number of nucleotides in the target-gap between S1 and S2. The US may be mismatched to all three variants. A single MNAzyme could be designed with a partzyme sensor arm that would hybridize the complement of US and cleave a single probe to detect Variant 1, 2 and/or 3.

Figure 6:
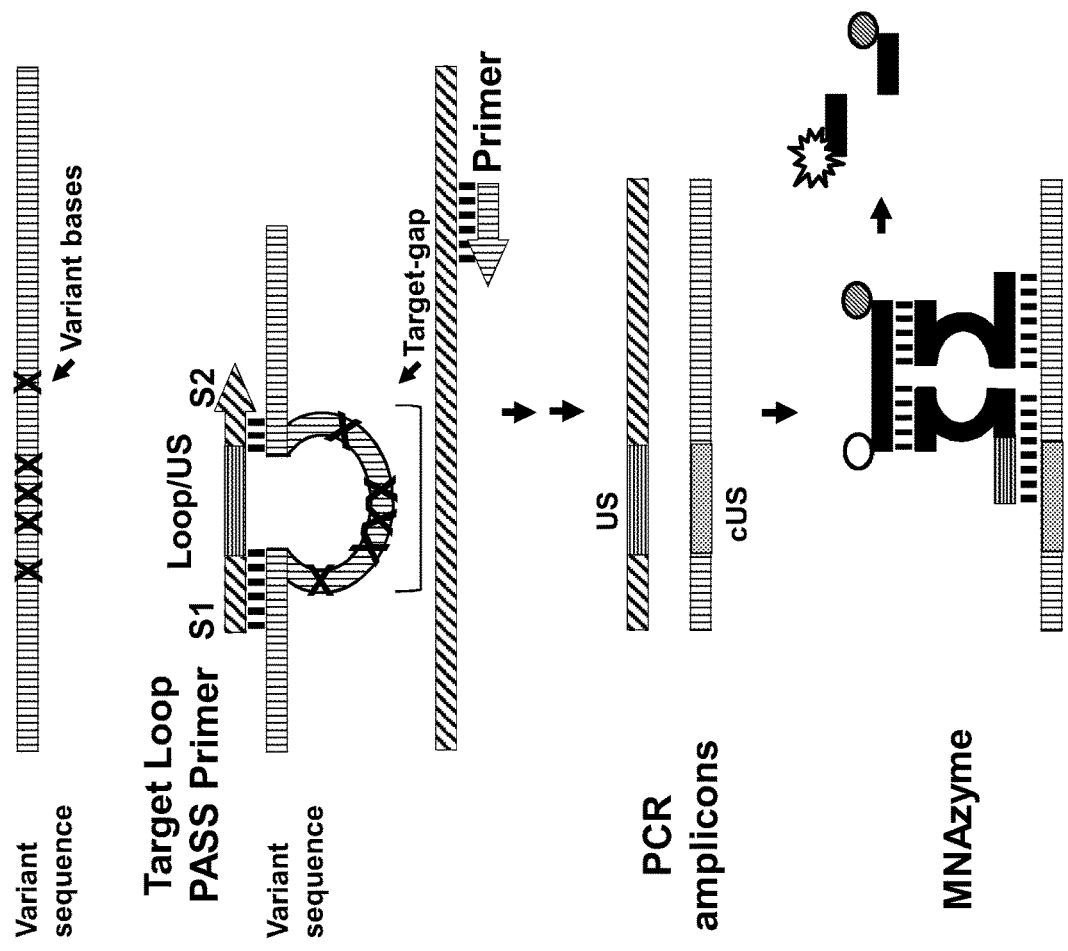

FIG. 6: Using PASS primers to loop out highly variable sequence: The US incorporated into amplicons via use of a PASS primer may also be used to remove areas of non-informative genetic variation that exist between conserved sequences to be detected. Target Loop PASS primers may be designed such that US of the PASS primer contains less nucleotides that those in the target-gap between S1 and S2. Amplification of DNA from Variant 1 using the target Loop PASS primer would replace the variant sequence in the target-gap with a smaller number of nucleotides in the US of the PASS primer. A single MNAzyme could be designed with a partzyme sensor arm that would hybridize the complement of US and cleave a single probe to detect any amplicons generated from the PASS primer.

Figure 7:
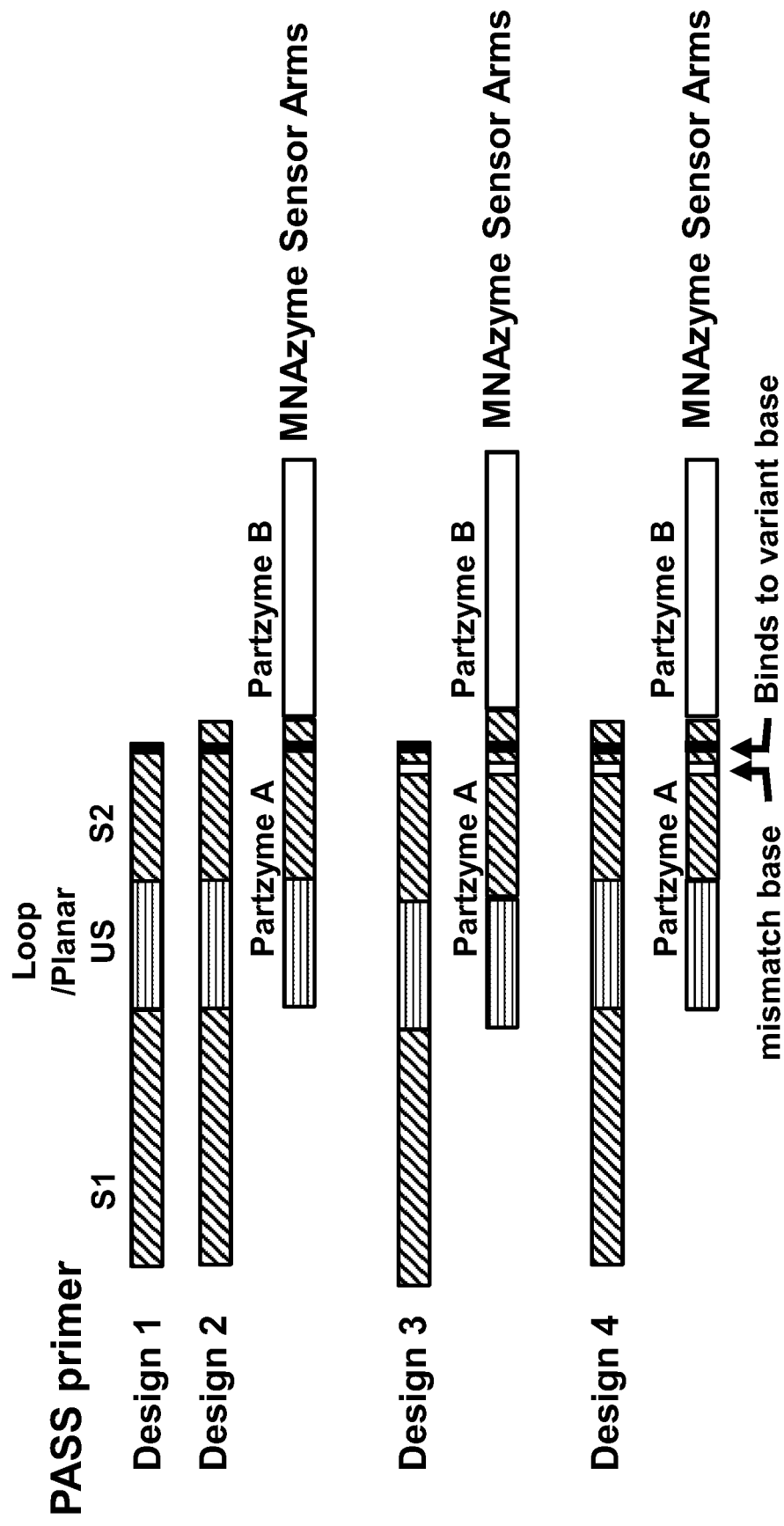

FIG. 7: Designs of PASS primers used to discriminate single nucleotide polymorphisms (SNPs) and/or acquired point mutations: PASS primers may be designed to discriminate single base changes such as SNPs or point mutations. In one embodiment, S2 of either a looped or planar PASS primer can be used to target and specifically bind to the SNP or point mutation. By way of example, the base matched to the SNP or point mutation in S2 of the PASS primer may be located at the 3' terminus of the primer (Design 1), 3 bases from the 3' end (Design 2), at the 3' terminus of the primer with a mismatch base inserted 3 bases from the 3' end (Design 3) or 3 bases from the 3' end with a mismatch base inserted 5 bases from the 3' end (Design 4). Partzyme A target sensor arms for MNAzymes are designed to match each PASS primer design whereas Partzyme B is constant for all designs.

Figure 8:
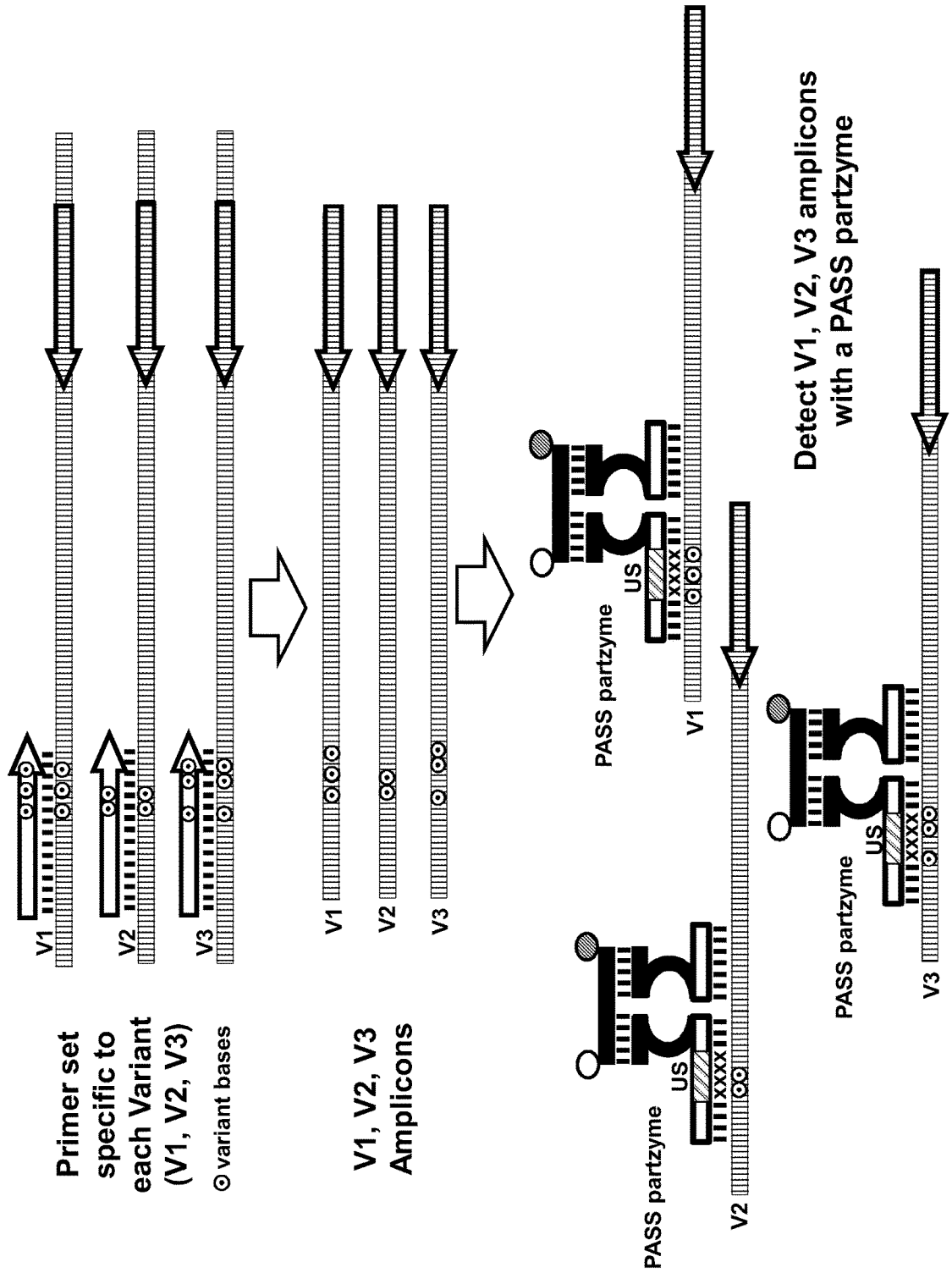

FIG. 8: Using PASS partzymes to detect variant strains with MNAzyme qPCR readout: Target sequences of interest may contain a string of variant bases, where the variants in each may be different to the others, for example, variant 1 (V1), variant 2 (V2) and variant 3 (V3) sequences. Primer sets can be designed to be specific for each variant sequence, V1, V2 and V3, and produce amplicons for each. The use of PASS partzymes provides a strategy to detect the sequences in real-time without discriminating between the variant strains. This involves using MNAzyme qPCR, whereby the MNAzyme may comprise a PASS partzyme. The PASS partzyme contains a portion of unique sequence (US) that is not complementary to the target sequence(s)/amplicon(s) of interest. The US is contained within the PASS partzyme sensor arm between two complementary target specific regions that are largely complementary to the target. The US in the partzyme is aligned with the variant region in V1, V2 and V3 that contains the variant bases.

The US within the PASS partzymes does not affect the formation of the active MNAzymes and thus the presence of any variant, or combination thereof, may result in the cleavage of a universal probe labelled with a fluorophore and quencher, producing a signal that can be monitored in real-time.

Figure 9:
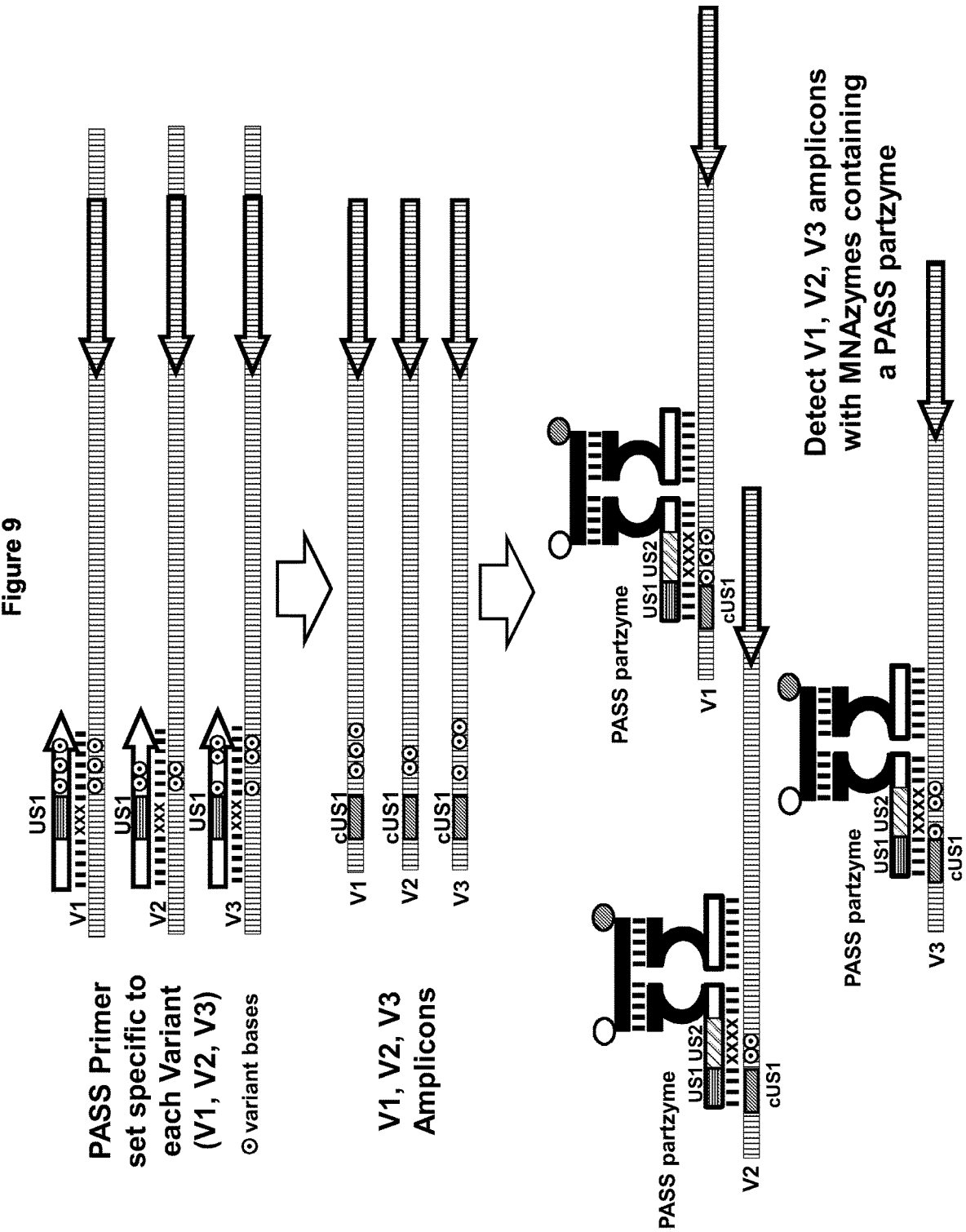

FIG. 9: Using PASS partzymes with PASS primers to detect variant strains with MNAzyme qPCR readout: Target sequences of interest may contain a string of variant bases, where the variants in each may be different to the others, for example, variant 1 (V1), variant 2 (V2) and variant 3 (V3) sequences. PASS primer sets can be designed to be specific for each variant sequence, V1, V2 and V3, but contain the same US (US1), resulting in amplicons for each still containing the variant bases but also the complement sequence to the same US (cUS1). The use of PASS partzymes provides a strategy to detect the sequences in real-time without discriminating between the variant strains. This involves using MNAzyme qPCR, whereby the MNAzyme may comprise a first PASS partzyme and a fully matched "standard" partzyme that bind adjacently on the amplified target sequences of interest. The first PASS partzyme sensor arm contains (i) a region fully matched to the conserved sequence of all the Variant amplicons, (ii) a unique sequence (US2) that is not complementary to any of the variant amplicons and which is aligned to the regions which differ between the Variant amplicons, and (iii) a region containing US1, which binds to the cUS1 in all amplicons generated by using the variant-specific PASS primer sets (all containing cUS1). This MNAzyme can recognize and bind to all variants.

The US sequences within the PASS partzymes do not affect the formation of the active MNAzymes and thus the presence of any variant sequence, or combinations thereof, may result in the cleavage of a universal probe labelled with a fluorophore and quencher, producing a signal that can be monitored in real-time.

Figure 10:
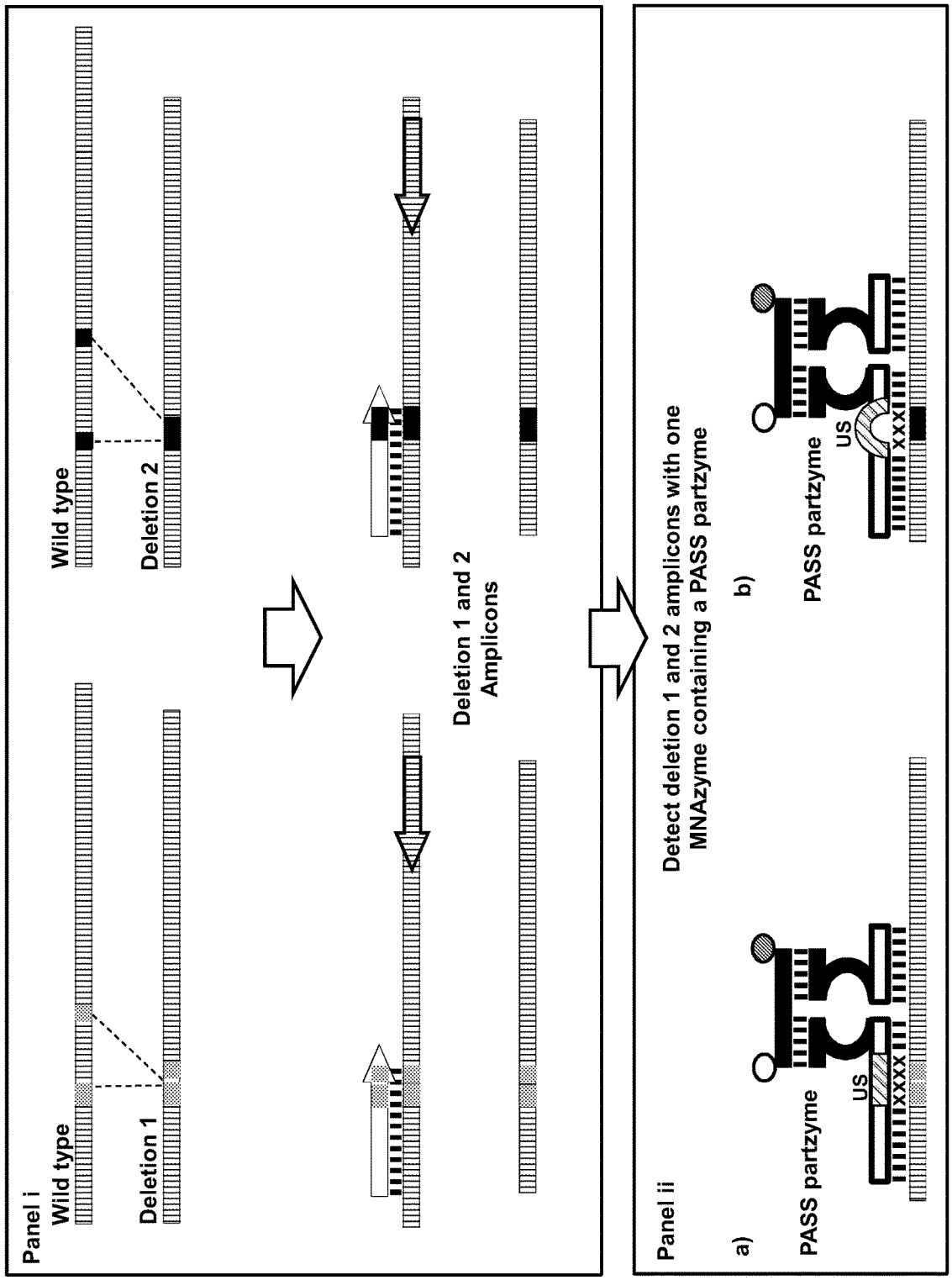

FIG. 10: Using PASS partzymes to detect variant deletion strains with MNAzyme qPCR readout: Variant target sequences of interest may be derived from wild type sequences where different regions have been deleted (Panel i, Deletion 1 and Deletion 2). Primer sets can be designed to be specific for each deletion variant sequence and produce amplicons for each. The use of PASS partzymes provides a strategy to detect the sequences in real-time without necessarily discriminating between the specific deletions. This may be achieved using MNAzyme qPCR, whereby the MNAzyme may comprise a first PASS partzyme and a second fully matched ("standard") partzyme which bind adjacently on the amplified target sequences of interest. The first PASS partzyme contains a region of sequence not complementary to the amplified target sequence, denoted the unique sequence (US), which is designed to align to where the region varies between deletion amplicons so that one MNAzyme can be used to detect all variants (Panel ii). The US present in the PASS partzyme can be in "planar" formation (Panel ii (a)) where the number of non-complementary bases in the PASS partzyme match the number of unbound bases in the amplified target sequence; or "looped" (Panel ii (b)) when the number of non-complementary bases in the partzyme is greater than the amplified target sequence and the partzyme sequence bulges or loops out; or alternatively the number of non-complementary bases in the partzyme is smaller than the amplified target sequence and the target sequence loops out.

The US within the PASS partzymes does not affect the formation of the active MNAzymes hence a universal probe labelled with a fluorophore and quencher can be cleaved producing a signal that can be monitored in real-time.

Figure 11:
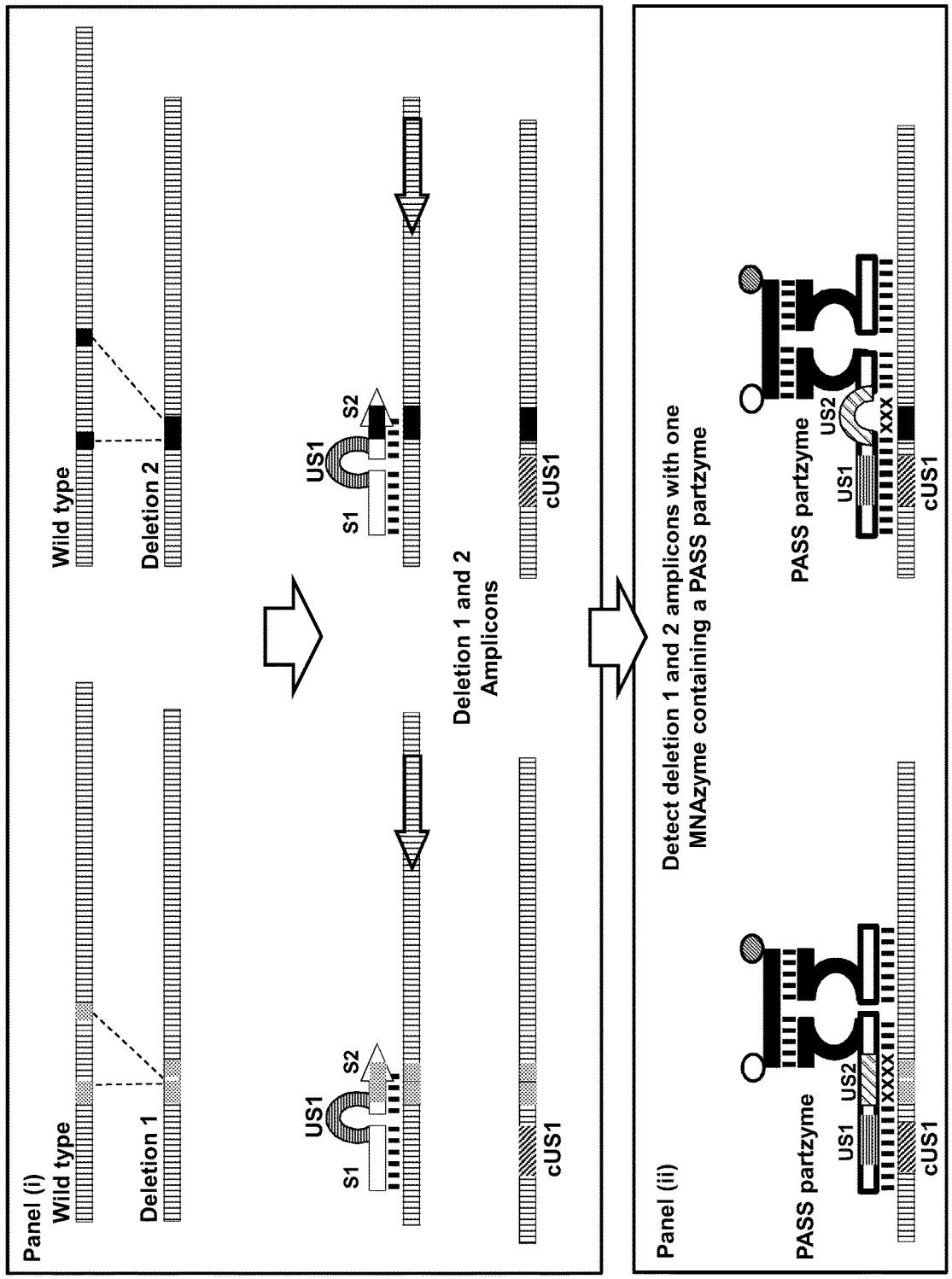

FIG. 11: Using PASS partzymes with PASS primers to detect variant strains with MNAzyme qPCR readout: Variant target sequences of interest may be derived from wild type sequences where different regions have been deleted (Panel (i), Deletion 1 and Deletion 2). PASS primer sets can be designed to be specific for each deletion variant sequence, Deletion 1 and Deletion 2, but may contain the same US (US1), resulting in amplicons for each deletion containing the deletion-specific variant bases as well as the complementary sequence to the same US (cUS1). An exemplary strategy for detecting the amplicons in real-time, without discriminating between the variant strains, may use PASS partzymes together with the PASS primers. This may involve using MNAzyme qPCR, whereby the MNAzyme may comprise a first PASS partzyme and a second fully matched ("standard") partzyme, which bind adjacently on the amplified target sequence of interest. The PASS partzyme contains a region of sequence not complementary to the amplified target sequence, denoted the unique sequence (US2) (which is designed to align to where the sequence varies between deletion amplions) and another region corresponding to US1, so that one MNAzyme can be used to detect all variants (Panel (ii)). The US2 present in the PASS partzyme can be in planar formation, where the number of non-complementary bases in the PASS partzyme match the number of unbound bases in the amplified target sequence or looped when the number of non-complementary bases in the PASS partzyme is greater or smaller than the amplified target sequence and the sequence bulges or loops out (Panel (ii)).

Since the US within the PASS partzymes does not affect the formation of the active MNAzymes a universal probe labelled with a fluorophore and quencher can be cleaved producing a signal that can be monitored in real-time.

Figure 12:
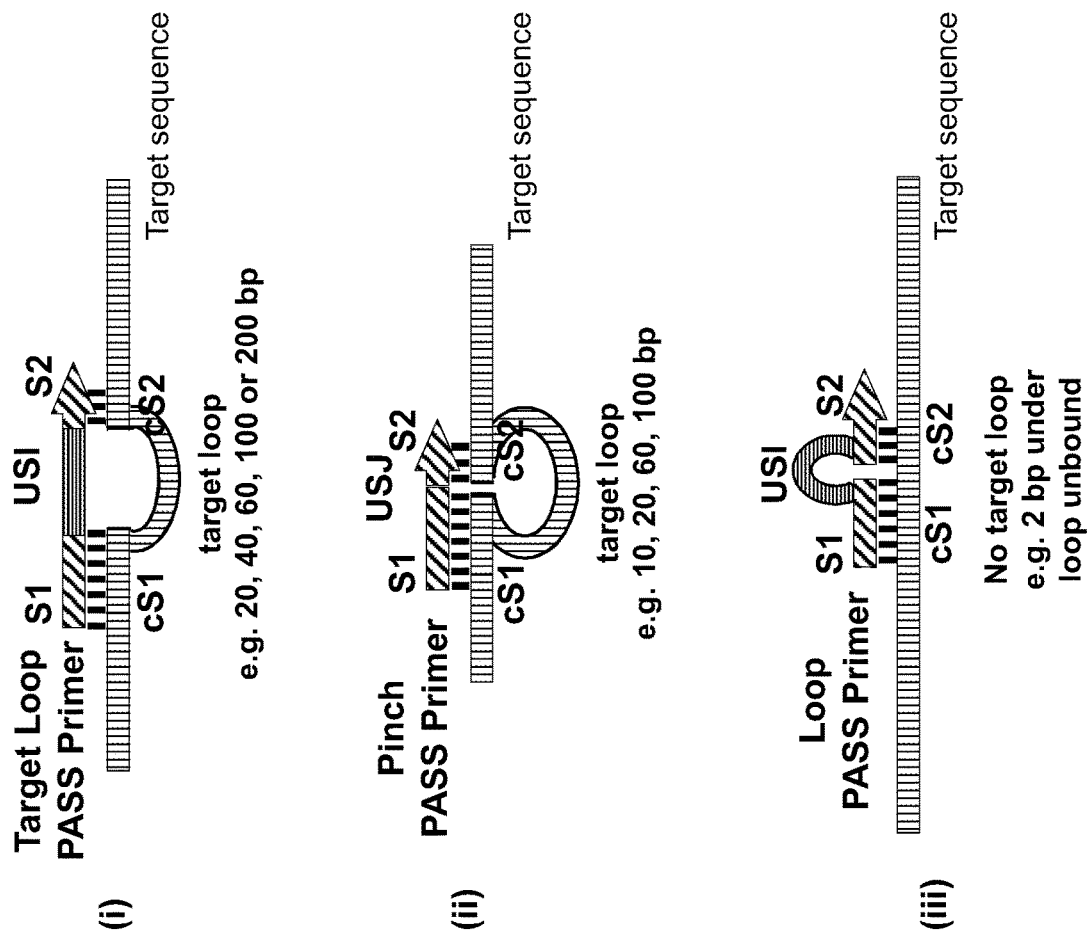

FIG. 12: Using Target Loop PASS primers or Pinch PASS primers to loop out different lengths of target sequence: The Unique Sequence Insert (USI) or Unique Sequence Junction (USJ) incorporated into amplicons via use of a PASS primer, Target Loop PASS primer or Pinch PASS primer may also be used to remove areas of sequence such as non-informative genetic variation that exists between conserved sequences to be detected.

PASS primers may be designed as, (i) Target Loop PASS primers such that the USI of the PASS primer contains less nucleotides than those in the target sequence located between cS1 and cS2 or (ii) the USJ of the Pinch PASS primer loops out target sequence located between cS1 and cS2. The length of target sequence looped out may be, for example, 10 bases, 20 bases, 40 bases, 60 bases, 100 bases or 200 bases (i or ii) which can be compared back to the original Loop PASS primer which, for example, may contain 2 unbound bases under the loop (iii).

Amplification of DNA using the Target Loop PASS primers or Pinch PASS primers would replace the looped out target sequence with the smaller number of nucleotides in the USI or USJ of the Target Loop PASS primer or Pinch PASS primer respectively. An MNAzyme could be designed with a partzyme sensor arm that would hybridize the complement of the USI or the USJ and cleave a reporter probe to detect any amplicons generated from the PASS primer or Pinch PASS primer.

Figure 13:
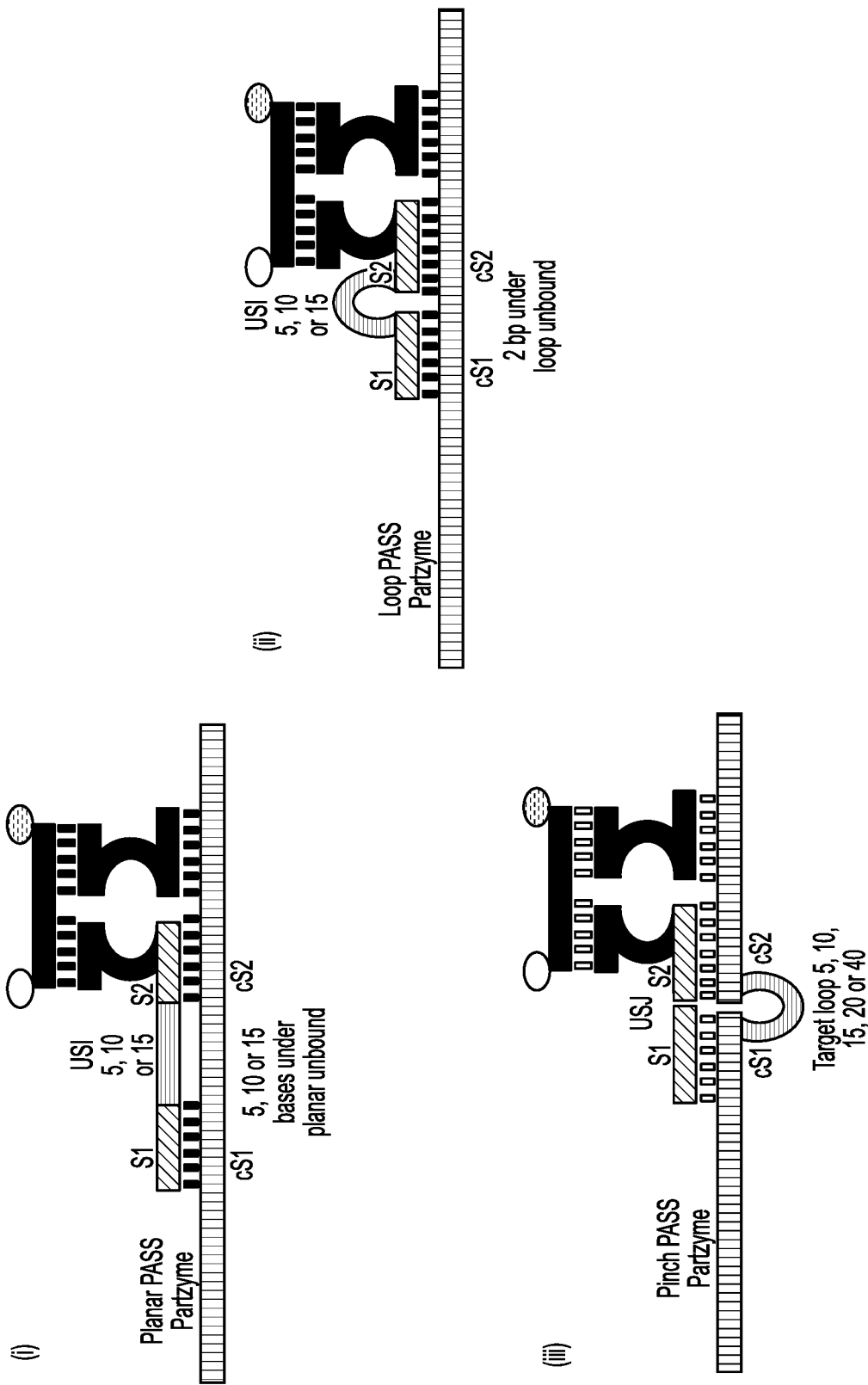

FIG. 13: Using PASS partzymes or Pinch PASS partzymes to loop out different lengths of target sequence: PASS partzymes may be designed such that (i) the USI of the Planar PASS partzyme contains the same number of nucleotides as those in the target sequence located between cS1 and cS2 which, by way of example, may be 5, 10 or 15 bases, (ii) the USI of the Loop PASS partzyme may contain more or less nucleotides than those in the target sequence located between cS1 and cS2 which, by way of example, the USI may be 5, 10 or 15 bases or (iii) the USJ of the Pinch PASS partzyme may loop out, by way of example, 5, 10, 15, 20 or 40 bases of the target sequence located between cS1 and cS2.

PASS partzymes can be used in MNAzyme qPCR, whereby the MNAzyme may comprise a first PASS partzyme or Pinch PASS partzyme and a fully matched ("standard") partzyme which bind adjacently on the amplified target sequence of interest. The USI or USJ sequence within the PASS partzymes does not affect the formation of the active MNAzymes hence a universal probe labelled with a fluorophore and quencher can be cleaved producing a signal that can be monitored in real-time.

Figure 14:
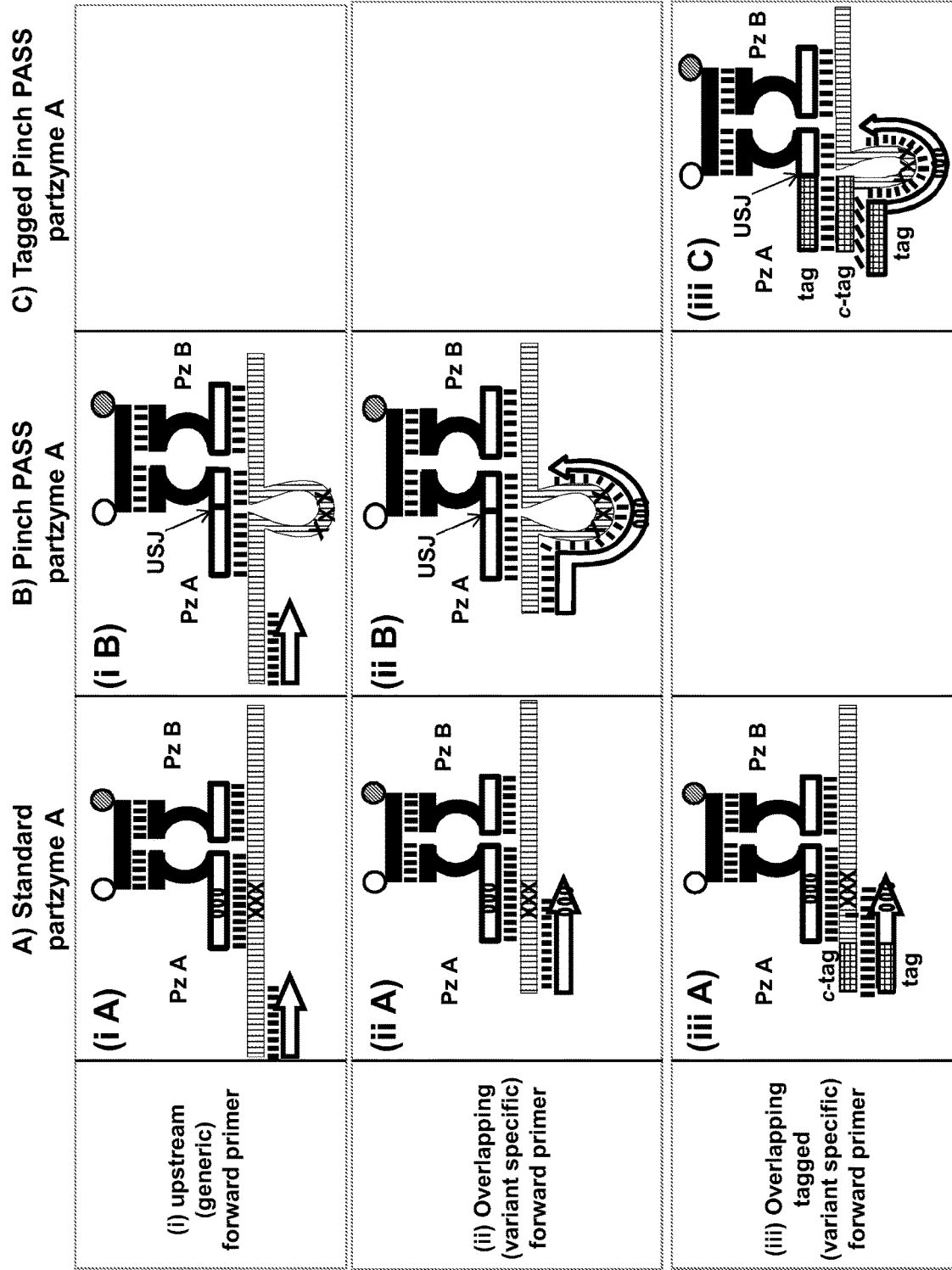

FIG. 14: Choice of primer and partzyme A combination for the omission or selection of variable regions in a genome. The development of Pinch PASS partzymes enables flexibility in the selection of the sequence to be detected by the MNAzyme which can be an advantage when target sequences contain variable regions. Many different primer and MNAzyme scenarios can be employed. Strategies include (i) an upstream generic forward primer that detects all variants including wild type which can be used with (i A) a downstream standard MNAzyme targeting a variable region wherein a different partzyme A (Pz A) can be designed for each variant but can be used with a common partzyme B (Pz B) to detect multiple variants; or with (i B) a Pinch PASS partzyme A, which pinches out the variable region at its unique sequence junction (USJ), allowing detection of all variants with a single MNAzyme. The "X" represents the variant bases and the "0" represents the complement of the variant bases. In another scenario, (ii) a variant specific, forward primer that overlaps with the MNAzyme can be used to selectively amplify variant over wild type sequence. When combined with a standard MNAzyme (ii A), detection of a specific variant is possible, however detection of multiple variants requires a specific primer and partzyme A set per variant (with a common Pz B). Alternatively, detection of the presence of any variant can be achieved by use of specific primers amplifying each variable region combined with a Pinch PASS partzyme A (ii B), which pinches out the variable region at its unique sequence junction (USJ), allowing detection of all variants with a single MNAzyme. Alternatively, (iii) a variant specific, forward primer that overlaps with the MNAzyme can be used to selectively amplify variant sequences, and each variant specific primer may contain a non-target related tag sequence on its 5' end which becomes incorporated into the amplicon for each variant. This reduces the competition between the MNAzyme and the primer for binding to the same strand of the amplicon and reduces competition between primers in a multiplex reaction. This tagged primer can be combined with (iii A) a standard MNAzyme to detect specific variants (each Pz A designed to detect a different variable region in the genome) or with (iii C) a tagged Pinch PASS partzyme A, such that the partzyme A pinches out the variable region at its unique sequence junction (USJ) and binds to the complement of the tag sequence in the amplicon (c-tag), thus reducing any binding competition between the forward primer and partzyme A and allowing detection of all variants with a single MNAzyme.

Figure 15:
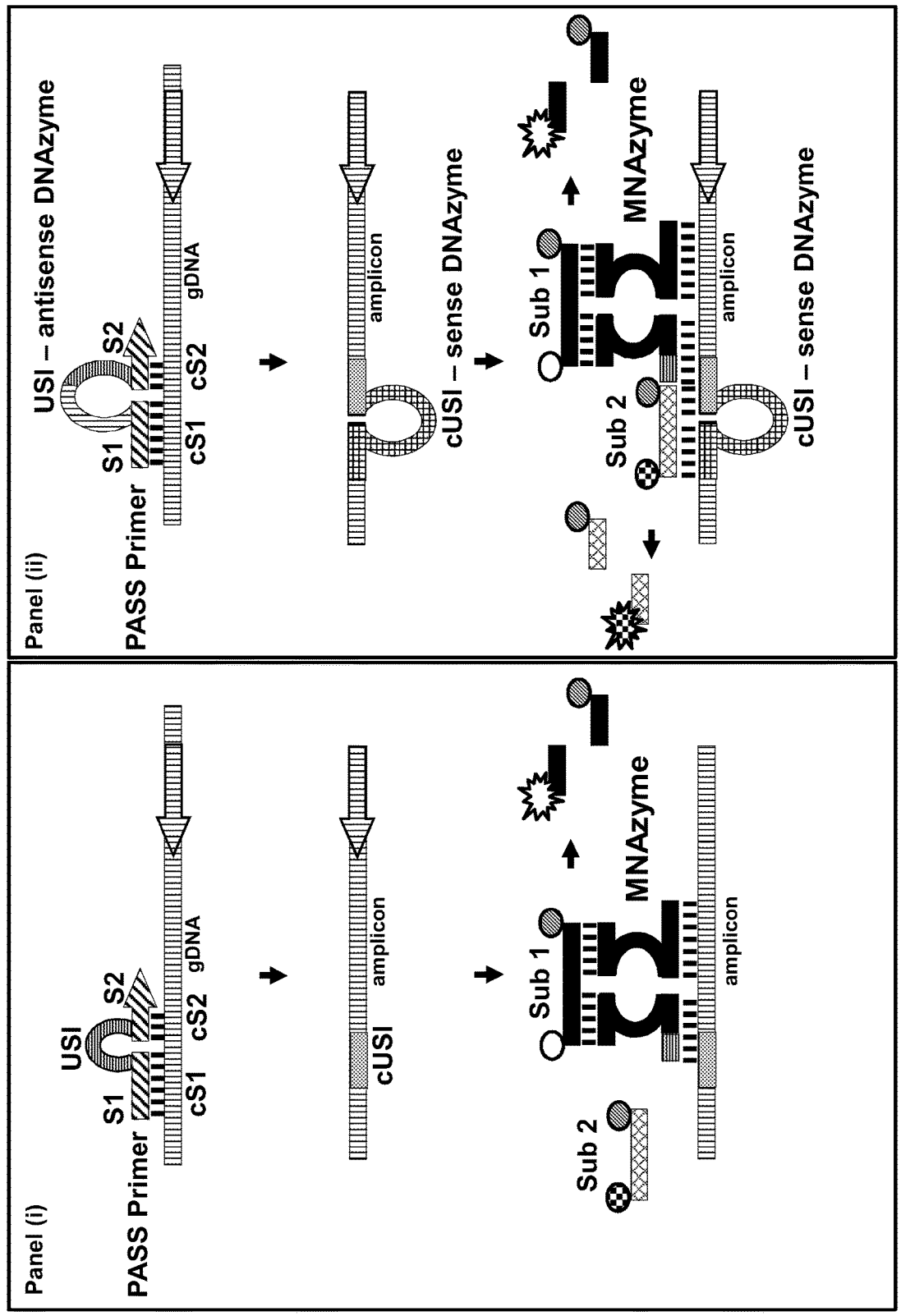

FIG. 15: PASS primers containing a US composed of an antisense DNAzyme. The unique sequence incorporated into amplicons via use of a PASS primer may also be used to insert functional sequences into the amplicon. PASS primers can be designed such that the unique sequence is composed of an inactive, antisense form of a DNAzyme while still being non-complementary to the target sequence. Upon amplification during PCR a catalytically active, sense DNAzyme is inserted into the amplicon and can cleave a substrate to produce a signal in real-time (FIG. 15 panel (ii)). In comparison, a standard PASS primer may have a US that has no catalytic potential and is non-complementary to the target sequence (FIG. 15 panel (i)). PASS primers can be combined with MNAzyme qPCR such that MNAzymes comprise a first partzyme that binds to the complement of the unique sequence (cUS) as well as amplified target sequence. The second partzyme can bind adjacently to the first partzyme on the amplicon of interest. The active MNAzyme would then cleave a substrate 1 (Sub 1) to produce a signal that can be monitored in real-time. A second substrate 2 (Sub 2) can be added to both reactions, but when a standard PASS partzyme is used the substrate 2 would remain uncleaved and not produce a signal (FIG. 15 panel (i)). However when the PASS primers are used that contain the antisense of the DNAzyme as the US, amplification results in formation of active DNAzymes that would cleave substrate 2 producing a signal that can be monitored in real-time (FIG. 15 panel (ii)). Substrate 2 could be labeled with a different fluorophore to substrate 1 so the two signals can be distinguished, or alternatively substrate 2 could be labeled with the same flurophore as substrate 1 to enhance the signal produced and decreasing the Ct value.

Figure 16:
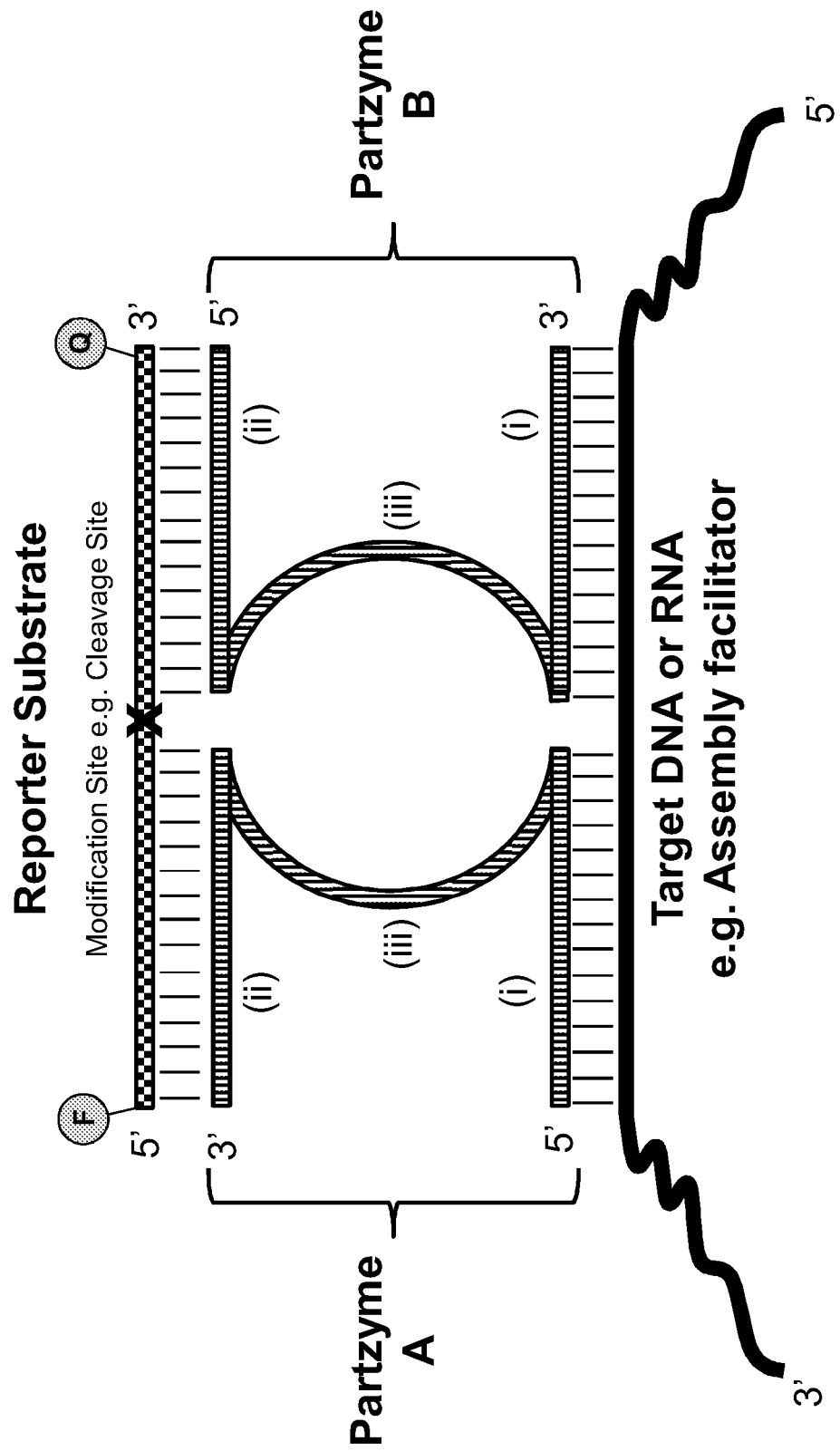

FIG. 16: A diagram depicting an exemplary design of a Multi-component nucleic acid (MNAzyme). By way of exemplary disclosure, an MNAzyme is comprised of two oligonucleotide components (partzyme A and partzyme B), which self assemble in the presence of an assembly facilitator, for example target DNA or RNA. When the two partzymes assemble in the presence of the assembly facilitator, a catalytically active MNAzyme forms which is capable of modifying (eg. cleaving or ligating) a substrate. The two component partzymes have (i) sensor arms, which bind to the assembly facilitator, (ii) substrate arms, which bind the substrate, and (iii) partial catalytic core sequences. The presence of an assembly facilitator molecule (eg. a target nucleic acid sequence) provides the "input" signal which directs the assembly of partzyme components in a highly specific fashion. In some embodiments, the assembly facilitator may be, for example, a target nucleic acid sequence present in a test sample. In other embodiments, the assembly facilitator may be, for example a synthetic oligonucleotide included in the milieu to direct the self-assembly of the partzyme components in the presence of a detectable entity or event. Modification of the substrate (substrate probe, reporter probe, or reporter substrate) by the assembled MNAzyme can provide a "detectable effect" which may be detected and/or quantified. For example, when the substrate is dual labelled with a fluorophore (F) and a quencher (Q), cleavage of the substrate by an active MNAzyme separates the fluorophore and the quencher resulting in a concomitant increase in fluorescence.

DEFINITIONS

As used in this application, the singular form "a", "an" and "the" include plural references unless the context clearly dictates otherwise. For example, the phrase "polynucleotide" also includes a plurality of polynucleotides.

As used herein, the term "comprising" means "including". Variations of the word "comprising", such as "comprise" and "comprises," have correspondingly varied meanings. Thus, for example, a polynucleotide "comprising" a sequence of nucleotides may consist exclusively of that sequence of nucleotides or may include one or more additional nucleotides.

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

As used herein, the term "subject" includes any animal of economic, social or research importance including bovine, equine, ovine, primate, avian and rodent species. Hence, a "subject" may be a mammal such as, for example, a human or a non-human mammal. Also encompassed are microorganism subjects including, but not limited to, bacteria, viruses, fungi/yeasts, protists and nematodes. A "subject" in accordance with the presence invention also includes infectious agents such as prions.

As used herein, the terms "protein" and "polypeptide" each refer to a polymer made up of amino acids linked together by peptide bonds and are used interchangeably. For the purposes of the present invention a "polypeptide" may constitute a full length protein or a portion of a full length protein.

As used herein, the terms "polynucleotide" and "nucleic acid" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof. The terms "polynucleotide" and "nucleic acid" "oligonucleotide" include reference to any specified sequence as well as to the sequence complementary thereto, unless otherwise indicated.

As used herein, the term "oligonucleotide" refers to a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme; primers such as those used for in vitro target amplification by methods such as PCR; and components of MNAzymes. The term "oligonucleotide" includes reference to any specified sequence as well as to the sequence complementary thereto, unless otherwise indicated. Oligonucleotides may comprise at least one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, -methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

As used herein, the terms "complementary", "complementarity", "match" and "matched" refer to the capacity of nucleotides (e.g. deoxyribonucleotides, ribonucleotides or combinations thereof) to hybridise to each other via either Watson-Crick base-pairing or wobble base pairing. Bonds can be formed via Watson-Crick base-pairing between adenine (A) bases and uracil (U) bases, between adenine (A) bases and thymine (C) bases, between cytosine (C) bases and guanine (G) bases. A wobble base pair is a non-Watson-Crick base pairing between two nucleotides in a polynucleotide duplex (e.g. guanine-inosine-uracil, inosine-adenine, and inosine-cytosine). Nucleotides referred to as "complementary" or that are the "complement" of each other are nucleotides which have the capacity to hybridise together by either Watson-Crick base pairing or by wobble base pairing between their respective bases.

As used herein, the terms "non-complementary", "not complementary", "mismatch" and "mismatched" refer to nucleotides (e.g. deoxyribonucleotides, ribonucleotides, combinations thereof) that lack the capacity to hybridize together by either Watson-Crick base pairing or by wobble base pairing between their respective bases.

As used herein, an "enzyme" refers to any molecule which can catalyze a chemical reaction (e.g. amplification of a polynucleotide, cleavage of a polynucleotide etc.)

As used herein, an "amplicon" refers to nucleic acid (e.g. DNA or RNA, or a combination thereof) that is a product of natural or artificial nucleic acid amplification or replication events including, but not limited to, PCR, RT-PCR, SDA, HDA, RPA, LAMP, RCA, TMA, 3SR or NASBA.

As used herein, the terms "nucleic acid enzyme", "catalytic nucleic acid", "nucleic acid with catalytic activity", and "catalytic nucleic acid enzyme" are used herein interchangeably and shall mean a DNA or DNA-containing molecule or complex, or an RNA or RNA-containing molecule or complex, or a combination thereof (i.e. DNA-RNA hybrid molecule or complex), which may recognize at least one substrate and catalyse a modification (such as ligation or cleavage) of the at least one substrate. The nucleotide residues in the catalytic nucleic acids may include the bases A, C, G, T, and U, as well as derivatives and analogues thereof. The terms above include uni-molecular nucleic acid enzymes which may comprise a single DNA or DNA-containing molecule (also known in the art as a "DNA enzyme", "deoxyribozyme" or "DNAzyme") or an RNA or RNA-containing molecule (also known in the art as a "ribozyme") or a combination thereof, being a DNA-RNA hybrid molecule which may recognize at least one substrate and catalyse a modification (such as ligation or cleavage) of the at least one substrate. The terms above include nucleic acid enzymes which comprise a DNA or DNA-containing complex or an RNA or RNA-containing complex or a combination thereof, being a DNA-RNA hybrid complex which may recognize at least one substrate and catalyse a modification (such as ligation or cleavage) of the at least one substrate. The terms "nucleic acid enzyme", "catalytic nucleic acid", "nucleic acid with catalytic activity", and "catalytic nucleic acid enzyme" include within their meaning MNAzymes.

As used herein, the terms "MNAzyme" and "multi-component nucleic acid enzyme" as used herein have the same meaning and refer to two or more oligonucleotide sequences (e.g. partzymes) which, only in the presence of an MNAzyme assembly facilitator (for example, a target), form an active nucleic acid enzyme that is capable of catalytically modifying a substrate. MNAzymes can catalyse a range of reactions including cleavage of a substrate, ligation of substrates and other enzymatic modifications of a substrate or substrates. An exemplary MNAzyme comprising partzyme A and partzyme B which has cleavage activity is depicted in FIG. 16. MNAzymes with endonuclease or cleavage activity are also known as "MNAzyme cleavers". With reference to FIG. 16, partzymes A and B each of which bind to an assembly facilitator (e.g. a target DNA or RNA sequence) through Watson-Crick base pairing. The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. Cleavage of a DNA/RNA chimeric reporter substrate is exemplified in the drawing. The MNAzyme may cleave the substrate between a fluorophore and a quencher dye pair, thus generating signal. The terms "multi-component nucleic acid enzyme" and "MNAzyme" comprise bipartite structures, composed of two molecules, or tripartite structures, composed of three nucleic acid molecules, or other multipartite structures, for example those formed by four or more nucleic acid molecules.

It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

As used herein, the terms "partzyme", "component partzyme" and "partzyme component" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a modification; a "sensor arm" domain, which may associate with and/or bind to an assembly facilitator; and a "substrate arm" domain, which may associate with and/or bind to a substrate. Partzymes may comprise at least one additional component including but not limited to an aptamer, referred to herein as an "apta-partzyme." A partzyme may comprise multiple components, including but not limited to, a partzyme component with a truncated sensor arm and a stabilizing arm component which stabilises the MNAzyme structure by interacting with either an assembly facilitator or a substrate.

The term Polynucleotide Assisted Sequence Switching (PASS) oligonucleotide as used herein refers to an oligonucleotide which comprises a 5' component that is complementary or substantially complementary to a nucleic acid target of interest, a central component comprising a "unique sequence" (also referred to herein as "US") of nucleotides that is not present in the nucleic acid target sequence, and a 3' component that is complementary or substantially complementary to the nucleic acid target of interest. The PASS oligonucleotide may be provided in the form of a primer (referred to herein as a "PASS primer"). The PASS oligonucleotide may be a sensor arm component of a partzyme (referred to herein as a "PASS partzyme") which may further comprise a partial catalytic domain and a substrate arm domain.

The terms "unique sequence insert" and "USI" and "unique insert sequence" and "US insert" are used interchangeably herein and have the same meaning. The term "unique sequence insert" refers to a sequence of nucleotides within a larger polynucleotide (e.g. a PASS oligonucleotide) that is not complementary to a target polynucleotide when the larger polynucleotide is hybridized with the target polynucleotide via complementary base pairing.

The terms "unique sequence junction" and "USJ" and "US junction" refer to a unique sequence of nucleotides formed by combining two component nucleotide sequences, each component being complementary to different portions of a target polynucleotide which are separated by intervening sequence.

The term "unique sequence" as used herein may include a "unique sequence insert" or a "unique sequence junction."

The terms "assembly facilitator molecule", "assembly facilitator", "MNAzyme assembly facilitator molecule", and "MNAzyme assembly facilitator" as used herein refer to entities that can facilitate the self-assembly of component partzymes to form a catalytically active MNAzyme by interaction with the sensor arms of the MNAzyme. As used herein, assembly facilitators may facilitate the assembly of MNAzymes which have cleavage, ligase or other enzymatic activities. In preferred embodiments an assembly facilitator is required for the self-assembly of an MNAzyme. An assembly facilitator may be comprised of one molecule, or may be comprised of two or more "assembly facilitator components" that may pair with, or bind to, the sensor arms of one or more oligonucleotide "partzymes". The assembly facilitator may comprise one or more nucleotide component/s which do not share sequence complementarity with sensor arm/s of the MNAzyme. The assembly facilitator may be a target. The target may be a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The nucleic acid may be amplified. The amplification may comprise one or more of: PCR, RT-PCR, SDA, HDA, RPA, LAMP, RCA, TMA, 3SR, NASBA or the ligase chain reaction.

The term "detectable effect" as used herein is an effect that can be detected or quantified as an indication that modification of substrate/s has occurred. The magnitude of the effect may be indicative of the quantity of an input such as an assembly facilitator (e.g. a target). The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, electrochemical methods, UV, visible light or infra red spectroscopy, enzymatic methods or any combination thereof.

The terms "polynucleotide substrate" and "substrate" as used herein include any single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases), which is capable of being recognized, acted upon or modified by an enzyme including a catalytic nucleic acid enzyme. A "polynucleotide substrate" or "substrate" may be modified by various enzymatic activities including but not limited to cleavage or ligation. Modification of a "polynucleotide substrate" or "substrate" may provide a "detectable effect" for monitoring the catalytic activity of a enzyme.

A "reporter substrate" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

As used herein, a "generic substrate" or a "universal substrate" is a substrate, for example, a reporter substrate, that is recognized by and acted on catalytically by a plurality of MNAzymes, each of which can recognize a different assembly facilitator. The use of such substrates facilitates development of separate assays for detection, identification or quantification of a wide variety of assembly facilitators using structurally related MNAzymes all of which recognize a universal substrate. These universal substrates can each be independently labelled with one or more labels. In preferred embodiments, independently detectable labels are used to label one or more universal substrates to allow the creation of a convenient system for independently or simultaneously detecting a variety of assembly facilitators using MNAzymes. In some embodiments, substrates cleaved by MNAzymes could be reconstituted, and hence recycled, using an MNAzyme or DNAzyme ligase. In some embodiments, substrate(s) cleaved or ligated by MNAzymes can be further used as components or modulators of additional MNAzyme(s) or DNAzyme(s).

The terms "probe" as used herein refers to an oligonucleotide that is used for detection of a target nucleic acid. Non-limiting examples of probes include TaqMan probes; Molecular Beacon probes; and nucleic acid enzyme substrates capable of catalytic modification by a nucleic acid enzyme.

The terms "generic probe" and "universal probe" as used herein refer to a probe that may be catalytically modified by a plurality of non-identical nucleic acid enzymes, thus facilitating the detection of one or more target nucleic acids.

A "generic probe" or "universal probe" as used herein may also be referred to as a "universal substrate". Universal substrates may in some embodiments be tethered to a solid support in different positions to provide a substrate array. In such embodiments, the tethered universal substrates may all be labelled with the same fluorophore. In certain cases, each universal substrate can be cleaved only by an MNAzyme formed in the presence of a specific MNAzyme assembly facilitator molecule and signal can be localised by positioning of the substrate on the surface, thus allowing specific detection of different assembly facilitators.

The term "product" refers to the new molecule or molecules that are produced as a result of enzymatic modification of a substrate. As used herein the term "cleavage product" refers to a new molecule produced as a result of cleavage or endonuclease activity by an enzyme. The term "ligation product" refers to a new molecule produced as a result of the ligation of substrates by an enzyme.

As used herein, use of the terms "melting temperature" and "Tm" in the context of a polynucleotide will be understood to be a reference to the melting temperature (Tm) as calculated using the Wallace rule, whereby Tm=2° C.(A+T)+4° C.(G+C) (see Wallace et al., (1979) Nucleic Acids Res. 6, 3543), unless specifically indicated otherwise.

As used herein, the term "base" will be understood to have the same meaning as the term "nucleotide".

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that each contains a subportion of the total kit components. The containers may be delivered to the intended recipient together or separately. Any delivery system comprising two or more separate containers that each contains a subportion of the total kit components are included within the meaning of the term "fragmented kit".

As used herein, a "combined kit" refers to a delivery system containing all of the components of a reaction assay in a single container (e.g. in a single box housing each of the desired components).

It will be understood that use the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

Abbreviations

The following abbreviations are used herein and throughout the specification:
MNAzyme: multi-component nucleic acid enzyme, or multipartite nucleic acid enzyme;
Partzyme: Partial enzyme containing oligonucleotide;
S1; Sequence one, located 5' of the US
S2; Sequence two, located 3' of the US
cS1; complement of sequence one, located 3' of the US
cS2; complement of sequence two, located 5' of the US
PASS; Polynucleotide Assisted Sequence Switching
US; Unique sequence
cUS; complement of unique sequence
USI; unique sequence insert
USJ; unique sequence junction
cUSI; complement of unique sequence insert
cUSJ; complement of unique sequence junction
ave; average
PCR: polymerase chain reaction;
gDNA: genomic DNA
rc: reverse complement
NTC: No template control
qPCR: Real-time quantitative PCR
Ct; Threshold cycle
$R^2$; Correlation coefficient
nM; Nanomolar
mM; Millimolar
μL; Microlitre
dNTP; Deoxyribonucleotide triphosphate ARMS: Amplification Refractory Mutation System
WE-ARMS: wobble-enhanced ARMS
NF-H$_2$O: nuclease-free water;
LNA: locked nucleic acid;
F: fluorophore;
Q: quencher;
N=A, C, T, G, or any analogue thereof;
N'=any nucleotide complementary to N, or able to base pair with N;
(N)$_x$: any number of N;
(N')$_x$: any number of N';
W: A or T;
R: A, G, or AA;
rN: any ribonucleotide base;
(rN)$_x$: any number of rN;
rR: A or G;
rY: C or U;
M: A or C;
H: A, C, or T;
D: G, A, or T;
JOE or 6-JOE: 6-carboxy-4',5'-dichloro-2',7'-dimethoxyfluorescein;
FAM or 6-FAM: 6-Carboxyfluorescein.
BHQ1: Black Hole Quencher 1
BHQ2: Black Hole Quencher 2
RT-PCR: reverse transcription polymerase chain reaction
SDA: strand displacement amplification
HDA: helicase dependent amplification
RIM: Recombinase Polymerase Amplification
LAMP: loop-mediated isothermal amplification
RCA: rolling circle amplification
TMA: transcription-mediated amplification
3SR: self-sustained sequence replication
NASBA: nucleic acid sequence based amplification
IB: Iowa Black® FQ
IBR: Iowa Black® RQ
shRNA: short hairpin RNA
siRNA: short interfering RNA
mRNA: messenger RNA
tRNA: transfer RNA
snoRNA: small nucleolar RNA
stRNA: small temporal RNA
smRNA: small modulatory RNA
pre-microRNA: precursor microRNA
pri-microRNA: primary microRNA

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

The present invention provides Polynucleotide Assisted Sequence Switching (PASS) oligonucleotides. The PASS oligonucleotides may be used as PASS primers to facilitate the introduction of unique specific sequence into amplicons. A unique sequence introduced into an amplicon by the oligonucleotide may be used to enhance the detection of small genetic variations (e.g. an SNP) in a given nucleic acid target, or alternatively to replace a region of variable sequence in an amplicon to improve the efficacy of amplification and/or detection of related sequences. The PASS oligonucleotide may be a sensor arm component of a PASS partzyme whereby the PASS partzyme sensor arm contains both 'unique sequence' which is non-complementary to one or a group of nucleic acid targets, as well as sequence that is complementary to the group of nucleic acid targets. A PASS partzyme sensor arm may thus in some embodiments hybridise with multiple different nucleic acid targets that differ from each other only by virtue of a component that is not capable of hybridising with the PASS partzyme sensor arm. The PASS partzyme may then interact with a second other partzyme comprising a sensor arm complementary to a different component of the nucleic acid target to form an MNAzyme capable of detecting multiple different nucleic acid sequences with similar efficiency.

Accordingly, certain embodiments of the present invention relate to oligonucleotides useful for the detection of nucleic acids. Also provided are compositions and kits comprising the oligonucleotides.

Other embodiments of the present invention relate to methods for detecting nucleic acids. The methods may be used to detect genetic polymorphisms in a given target nucleic acid, or alternatively to avoid incorporating undesirable region(s) of a target sequence into amplicons by replacing those region(s) with a unique sequence from the oligonucleotide primer. The methods may comprise amplifying a target sequence using an oligonucleotide primer (e.g. a PASS primer) and detecting amplicons produced. The amplicons may comprise a unique sequence insert or junction derived from the oligonucleotide primer that is foreign to the target sequence amplified. Alternatively, the methods may comprise amplifying a target sequence with an oligonucleotide primer and/or detecting the target sequence using an MNAzyme comprising PASS partzyme(s).

PASS Oligonucleotides

PASS oligonucleotides of the present invention comprise a unique sequence (US) that is non-complementary to sequence present in a target polynucleotide. The US may be provided in the form of a unique sequence insert (USI) or a unique sequence junction (USJ). The PASS oligonucleotides may be used as primers for polymerase-based enzymatic reactions (PASS primers) and/or included as a sensor arm component and/or substrate arm component of a partzyme (PASS partzyme).

In some embodiments the PASS oligonucleotides may comprise at least two components. One component may be complementary or substantially complementary to a target polynucleotide, whereas the other component may be non-complementary or substantially non-complementary to that target oligonucleotide.

In some embodiments the PASS oligonucleotides may further comprise three components. A first and second component may be complementary or substantially complementary to a target polynucleotide, whereas a third component may be non-complementary or substantially non-complementary to the same target polynucleotide. The first and second components of the oligonucleotide may be complementary or substantially complementary to different portions of the target oligonucleotide. The third component of the oligonucleotide that is non-complementary to the target may be located between first and second components of the oligonucleotide.

In some embodiments, the number of nucleotides in the third component may be equal to the number of unhybridised nucleotides in the target polynucleotide which are located between portions of the target polynucleotide hybridised to the first and second components. PASS oligonucleotides having this feature are also referred to herein as planar PASS oligonucleotides.

In other embodiments, the number of nucleotides in the third component exceeds the number of unhybridised nucleotides in the target polynucleotide which are located between portions of the target polynucleotide hybridised to the first and second components. In such cases, unhybridised nucleotides of the PASS oligonucleotide may form a loop structure. PASS oligonucleotides having this feature are also referred to herein as loop PASS oligonucleotides.

In still other embodiments, the number of nucleotides in the third component is less than the number of unhybridised nucleotides in the target polynucleotide which are located between portions of the target polynucleotide hybridised to the first and second components. PASS oligonucleotides having this feature are also referred to herein as target loop PASS oligonucleotides.

For example, the third component may comprise between 1 and 300 nucleotides, 1 and 250 nucleotides, 1 and 200 nucleotides, 1 and 150 nucleotides, 1 and 100 nucleotides, 1 and 75 nucleotides, 1 and 50 nucleotides 1 and 25 nucleotides, 5 and 300 nucleotides, 5 and 250 nucleotides, 5 and 200 nucleotides, 5 and 150 nucleotides, 5 and 100 nucleotides, 5 and 75 nucleotides, 5 and 50 nucleotides, 5 and 25 nucleotides, 10 and 300 nucleotides, 10 and 250 nucleotides, 10 and 200 nucleotides, 10 and 150 nucleotides, 10 and 100 nucleotides, 10 and 75 nucleotides, 10 and 50 nucleotides, or 10 and 25 fewer nucleotides than the number of unhybridised nucleotides in the target polynucleotide which are located between portions of the target polynucleotide hybridised to the first and second components. In such cases, unhybridised nucleotides of the target polynucleotide positioned between the first and second components may form a loop structure. The loop structure may comprise between 1 and 300 nucleotides, 1 and 250 nucleotides, 1 and 200 nucleotides, 1 and 150 nucleotides, 1 and 100 nucleotides, 1 and 75 nucleotides, 1 and 50 nucleotides 1 and 25 nucleotides, 5 and 300 nucleotides, 5 and 250 nucleotides, 5 and 200 nucleotides, 5 and 150 nucleotides, 5 and 100 nucleotides, 5 and 75 nucleotides, 5 and 50 nucleotides 5 and 25 nucleotides, 10 and 300 nucleotides, 10 and 250 nucleotides, 10 and 200 nucleotides, 10 and 150 nucleotides, 10 and 100 nucleotides, 10 and 75 nucleotides, 10 and 50 nucleotides, or 10 and 25 nucleotides. The loop structure may comprise 10, 20, 30, 40, 50, 60, 100 or 200 nucleotides (FIG. 12).

In some embodiments, the first component may terminate at the 5' end of the PASS oligonucleotide and the second component may terminate at the 3' end of the PASS oligonucleotide. The 5' component may be shorter than the 3' component. In other embodiments, the 5' component may be longer than the 3' component. In other embodiments the central component may be shorter than the 5' component and/or the 3' component. In still other embodiments the central component may be longer than the 5' component and/or the 3' component.

A PASS oligonucleotide may further comprise additional non-complementary sequence which may be located either 5' of the 5' component and/or 3' of the 3' component.

By way of non-limiting example only, the 5' component, 3' component and/or central component of a PASS oligonucleotide may be less than 75, less than 70, 60, 50, 45, 40, 35, 30, 25, 20, 17, 55, 13, 10, 9, 8, 7, 6 or less than 5 nucleotides in length. For example, the central component may be 10, 9, 8, 7, 6, 5, 4, 3, 2 or 1 nucleotide/s in length. In alternative embodiments, the PASS oligonucleotides may comprise first and second components, each of which is complementary or substantially complementary to a distinct portion of the target polynucleotide. The distinct portions of the target polynucleotide are separated by intervening nucleotide/s. Accordingly, upon hybridisation of the PASS oligonucleotide to the target polynucleotide by complementary base pairing, non-contiguous nucleotides of the target polynucleotide are juxtaposed creating a USJ. The bringing together of spatially-separated nucleotide sequence components in the target polynucleotide may form a loop structure in the target polynucleotide. PASS oligonucleotides having these features are also referred to herein as pinch PASS oligonucleotides. The loop structure in the target polynucleotide may comprise between 1 and 100 nucleotides, 1 and 75 nucleotides, 1 and 50 nucleotides 1 and 25 nucleotides, 5 and 100 nucleotides, 5 and 75 nucleotides, 5 and 50 nucleotides 5 and 25 nucleotides, 10 and 100 nucleotides, 10 and 75 nucleotides, 10 and 50 nucleotides, or 10 and 25 nucleotides. The loop structure may comprise 10, 20, 30, 40, 50 or 60 nucleotides.

A PASS oligonucleotide of the present invention may be a component of a partzyme (PASS partzyme). For example, sensor and/or substrate arm/s of the PASS partzyme may comprise a PASS oligonucleotide. Accordingly, PASS partzymes may be capable of hybridising to a target polynucleotide and combining with a second partzyme capable of hybridising to an adjacent portion of the target polynucleotide to assemble into MNAzyme capable of modifying a substrate providing a detectable event.

A PASS partzyme of the present invention may comprise a sensor arm and/or a substrate arm comprising or consisting of a planar PASS oligonucleotide, a loop PASS oligonucleotide, a target loop PASS oligonucleotide, or a pinch PASS oligonucleotide as described herein.

A PASS partzyme comprising a sensor arm and/or a substrate arm comprising or consisting of a target loop PASS oligonucleotide or a pinch PASS oligonucleotide may cause the formation of a loop structure in a polynucleotide hybridised to the sensor arm and/or a substrate arm. The loop structure in the target polynucleotide may comprise between 1 and 60 nucleotides, 1 and 50 nucleotides, 1 and 40 nucleotides, 1 and 30 nucleotides 1 and 20 nucleotides, 1 and 10 nucleotides, 5 and 60 nucleotides, 5 and 50 nucleotides, 5 and 40 nucleotides, 5 and 30 nucleotides 5 and 20 nucleotides, 5 and 10 nucleotides, 10 and 60 nucleotides, 10 and 50 nucleotides, 10 and 40 nucleotides, 10 and 30 nucleotides, or 10 and 20 nucleotides. The loop structure in the target polynucleotide may comprise 1, 2, 3, 4, 5, 6, 7, 8, 9, 10, 15, 20, 25, 30, 35, 40, 45, 50, 55 or 60 nucleotides (FIG. 13).

Reference to a sequence of nucleotides that is "substantially complementary" to another sequence of nucleotides herein may mean that a first sequence is at least 60%, 65%, 70%, 75%, 80%, 85%, 90%, 95%, 97%, 98% or 99% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

A sequence of nucleotides that is "complementary" to another sequence of nucleotides herein may mean that a first sequence is 100% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

Reference to a sequence of nucleotides that is "substantially non-complementary" to another sequence of nucleotides herein may mean that a first sequence is less than 1%, 2%, 3%, 4%, 5%, 10%, 15%, 20%, 25%, 30%, 35%, or 40% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

A sequence of nucleotides that is "non-complementary" to another sequence of nucleotides herein may mean that a first sequence is 0% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

A PASS oligonucleotide as provided herein may be of any suitable length, depending on the desired application, By way of non-limiting example only the oligonucleotide may be less than 100, less than 75, less than 70, 60, 50, 45, 40, 35, 30, 25, 20, 17, 55, 13, 10, 9, 8, 7, 6 or less than 5 nucleotides in length.

Non-limiting examples of target nucleic acids (i.e. a polynucleotide) to which PASS oligonuceotides may bind include DNA, methylated DNA, alkylated DNA, complementary DNA (cDNA), RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases).

Accordingly, the PASS oligonucleotides provided herein may comprise or consist of DNA, methylated DNA, alkylated DNA, complementary DNA (cDNA), RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases).

In certain embodiments, PASS oligonucleotides of the present invention may be used as primers in the amplification of a target sequence of nucleic acids.

Figure 1:
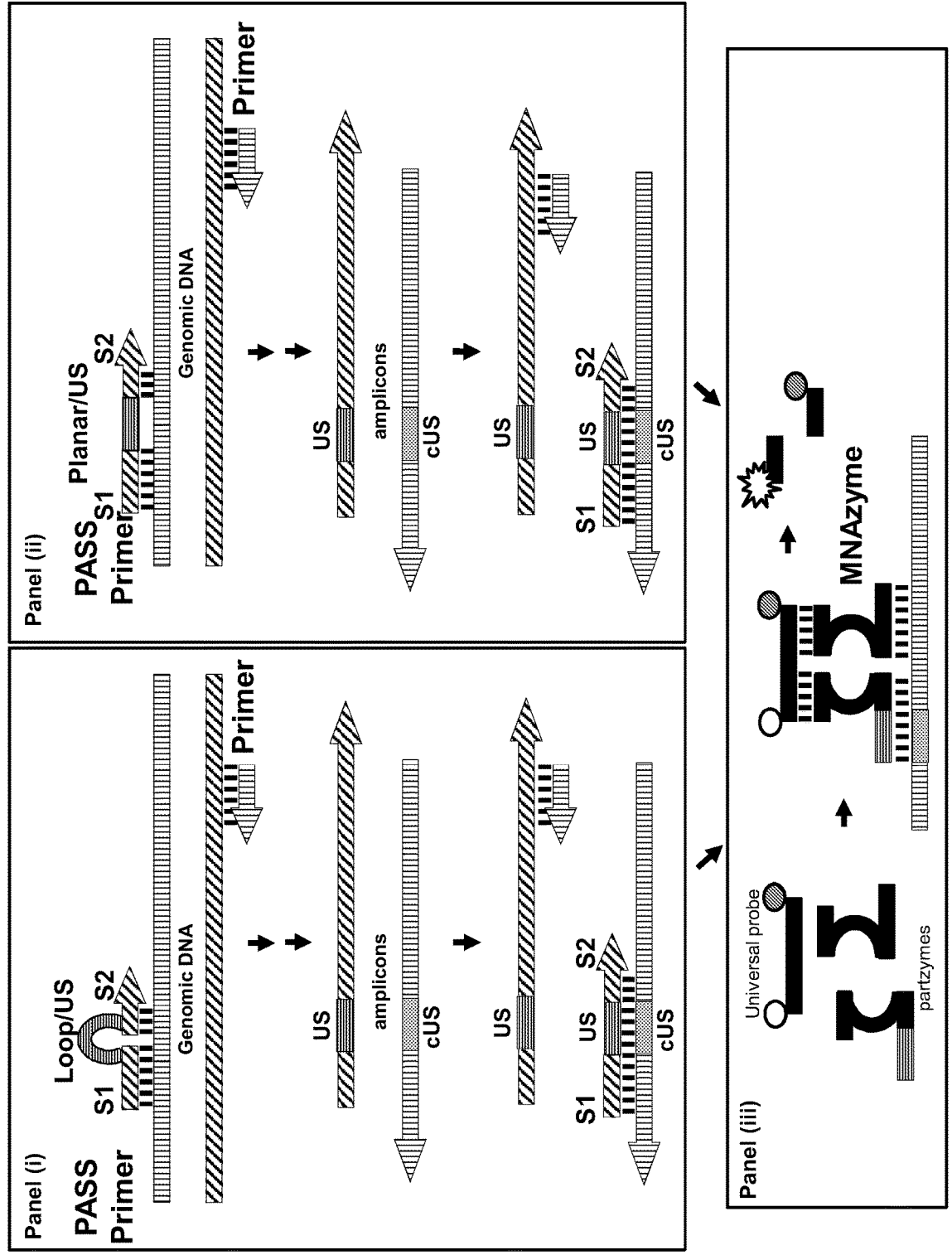
FIG. 1: Polynucleotide Assisted Sequence Switching (PASS) primer with MNAzyme readout: An exemplary PASS PCR strategy is illustrated which involves a PASS primer that contains a portion of unique sequence that is not complementary to the target sequence of interest. The unique sequence (US) sits between two sequences (S1 and S2) in the PASS primer, both of which are largely complementary to the target. S1 is the region of the PASS primer that is complementary to the target and 5' to the US. S2 is the region of the PASS primer that is largely complementary to the target and is 3' to the US. PASS primers can be designed to produce different conformations when bound to the target sequence. For example, when the number of bases in the target sequence between the binding sites of S1 and S2 (target-gap) is less than the number of bases in the US, then the US will "loop" out when the PASS primer binds to the target (Panel (i)). When the number of bases in the target between the binding sites of S1 and S2 is the same as the number of bases in the US, then the US does not loop out but rather forms a "planar" non-complementary region (Panel (ii)). In another embodiment, the number of bases in the target sequence between the binding sites of S1 and S2 may be more than the number of bases in the US, in this scenario the target sequence will loop out when the PASS primer binds to the target sequence. Through successive rounds of PCR the US is incorporated into one strand of the PCR amplicon and the complement of the US (cUS) is incorporated into the opposite strand of the PCR amplicon. The amplicons generated by PASS primers with either a loop (Panel (i)) or a planar region (Panel (ii)) of US can be detected by many strategies. By way of example this figure shows detection using MNAzymes (Panel (iii)).

Referring to the embodiments shown in FIG. 1, PASS primers may comprise three regions. The 5' component of the primer (S1) contains sequence that is substantially complementary to the nucleic acid target of interest, the middle component of the primer is a non-target specific unique sequence (US) and the 3' component of the primer (S2) contains sequence that is substantially complementary to the nucleic acid target of interest. S1 and S2 may be designed such that S2 binds further towards the 5' of the target sequence than S1. As shown in panel (i) the number of nucleotides in the gap between the areas of the target to which S1 and S2 bind may be less than than the number of bases in the US, so that the US forms a loop when the PASS primer binds to the target (FIG. 1, Panel (i)). Alternatively, there may be a gap between the target sequence bound by S1 and S2 as shown in FIG. 1 panel (ii). The US may comprise the same number of nucleotides as the gap between S1 and S2 (FIG. 1, Panel (ii)), fewer nucleotides, or more nucleotides (FIG. 1, Panel (i)).

In some embodiments, the melting temperature ("Tm") of S1 is higher than the Tm than S2.

Thus, in certain embodiments PASS oligonucleotides may have three regions, namely, (i) a 5' region (S1) having a Tm higher than the a 3' region (S2) that is complementary or substantially complementary to a first component of a target nucleic acid and capable of annealing to the target; (ii) a 3' region (S2) which may have a lower Tm than S1 and which is complementary or substantially complementary to the target; and (iii) an intervening region (US) located between S1 and S2 comprising a unique sequence (US) that is non-complementary or substantially non-complementary to the target.

In general, when a PASS primer is used to amplify a sequence of interest, the US is incorporated into resulting amplicons (FIG. 1, Panels (i), (ii) and (iii)). The US may be designed for various purposes such as, for example, to aid in the detection of the amplicons using a Molecular Beacon or an MNAzyme partzyme designed to bind to US or the complement of the US (FIG. 1, Panel (iii)). The MNAzyme partzyme or the Molecular Beacon may or may not also bind to target sequence amplified from the 3' end of the PASS primer.

Specific and non-limiting examples of PASS primers include those comprising a sequence as defined in any one of SEQ ID NOs 10, 11, 13, 14, 16, or 17.

Exemplary Applications of PASS Oligonucleotides

Target Amplification with PASS Primers

PASS oligonucleotides of the present invention may be used as primers (PASS primers) to amplify target nucleic acid sequences and to incorporate unique sequences (US) into resulting amplicons. No particular limitation exists in relation to amplification techniques to which the PASS primers may be applied. Amplicons generated by various reactions utilising the PASS oligonucleotides may be detected using any known technique. Non-limiting examples include those detection techniques using a signal provided by a dye that binds to double-stranded DNA (e.g. SYBR green), and/or those using an amplicon sequence specific-probe (e.g. molecular beacons, minor groove binder (MGB) probes, TaqMan® probes).

In general, nucleic acid amplification techniques utilise enzymes (e.g. polymerases) to generate copies of a target nucleic acid that is bound specifically by one or more oligonucleotide primers. Non-limiting examples of amplification techniques in which PASS oligonucleotides may be used include one or more of the polymerase chain reaction (PCR), the reverse transcription polymerase chain reaction (RT-PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA).

The introduction of a US from a PASS oligonucleotide described herein into an amplicon may aid in better discrimination of single base differences such as single nucleotide polymorphisms or acquired point mutations. For example, PASS primers may be designed to enhance discrimination between variant sequences, such as SNPs or mutations (e.g. point mutations).

Referring to FIG. 2, PASS primers may be designed to enhance discrimination of single base changes such as SNPs or point mutations. For example, the 3' component (S2) of either a loop PASS primer (FIG. 2 panel (i)) or a planar PASS primer (FIG. 2 panel (ii)) can be used to target and specifically bind to the SNP or point mutation. The base matched to the SNP or point mutation in S2 of the PASS primer may be located at the 3' terminus of the primer (FIG. 2 top of Panels (i) and (ii)), or may be located at other positions within S2 such as, for example, 1, 2, 3, 4, 5 or more than 5 bases 5' of the 3' terminus of the primer. Further, additional bases may be mismatched between S2 and the target sequence of interest to aid in better discrimination of the SNP (FIG. 2 bottom of Panels (i) and (ii)). For example, 1, 2, or 3 bases may be mismatched between S2 and the target sequence. The mismatched base or bases may be located, for example, 1, 2, 3, 4, 5 or more than 5 bases 5' of the 3' terminus of the primer.

PASS primers can be designed to enhance discrimination between variant sequences (e.g. SNPs or mutations) in multiplex reactions involving a plurality of target polynucleotides. In these embodiments, two or more PASS primers comprising different target polynucleotide binding specificities may be used for the detection of different target polynucleotides. To discern between amplicons derived from different polynucleotide targets, the central component (US) of a first PASS primer with specificity for one polynucleotide may differ from the central component (US) of a second PASS primer with specificity for the other different target polynucleotide.

Detection of, and discrimination between, two sequences which vary by only a single base is illustrated in FIG. 3. Variant 1 is denoted by a circle in the left hand panel and Variant 2 denoted by a triangle in the right hand panel. S2 of PASS Primer 1 is specifically matched to Variant 1, and the US of PASS primer 1 is a first US (US1) in a loop format (loop 1). S2 of PASS primer 2 is specifically matched to Variant 2, and the US of PASS primer 2 is a second US (US2) in a loop format (loop 2). Use of these PASS primers in PCR results in amplicons for each variant that differ in sequence by both the (a) the variant base and (b) the US incorporated via the PASS primer. The different amplicons may be detected using any suitable means. In the embodiment shown in FIG. 3, detection could be achieved using a multiplex MNAzyme qPCR reaction.

Unique sequence (US) from PASS primers may be incorporated into amplicons for the purpose of "skipping" or removing areas of non-informative genetic variation that exist between target conserved sequences to be detected. This may facilitate, for example, the detection of multiple strains of a single virus or bacterium where conserved regions are separated by variable regions of sequence. In such embodiments, it may not be necessary to discern between amplicons derived from different polynucleotide targets in which case the central component (US) of different PASS primers may be identical. Alternatively, the sequences of the central component (US) from different PASS primers may differ in order to discern between the sources of amplicons.

By way of non-limiting example only, a SNP (SNP-1) that predicts response to a particular therapy may immediately be downstream of a SNP (SNP-2) that provides no useful information on therapeutic response. The design of ARMS primers to SNP-1 would be complicated by the presence of multiple alleles for SNP-2. A PASS primer could be designed with S2 specific for the informative allele for SNP-1. The PASS primer would be designed to the target such that S1 and S2 would leave un-hybridized target sequence between them. This un-hybridized target sequence would contain SNP-2. During amplification with the PASS primer, the unique sequence (US) in the PASS primer would replace the sequence of SNP-2, removing this extraneous variation from the reaction. Discrimination between different alleles of SNP-1 could be achieved using two PASS primers. Allele 1 of the SNP would be amplified by PASS Primer 1 which would contain S2 specifically matched to Allele 1, and US1. PASS Primer 2 would amplify Allele 2 of the SNP. PASS Primer 2 would contain S2 specifically matched to Allele 2 and US2 (a different sequence to US1). Use of these PASS primers in PCR would result in amplicons for each variant that differ in sequence by both the (a) the variant base and (b) the US incorporated via the PASS primer, but without the variant of SNP-2. The amplicons from PASS Primer 1 and PASS Primer 2 could be detected using MNAzymes as described in FIG. 3 (see MNAzyme 1 and MNAzyme 2).

Referring specifically to the embodiments shown in FIGS. 5 and 6, PASS primers may be designed such that S1 and S2 are complementary or substantially complementary to two conserved, non-adjacent sequences of a target (FIG. 5, PASS primer). The gap in the target sequence between the areas that hybridize to S1 and S2 (target-gap) may contain differences in sequence between three variants to be detected. The variants may be viral or bacterial strains. The US of the PASS primer may be designed to contain the same number of nucleotides in the target-gap between S1 and S2 (FIG. 5) or the US of the PASS primer may be designed to contain less nucleotides than those in the target-gap between S1 and S2 (FIG. 6).

Amplification of DNA from Variants 1, 2 and 3 in FIG. 5 with the PASS primer in FIG. 5 may result in amplicons with exactly the same sequence irrespective of the variation in the target-gap. The US from the PASS primer may replace the genetic variation in the target-gap between S1 and S2. Thus a method for detecting all amplicons produced may rely on the detection of a single US, regardless of the amplicons being amplified from different target polynucleotides. For example, as shown in FIG. 5, an MNAzyme may be designed with a partzyme sensor arm that hybridises the complement of the US (cUS, FIG. 5) and cleaves a single probe to detect Variant 1, 2 and 3 of, for example, a virus or bacterium.

Referring specifically to FIG. 6, amplification of DNA from Variant 1 using the target loop PASS primer shown would replace the variant sequence in the target-gap with the smaller number of nucleotides in the US of the PASS primer. Other strains of virus or bacteria that had variation in this same target-gap region would also be effectively amplified using this PASS primer. The resulting amplicons would all have the same sequence, regardless of the sequence of the target-gap. A single MNAzyme could be designed with a partzyme sensor arm that would hybridize to the complement of the US (cUS, FIG. 6) and cleave a single probe to detect any amplicons generated from the PASS primer.

The skilled addressee will readily understand that the applications of PASS oligonucleotides/primers described above are provided for the purpose of non-limiting exemplification only. The PASS oligonucleotides/primers disclosed may be used in any primer-based nucleic acid amplification technique and the invention is not so limited to those embodiments specifically described.

Detection of Amplicons Generated Using PASS Primers

As discussed above, PASS primers of the present invention may be utilised in any polynucleotide amplification technique, non-limiting examples of which include the PCR, RT-PCR, SDA, HDA, RPA. LAMP, RCA, TMA, 3SR, or NASBA.

Amplicons generated by techniques that utilise PASS primers may be detected using any suitable method known in the art.

Non-limiting examples include the use of labelled probes, the incorporation of detectable labels into the primers, the use of catalytic nucleic acids, and the like.

For example, the amplicons may be detected by (SYBR Green with melt curve analysis) where the difference in Tm between a unique sequence (US1) of a first PASS primer and the Tm of a unique sequence (US2) from a second PASS primer would provide a greater difference in the melt temperature of the amplicons. Additionally or alternatively, molecular beacons may be used where the molecular beacons are designed to encompass US1 or US2. Additionally or alternatively, MNAzymes may be used to detect the amplicons.

In certain embodiments, the detection method utilised may be designed to detect a central component (US) of PASS primers incorporated into amplicons, or a component of the US. This may be particularly advantageous in multiplex assays aimed at detecting amplicons derived from distinct polynucleotides. For example, it may allow for easier discrimination between small genetic variations in distinct target polynucleotides such as SNPs and other mutations.

Additionally or alternatively, the detection method utilised may be designed to detect a 5' (S1) and/or 3' (S2) component of PASS primers incorporated into amplicons.

Although it may be preferable in many applications to detect the amplicons using sequence-specific techniques (e.g. techniques based on the specific sequence of a central component of a PASS oligonucleotide incorporated into an amplicon), other techniques are also contemplated. For example, in embodiments where amplification is not carried out for the purpose of discerning amplicons derived from different target polynucleotides it may well be sufficient to detect amplicons produced by virtue of its size. This may be the case, for example, when amplification involves removing areas of non-informative genetic variation that exist between target conserved sequences that are to be detected.

An MNAzyme may be utilised to detect amplicons generated using PASS primers using techniques such as PCR, RT-PCR, SDA, HDA, RPA, TMA, LAMP, RCA, 3SR, and NASBA. The MNAzyme may comprise one or more PASS partzyme(s). MNAzymes are multi-component nucleic acid enzymes which are assembled and are only catalytically active in the presence of an assembly facilitator which may be, for example, a target to be detected such as an amplicon generated from a polynucleotide sequence using PASS primers. MNAzymes are composed of multiple part-enzymes, or partzymes, which self-assemble in the presence of one or more assembly facilitators and form active MNAzymes which catalytically modify substrates (FIG. 16). The substrate and assembly facilitators (target) are separate nucleic acid molecules. The partzymes have multiple domains including (i) sensor arms which bind to the assembly facilitator (such as a target nucleic acid); (ii) substrate arms which bind the substrate, and (iii) partial catalytic core sequences which, upon assembly, combine to provide a complete catalytic core. MNAzymes can be designed to recognize a broad range of assembly facilitators including, for example, different target nucleic acid sequences. In response to the presence of the assembly facilitator, MNAzymes modify their substrates. This substrate modification can be linked to signal generation and thus MNAzymes can generate an enzymatically amplified output signal. The assembly facilitator may be a target nucleic acid present in a biological or environmental sample (e.g. an amplicon generated from a polynucleotide target using PASS primers). In such cases, the detection of the modification of the substrate by the MNAzyme activity is indicative of the presence of the target. Several MNAzymes capable of cleaving nucleic acid substrates have been reported and additional MNAzymes which can ligate nucleic acid substrates are also known in the art. MNAzymes and modified forms thereof are known in the art and disclosed in PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety).

For example, either or both sensor arms of an MNAzyme may be complementary or substantially complementary to a PASS primer, or a component thereof. In certain embodiments, one sensor arm of the MNAzyme is complementary or substantially complementary to the central component (US) of a PASS primer or a component thereof, and is also complementary to a portion of the remainder of an amplicon comprising the central component. The second sensor arm of the MNAzyme is complementary to a different portion of the same amplicon that is not complementary to the first sensor arm and that does not contain the US.

MNAzymes may be used in multiplex assays designed to detect the presence of multiple distinct amplicons comprising different central components (US) derived from different PASS primers. For example, the sensor arm or sensor arms of a first MNAzyme may be specific for a first amplicon comprising a first central component (US) derived from a first PASS primer capable of binding to and facilitating amplification of a first polynucleotide target, and the sensor arm or sensor arms of a second MNAzyme may be specific for a second amplicon comprising a second central component (US) derived from a second PASS primer capable of binding to and facilitating amplification of a second polynucleotide target comprising a sequence that is distinct from the first polynucleotide target. This facilitates the detection of multiple distinct amplicons derived from distinct polynucleotide targets in a single assay. The skilled person would readily understand that additional MNAzymes with specificities for additional distinct amplicons derived from other distinct polynucleotide targets could also be incorporated into such assays.

By way of non-limiting example only, reference is made to FIG. 3 wherein MNAzyme 1 may be designed to detect Variant 1 amplicons by designing a partzyme sensor arm that is comprised of sequence which is specific for both the Variant 1 and the complement of US1. MNAzyme 1 may be designed to cleave a universal probe 1 (Sub 1) labeled with fluorophore 1 only in the presence of amplicons of Variant 1. MNAzyme 2 may be designed to detect Variant 2 amplicons by designing a partzyme sensor arm that is comprised of sequence which is specific for both the Variant 2 and the complement of US 2. MNAzyme 2 can be designed to cleave a universal probe 2 (Sub 2) labeled with fluorophore 2 only in the presence of amplicons with Variant 2. In this strategy, real-time detection, discrimination and quantification of both Variants 1 and 2 can occur simultaneously in the one reaction tube. FIG. 7 shows exemplary designs of PASS primers designed for the selective amplification of variant bases such as SNPs or point mutations in target polynucleotides. Amplicons generated by the PASS primers may be detected, for example, by MNAzymes. PASS primers may be designed to discriminate single base changes such as SNPs or point mutations. For example, S2 as shown in looped and planar PASS primers in FIG. 7 can be used to target and specifically bind to the SNP or point mutation. The nucleotide matched to the SNP or point mutation in S2 of the PASS primer may be located at the 3' terminus of the primer (Design 1), 3 nucleotides from the 3' end (Design 2), at the 3' terminus of the primer with a mismatch nucleotide inserted 3 bases from the 3' end (Design 3) or 3 nucleotides from the 3' end with a mismatch nucleotide inserted 5 bases from the 3' end (Design 4). An MNAzyme may be used to detect amplicons generated with the PASS primers.

Partzyme A target sensor arms are shown to match each PASS primer design and Partzyme B is shown as constant for all designs.

The skilled person will readily recognise that planar, loop, target loop and pinch PASS primers can be used in accordance with the exemplary design shown in FIG. 7. The skilled person will also recognise that the position of the nucleotide matched to the SNP and/or mismatch nucleotide shown in the S2 component may be varied. For example, either may be at the 3' terminus, or 1, 2, 3, 4 or 5 nucleotides from the 3' terminus.

Detection of Amplicons Using PASS Partzymes

MNAzymes comprising PASS partztyme(s) may be used to detect target nucleic acids and target nucleic acid amplicons. The target nucleic acid amplicons may be generated using any suitable technique. In some embodiments, the target nucleic acid amplicons may be generated with techniques that utilise PASS primers.

Referring to the exemplary embodiment shown in FIG. 8, PASS partzymes can be designed to detect multiple amplicons derived from related variant sequences. By way of non-limiting example only, target sequences of interest may contain a string of variant nucleotides that differ in different targets (depicted as variant 1 (V1), variant 2 (V2) and variant 3 (V3) sequences in FIG. 8). Primer sets may be designed to be specific for each variant sequence, V1, V2 and V3, and produce amplicons for each. PASS partzymes provide a strategy for detection of the sequences in real-time without discriminating between the variant strains. This involves using MNAzyme qPCR, whereby the MNAzyme may comprise a PASS partzyme. By way of example a PASS partzyme may comprise a portion of unique sequence (US) that is not complementary to the target sequence(s)/amplicon(s) of interest. The US may be positioned within the PASS partzyme sensor arm between two regions that are complementary to the targets. The US in the partzyme may be aligned with the variant region in V1, V2 and V3 that contains the variant bases. A single PASS partzyme with this design could bind to amplicons from V1, V2 and V3 with equal or similar efficiency allowing their simultaneous detection.

Still referring to the exemplary embodiment shown in FIG. 8, the US within the PASS partzymes does not prevent the formation of active MNAzymes and thus the presence of any variant, or combination thereof, may result in the cleavage of a universal probe providing a detectable event. For example, when the probe is labelled with a fluorophore and quencher this may produce a signal that can be monitored in real-time.

The skilled person will recognise that the sensor arm of the PASS partzyme shown in FIG. 8 can comprise or consist of a planar PASS oligonucleotide, a loop PASS oligonucleotide, a target loop PASS oligonucleotide, or a pinch PASS oligonucleotide as described herein, each designed to avoid complementary base hybridization to the variant region of the amplicons.

Referring now to the exemplary embodiment depicted in FIG. 10, PASS partzymes may be designed to detect variant deletion strains with MNAzyme qPCR readout whereby the Variant target sequences of interest may be derived from a group of wild type sequences comprising members with unidentical deleted regions (FIG. 10 Panel i, Deletion 1 and Deletion 2). Primer sets may be designed to be specific for each deletion variant sequence and produce amplicons for each. The use of PASS partzymes provides a strategy to detect the sequences in real-time without necessarily discriminating between the specific deletions. This may be achieved using MNAzyme qPCR, whereby the MNAzyme may comprise a first PASS partzyme and a fully matched ("standard") partzyme which bind adjacently on the amplified target sequence of interest. The PASS partzyme may comprise a region of sequence that is not complementary to the target sequence, denoted the unique sequence (US), which is designed to align where the region varies between deletion amplicons such that one MNAzyme can be used to detect all variants (FIG. 10 Panel ii). The US present in the PASS partzyme may be in a planar form where the number of non-complementary bases in the sensor arm of the PASS partzyme matches the number of unhybridised nucleotides in the target sequence (FIG. 10 Panel ii (a)). Alternatively, the US present in the PASS partzyme sensor arm may be in a loop form where the number of non-complementary/unhybridised nucleotides in the sensor arm of the PASS partzyme is greater than the number of non-complementary/unhybridised nucleotides in the target sequence sequence (FIG. 10 Panel ii (b)).

The skilled person will recognise that although FIG. 10 depicts the use of planar and loop PASS oligonucleotides, the sensor arm of the PASS partzyme shown in FIG. 10 may comprise or consist of a target loop PASS oligonucleotide or a pinch PASS oligonucleotide as described herein, each designed to avoid complementary base hybridisation to the variable deleted region of the amplicons.

A single PASS partzyme could bind to amplicons generated by amplification deletion variant 1 and 2 with equal or similar efficiency thus allowing their simultaneous detection.

The US within the PASS partzymes does not prevent the formation of the active MNAzymes hence a universal probe labelled with a fluorophore and quencher can be cleaved providing a detectable event. This may in turn provide a signal that can be monitored in real-time.

In yet another exemplary embodiment, depicted in FIG. 9, detection of target may be achieved using a combination of PASS partzymes with PASS primers. Target sequences of interest may contain a sequence of variant nucleotides, where the variant nucleotide sequence in different targets is not the same, for example, variant 1 (V1), variant 2 (V2) and variant 3 (V3) sequences. PASS primer sets may be designed to be specific for each variant sequence, V1, V2 and V3, and may further comprise the same US (US1), such that amplification produces amplicons for each variant which contain (i) the variant bases and (ii) the complementary sequence to the common US (cUS1) and the sequence conserved between variants. The combined use of these PASS primers with PASS partzymes provides a strategy to detect all variant sequences in real-time without discriminating between the variant strains. This involves using MNAzyme qPCR, whereby the MNAzyme may comprise a first PASS partzyme and a fully matched "standard" partzyme that bind adjacently on the amplified target sequence of interest. The PASS partzyme sensor arm depicted comprises (i) a region fully matched to the conserved sequence of the all variant amplicons, (ii) a unique sequence (US2) which is not complementary to any of the variant amplicons and which is aligned to the regions which differs between the variant amplicons, and (iii) a region comprising US1, which can bind to all amplicons generated by using the variant-specific primer sets (all comprising cUS). This MNAzyme can recognize and hybridise to all variants.

A single PASS partzyme of either design could bind to amplicons generated by amplification of variant sequences with equal or similar efficiency thus allowing their simultaneous detection. The skilled person will recognise that although FIG. 9 depicts the use of planar PASS primers, the PASS primers shown in FIG. 9 may be substituted for loop PASS primers, target loop PASS primers, or pinch PASS primers as described herein, each designed to provide a US in the copy of the target sequence generated. The skilled person will also recognise that although FIG. 9 depicts a planar PASS partzyme conformation, the sensor arm may be substituted for an equivalent version comprising a loop or target loop PASS oligonucleotide in which US2 is non-complementary to the variable sequence of the amplicons, or alternatively a pinch PASS oligonucleotide sensor arm facilitating removal of the variable sequence as an available binding region in the amplicon for the sensor arm.

The plurality of US within each PASS partzyme do not prevent the formation of the active MNAzymes and thus the presence of any variant, or combination thereof, may result in the cleavage of a universal probe providing a detectable event. For example, when the probe is labelled with a fluorophore and quencher this may produce a signal that can be monitored in real-time.

In a further embodiment illustrated in FIG. 11 PASS partzymes may be used with PASS primers to detect variant deletions. Variant target sequences of interest may be derived from wild type sequences where different regions have been deleted (FIG. 11 Panel i, Deletion 1 and Deletion 2). PASS primer sets may be designed to be specific for each deletion variant sequence, Deletion 1 and Deletion 2, but may further comprise the same US (US1), resulting in amplicons for each deletion containing the deletion-specific variant bases as well as the complement sequence to the same US (cUS1) and the conserved common target sequence. An exemplary strategy for detection of the amplicons in real-time, without discriminating between the variant deletions, uses PASS partzymes together with the PASS primers. This may involve using MNAzyme qPCR, whereby the MNAzyme may comprise a first PASS partzyme and a fully matched ("standard") partzyme, which bind adjacently on the amplified target sequence of interest. The PASS partzyme may comprise (i) a region of sequence not complementary to the amplified target sequence, denoted as the unique sequence (US2) (Panel ii) which is designed to align where the sequence varies between deletion amplicons; (ii) another region corresponding to US1, so that one MNAzyme can be used to detect all variants (Panel ii) and (iii) common complementary sequence that is conserved in all deletion amplicons. The US2 present in the PASS partzyme may be in planar formation where the number of non-complementary bases in the PASS partzyme matches the number of unbound bases in the target sequence. Alternatively, the US2 present in the PASS partzyme may be in a looped conformation whereby the number of non-complementary bases in the partzyme is greater than the number in the target sequence resulting in the sequence bulging or looping out (Panel ii). A single PASS partzyme of either design could bind to amplicons generated by amplification of deletion variants with equal or similar efficiency thus allowing their simultaneous detection.

The skilled person will recognise that although FIG. 11 depicts the use of loop PASS primers, the PASS primers shown in FIG. 11 may be substituted for planar PASS primers, target loop PASS primers or pinch PASS primers as described herein, each designed to provide a US in the copy of the target sequence generated. The skilled person will also recognise that although FIG. 11 depicts planar and loop PASS partzyme conformations, the sensor arm may be substituted for an equivalent version comprising a a target loop PASS oligonucleotide in which US2 is non-complementary to the variable deleted sequence of the amplicons, or alternatively a pinch PASS oligonucleotide sensor arm facilitating removal of the variable deleted sequence as an available binding region in the amplicon for the sensor arm.

Since the US within the PASS partzymes does not affect the formation of the active MNAzymes a universal probe labelled with a fluorophore and quencher can be cleaved producing a signal that can be monitored in real-time.

Referring now to FIG. 14, amplification of target sequences using one or more primers may provide target sequence amplicons comprising the primer(s) and the target sequence. In such cases, MNAzymes may be designed to detect the amplicons. The MNAzymes may comprise a PASS partzyme as shown in FIGS. 14B and 14C. For example, as shown in FIGS. 14 (i), 14A (i) and 14B (i), the MNAzyme may be designed such that the sensor arm of either or both partzyme component(s) hybridizes by base pair complementarity to a region of the amplicon that does not comprise the primer sequence or a sequence complementary to the primer sequence (e.g. in a region between two termini of an amplicon each terminus comprising a separate primer sequence, or each terminus comprising a sequence complementary to a separate primer sequence). Alternatively, the MNAzyme may be designed such that the sensor arm of either or both partzyme component(s) hybridizes to a region of the amplicon that comprises a primer sequence or sequence complementary to the primer sequence (FIG. 14 (ii)/(iii), 14A (ii)/(iii), 14B (ii) and 14C (iii)). In such cases, the sensor arm that hybridizes to the primer sequence may be a component of a PASS partzyme. For example, as shown in FIGS. 14B (i)/(ii) and 14C (iii), a pinch PASS partzyme may be used resulting in the looping out of a portion of the primer sequence and optionally of additional sequence of the amplicon upstream or downstream of the primer sequence. In some embodiments, the target sequence amplicons may comprise primer(s) comprising a tag sequence (FIG. 14 (iii), 14A (iii), 14C (iii)). The MNAzyme may be designed such that the sensor arm of either or both partzyme component(s) hybridizes to a region of the amplicon that comprises the tag sequence or sequence complementary to the tag sequence. In such cases, the sensor arm that hybridizes to the primer sequence may be a component of a PASS partzyme. For example, as shown in FIG. 14C (iii), a pinch PASS partzyme may be used resulting in the looping out of a portion of the primer sequence and optionally of additional tag sequence and optionally of sequence of the amplicon upstream or downstream of the primer sequence. The skilled person will readily recognise that planar, loop, target loop and pinch PASS partzymes can be used in accordance with the exemplary methods described herein.

Detection of Non-Amplified Target Nucleic Acids Using PASS Partzymes

PASS partzymes of the present invention may be used to detect nucleic acids that have not been previously amplified using polymerase-based amplification techniques.

For example, PASS partzymes can be designed to detect variant target sequences. By way of non-limiting example only, target sequences of interest may contain a variant region that differs in different targets. The variable region may comprise nucleotide substitution(s), insertion(s) and/or deletion(s). A PASS partzyme may comprise a portion of unique sequence (US) that is not complementary to any of the target sequences, or at least none of the variable regions within a given population of variant target sequences. The US may be positioned between two regions of the PASS partzyme sensor arm that are each complementary to one or more target sequences. One of the complementary regions may be capable of hybridizing to target sequence(s) by complementary base pairing 3' of the variant region of the target(s), while the other may be capable of hybridizing to the same target sequence(s) by complementary base pairing 5' of the variable region in the target(s). In this manner, hybridization of the PASS partzyme to the target(s) comprising the variable region may align the US with the variant region to which the US may remain unhybridized. A single PASS partzyme with this design could thus bind to multiple different targets with equal or similar efficiency allowing their simultaneous detection. In general, detection can be facilitated by the addition of a second partzyme comprising a sensor arm that is complementary to a portion of the target sequence immediately adjacent to the portion of the target sequence hybridized by the PASS partzyme, thereby facilitating the assembly of a catalytically active MNAzyme capable of modifying a substrate to provide a detectable signal. The skilled person will recognise that the sensor arm of the PASS partzyme may comprise or consist of a planar PASS oligonucleotide, a loop PASS oligonucleotide, a target loop PASS oligonucleotide, or a pinch PASS oligonucleotide as described herein, each designed to avoid complementary base hybridization to the variant region of the target sequences.

Use of PASS Oligonucleotides to Incorporate Functional Nucleic Acids into Amplicons PASS oligonucleotides may be used to incorporate functional sequences into amplicons. The functional sequences may be formed by virtue of a PASS oligonucleotide (e.g. a PASS primer) incorporating a US or UJS into an amplicon, wherein a sequence that is complementary to the new US, or a new sequence formed by the UJS, has functional capacity. For example, the incorporated sequence may be that of a DNAzyme or ribozyme.

Referring now to FIG. 15 and in particular FIG. 15 panel (ii), a PASS primer comprising a US can be used to amplify a target nucleic acid (e.g. genomic DNA) and in doing so incorporate a US into the amplicon. The US of the PASS primer may comprise an inactive, antisense form of a functional nucleic acid. Upon amplification of the target nucleic acid a catalytically active, sense form of the functional nucleic acid is inserted into amplicons. The skilled person will readily recognize that planar, loop, and target loop PASS primers can be used to achieve the outcome of incorporating a functional nucleic acid into the amplicon produced via a US. In an alternative embodiment, a pinch PASS primer may be used to generate a UJS in the amplicon and in doing so create a functional nucleic acid within the amplicon.

As shown in the exemplary embodiment of FIG. 15 panel (ii), the US which comprises an inactive, antisense form of a catalytic nucleic acid (in this case a DNAzyme) used resulting in amplicons comprising functionally active sense forms of the US. The functionally active sense forms of the catalytic nucleic acid present in the amplicons are capable of cleaving a substrate to produce a detectable signal, thus notifying of the presence of the amplicons so generated. As shown in the lowest portion of FIG. 15 panel (ii), an MNAzyme may optionally be used to aid in the detection of the amplicon comprising the functional catalytic nucleic acid (in this case a DNAzyme). For example, an MNAzyme can be used that comprises a first partzyme capable of hybridizing by complementary base pairing adjacently or substantially adjacently to the substrate for the functional catalytic nucleic acid as well as portion of the amplicon. The second partzyme component of the MNAzyme may hybridize to the amplicon (again by complementary base pairing) adjacent to the first partzyme facilitating the assembly of a catalytically active MNAzyme capable of cleaving the same or a different substrate as the catalytic nucleic acid present in amplicon, thereby generating additional detectable signal indicative of the presence of the amplicons.

Diagnostic Applications

PASS oligonucleotides may be used for diagnostic and/or prognositic purposes in accordance with the methods described herein. The diagnostic and/or prognostic methods may be performed ex vivo or in vitro. However, the methods of the present invention need not necessarily be used for diagnostic and/or prognositic purposes, and hence applications that are not diagnostic or prognostic are also contemplated.

In some embodiments, the methods described herein may be used to diagnose infection in a subject. For example, the methods may be used to diagnose infection by bacteria, viruses, fungi/yeast, protists and/or nematodes in the subject. In one embodiment, the virus may be an enterovirus. The subject may be a bovine, equine, ovine, primate, avian or rodent species. For example, the subject may be a mammal, such as a human, dog, cat, horse, sheep, goat, or cow. The subject may be afflicted with a disease arising from the infection. For example, the subject may have meningitis arising from an enterovirus infection. Accordingly, methods of the present invention may in certain embodiments be used to diagnose meningitis.

The methods of the present invention may be performed on a sample. The sample may be derived from any source. For example, the sample may be obtained from an environmental source, an industrial source, or by chemical synthesis.

It will be understood that a "sample" as contemplated herein includes a sample that is modified from its original state, for example, by purification, dilution or the addition of any other component or components.

The methods of the present invention including, but not limited to diagnostic and/or prognostic methods, may be performed on a biological sample. The biological sample may be taken from a subject. Stored biological samples may also be used. Non-limiting examples of suitable biological samples include whole blood or a component thereof (e.g. blood cells, plasma, serum), urine, saliva, lymph, bile fluid, sputum, tears, cerebrospinal fluid, bronchioalveolar lavage fluid, synovial fluid, semen, ascitic tumour fluid, breast milk and pus.

Kits

The present invention provides kits comprising one or more agents for performing methods of the present invention. Typically, kits for carrying out the methods of the present invention contain all the necessary reagents to carry out the method.

In some embodiments the kits may comprise oligonucleotide components capable of forming an MNAzyme in the presence of an appropriate assembly facilitator (e.g. an amplicon comprising a PASS primer as described herein). For example, the kit may comprise at least a first and second oligonucleotide component comprising a first and second partzyme, and a second container comprising a substrate, wherein self-assembly of the first and second partzymes, and the substrate, into an MNAzyme requires association of an assembly facilitator (e.g. an amplicon) present in a test sample. Accordingly, in such embodiment, the first and second partzymes, and the substrate, may be applied to the test sample in order to determine the presence of one or more target amplicons.

In general, the kits comprise at least one PASS oligonucleotide provided herein. The kits may therefore comprise PASS oligonucleotides such as, for example, planar PASS oligonucleotides, loop PASS oligonucleotides, target loop PASS oligonucleotides and/or pinch PASS oligonucleotides.

Additionally or alternatively, the kits may comprise PASS primers such as, for example, planar PASS primers, loop PASS primers, target loop PASS primers and/or pinch PASS primers.

Additionally or alternatively, the kits may comprise PASS partzymes comprising a sensor arm and/or substrate arm that comprises or consists of a PASS oligonucleotide as described herein (e.g. a planar PASS oligonucleotide, loop PASS oligonucleotide, target loop PASS oligonucleotides or pinch PASS oligonucleotide). The kits may further comprise standard partzymes designed to complement the PASS partzymes in the context of binding the same target polynucleotide and facilitating the assembly of a catalytically active MNAzyme capable of modifying a substrate to provide a detectable signal.

Typically, the kits of the present invention will also comprise other reagents, wash reagents, enzymes and/or other reagents as required in the performance of the methods of the invention such as PCR or other nucleic acid amplification techniques.

The kits may be fragmented kits or combined kits as defined herein.

Fragmented kits comprise reagents that are housed in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent.

Combined kits comprise all of the components of a reaction assay in a single container (e.g. in a single box housing each of the desired components).

A kit of the present invention may also include instructions for using the kit components to conduct the appropriate methods. Kits and methods of the invention may be used in conjunction with automated analysis equipment and systems, for example, including but not limited to, real time PCR machines.

For application to amplification, detection, identification or quantitation of different targets, a single kit of the invention may be applicable, or alternatively different kits, for example containing reagents specific for each target, may be required. Methods and kits of the present invention find application in any circumstance in which it is desirable to detect, identify or quantitate any entity.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to the following specific examples, which should not be construed as in any way limiting.

Example 1: Use of MNAzymes to Detect Sequence Inserted into Amplicons Via PASS Primers The PASS PCR strategy involves a primer which has a region containing a unique sequence that is not complementary to the target sequence of interest. The unique sequence (US) present in the PASS primer may be either looped out or planar when the PASS primer binds the target (FIG. 1).

In this example, PASS primers are combined with MNAzyme qPCR whereby the MNAzyme comprises a first partzyme that binds to the complement of the unique sequence (cUS) as well as amplified target sequence of interest while the second partzyme binds adjacently to the first partzyme to amplified target sequence of interest. The point at which partzyme A binds directly adjacent to partzyme B on the target sequence of interest is referred to as the partzyme junction. Formation of active MNAzymes from partzyme components results in the cleavage of the universal probe labeled with fluorophore and quencher dye pair, producing a signal that can be monitored in real-time.

Primers and partzymes were designed to determine if various scenarios of overlap between the S2 domain of the PASS primer (FIG. 1) and the complementary partyzme sequence were compatible with detection of the CCB gene. This resulted in the 3' end of the PASS primer binding either 5 bases from the partzyme junction, 3 bases from the partyzme junction or at the partzyme junction. PASS primers and non-PASS "standard" primers were designed for each scenario.

1.1. Partzyme Oligonucleotides

Partzymes were designed to specifically target the CCB gene and/or any cUS introduced into the amplicon via a PASS primer. In the following sequences the bases in bold hybridize with the target sequence of interest and bases underlined hybridise to the cUS and contain the US, insert 2 (i2). The "-P" indicates 3' phosphorylation of the oligonucleotide. All sequences are written 5' to 3'.

SEQ ID NO: 1 partzyme A CCBA/72-P:
ATGGTCATCTCCAGAGCCCAACAACGAGAGGCGTGAT

SEQ ID NO: 2 partzyme B CCBB/72-P:
CTGGGAGGAGAGGCTAGCTGGTCCATGGCTTCTGGGTA

SEQ ID NO: 3 partzyme A CCB_1i2A/72-P:
<u>AGACATACTA</u>CTCCAGAGCCCAACAACGAGAGGCGTGAT SEQ ID NO: 4 partzyme A CCB_2i2A/72-P:
<u>AGACATACTA</u>CCAGAGCCCAACAACGAGAGGCGTGAT SEQ ID NO: 5 partzyme A CCB_3i2A/72-P:
ATG<u>AGACATACTA</u>GAGCCCAACAACGAGAGGCGTGAT 1.2. Reporter Substrate The reporter substrate for this example is shown below with the sequence written 5' to 3'. In the current example, the substrate was end labelled with a FAM moiety at the 5' end (indicated by a "F" in the name of the substrate below) and an Iowa Black® FQ quencher moiety at the 3' end (indicated by a "IB" in the name of the substrate below). Cleavage of the substrate was monitored at 530 nm (FAM emission wavelength) with excitation at 485 nm (FAM excitation wavelength). The lower case bases represent RNA and the upper case bases represent DNA.

```
SEQ ID NO: 6 Substrate Sub72-FIB:
ATCACGCCTCguCTCCTCCCAG
```

1.3. PCR Primers for Amplification of CCB DNA

The target sequence for this example was generated by in vitro amplification of human genomic DNA (gDNA) using the oligonucleotide PCR primers listed below. PASS primers are designed such that the US loops out on binding of the primer to the target are called "Loop". PASS primers where the US does not loop out on binding of the primer to the target are called "Planar". All sequences are written 5' to 3'. In the following sequences the bases underlined are the US.

```
SEQ ID NO: 7 Reverse primer 3CCB:
CTCAGGAATTTCCCAGCTAC

SEQ ID NO: 8 Forward primer 5CCB:
GTCTCAGTTCTTCTTGGATG

SEQ ID NO: 9 Forward primer 5CCB_1:
CTTGGATGGTCATCTCCAGA

SEQ ID NO: 10 Forward PASS primer 5CCB_1i2Loop:
AGTTCTTCTTGGATGGTCATAGACATACTACTCCAGA SEQ ID NO: 11 Forward PASS primer 5CCB_1i2Planar
CTCTTGTCTCAGTTCTTCTTAGACATACTACTCCAGA SEQ ID NO: 12 Forward primer 5CCB_2:
GGATGGTCATCTCCAGAGC SEQ ID NO: 13 Forward PASS primer 5CCB_2i2Loop:
TTCTTCTTGGATGGTCATCTAGACATACTACCAGAGC SEQ ID NO: 14 Forward PASS primer 5CCB_2i2Planar:
CTTGTCTCAGTTCTTCTTGGAGACATACTACCAGAGC SEQ ID NO: 15 Forward primer 5CCB_3:
TGGTCATCTCCAGAGCCCA SEQ ID NO: 16 Forward PASS primer 5CCB_3i2Loop:
CTTCTTGGATGGTCATCTCCAAGACATACTAGAGCCCA SEQ ID NO: 17 Forward PASS primer 5CCB_3i2Planar:
GTCTCAGTTCTTCTTGGATGAGACATACTAGAGCCCA
```

1.4. Target Sequence

Human gDNA extracted from the IM9 cell line (Promega) was used as template for amplification of the CCB gene.

1.5. Reaction Components: Amplification and Detection of Target Sequence

Real-time amplification and detection of the target sequence was performed in a total reaction volume of 25 µL. The reactions were conducted in a Mx3005p (Stratagene). The cycling parameters were 95° C. for 2 minutes, 5 cycles of 95° C. for 15 seconds and 55° C. for 30 seconds, 40 cycles of 95° C. for 15 seconds and 52° C. for 60 seconds (data collected at the 52° C. step). All reactions were run in duplicate and contained 40 nM forward primer, 100 nM partzyme A (the combinations as listed in Table 1), 200 nM of reverse primer (3CCB), 200 nM partzyme B (CCBB/72-P), 200 nM substrate (Sub72-FIB), 8 mM MgCl$_2$, 200 µM of each dNTP, 10 units RiboSafe RNAse Inhibitor (Bioline), 1× ImmoBuffer (Bioline), 2 units of MyTaq™ HS DNA polymerase (Bioline) and either gDNA template (50 ng) or no target (nuclease free H$_2$O (NF H$_2$O)).

TABLE 1

| Forward primer and partzyme A combinations | | | |
|---|---|---|---|
| Reaction type | Contents | Forward Primer | Partzyme A |
| (i) 3' end of forward primer is 5 bases from partzyme junction | | | |
| 1_Positive control | Standard (non PASS primer) with matched partzyme A | 5CCB_1 | CCBA/72-P |
| 1_Negative control | Standard (non PASS primer) with US containing partzyme A | 5CCB_1 | CCB_1i2A/72-P |
| 1_Test 1 Loop | Loop PASS primer with matched partzyme A | 5CCB_1i2Loop | |
| 1_Test 2 Planar | Planar PASS primer with matched partzyme A | 5CCB_1i2Planar | |
| (ii) 3' end of forward primer is 3 bases from partzyme junction | | | |
| 2_Positive control | Standard (non PASS primer) with matched partzyme A | 5CCB_2 | CCBA/72-P |
| 2_Negative control | Standard (non PASS primer) with US containing partzyme A | 5CCB_2 | CCB_2i2A/72-P |
| 2_Test 1 Loop | Loop PASS primer with matched partzyme A | 5CCB_2i2Loop | |
| 2_Test 2 Planar | Planar PASS primer with matched partzyme A | 5CCB_2i2Planar | |
| (iii) 3' end of forward primer is at partzyme junction | | | |
| 3_Positive control | Standard (non PASS primer) with matched partzyme A | 5CCB_3 | CCBA/72-P |
| 3_Negative control | Standard (non PASS primer) with US containing partzyme A | 5CCB_3 | CCB_3i2A/72-P |
| 3_Test 1 Loop | Loop PASS primer with matched partzyme A | 5CCB_3i2Loop | |
| 3_Test 2 Planar | Planar PASS primer with matched partzyme A | 5CCB_3i2Planar | |

1.6. Results: Amplification of Target and Cleavage of Reporter Substrate

The positive control "standard" forward primers (non-PASS primers i.e. do not contain a US) were used to produce amplicons for the real-time detection and quantification of CCB by MNAzymes binding only to the target sequence of interest. This reaction showed an increase in fluorescence over time when the target sequence used was human gDNA amplified via PCR (FIG. 4 (i)-(iii), Positive Control). The fluorescence of the no-DNA target control was lower than that in the DNA target-containing reactions and did not increase during the reaction. This demonstrates that the increase in fluorescence produced in target-containing reactions is due to target dependent assembly of catalytically active MNAzyme that then cleaved the reporter substrate.

When the forward primer was a PASS primer and the partzyme A bound to both the cUS and the target specific sequence, an increase in fluorescence was seen over time (FIG. 4 (i)-(iii), Test 1 & Test 2). Further, the signal was similar to the Positive Control for reactions containing both the Loop and Planar type of PASS primer. There was a slight delay in signal generation observed for reactions where the PASS primer started at the partzyme junction when the Planar PASS primer was used compared to the standard non-PASS and Loop PASS primer (FIG. 4 (iii) Test 2 Planar).

The fluorescence of the negative control reactions, containing standard non-PASS forward primer (i.e. normal primers) and partzyme A containing both the US and the target specific sequence, was lower than the Test 1, Test 2 and Positive Control reactions and did not cross the threshold in reactions show in panels (i) and (iii) of FIG. 4. However the Negative Control in the reaction shown in Panel (ii) of FIG. 4 shows a slight increase in fluorescence above the threshold. This is not unexpected as there is some homology between the US in the partzyme arm and the CCB target sequence amplified for this design, and this homology may stabilise the partzyme arm enough for the MNAzmye to form albeit inefficiently.

All scenarios of overlap between the partzyme A and the S2 domain of the PASS primer were well tolerated with strong signal seen for Test 1 and Test 2 (FIG. 4 (i)-(iii)).

These results indicate that a US can be inserted into PCR amplicons via PASS primers (by a loop or a Planar PASS type primer) and these amplicons can be subsequently detected with MNAzymes, and that overlap between S2 of the PASS primer and the partyzme A are well tolerated.

Example 2: Use of PASS Primers Combined with MNAzymes to Detect Single Bases Changes in Sequence PASS primers can be designed to discriminate between two sequences that vary by a single base, such that the target-specific 3' end (S2) contains the variant base (FIG. 2 (i) and (ii) top) and may also contain a mismatch base located 5' of the variant base (FIG. 2 (i) and (ii) bottom). Further the US can be different for each variant adding another level of selectivity and specificity (FIG. 3).

In this example, the KRAS point mutation in codon 12 referred to as G12V is assayed against the wild type KRAS sequence, G12. The variant base for the wild type on codon 12 (G12; GGT) is the G at position 2 and for the mutant (G12V; GTT) the variant base is a T at position 2 of codon 12. PASS primers containing either a loop or planar US were designed to be specific for either the G12V or the G12 sequence. The variant base was located in S2 either at the 3' end (FIG. 7, Design 1) or three bases from the 3' end (FIG. 7, Design 2). Design 1 and 2 were compared to Designs 3 and 4 which also had a mismatch (M) inserted two bases 5' of the variant base, respectively (FIG. 7, Designs 3 and Design 4). A different US is inserted into the PASS primer for the wild type (US1) compared to the variant (US2).

The PASS primers are combined with MNAzyme qPCR, whereby MNAzymes comprise a first partzyme that binds to the complement of the unique sequence (cUS), as well as amplified target sequence that is tailored for each variant base (wild type or mutant, with or without mismatch) (FIG. 7). The second partzyme binds adjacently to the first partzyme on the amplified target sequence of interest.

PASS primers and partzymes were designed to determine if the various scenarios were specific for the variant bases of the KRAS, wild type G12 or point mutation G12V.

2.1. Partzyme Oligonucleotides

Partzymes were designed to specifically target the wild type G12 or mutant G12V alleles of the KRAS gene plus any cUS introduced via a PASS primer. In the following sequences the bases in bold hybridize with the target sequence of interest and bases underlined are the unique sequences (wild type insert i1 and variant insert i2) which are mismatched with respect to the starting template. Some partzyme A's have a longer (L) 3' target specific region. Bases in bold and italicised represent the variant bases and bases underlined and in italics represent an additional mismatched base. The "-P" indicates 3' phosphorylation of the oligonucleotide. All sequences are written 5' to 3'.

```
SEQ ID NO: 18 partzyme B KRAS_B/55-P:
GAGCTGGGGAGGCTAGCTGCGTAGGCAAGAGTGCCTT

SEQ ID NO: 19 partzyme A G12_i1A/55-P:
CACAATCAGTGAGCTGGTGACAACGAGAGGTGCGGT

SEQ ID NO: 20 partzyme A G12_Mi1A/55-P:
CACAATCAGTGAGCAGGTGACAACGAGAGGTGCGGT

SEQ ID NO: 21 partzyme A G12_LMi1A/55-P:
CACAATCAGTTGGAGCAGGTGACAACGAGAGGTGCGGT

SEQ ID NO: 22 partzyme A G12V_i2A/55-P:
AGACATACTAGAGCTGTTGACAACGAGAGGTGCGGT

SEQ ID NO: 23 partzyme A G12V_Mi2A/55-P:
AGACATACTAGAGCCGTTGACAACGAGAGGTGCGGT

SEQ ID NO: 24 partzyme A G12V_LMi2A/55-P:
AGACATACTATGGAGCCGTTGACAACGAGAGGTGCGGT
```

2.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

```
SEQ ID NO: 25 Substrate Sub55-FIB:
ACCGCACCTCguCCCCAGCTC
```

2.3. PCR Primers for Amplification of KRAS DNA

In vitro amplification of the KRAS gene in human gDNA was performed using the oligonucleotide PCR primers listed below. PASS primers were designed so that the forward primer, specific for the wild type contained US, insert 1 (i1) and the forward primer specific for the mutant contained US, insert 2 (i2). Some forward primers have a longer (L) 3' target specific region. In the following sequences the bases in bold hybridize with the target sequence, bases underlined are the unique sequences which are mismatched with respect to the starting template, bases bold and underlined are the variant base and bases italicised represent an additional base mismatched (M) to both targets. All sequences are written 5' to 3'.

SEQ ID NO: 26 Reverse primer 3KRAS:
GGTCCTGCACCAGTAATATGC

SEQ ID NO: 27 Forward PASS primer 5G12_1i1Loop:
ATATAAACTTGTGGTAGTTGCACAATCAGTGAGCTGG SEQ ID NO: 28 Forward PASS primer 5G12_1i1Planar:
GAAAATGACTGAATATAAACTTCACAATCAGTGAGCTGG SEQ ID NO: 29 Forward PASS primer 5G12_2i1Loop:
ATATAAACTTGTGGTAGTTGCACAATCAGTGAGCTGGTG SEQ ID NO: 30 Forward PASS primer 5G12_2i1Planar:
GAAAATGACTGAATATAAACTTCACAATCAGTGAGCTGGTG SEQ ID NO: 31 Forward PASS primer 5G12_LM3i1Loop:
TGATATAAACTTGTGGTAGTCACAATCAGTTGGAGCAGG SEQ ID NO: 32 Forward PASS primer 5G12_LM3i1Planar:
CTGAAAATGACTGAATATAAACCACAATCAGTTGGAGCAGG SEQ ID NO: 33 Forward PASS primer 5G12_M4i1Loop:
ATATAAACTTGTGGTAGTTGCACAATCAGTGAGCAGGTG SEQ ID NO: 34 Forward PASS primer 5G12_M4i1Planar:
GAAAATGACTGAATATAAACTTCACAATCAGTGAGCAGGTG SEQ ID NO: 35 Forward PASS primer 5G12V_1i2Loop:
ATATAAACTTGTGGTAGTTGAGACATACTAGAGCTGT SEQ ID NO: 36 Forward PASS primer 5G12V_1i2Planar:
GAAAATGACTGAATATAAACTTAGACATACTAGAGCTGT SEQ ID NO: 37 Forward PASS primer 5G12V_2i2Loop:
ATATAAACTTGTGGTAGTTGAGACATACTAGAGCTGTTG SEQ ID NO: 38 Forward PASS primer 5G12V_2i2Planar:
GAAAATGACTGAATATAAACTTAGACATACTAGAGCTGTTG SEQ ID NO: 39 Forward PASS primer 5G12V_LM3i2Loop:
TGATATAAACTTGTGGTAGTAGACATACTATGGAGCCGT SEQ ID NO: 40 Forward PASS primer 5G12V_LM3i2Planar:
CTGAAAATGACTGAATATAAACAGACATACTATGGAGCCGT SEQ ID NO: 41 Forward PASS primer 5G12V_M4i2Loop:
ATATAAACTTGTGGTAGTTGAGACATACTAGAGCCGTTG SEQ ID NO: 42 Forward PASS primer 5G12V_M4i2Planar:
GAAAATGACTGAATATAAACTTAGACATACTAGAGCCGTTG

2.4. Target Sequences

Human gDNA extracted from the K562 cell line was used as template for in vitro amplification of the wild type KRAS gene and gDNA extracted from the SW620 cell line was used for in vitro amplification of KRAS containing the point mutation G12V.

2.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C.). All reactions were run in duplicate and contained 40 nM forward primer and 100 nM partzyme A (combinations outlined in Table 2), 200 nM of reverse primer (3KRAS), 200 nM partzyme B (KRAS_B/55-P), 200 nM substrate (Sub55-FIB), 8 mM MgCl$_2$, 200 μM of each dNTP, 10 units RiboSafe RNAase Inhibitor (Bioline), 1× ImmoBuffer (Bioline), 2 units of MyTaq™ HS DNA polymerase (Bioline) and either K562 or SW620 gDNA template (50 ng) or no target (NF H$_2$O).

TABLE 2

Primer/partzyme combinations for wild type and mutant.

| Design | Forward Primer | Partzyme A | Template | Reaction type |
|---|---|---|---|---|
| G12 (Wild type systems) | | | | |
| Design 1 Variant (wild type) base at end | 5G12_1i1Loop | G12_i1A/55-P | K562 | Test |
| | | | SW620 | Negative control |
| | | | H$_2$0 | No template |
| | 5G12_1i1Planar | | K562 | Test |
| | | | SW620 | Negative control |
| | | | H$_2$0 | No template |
| Design 2 Variant (wild type) base 3rd from 3' end | 5G12_2i1Loop | | K562 | Test |
| | | | SW620 | Negative control |
| | | | H$_2$0 | No template |
| | 5G12_2i1Planar | | K562 | Test |
| | | | SW620 | Negative control |
| | | | H$_2$0 | No template |
| Design 3 Variant (wild type) base at end & mismatch 2 bases 5' of variant | 5G12_LM3i1Loop | G12_LMi1A/55-P | K562 | Test |
| | | | SW620 | Negative control |
| | | | H$_2$0 | No template |
| | 5G12_LM3i1Planar | | K562 | Test |
| | | | SW620 | Negative control |
| | | | H$_2$0 | No template |
| Design 4 Variant (wild type) | 5G12_M4i1Loop | G12_Mi1A/55-P | K562 | Test |
| | | | SW620 | Negative control |
| | | | H$_2$0 | No template |

TABLE 2-continued

Primer/partzyme combinations for wild type and mutant.

| Design | Forward Primer | Partzyme A | Template | Reaction type |
|---|---|---|---|---|
| base 3rd from 3' end & mismatch 2 bases 5' of variant | 5G12_M4i1Planar | | K562 | Test |
| | | | SW620 | Negative control |
| | | | H$_2$0 | No template |
| G12V (mutant systems) | | | | |
| Design 1 Variant (mutant) base at end | 5G12V_1i2Loop | G12V_i2A/55-P | SW620 | Test |
| | | | K562 | Negative control |
| | | | H$_2$0 | No template |
| | 5G12V_1i2Planar | | SW620 | Test |
| | | | K562 | Negative control |
| | | | H$_2$0 | No template |
| Design 2 Variant (mutant) base 3rd from 3' end | 5G12V_2i2Loop | | SW620 | Test |
| | | | K562 | Negative control |
| | | | H$_2$0 | No template |
| | 5G12V_2i2Planar | | SW620 | Test |
| | | | K562 | Negative control |
| | | | H$_2$0 | No template |
| Design 3 Variant (mutant) base at end & mismatch 2 bases 5' of variant | 5G12V_LM3i2Loop | G12V_LMi2A/55-P | SW620 | Test |
| | | | K562 | Negative control |
| | | | H$_2$0 | No template |
| | 5G12V_LM3i2Planar | | SW620 | Test |
| | | | K562 | Negative control |
| | | | H$_2$0 | No template |
| Design 4 Variant (mutant) base 3rd from 3' end & mismatch 2 bases 5' of variant | 5G12V_M4i2Loop | G12V_Mi2A/55-P | SW620 | Test |
| | | | K562 | Negative control |
| | | | H$_2$0 | No template |
| | 5G12V_M4i2Planar | | SW620 | Test |
| | | | K562 | Negative control |
| | | | H$_2$0 | No template |

2.6. Results: Amplification of Target and Cleavage of Reporter Substrate

The forward PASS primers and the partzyme As specific for either the G12 and cUS1, or G12V and cUS2, amplified and detected the specific KRAS alleles resulting in an increase in fluorescence over time which reached the threshold Ct values as shown in Table 3. In reactions containing wild type G12 primer/partzyme Design 1 (Planar and Loop), Design 3 (Planar and Loop), and Design 4 (Planar) the Ct values for the "Test" DNA (K562) indicated successful amplification and detection of the wild type KRAS allele in K562, whereas the lack of signal for the Negative Control (SW620) indicated the mutant allele is not detected with these systems. These systems allow complete discrimination between wild type and mutant KRAS in gDNA. Reactions containing wild type G12 primer/partzyme Design 2 (Planar and Loop), and Design 4 (Loop) the Ct values for the "Test" DNA (K562) indicated successful amplification and detection of the wild type KRAS allele in K562. The signal for the Negative Control (SW620) reached threshold Ct values as shown in Table 3 indicating that some background signal was produced when mutant template was used, however, the ΔCt values were sufficiently high to allow clear discrimination of wild type and mutant sequences.

In reactions containing G12V primer/partzyme Designs 3 (Loop), the Ct values for the "Test" DNA (SW620) indicated successful amplification and detection of the mutant KRAS allele in SW620, whereas the lack of signal for the Negative Control (K562) indicated the wild type allele is not detected with this system. This system allowed complete discrimination between mutant and wild type KRAS in gDNA. Reactions containing mutant G12V primer/partzyme Designs 1, 2 and 4 (Planar and Loop) and Designs 3 (Planar), the Ct values for the "Test" DNA (SW620) indicated successful amplification and detection of the mutant KRAS allele in SW620. The signal for the Negative Control (K562) reached threshold Ct values as shown in Table 3 indicating that some background signal was produced when wild type template was used, however, the ΔCt values were sufficiently high to allow clear discrimination of mutant and wild type sequences.

In all systems no amplification was observed in the No Template Controls which lacked gDNA.

These results indicate that a US can be inserted into PCR amplicons via PASS primers (by a Loop or a Planar PASS type primer) and these amplicons can be subsequently detected with MNAzymes. The partzymes specifically detect amplicons containing the variant base and accompanying inserted Unique Sequence.

TABLE 3

| | | | | | |
|---|---|---|---|---|---|
| Ct values for wild type (variant G) and mutant (variant T) combinations | | | | | |
| Target | Design | US inserted | Reaction type | Ct (ave) | ΔCt |
| G12 Wild type | Design 1 Variant (wild type) | Loop | Test | 25.0 | >15.0 |
| | | | Negative control | No Ct | |
| | | | No template | | |

TABLE 3-continued

Ct values for wild type (variant G) and mutant (variant T) combinations

| Target | Design | US inserted | Reaction type | Ct (ave) | ΔCt |
|---|---|---|---|---|---|
| | base at end | Planar | Test | 24.3 | >15.7 |
| | | | Negative control | No Ct | |
| | | | No template | | |
| | Design 2 Variant (wild type) | Loop | Test | 21.8 | 6.7 |
| | | | Negative control | 28.5 | |
| | | | No template | No Ct | |
| | base 3rd from 3' end | Planar | Test | 21.5 | 6.1 |
| | | | Negative control | 27.6 | |
| | | | No template | No Ct | |
| | Design 3 Variant (wild type) base at end; Mismatch 2 bases 5' of variant | Loop | Test | 24.6 | >15.4 |
| | | | Negative control | No Ct | |
| | | | No template | No Ct | |
| | | Planar | Test | 20.8 | >19.2 |
| | | | Negative control | No Ct | |
| | | | No template | | |
| | Design 4 Variant (wild type) base 3rd from 3' end; Mismatch 2 bases 5' of variant | Loop | Test | 24.7 | 12.9 |
| | | | Negative control | 37.6 | |
| | | | No template | No Ct | |
| | | Planar | Test | 24.8 | >15.2 |
| | | | Negative control | No Ct | |
| | | | No template | | |
| G12V mutant | Design 1 Variant (mutant) base at end | Loop | Test | 22.9 | 14.0 |
| | | | Negative control | 36.9 | |
| | | | No template | No Ct | |
| | | Planar | Test | 22.6 | 13.7 |
| | | | Negative control | 36.4 | |
| | | | No template | No Ct | |
| | Design 2 Variant (mutant) | Loop | Test | 20.0 | 7.1 |
| | | | Negative control | 27.1 | |
| | | | No template | No Ct | |
| | base 3rd from 3' end | Planar | Test | 20.0 | 6.6 |
| | | | Negative control | 26.6 | |
| | | | No template | No Ct | |
| | Design 3 Variant (mutant) base at end; Mismatch 2 bases 5' of variant | Loop | Test | 25.3 | >14.7 |
| | | | Negative control | No Ct | |
| | | | No template | No Ct | |
| | | Planar | Test | 22.8 | 13.9 |
| | | | Negative control | 36.7 | |
| | | | No template | No Ct | |
| | Design 4 Variant (mutant) base 3rd from 3' end; Mismatch 2 bases 5' of variant | Loop | Test | 25.0 | 10.4 |
| | | | Negative control | 35.4 | |
| | | | No template | No Ct | |
| | | Planar | Test | 24.3 | 12.1 |
| | | | Negative control | 36.5 | |
| | | | No template | No Ct | |

N.B. When no Ct was produced for a negative control sample the final Ct of 50 was used to produce the ΔCt and a greater than symbol (>) placed in front to indicate that the ΔCt would be expected to be higher than this value.

Example 3: Comparing the Specificity of PASS Primers to Wobble-Enhanced ARMS Primers Both Combined with MNAzymes to Detect Single Bases Changes in Sequence In this example, the KRAS point mutation in codon 12 referred to as G12V is assayed against the wild type KRAS sequence, G12. Planar PASS primers were designed to be specific for either the G12V or the G12 sequence. The variant base (G for wild type and T for mutant) was located in the 3' target specific region (S2), at the 3' end and a mismatch was inserted 2 bases 5' of the variant base (FIG. 7, Design 3). A different US is contained in the PASS primer for the wild type (US1) and the mutant (US2) sequences. These PASS primers were compared to wobble-enhanced ARMS (WE-ARMS) primers (see Hamfjord et al, (2011), "*Wobble-enhanced ARMS Method for Detection of KRAS and BRAF Mutations*", Diagn Mol Pathol; 20:158-165), whereby primers are designed that are sequence-specific for G12V or G12 plus they contain an introduced mismatch with respect to both alleles to help discriminate between the KRAS sequences that differ by a single base. For the WE-ARMS primers used in this example, the variant (mutant or wild type) base is located at the 3' end and a mismatch is inserted 2 bases 5' of the variant base.

The PASS primers are combined with MNAzyme qPCR whereby MNAzymes comprise a first partzyme that binds to the complement of the, unique sequence (cUS), variant base (wild type or mutant) and mismatched base as well as amplified target sequence. The second partzyme binds adjacently to the first partzyme, hybridizing to the amplified target sequence of interest. The WE-ARMS primers were combined with MNAzymes whereby a first partzyme binds to the amplified target sequence and the complement of the, variant base (wild type or mutant) and mismatched base. The second partzyme binds adjacently to the first partzyme, hybridizing to the amplified target sequence of interest.

PASS primers were compared to WE-ARMS primers for capacity to discriminate the single base change between target G12 and G12V.

3.1. Partzyme Oligonucleotides

Partzymes were designed to specifically target the G12 or G12V sequence and any mismatch introduced via a primer and cUS introduced via a PASS primer. In the following sequences the bases in bold hybridize with the target sequence of interest and bases underlined are the unique sequences (wild type insert i1 and variant insert i2) which are mismatched with respect to the starting template. Some partzyme A's have a longer (L) 3' target specific region. Bases in bold and italicised represent the variant bases (wild type or mutant) and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 21 partzyme A G12_LMi1A/55-P:
CACAATCAGTTGGAGCAG<sup>G</sup>TGACAACGAGAGGTGCGGT SEQ ID NO: 24 partzyme A G12V_LMi2A/55-P:
AGACATACTATGGAGCCGTTGACAACGAGAGGTGCGGT SEQ ID NO: 43 partzyme A G12_MA/55-P:
TGGTAGTTGGAGCAG<sup>G</sup>TGACAACGAGAGGTGCGGT SEQ ID NO: 44 partzyme A G12V_MA/55-P:
TGTGGTAGTTGGAGCCGTTGACAACGAGAGGTGCGGT

3.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

SEQ ID NO: 25 Substrate Sub55-FIB:
ACCGCACCTCguCCCCAGCTC

3.3. PCR Primers for Amplification of KRAS DNA

In vitro amplification of human gDNA was performed using the oligonucleotide PCR primers listed below. PASS primers are designed so that the G12 specific forward primers contain US insert 1 (i1), and the G12V specific forward primers contain US insert 2 (i2). Some forward primers have a longer (L) target specific region. In the following sequences the bases in bold hybridize with the target sequence, bases underlined are the unique sequences which are mismatched with respect to the starting template, bases bold and underlined are the variant base and bases italicised represent an additional base mismatched (M) to both targets. All sequences are written 5' to 3'.

SEQ ID NO: 26 Reverse primer 3KRAS:
GGTCCTGCACCAGTAATATGC

SEQ ID NO: 32 Forward PASS primer 5G12_LM3i1Planar:
CTGAAAATGACTGAATATAAACCACAATCAGTTGGAGCAGG

SEQ ID NO: 40 Forward PASS primer 5G12V_LM3i2Planar:
CTGAAAATGACTGAATATAAACAGACATACTATGGAGCCGT

SEQ ID NO: 45 Forward WE-ARMS primer 5G12_M:
TTGTGGTAGTTGGAGCAGG

SEQ ID NO: 46 Forward WE-ARMS primer 5G12V_M:
CTTGTGGTAGTTGGAGCCGT

3.4. Target Sequences

Human gDNA extracted from the K562 cell line was used as template for in vitro amplification of the wild type gene and gDNA extracted from the SW620 cell line was used for in vitro amplification of the point mutation G12V.

3.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C. step). All reactions were run in duplicate and contained 40 nM forward primer and 100 nM partzyme A (combinations outlined in Table 4), 200 nM of reverse primer (3KRAS), 200 nM partzyme B (KRAS_B/55-P), 200 nM substrate (Sub55-FIB), 8 mM MgCl$_2$, 200 μM of each dNTP, 10 units RiboSafe RNAase Inhibitor (Bioline), 1× ImmoBuffer (Bioline), 2 units of MyTaq™ HS DNA polymerase (Bioline) and either K562 or SW620 gDNA template (50 ng) or no target (NF H$_2$O).

TABLE 4 primer/partzyme combinations for wild type and variant

| Design | Forward Primer | Partzyme A | Template | Reaction type |
|---|---|---|---|---|
| G12 | | | | |
| Design 3 | 5G12_LM3i1 | G12_LMi1A/55-P | K562 | Test |
| Variant wild type base at end | Planar | | SW620 | Negative control |
| Mismatch 2 bases 5' of variant | | | H$_2$0 | No template |
| WE-ARMS | 5G12_M | G12_MA/55-P | K562 | Test |
| Variant base wild type at end | | | SW620 | Negative control |
| Mismatch 2 bases 5' of variant | | | H$_2$0 | No template |

TABLE 4-continued primer/partzyme combinations for wild type and variant

| Design | Forward Primer | Partzyme A | Template | Reaction type |
|---|---|---|---|---|
| Cross reactivity control Wild type PASS primer with variant partzyme A | 5G12_LM3i1 Planar | G12V_LMi2A/55-P G12V | K562 SW620 H$_2$0 | Test Negative control No template |
| Design 3 Variant (mutant) base at end Mismatch 2 bases 5' of variant | 5G12V_LM3 i2Planar | G12V_LMi2A/55-P | SW620 K562 H$_2$0 | Test Negative control No template |
| WE-ARMS Variant (mutant) base at end Mismatch 2 bases 5' of variant | 5G12V_M | G12V_MA/55-P | SW620 K562 H$_2$0 | Test Negative control No template |
| Cross reactivity control Variant PASS primer with wild type partzyme A | 5G12V_LM3 i2Planar | G12_LMi1A/55-P | SW620 K562 H$_2$0 | Test Negative control No template |

3.6. Results: Amplification of Target and Cleavage of Reporter Substrate

The results of amplification using PASS primers and WE-ARMS primers followed by detection using primer-specific partzymes are shown in Table 5.

TABLE 5

Ct values for G12 and G12V combinations

| Target | Design | US inserted | Reaction type | Ct (Ave) | ΔCt |
|---|---|---|---|---|---|
| G12 | PASS Design 3 Variant wild type base at end Mismatch 2 bases 5' of variant | Planar | Test Negative control No template | 22.3 No Ct | >17.7 |
| | WE-ARMS Variant wild type base at end Mismatch 2 bases 5' of variant | n/a | Test Negative control No template | 28.3 No Ct | >11.7 |
| | Cross reactivity G12 PASS primer with G12V partzyme | Planar | Test Negative control No template | No Ct | n/a |
| G12V | PASS Design 3 Variant mutant base at end Mismatch 2 bases 5' of variant | Planar | Test Negative control No template | 24.0 39.4^ No Ct | 15.4 |
| | WE-ARMS Variant mutant base at end Mismatch 2 bases 5' of variant | n/a | Test Negative control No template | 21.6 36.4 No Ct | 14.8 |
| | Cross reactivity G12V PASS primer with G12 partzyme | Planar | Test Negative control No template | No Ct | n/a |

^Only one of 2 replicates produced a signal, therefore the final cycle number of 40 was used to average Ct value.
N.B. When no Ct was produced for a negative control sample the final Ct of 50 was used to produce the ΔCt and a greater than symbol (>) placed in front to indicate that the ΔCt would be expected to be higher than this value.

The PASS primer matched to the wild type variant amplified the G12 allele in Test K562 DNA and this was detected by the MNAzyme containing a partzyme A matched to wild type amplicon and US1. This wild type PASS primer/partzyme system was specific for wild type allele and no signal was generated when Negative Control template (SW620) was used. No cross reactivity was seen when partzyme A specific for the variant mutant and US2 were used in conjunction with the wild type PASS primer.

The WE-ARMS primer matched to the wild type variant amplified the G12 allele in Test K562 DNA which was detected by the MNAzyme containing a partzyme A matched to wild type amplicon. This wild type ARMS primer/partzyme system was specific for wild type allele and no signal was generated when Negative Control template (SW620) was used.

The PASS primer matched to the mutant variant amplified the G12V allele in Test SW620 DNA and this was detected by the partzyme matched to mutant amplicon and US2. This mutant PASS primer/partzyme system preferentially amplified and detected the mutant allele and signal was only generated late in the reaction when Negative Control template (K562) was used. The difference in Ct between mutant SW620 and wild type K562 DNA was greater than 15 cycles (Table 5), demonstrating PASS primer and matching partzyme As allow discrimination between mutant and wild type alleles. No cross reactivity was seen when partzymes specific for the variant wild type and US1 were used in conjunction with the mutant PASS primer.

The WE-ARMS primer matched to the mutant variant amplified the G12V allele in Test SW620 DNA and this was detected by the partzyme matched to mutant amplicon. This mutant WE-ARMS primer/partzyme system preferentially amplified and detected the mutant allele and signal was only generated late in the reaction when Negative Control template (K562) was used. The difference in Ct between mutant SW620 and wild type K562 DNA was greater than 14 cycles (Table 5), demonstrating ARMS primer and matching partzymes allow discrimination between mutant and wild type alleles.

No amplification was detected using any primer/partzyme pair when no template (no DNA) was added.

The data in this example demonstrates the capacity of PASS primers to perform in a manner similar or superior to an alternative technology for detection of single base changes (ARMS) which is well known in the art.

Example 4: Comparing the Sensitivity of PASS Primers to Wobble-Enhanced ARMS (WE-ARMS) Primers Both Combined with MNAzymes to Detect Single Bases Changes in a Sequence In this example, the KRAS point mutation in codon 12 referred to as G12V is assayed using serial dilutions of the G12V template in a background of wild type KRAS template. Dilutions of 1 in 10, 100 and 1000 of G12V in a background of wild type were tested.

The design 3 (FIG. 7) planar PASS primers are used for the amplification of G12V sequence. This was compared to the G12V WE-ARMS primers. The PASS primers are combined with MNAzyme qPCR whereby MNAzymes comprise a first partzyme that binds to the complement of the unique sequence (cUS) as well as amplified target sequence containing the complement of, the variant (mutant) base and the mismatched base. The second partzyme binds adjacently to the first partzyme within amplified target sequence of interest. The WE-ARMS primers are combined with MNAzymes whereby a first partzyme binds to amplified target sequence containing the complement of the variant (mutant) base and the mismatched base. The second partzyme binds adjacently to the first partzyme within the amplified target sequence of interest.

PASS primers were compared to WE-ARMS primers to investigate the efficiency, linearity and sensitivity of each strategy.

4.1. Partzyme Oligonucleotides

Partzymes were designed to specifically target the G12V sequence and any mismatch introduced via a primer as well as cUS in the case of the PASS primer. In the following sequences the bases in bold hybridize with the target sequence of interest and bases underlined are the US (insert i2) which is mismatched with respect to the starting template. Some partzyme A's have a longer (L) target specific region. Bases in bold and italicised represent the variant (mutant) bases and bases underlined and in italics represent an additional mismatched base. The "-P" indicates 3' phosphorylation of the oligonucleotide. All sequences are written 5' to 3'.

```
SEQ ID NO: 18 partzyme B KRAS_B/55-P:
GAGCTGGGGAGGCTAGCTGCGTAGGCAAGAGTGCCTT

SEQ ID NO: 24 partzyme A G12V_LMi2A/55-P:
AGACATACTATGGAGCCGTTGACAACGAGAGGTGCCGGT SEQ ID NO: 44 partzyme A G12V_MA/55-P:
TGTGGTAGTTGGAGCCGTTGACAACGAGAGGTGCCGGT
```

4.2. Reporter Substrate

In the current example, the substrate were end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

```
SEQ ID NO: 25 Substrate Sub55-FIB:
ACCGCACCTCguCCCCAGCTC
```

4.3. PCR Primers for Amplification of KRAS DNA

In vitro amplification of human gDNA was performed using the oligonucleotide PCR primers listed below. In the following sequences the bases in bold hybridize with the target sequence, bases underlined are the US (insert i2) which are mismatched with respect to the starting template, bases bold and underlined are the variant base and bases italicised represent an additional base mismatched (M) to both targets. All sequences are written 5' to 3'.

```
SEQ ID NO: 26 Reverse primer 3KRAS:
GGTCCTGCACCAGTAATATGC

SEQ ID NO: 40 Forward PASS primer
5G12V_LM3i2Planar:
CTGAAAATGACTGAATATAAACAGACATACTATGGAGCCGT

SEQ ID NO: 46 Forward WE-ARMS primer 5G12V_M:
CTTGTGGTAGTTGGAGCCGT
```

4.4. Target Sequences

Human gDNA extracted from the SW620 cell line was used as template for in vitro amplification of the point mutation G12V. A calibration curve was made by serially diluting SW620 gDNA in a constant background of the wild type gDNA extracted from the K562 cell line.

4.5. Reaction Components: Amplification and Quantitation of Target Sequence Real-time amplification and quantitation of the target sequence was performed in a total reaction volume of 25 µL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C. step). All reactions were run in duplicate and contained 40 nM forward primer and 100 nM partzyme A (combinations outlined in Table 6), 200 nM of reverse primer (3KRAS), 200 nM partzyme B (KRAS_B/55-P), 200 nM substrate (Sub55-FIB), 8 mM MgCl$_2$, 200 µM of each dNTP, 10 units RiboSafe RNAase Inhibitor (Bioline), 1× ImmoBuffer (Bioline), 2 units of MyTaq™ HS DNA polymerase (Bioline) and either SW620 gDNA template (50 ng), SW620 gDNA template diluted 1 in 10, 1 in 100 or 1 in 1000 in a constant background of K562 gDNA template (50 ng), K562 gDNA template (50 ng) or no target (NF H$_2$O).

TABLE 6

Primer/partzyme combinations for the variant assays

| Design | Forward Primer | Partzyme A |
| --- | --- | --- |
| PASS primer | 5G12V_LM3i2Planar | G12V_LMi2A/55-P |
| WE-ARMS primer | 5G12V_M | G12V_MA/55-P |

4.6. Results: Amplification of Target and Cleavage of Reporter Substrate

The PASS and WE-ARMS forward primers were used to produce amplicons for the real-time detection and quantification of the KRAS point mutation (G12V). MNAzymes were designed to be specific for the specific PASS or ARMS primers used to detect the mutant sequence. This reaction showed an increase in fluorescence over time when the reaction contained target sequence specific for G12V (Table 7).

The SW620 gDNA template, containing the G12V mutation, was serially diluted 10-fold in a background of K562 template which contains the wild type (G12) sequence. The serial dilutions of gDNA were amplified with either a PASS or WE-ARMS forward primer. Standard curves were generated for both PASS and WE-ARMS primers by plotting the log of the gDNA concentration against the threshold cycle (Ct) resulting in a linear plot. The average Ct values of each dilution series are shown in Table 7. The correlation coefficient ($R^2$), and reaction efficiency for each target are also shown in Table 7. The linearity of both primers is comparable whereas the PASS primer has a greater efficiency (103%) than the WE-ARMS primer (78%). Optimal efficiencies should fall within the range of 90 to 110%.

Both primers sets were able to detect the G12V sequence when diluted 1 in 1000 in a background of G12. For the WE-ARMS primer the signal of the negative control K562 template was only 1.3 Cts behind the Ct of the sample diluted 1 in 1000 (SW620 in K562 DNA), whereas PASS primers produced a signal that was 4.8 Cts behind the Ct of the sample diluted 1 in 1000 (Table 7) indicating a greater specificity of this PASS primer/partzyme system for G12V mutant DNA than observed with this ARMS system.

The fluorescence of the no template control did not increase during the reaction. This demonstrates that the increase in fluorescence produced in target-containing reactions is due to target dependent assembly of catalytically active MNAzyme that then cleaved the reporter substrate.

TABLE 7

Ct values for G12V PASS vs. WE-ARMS primer

| | Template | PASS primer | WE-ARMS primer |
| --- | --- | --- | --- |
| Ct (Ave) | 50 ng SW620 | 24.7 | 22.2 |
| | 1 in 10 | 28.2 | 26.6 |
| | 1 in 100 | 31.2 | 30.9 |
| | 1 in 1000 | 34.6 | 34.1 |
| | 50 ng K562 | 39.4^ | 35.4 |
| | NTC | No Ct | No Ct |
| ΔCt | 50 ng SW620 to K562 | 14.7 | 13.2 |
| | 1 in 1000 to K562 | 4.8 | 1.3 |
| Standard curve | Efficiency | 103% | 78% |
| | Linearity ($R^2$) | 0.990 | 0.993 |

^Only one of 2 replicates produced a signal, therefore the final cycle number of 40 was used to average Ct value.

Example 5: Multiplexing Wild Type and Mutant Alleles of KRAS Codon 12 Using PASS Primers Combined with MNAzyme Detection to Discriminate Single Base Changes in Each Sequence The KRAS point mutation in codon 12 referred to as G12V differs from the wild type (G12) by one nucleotide. This example combines the detection of the wild type G12 and mutant G12V alleles in a multiplex reaction. Templates for the assay included serial dilutions of G12V template (SW480 DNA) in a background of G12 template (K562 DNA) at ratios of 1 in 10, 100 and 1000; or G12 template (K562 DNA) in a background of G12V template (SW480 DNA) at ratios of 1 in 10, 100 and 1000.

A planar PASS primer based on design 3 (FIG. 7) was used for the specific amplification of G12 sequence and a Loop PASS primer based on design 3 (FIG. 7) was used for the specific amplification of G12V sequence. A different US is inserted into the PASS primer for the wild type (US1) verse the mutant (US2). The PASS primers are combined with MNAzyme qPCR whereby the MNAzyme for the detection of the G12 amplicon comprises a first partzyme that binds to the complement of, the unique sequence 1 (cUS1), the wild type variant base, and the additional mismatch base as well as amplified target sequence. The MNAzyme for the detection of the G12V amplicon comprises a first partzyme that binds to the complement of, the unique sequence 2 (cUS2), the mutant variant base, and the additional mismatch base as well as amplified target sequence. The two "first partzymes" bind to different partial substrate sequences labelled with different fluorophores to enable monitoring of the accumulation of wild type and mutant amplicons separately. The second partzyme for both the G12 and G12V binds adjacently to the first partzyme on the amplified target sequence of interest; this partzyme is identical for both the G12 and G12V MNAzymes, binding to the same partial substrate sequence for both.

The use of PASS primers in a multiplex reaction combining the simultaneous amplification and detection of a wild type (G12) and a mutant (G12V) sequences was investigated to determine the effect on sensitivity and specificity of each assay.

5.1. Partzyme Oligonucleotides

Partzyme A was designed to specifically target the G12V or G12 sequence and any mismatch and cUS introduced via a PASS primer. In the following sequences the bases in bold hybridize with the target sequence of interest and bases underlined are the unique sequences which are mismatched with respect to the starting template. Bases in bold and italicised represent the variant mutant or wild type bases and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 21 partzyme A G12_LMi1A/55-P:
CACAATCAGTTGGAGCAGGTGACAACGAGAGGTGCGGT SEQ ID NO: 47 partzyme A G12V_LMi2A/6-P:
AGACATACTATGGAGCCCGTTGACAACGAGAGGCGTGAT

5.2. Reporter Substrates

The reporter substrates for this example are shown below with the sequences written 5' to 3'. In the current example, the Sub55 was end labelled with a Quasar 670 moiety at the 5' end (indicated by a "Q670" in the name of the substrate below) and a Black Hole Quencher® 2 moiety at the 3' end (indicated by a "B2" in the name of the substrate below) and was designated Sub55-Q670B2. Cleavage of the Sub55-Q670B2 was monitored between 675-690 nm (Quasar 670 emission wavelength range on the CFX96 (BioRad)) with excitation between 620-650 nm (Quasar 670 excitation wavelength range on the CFX96 (BioRad)). The Sub6_55 was end labelled with a FAM moiety at the 5' end (indicated by a "F" in the name of the substrate below) and an Iowa Black® FQ quencher moiety at the 3' end (indicated by a "IB" in the name of the substrate below. and was designated Sub6_55-FIB. Cleavage of the Sub6_55-FIB was monitored between 510-530 nm (FAM emission wavelength range on the CFX96 (BioRad)) with excitation between 450-490 nm (FAM excitation wavelength range on the CFX96 (BioRad)). These substrates have one arm which is common to both (3' of the RNA bases) and this binds to the partzyme which is common to both MNAzymes. The second substrate arm (5' of the RNA bases) binds specific to the partzyme which detects the sequences derived from amplification by either the wild type or mutant PASS primers. The lower case bases represent RNA and the upper case bases represent DNA. The reporter substrates for this example are shown below with the sequence, 5' to 3'

```
SEQ ID NO: 25 Substrate Sub55-Q670B2:
ACCGCACCTCguCCCCAGCTC

SEQ ID NO: 48 Substrate Sub6_55-FIB:
ATCACGCCTCguCCCCAGCTC
```

5.3. PCR Primers for Amplification of KRAS DNA

The target sequence for this example was generated by in vitro amplification of human gDNA using the oligonucleotide PCR primers listed below. In the following sequences the bases in bold hybridize with the target sequence, bases underlined are the unique sequences (G12 inset i1 and G12V insert i2) which are mismatched with respect to the starting template, bases bold and underlined are the variant base and bases italicised represent an additional base mismatched (M) to both targets. All sequences are written 5' to 3'.

```
SEQ ID NO: 26 Reverse primer 3KRAS:
GGTCCTGCACCAGTAATATGC

SEQ ID NO: 49 Forward PASS primer
5G12_LM3i1LPlanar:
CTGCTGAAAATGACTGAATATAAACCACAATCAGTTGGAGCAGG SEQ ID NO: 50 Forward PASS primer
5G12V_LM3i2LLoop:
GACTGAATATAAACTTGTGGTAGTAGACATACTATGGAGCCGT
```

5.4. Target Sequences

Human gDNA extracted from the K562 cell line was used as template for in vitro amplification of the wild type KRAS G12. A calibration curve was made by serially diluting K562 in a constant background of the mutant gDNA, SW480. Human gDNA extracted from the SW480 cell line was used as template for in vitro amplification of the point mutation G12V. A calibration curve was made by serially diluting SW480 gDNA in a constant background of the wild type gDNA, K562.

5.5. Reaction Components: Multiplex Amplification and Quantitation of Target Sequences Real-time amplification and quantitation of the target sequences was performed in a total reaction volume of 25 µL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 50 cycles of 95° C. for 15 seconds and 54° C. for 50 seconds (data collected at the 54° C. step). Reactions were run in duplicate or quadruplicate and contained 40 nM each of forward primer (5G12_LM3i1LPlanar and 5G12V_LM3i2LLoop), 100 nM of each partzyme A (G12_LMilA/55-P and G12V_LMi2A/6-P) and 200 nM of each substrate (Sub6_55-FIB and Sub55-Q670B2). As well as 400 nM of reverse primer (3KRAS), 400 nM partzyme B (KRAS_B/55-P), 8 mM MgCl$_2$, 200 µM of each dNTP, 10 units RiboSafe RNAase Inhibitor (Bioline), 1× ImmoBuffer (Bioline), 2 units of MyTaq™ HS DNA polymerase (Bioline) and either SW480 or K562 gDNA template (50 ng) or SW480 gDNA template diluted 1 in 10, 1 in 100 or 1 in 1000 in a constant background of K562 gDNA template (50 ng) or K562 gDNA template diluted 1 in 10, 1 in 100 or 1 in 1000 in a constant background of SW480 gDNA template (50 ng) or no target (NF H$_2$O).

5.6. Results: Multiplex Amplification of Targets and Cleavage of Reporter Substrates The amplification and detection of G12 and G12V occurred simultaneously using PASS primers and Partzymes A specific for each in allele. DNA samples were serially diluted 10-fold as either SW480 (G12V) in a background of K562 (G12) or K562 (G12) in a background of SW480 (G12V). The Ct values shown in Table 8 are an average of the results for duplicate (n=2) or quadruplicate reactions (n=4).

Both PASS primer sets for either G12 or G12V were sensitive, detecting the specific sequence when diluted 1 in 1000 in a background of the other template. The multiplex assays was highly specific with no signal produced in the negative control reactions for both the wild type and variant (when only template specific for G12V (SW480) or G12 (K562) respectively was present (Table 8).

The fluorescence of the no template control was lower than that in the DNA target-containing reactions for all combinations tested and did not increase during the reaction. This demonstrates that the increase in fluorescence produced in target-containing reactions is due to target dependent assembly of catalytically active MNAzyme that then cleaved the reporter substrate.

TABLE 8

| | Ct values for wild type (G12) and variant (G12V) PASS primer multiplex | | |
|---|---|---|---|
| | Template | G12 (Q670) | G12V (FAM) |
| G12V template diluted in a background of G12 | 1 in 10 (SW480 in K562) (n = 2) | 21.1 | 27.9 |
| | 1 in 100 (SW480 in K562) (n = 2) | 20.9 | 33.9 |
| | 1 in 1000 (SW480 in K562) (n = 2) | 20.8 | 40.1 |
| G12 template diluted in a background of G12V | 1 in 10 (K562 in SW480) (n = 2) | 24.7 | 22.4 |
| | 1 in 100 (K562 in SW480) (n = 2) | 29.3 | 22.2 |
| | 1 in 1000 (K562 in SW480) (n = 2) | 36.8 | 22.1 |
| Control reactions | 50 ng K562 (n = 4) | 20.8 | No Ct |
| | 50 ng SW620 (n = 4) | No Ct | 22.5 |
| | NTC (n = 4) | No Ct | No Ct |

This example demonstrates the use of multiple unique sequences in a multiplex reaction. This results in generation of amplicons which contain a very different sequence in the region bound by partzyme A even though the original template only contained a single base difference. The PASS primer/matching partzyme strategy allows a greater level of multiplexing since the strategy greatly increases the difference in sequence of amplicons from closely related targets.

Example 6: Comparing Different Unique Sequence Inserts in PASS Primers and Combined with MNAzymes to Detect Single Base Changes in Sequence PASS primers can be designed to discriminate between two sequences that vary by a single base, such that the target-specific 3' end (S2) contains the variant base (FIG. 2 (*i*) and (*ii*) top). Further the US can be different for each variant adding another level of selectivity and specificity (FIG. 3).

In this example, three different unique sequences were inserted into the PASS primer for both the KRAS point mutation in codon 12 referred to as G12V and the wild type KRAS sequence, G12. PASS primers containing the US in either a loop or planar formation were designed to be specific for either the G12V or the G12 sequence and the specific primers also contained the US insert, i1, i2, i3 or i3a. The variant base for both the mutant and the wild type was located in S2 at the 3' end (FIG. 7 Design 1).

The PASS primers are combined with MNAzyme qPCR whereby MNAzymes comprise a first partzyme that binds to the complement of the unique sequence (cUS) as well as amplified target sequence that is tailored for each variant base (wild type or mutant). The second partzyme binds adjacently to the first partzyme on the amplified target sequence of interest.

PASS primers and partzymes were designed for each US to determine if the various scenarios improved reaction efficiency and specificity for the KRAS wild type G12 or point mutation G12V.

6.1. Partzyme Oligonucleotides

Partzymes were designed to specifically target the wild type G12 or mutant G12V alleles of the KRAS gene plus any cUS introduced via a PASS primer. In the following sequences the bases in bold hybridize with the target sequence of interest and bases underlined are the unique sequences (inserts i1, i2 or i3) which are mismatched with respect to the starting template. Bases in bold and italicised represent the variant bases. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 19 partzyme A G12_i1A/55-P:
CACAATCAGT**GAGCTG*G*T G**ACAACGAGAGGTGCGGT SEQ ID NO: 51 partzyme A G12_i2A/55-P:
AGACATACTA**GAGCTG*G*TG**ACAACGAGAGGTGCGGT SEQ ID NO: 52 partzyme A G12_i3A/55-P:
CGTTGGCTAC**GAGCTG*G*TG**ACAACGAGAGGTGCGGT SEQ ID NO: 53 partzyme A G12V_i1A/55-P:
CACAATCAGT**GAGCTG*T*TG**ACAACGAGAGGTGCGGT SEQ ID NO: 22 partzyme A G12V_i2A/55-P:
AGACATACTA**GAGCTG*T*TG**ACAACGAGAGGTGCGGT SEQ ID NO: 54 partzyme A G12V_i3A/55-P:
CGTTGGCTAC**GAGCTG*T*TG**ACAACGAGAGGTGCGGT

6.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

SEQ ID NO: 25 Substrate Sub55-FIB:
ACCGCACCTCguCCCCAGCTC

6.3. PCR Primers for Amplification of KRAS DNA

In vitro amplification of the KRAS gene in human gDNA was performed using the oligonucleotide PCR primers listed below. PASS primers are designed so that the forward primer, specific for the wild type contained US inserts, i1, i2 i3 or i3a and the forward primer specific for the mutant contained US inserts, i1, i2 or i3. In the following sequences the bases in bold hybridize with the target sequence, bases underlined are the unique sequences which are mismatched with respect to the starting template and bases bold and underlined are the variant base. All sequences are written 5' to 3'.

SEQ ID NO: 26 Reverse primer 3KRAS:
GGTCCTGCACCAGTAATATGC

SEQ ID NO: 27 Forward PASS primer 5G12_i1iLoop:
ATATAAACTTGTGGTAGTTGCACAATCAGTGAGCTGG

SEQ ID NO: 28 Forward PASS primer 5G12_i1iPlanar:
GAAAATGACTGAATATAAACTTCACAATCAGTGAGCTGG

SEQ ID NO: 55 Forward PASS primer 5G12_i1i2Loop:
ATATAAACTTGTGGTAGTTGAGACATACTAGAGCTGG

SEQ ID NO: 56 Forward PASS primer 5G12_i1i2Planar:
GAAAATGACTGAATATAAACTTAGACATACTAGAGCTGG

SEQ ID NO: 57 Forward PASS primer 5G12_i1i3Loop:
ATATAAACTTGTGGTAGTTGCGTTGGCTACGAGCTGG

SEQ ID NO: 58 Forward PASS primer 5G12_i1i3aPlanar:
GAAAATGACTGAATATAAACTTACGTTGGCTACGAGCTGG

SEQ ID NO: 59 Forward PASS primer 5G12V_i1iLoop:
ATATAAACTTGTGGTAGTTGCACAATCAGTGAGCTGT

SEQ ID NO: 60
Forward PASS primer 5G12V_i1iPlanar:
GAAAATGACTGAATATAAACTTCACAATCAGTGAGCTGT

-continued

SEQ ID NO: 35 Forward PASS primer
5G12V_1i2Loop:
ATATAAACTTGTGGTAGTTGAGACATACTAGAGCTGT SEQ ID NO: 36 Forward PASS primer
5G12V_1i2Planar:
GAAAATGACTGAATATAAACTTAGACATACTAGAGCTGT SEQ ID NO: 61
Forward PASS primer 5G12V_1i3Loop:
ATATAAACTTGTGGTAGTTGCGTTGGCTACGAGCTGT -continued SEQ ID NO: 62 Forward PASS primer
5G12V_1i3Planar:
GAAAATGACTGAATATAAACTTCGTTGGCTACGAGCTGT

6.4. Target Sequences

Human gDNA extracted from the K562 cell line was used as template for in vitro amplification of the wild type KRAS gene and human gDNA extracted from the SW620 cell line was used for in vitro amplification of KRAS containing the point mutation G12V.

6.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C.). All reactions were run in duplicate and contained 40 nM forward primer and 100 nM partzyme A (combinations outlined in Table 9), 200 nM of reverse primer (3KRAS), 200 nM partzyme B (KRAS_B/55-P), 200 nM substrate (Sub55-FIB), 8 mM MgCl$_2$, 200 μM of each dNTP, 10 units RiboSafeRNAase Inhibitor (Bioline), 1× ImmoBuffer (Bioline), 2 units of MyTaq™ HS DNA polymerase (Bioline) and either K562 or SW620 gDNA template (50 ng) or no target (NF H$_2$O).

TABLE 9

Primer and partzyme combinations for wild type and mutant

| Target | Unique sequence | Forward Primer | Partzyme A | Template | Reaction type |
|---|---|---|---|---|---|
| Wild type G12 | Insert 1 | 5G12_1i1Loop | G12_i1A/55-P | K562 | Test |
| | | | | SW620 | Negative control |
| | | | | H$_2$0 | No template |
| | | 5G12_1i1Planar | | K562 | Test |
| | | | | SW620 | Negative control |
| | | | | H$_2$0 | No template |
| | Insert 2 | 5G12_1i2Loop | G12_i2A/55-P | K562 | Test |
| | | | | SW620 | Negative control |
| | | | | H$_2$0 | No template |
| | | 5G12_1i2Planar | | K562 | Test |
| | | | | SW620 | Negative control |
| | | | | H$_2$0 | No template |
| | Insert 3 or 3a | 5G12_1i3Loop | G12_i3A/55-P | K562 | Test |
| | | | | SW620 | Negative control |
| | | | | H$_2$0 | No template |
| | | 5G12_1i3aPlanar | | K562 | Test |
| | | | | SW620 | Negative control |
| | | | | H$_2$0 | No template |
| Mutant G12V | Insert 1 | 5G12V_1i1Loop | G12V_i1A/55-P | SW620 | Test |
| | | | | K562 | Negative control |
| | | | | H$_2$0 | No template |
| | | 5G12V_1i1Planar | | SW620 | Test |
| | | | | K562 | Negative control |
| | | | | H$_2$0 | No template |
| | Insert 2 | 5G12V_1i2Loop | G12V_i2A/55-P | SW620 | Test |
| | | | | K562 | Negative control |
| | | | | H$_2$0 | No template |
| | | 5G12V_1i2Planar | | SW620 | Test |
| | | | | K562 | Negative control |
| | | | | H$_2$0 | No template |
| | Insert 3 | 5G12V_1i3Loop | G12V_i3A/55-P | SW620 | Test |
| | | | | K562 | Negative control |
| | | | | H$_2$0 | No template |
| | | 5G12V_1i3Planar | | SW620 | Test |
| | | | | K562 | Negative control |
| | | | | H$_2$0 | No template |

6.6. Results: Amplification of Target and Cleavage of Reporter Substrate

PASS primers containing different US were used to produce amplicons for the real-time detection of the KRAS wild type and point mutation (G12V). This reaction showed an increase in fluorescence over time when the target sequence used was Test human gDNA (K562 and SW620 respectively) amplified via PCR. The fluorescence of the no template control was lower than that in the DNA target-containing reactions and did not increase during the reaction. This demonstrates that the increase in fluorescence produced in target-containing reactions is due to target dependent assembly of catalytically active MNAzyme that then cleaved the reporter substrate.

In reactions containing wild type G12 PASS primer (Planar or Loop) comprising US inserts, i1, i2, i3 (Loop) or i3a (Planar), the Ct values for the "Test" DNA (K562)

indicated successful amplification and detection of the wild type KRAS allele in K562, whereas the lack of signal for the Negative Control (SW620) indicated the mutant allele is not detected with these systems. The PASS primer assays (Loop and Planar) containing US inserts, i3 or i3a had a lower Ct than for US inserts, i1 and i2 (Table 10).

the experiment demonstrated that a variety of different unique insert sequences can be used for amplification and detection of the same target, or on different targets. As such, the unique sequences can also be considered as universal unique sequences since they may be incorporated in a vast array of analytical assays.

TABLE 10

Ct values for PASS primer and partzyme combinations for wild type and mutant assays

| Target | Design | US inserted | Reaction type | Ct (ave) | ΔCt from Test |
|---|---|---|---|---|---|
| Wild type G12 | Insert 1 | Loop | Test | 24.8 | n/a |
| | | | Negative control | No Ct | |
| | | | No template | | |
| | | Planar | Test | 24.1 | n/a |
| | | | Negative control | No Ct | |
| | | | No template | | |
| | Insert 2 | Loop | Test | 25.4 | n/a |
| | | | Negative control | No Ct | |
| | | | No template | | |
| | | Planar | Test | 26.6 | n/a |
| | | | Negative control | No Ct | |
| | | | No template | | |
| | Insert 3 or 3a | Loop | Test | 22.7 | n/a |
| | | | Negative control | No Ct | |
| | | | No template | | |
| | | Planar | Test | 23.7 | n/a |
| | | | Negative control | No Ct | |
| | | | No template | | |
| Mutant G12V | Insert 1 | Loop | Test | 21.5 | 12.6 |
| | | | Negative control | 34.1 | |
| | | | No template | No Ct | |
| | | Planar | Test | 21.5 | 11.2 |
| | | | Negative control | 32.7 | |
| | | | No template | No Ct | |
| | Insert 2 | Loop | Test | 22.7 | 13.5 |
| | | | Negative control | 36.2 | |
| | | | No template | No Ct | |
| | | Planar | Test | 22.5 | 13.9 |
| | | | Negative control | 36.4 | |
| | | | No template | No Ct | |
| | Insert 3 | Loop | Test | 20.8 | 12.7 |
| | | | Negative control | 33.5 | |
| | | | No template | No Ct | |
| | | Planar | Test | 21.0 | 12.8 |
| | | | Negative control | 33.8 | |
| | | | No template | No Ct | |

In reactions containing G12V PASS primer (Planar or Loop) comprising US inserts, i1, i2 or i3, the Ct values for the "Test" DNA (SW620) indicated successful amplification and detection of the mutant KRAS allele in SW620. The signal for the Negative Control (K562) reached threshold Ct values as shown in Table 10 indicating that some background signal was produced when wild type template was used, however, the ΔCt values were sufficiently high to allow clear discrimination of mutant and wild type sequences. The PASS primer assays (Loop and Planar) containing US insert i3 had slightly lower Cts than for US inserts, i1 and i2 (Table 10), however the ΔCt was greater with US insert, i2.

Overall, all three US inserts were suitable for analysis of both wild type and mutant KRAS target sequences. There were differences in the results with slightly more variability observed in the wild type assay than for the mutant evident by the greater range of Ct values obtained. For both assays the incorporation of US insert, i3 resulted in lower Ct values while US insert, i2 resulted in higher Ct values. However, Example 7: Comparing the Specificity and Sensitivity of a PASS Primer Designed to Amplify the Complement Strand to that Obtained Using a PASS Primer Designed to Amplify the Reverse Complement of KRAS Under Standard and Fast Thermocycling Conditions In previous examples, the PASS primer designed to specifically amplify the KRAS point mutation in codon 12 referred to as G12V targeted the complement strand. This resulted in the PASS primer ending with a thymine (T) and having a T:C mismatch with the wild type KRAS sequence. If the PASS primer is designed to target the reverse strand, the PASS primer would then end with an A changing the mismatch with the wild type to an A:G.

In this example, the assay amplifying the complement strand for G12V used the PASS primer (5G12V_LM3i2Planar, SEQ ID NO. 40) which has been shown to work robustly and specifically in previous examples and this was compared to the assay amplifying the reverse complement strand of G12V (rcG12V) (5rcG12V_LM3 i1Loop, SEQ ID No. 66) which provides a robust and sensitive PASS primer for the amplification of rcG12V. The PASS primers are combined with MNAzyme qPCR whereby MNAzymes comprise a first partzyme that binds to the complement of the unique sequence (cUS) as well as amplified target sequence containing the complement of, the variant (mutant) base and the mismatched base. The second partzyme binds adjacently to the first partzyme within amplified target sequence of interest. Further a fast thermocycling protocol was compared to the standard protocol that had been used in previous experiments to assess any impact on specificity.

PASS primers for the amplification of the complement or reverse complement strands, both of which incorporated the format of design 3 (FIG. 7), were compared using two thermocycling conditions to investigate the efficiency, linearity and sensitivity of each strategy.

7.1. Partzyme Oligonucleotides

Partzymes were designed to specifically target the complement or reverse complement (rc) of the G12V sequence and any mismatch and cUS introduced by the PASS primer. In the following sequences, the bases in bold hybridize with the target sequence of interest and bases underlined are the unique sequences (G12V insert i2 and rcG12V insert i1) which are mismatched with respect to the starting template. The partzyme A's have a longer (L) target specific region. Bases in bold and italicised represent the variant (mutant) bases and bases underlined and in italics represent an additional mismatched base. The "-P" indicates 3' phosphorylation of the oligonucleotide. All sequences are written 5' to 3'.

```
SEQ ID NO: 18 partzyme B KRAS_B/55-P:
GAGCTGGGGAGGCTAGCTGCGTAGGCAAGAGTGCCTT

SEQ ID NO: 24 partzyme A G12V_LMi2A/55-P:
AGACATACTATGGAGCCGTTGACAACGAGAGGTGCGGT SEQ ID NO: 63 partzyme B rcKRAS_B/55-P:
GAGCTGGGGAGGCTAGCTGCTCCAACTACCACAAGTTT SEQ ID NO: 64 partzyme A rcG12V_LMi1A/55-P:
ACAATCAGTCCTACGCGAACAACAACGAGAGGTGCGGT
```

7.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

```
SEQ ID NO: 25 Substrate Sub55-FIB:
ACCGCACCTCguCCCCAGCTC
```

7.3. PCR Primers for Amplification of KRAS DNA

In vitro amplification of human gDNA was performed using the oligonucleotide PCR primers listed below. In the following sequences the bases in bold hybridize with the target sequence, bases underlined are the unique sequences (G12V insert i2 and rcG12V insert i1) which are mismatched with respect to the starting template, bases bold and underlined are the variant base and bases italicised represent an additional base mismatched (M) to both targets. All sequences are written 5' to 3'.

```
SEQ ID NO: 26 Reverse primer 3KRAS_3:
GGTCCTGCACCAGTAATATGC

SEQ ID NO: 87 Forward PASS primer
5G12V_LM4i2Planar:
CTGCTGAAAATGACTGAATATAAACAGACATACTATGGAGCCGT SEQ ID NO: 65 Reverse primer 3rcKRAS:
TATTAAAAGGTACTGGTGGAGTA SEQ ID NO: 66 Forward PASS primer
5rcG12V_LM3i1Loop:
CTGTATCGTCAAGGCACTCTTCACAATCAGTCCTACGCGAA
```

7.4. Target Sequences

Human gDNA extracted from the SW480 cell line was used as template for in vitro amplification of the point mutation G12V. A calibration curve was made by serially diluting SW480 in a constant background of the wild type gDNA, extracted from the K562 cell line. Human gDNA extracted from the cell lines Calu1, A549, MDA-MB231 and HCT116 were used as negative control template for other KRAS variants G12C, G12S, G13D and G13D respectively.

7.5. Reaction Components: Amplification and Quantitation of Target Sequence

Real-time amplification and quantitation of the target sequence was performed in a total reaction volume of 25 µL The reactions were conducted in a CFX96™ Real-Time PCR detection System (BioRad). The cycling parameters were either;

1) "Standard" thermocyling; 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C. step) or 2) "Fast" thermocyling; 95° C. for 2 minutes, 10 cycles of 95° C. for 5 seconds and 64° C. for 20 seconds (minus 1° C. per cycle), 40 cycles of 95° C. for 5 seconds and 54° C. for 20 seconds (data collected at the 54° C. step).

Reactions were set up with primers and partzymes as in Table 11. Each set of reaction conditions was tested in duplicate and contained 40 nM forward primer, 200 nM of reverse primer, 100 nM of partzyme A, 200 nM of partzyme B, 200 nM substrate (Sub55-FIB), 8 mM MgCl$_2$, 200 µM of each dNTP, 10 units RiboSafe RNase inhibitor (Bioline), 1x ImmoBuffer (Bioline), 2 units of MyTaq™ HS DNA polymerase (Bioline) and either SW480 gDNA template (35 ng) or SW480 gDNA template diluted 1 in 10, 1 in 100 or 1 in 1000 in a constant background of K562 gDNA template (35 ng) or gDNA of the negative controls, K562, Calu1, A549, MDA-MB231 and HCT-116 (35 ng) or no target (NF H$_2$O).

TABLE 11

Primer/partzyme combinations for the variant assays

| Assay | Partzyme A | Partzyme B | Primers |
|---|---|---|---|
| G12V | G12V_LMi2A/55-P | KRAS_B/55-P | 5G12V_LM4i2Planar and 3KRAS |
| rcG12V | rcG12V_LMi1A/55-P | rcKRAS_B/55-P | 5rcG12V_LM3i1Loop and 3rcKRAS |

7.6. Results: Amplification of Target and Cleavage of Reporter Substrate

For all reactions the fluorescence of the no template control was lower than that in the DNA target-containing reactions. This demonstrates that the increase in fluorescence produced in target-containing reactions is due to target dependent assembly of catalytically active MNAzymes that then cleaved the universal reporter substrate.

The forward PASS primers designed to amplify either the complement or reverse complement strand were used to produce amplicons for the real-time detection and quantification of the KRAS point mutation G12V. MNAzymes were designed to be specific for either the complement or the reverse complement strand and the associated US introduced by the specific PASS primer used to detect the mutant sequence. This reaction showed an increase in fluorescence over time when the reaction contained target sequence specific for G12V (Table 12).

TABLE 12

Ct values for G12V vs rcG12V PASS primer assays

| | G12V | | rcG12V | |
|---|---|---|---|---|
| Template | Ct (Ave) | ΔCt from SW480 (G12V) | Ct (Ave) | ΔCt from SW480 (G12V) |
| Standard thermocycling | | | | |
| SW480 (G12V) | 23.1 | | 20.3 | |
| 1 in 10 | 26.1 | | 23.7 | |
| 1 in 100 | 29.3 | | 27.2 | |
| 1 in 1000 | 32.4 | | 30.9 | |
| K562 (WT) | 35.7 | 12.6 | 39.7 | 19.4 |
| NTC | No Ct | — | No Ct | — |
| Calu1 (G12C) | 34.3 | 11.3 | 48.5^ | 28.2 |
| A549 (G12S) | 37.7 | 14.6 | No Ct | — |
| MB231 (G13D) | 40.8 | 17.8 | 42.9^ | 22.6 |
| HCT116 (G13D) | 37.7 | 14.7 | No Ct | — |
| Efficiency | 109% | | 91.4% | |
| Linearity | 0.999 | | 0.992 | |
| Fast thermocycling | | | | |
| SW480 (G12V) | 25.1 | | 22.8 | |
| 1 in 10 | 28.2 | | 26.3 | |
| 1 in 100 | 31.4 | | 29.5 | |
| 1 in 1000 | 34.9 | | 24.5 | |
| K562 (WT) | 39.6 | 14.5 | 45.4 | 22.6 |
| NTC | No Ct | — | No Ct | — |
| Calu1 (G12C) | 38.2 | 13.1 | No Ct | — |
| A549 (G12S) | 41.4 | 16.3 | No Ct | — |
| MB231 (G13D) | 43.9 | 18.8 | No Ct | — |
| HCT116 (G13D) | 42.1 | 16.9 | 48.1^ | 25.3 |
| Efficiency | 103% | | 85% | |
| Linearity | 0.997 | | 0.989 | |

^Only one of 2 replicates produced a signal; Ct value not averaged

The SW480 DNA template, specific for G12V, was serially diluted 10-fold in a background of wild type K562 template. The serial dilutions of DNA were amplified with either the complement or the reverse complement forward PASS primer. Both primers sets were able to detect the G12V sequence when diluted 1 in 1000 in a background of wild type template. Standard curves were generated for both PASS primers by plotting the log of the DNA concentration against the threshold cycle resulting in a linear plot, the Ct of each dilution is shown in Table 12. The Ct values shown in the table are an average of the results for duplicate reactions. The correlation coefficient ($R^2$), and reaction efficiency for each target are also shown in Table 12.

Under standard thermocycling conditions, the difference in Cts (ΔCt) for the PASS primer designed to the complement strand between the top standard (35 ng) and the signal of the negative controls wild type (K562), G12C (Calu1), G12S (A549) and G13D (MDA-MB231 and HCT116), was smaller than for the PASS primer designed to the reverse complement strand (rcG12V). Further some of the negative controls for the rcG12V assay did not produce a Ct value (Table 12). This indicates that the rcG12V PASS primer assay may be more specific under these experimental conditions.

When the Ct values generated under fast thermocycling conditions were compared to the standard thermocycling conditions for both the G12V and rcG12V assays there is an increase in the ΔCts, indicating that the shorter cycling times improve the specificity of both reactions (Table 12) under these experimental conditions. However, for the rcG12V assay faster cycling times reduced the efficiency and linearity of the reaction (Table 12).

The complement and the reverse complement PASS primer assays for the amplification and detection of G12V displayed good sensitivity, detecting down to 1 G12V (~10 copies) in a background of 1000 wild type (~10,000 copies) under both standard and fast thermocycling. Overall, the rcG12V assay was more specific than the G12V. Reducing the cycling times decreased the linearity and efficiency of the rcG12V reaction whereas faster cycling times increased the specificity of the G12V assay without impacting the linearity and efficiency.

This example demonstrates that the specificity of an assay for a single base change can be influenced by the strand that the PASS primer binds and amplifies. Further modifying experimental conditions such as cycling times can be used to improve the specificity of the reaction.

Example 8: Investigating the Influence of the Number of Bases not Bound in the Target Sequence Under the Looped Unique Sequence of a PASS Primer In this example, the reverse complement strand of the KRAS point mutation in codon 12 referred to as rcG12V is used to test Loop PASS primers that were designed to contain 0, 1, 2, 3, 4, or 5 unbound base gap in the target sequence under the loop between S1 and S2 (in prior examples there was one or no base gap between S1 and S2). Two different designs for rcG12V were used, (i) the variant base "A" was located in the 3' target specific region (S2) at the 3' end and S2 had a Tm of 26° C., and a mismatch was inserted 2 bases 5' of the variant base (FIG. 7, Design 3) and (ii) the variant base "A" was located in the 3' target specific region (S2), 3 bases from the 3' end and S2 had a Tm of 20° C., and a mismatch was inserted 2 bases 5' of the variant base (FIG. 7, Design 4).

The PASS primers are combined with MNAzyme qPCR whereby MNAzymes comprise a first partzyme that binds to the complement of the unique sequence (cUS), variant base and mismatch base as well as amplified target sequence. The second partzyme binds adjacently to the first partzyme, hybridizing to the amplified target sequence of interest.

PASS primers with different size gaps, between S1 and S2 when they are bound to the target sequence, were compared for their capacity to discriminate the single base change between target G12 and G12V.

8.1. Partzyme Oligonucleotides

Partzymes were designed to specifically target amplicons of the reverse complement of the G12V sequence and any mismatch and cUS introduced via a PASS primer. In the following sequences the bases in bold hybridize with the target sequence of interest and bases underlined are the unique sequence which is mismatched with respect to the starting template. Bases in bold and italicised represent the variant base and bases underlined and in italics represent an additional mismatched base. The "-P" indicates 3' phosphorylation of the oligonucleotide. All sequences are written 5' to 3'.

```
SEQ ID NO: 63 partzyme B rcKRAS_B/55-P:
GAGCTGGGGAGGCTAGCTGCTCCAACTACCACAAGTTT SEQ ID NO: 67 partzyme A rcG12V_M3i2A/55-P:
AGACATACTACTACGACAACAACAACGAGAGGTGCGGT SEQ ID NO: 68 partzyme A rcG12V_M4i2A/55-P:
AGACATACTAGCAAACAACAACGAGAGGTGCGGT
```

8.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

```
SEQ ID NO: 25 Substrate Sub55-FIB:
ACCGCACCTCguCCCCAGCTC
```

8.3. PCR Primers for Amplification of KRAS DNA

In vitro amplification of human gDNA was performed using the oligonucleotide PCR primers listed below. PASS primers are designed so that the G12V specific forward primers contain US (insert i2). In the following sequences the bases in bold hybridize with the target sequence, bases underlined are the unique sequences which are mismatched with respect to the starting template, bases bold and underlined are the variant base, bases italicised represent an additional mismatched base (M) and the number in brackets after the word Loop indicates the numbers of unbound bases in the target sequence between S1 and S2. All sequences are written 5' to 3'.

```
SEQ ID NO: 69 Reverse primer 3rcKRAS_2:
TACGATACACGTCTGCAGTCA

SEQ ID NO: 70 Forward PASS primer
5rcG12V_M3i2Loop(1):
TGTATCGTCAAGGCACTCTTGAGACATACTACTACGACAA SEQ ID NO: 71 Forward PASS primer
5rcG12V_M3i2Loop(2):
CTGTATCGTCAAGGCACTCTTAGACATACTACTACGACAA SEQ ID NO: 72 Forward PASS primer
5rcG12V_M3i2Loop(3):
GCTGTATCGTCAAGGCACTCTAGACATACTACTACGACAA SEQ ID NO: 73 Forward PASS primer
5rcG12V_M3i2Loop(4):
GCTGTATCGTCAAGGCACTCAGACATACTACTACGACAA SEQ ID NO: 74 Forward PASS primer
5rcG12V_M4i2Loop(0):
GTCAAGGCACTCTTGCCTACAGACATACTAGCAAACA SEQ ID NO: 75 Forward PASS primer
5rcG12V_M4i2Loop(1):
CGTCAAGGCACTCTTGCCTAAGACATACTAGCAAACA SEQ ID NO: 76 Forward PASS primer
5rcG12V_M4i2Loop(2):
TCGTCAAGGCACTCTTGCCTAGACATACTAGCAAACA SEQ ID NO: 77 Forward PASS primer
5rcG12V_M4i2Loop(3):
ATCGTCAAGGCACTCTTGCCAGACATACTAGCAAACA SEQ ID NO: 78 Forward PASS primer
5rcG12V_M4i2Loop(4):
GTATCGTCAAGGCACTCTTGCAGACATACTAGCAAACA SEQ ID NO: 79 Forward PASS primer
5rcG12V_M4i2Loop(5):
TGTATCGTCAAGGCACTCTTGAGACATACTAGCAAACA
```

8.4. Target Sequences

Human gDNA extracted from the K562 cell line was used as template for in vitro amplification of the wild type gene and human gDNA extracted from the SW620 cell line was used for in vitro amplification of the point mutation G12V.

8.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C. step). All reactions were run in duplicate and contained 40 nM forward primer and 100 nM partzyme A (combinations outlined in Table 13), 200 nM of reverse primer (3rcKRAS_2), 200 nM partzyme B (rcKRAS_B/55-P), 200 nM substrate (Sub55-FIB), 8 mM $MgCl_2$, 200 μM of each dNTP, 10 units RiboSafe RNAase Inhibitor (Bioline), 1x ImmoBuffer (Bioline), 2 units of MyTaq™ HS DNA polymerase (Bioline) and either K562 or SW620 gDNA template (50 ng) or no target (NF $H_2O$).

TABLE 13

Primer/partzyme combinations for variant assays

| Design | Forward Primer | Partzyme A | Template | Reaction type |
|---|---|---|---|---|
| Design 3 Variant (mutant) base at end; Mismatch 2 bases 5' of variant | 5rcG12V_M3i2Loop(1) 5rcG12V_M3i2Loop(2) 5rcG12V_M3i2Loop(3) 5rcG12V_M3i2Loop(4) | rcG12V_M3i2A/55-P | SW620 K562 H$_2$0 | Test Negative control No template |
| Design 4 Variant (mutant) base 3$^{rd}$ base from 3' end; Mismatch 2 bases 5' of variant | 5rcG12V_M4i2Loop(0) 5rcG12V_M4i2Loop(1) 5rcG12V_M4i2Loop(2) 5rcG12V_M4i2Loop(3) 5rcG12V_M4i2Loop(4) 5rcG12V_M4i2Loop(5) | rcG12V_M4i2A/55-P | SW620 K562 H$_2$0 | Test Negative control No template |

8.6. Results: Amplification of Target and Cleavage of Reporter Substrate

The results of amplification using PASS primers followed by detection using primer-specific partzymes are shown in Table 14.

TABLE 14

Ct values for rcG12V Loop PASS primer combinations

| Design | Ct (Ave) Test | Ct (Ave) Negative control | Ct (Ave) No template | ΔCt (Negative minus Test) |
|---|---|---|---|---|
| *PASS Design 3 Variant base at 3' end; mismatch 2 bases 5' of variant* | | | | |
| 1 base gap | 20.4 | No Ct | No Ct | n/a |
| 2 base gap | 21.5 | No Ct | No Ct | n/a |
| 3 base gap | 20.4 | No Ct | No Ct | n/a |
| 4 base gap | 20.1 | No Ct | No Ct | n/a |
| *PASS Design 4 Variant base 3 bases from 3' end; mismatch 2 bases 5' of variant* | | | | |
| 0 base gap | 33.5 | No Ct | No Ct | n/a |
| 1 base gap | 31.6 | No Ct | No Ct | n/a |
| 2 base gap | 32.0 | No Ct | No Ct | n/a |
| 3 base gap | 26.6 | No Ct | No Ct | n/a |
| 4 base gap | 24.6 | 37.5˙ | No Ct | 12.9 |
| 5 base gap | 25.3 | No Ct | No Ct | n/a |

˙Only one of 2 replicates produced a signal; Ct not averaged

In all combinations the PASS primer matched to the mutant variant amplified the G12V allele in Test SW620 DNA and this was detected by the partzyme matched to mutant and US2. No amplification was detected using any primer/partzyme pair when no template (no DNA) was added. This mutant PASS primer/partzyme system preferentially amplified and detected the mutant allele and only one combination produced signal when the Negative Control template (K562) was used (Table 14).

The PASS primer based on design 3 (FIG. 7) with a Tm of 26° C. showed very little difference in amplification of the G12V target sequence when different base gaps (1 to 4) unbound to the target sequence located under the loop region of the PASS primer were compared (Table 14).

The PASS primer based on design 4 (FIG. 7) with a Tm of 20° C. displayed an improved Ct value when a 3, 4 or 5 base gap occurred under the loop region of the PASS primer. However, this also resulted in a signal being detected for the negative control (wild type) reaction, albeit with a ΔCt of 12.9 (Table 14). This may indicate that PASS primers with shorter S2 regions may benefit from the presence of a larger number of base gaps unbound to the target sequence between S1 and S2 under the loop region; whereas PASS primers with an S2 region that is longer and has a higher Tm, the number of base gaps under the loop region between S1 and S2 has little impact.

Overall this experiment combined with previous experiments demonstrates that there can be flexibility of design and that Loop PASS primers can function with various number of unbound bases in the region of the target that lies between the complement of the S1 and S2 regions of the primer.

Example 9: Comparing the Cross Reactivity of PASS Primers to WE-ARMS Primers when Both Primer Types were Combined with MNAzymes in an Assay Designed to Detect Single Base Changes in a Sequence Amplification of a variant (mutant) sequence with a WE-ARMS primer produces an amplicon that would be different from the wild type sequence by the mutant base and the added mismatched base. In comparison, amplification of a mutant sequence with a PASS primer produces an amplicon that would not only differ from the wild type sequence by the mutant and mismatch base but also the inserted US. When the mutant amplicon amplified by a WE-ARMS primer is detected in real-time by an MNAzyme the partzyme A would only differ from the wild type sequence by the mutant and mismatch base whereas for an amplicon generated by a PASS primer the partzyme A would also contain the US which is different to the original wild type sequence. Further if it was desirable to also amplify and detect the wild type in the same well, a different US could be used compared to the mutant, creating greater sequence diversity and improving the ability of the MNAzyme to discriminate between mutant and wild type amplicons.

In this example, the WE-ARMS and PASS primer systems are tested for any cross reactivity when a primer specific for the mutant is mixed with a partzyme A specific for the wild type and vice versa. This involves amplification of the reverse complement of the KRAS point mutation in codon 12 referred to as, rcG12V, and the wild type KRAS sequence, rcG12. PASS primers were designed to be specific for either the rcG12V or the rcG12 sequence. The variant base for the mutant was located in the 3' target specific region (S2), at the 3' end, and a mismatch base was inserted 4 bases from the 3' end. The variant base for the wild type was located 3 bases from the 3' end with a mismatch base inserted 5 bases from the 3' end. A different US is contained in the PASS primer for the wild type (insert i4) and the mutant (insert i1) sequences. These PASS primers were compared to wobble-enhanced ARMS (WE-ARMS) primers (see Hamfjord et al, (2011), "*Wobble-enhanced ARMS Method for Detection of KRAS and BRAF Mutations*", Diagn Mol Pathol; 20:158-165), whereby primers are designed that are sequence-specific for rcG12V or rcG12 plus they contain an induced mismatch with respect to both alleles to help discriminate between the KRAS sequences that differ by a single base. For the WE-ARMS primers used in this example, the variant (mutant or wild type) base is located at the 3' end and a mismatch is inserted 5 bases from the 3' end.

The PASS primers are combined with MNAzyme qPCR whereby MNAzymes comprise a first partzyme that binds to the complement of the, unique sequence (cUS), variant base (wild type or mutant) and mismatched base as well as the amplified target sequence. The second partzyme binds adjacently to the first partzyme, hybridizing to the amplified target sequence of interest. The WE-ARMS primers were combined with MNAzymes whereby a first partzyme binds to the amplified target sequence containing the complement of the, variant base (wild type or mutant) and mismatched base. The second partzyme binds adjacently to the first partzyme, hybridizing to the amplified target sequence of interest.

PASS primers were compared to WE-ARMS primers for their capacity to cross react when the primers are mismatched with partzymes.

9.1. Partzyme Oligonucleotides

Partzymes were designed to specifically target the rcG12 or rcG12V sequence and any mismatch introduced via a primer and cUS introduced via a PASS primer. In the following sequences the bases in bold hybridize with the target sequence of interest and bases underlined are the unique sequences (wild type insert i4 and variant insert i1) which are mismatched with respect to the starting template. Some partzyme A's have a longer (L) 3' target specific region. Bases in bold and italicised represent the variant bases (wild type or mutant) and bases underlined and in italics represent an additional mismatched base. The "-P" indicates 3' phosphorylation of the oligonucleotide. All sequences are written 5' to 3'.

```
SEQ ID NO: 63 partzyme B rcKRAS_B/55-P:
GAGCTGGGGAGGCTAGCTGCTCCAACTACCACAAGTTT SEQ ID NO: 80 partzyme A rcG12_LMi4A/55-P:
TCAATACCATTACGCGACCAACAACGAGAGGTGCGGT SEQ ID NO: 88 partzyme A rcG12V_LMa4i1A/55-P:
ACAATCAGTCCTACGACAACAACAACGAGAGGTGCGGT SEQ ID NO: 81 partzyme A rcG12_MA/55-P:
TCTTGCCTACGCGACCAACAACGAGAGGTGCGGT
```

```
-continued
SEQ ID NO: 82 partzyme A rcG12V_MA/55-P:
CTCTTGCCTACGCAAACAACAACGAGAGGTGCGGT
```

9.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The lower case bases represent RNA and the upper case bases represent DNA. The reporter substrate for this example is shown below with the sequence, 5' to 3'.

```
SEQ ID NO: 25 Substrate Sub55-FIB:
ACCGCACCTCguCCCCAGCTC
```

9.3. PCR Primers for Amplification of KRAS DNA

In vitro amplification of human gDNA was performed using the oligonucleotide PCR primers listed below. PASS primers are designed so that the rcG12 specific forward primers contain US insert, i4, and the rcG12V specific forward primers contain US insert, i1. Some forward primers have a longer (L) target specific region. In the following sequences the bases in bold hybridize with the target sequence, bases underlined are the unique sequences which are mismatched with respect to the starting template, bases bold and underlined are the variant base and bases italicised represent an additional base mismatched (M) to both targets. All sequences are written 5' to 3'.

```
SEQ ID NO: 69 Reverse primer 3rcKRAS_2:
TACGATACACGTCTGCAGTCA

SEQ ID NO: 83 Forward PASS primer
5rcG12_LM4i4Loop:
TGTATCGTCAAGGCACTCTTGTCAATACCATTACGCGACCA SEQ ID NO: 99 Forward PASS primer
5rcG12V_LM3a4i1Loop:
CTGTATCGTCAAGGCACTCTTCACAATCAGTCCTACGACAA SEQ ID NO: 84 Forward WE-ARMS
primer 5rcG12_M:
GCACTCTTGCCTACGCGAC SEQ ID NO: 85 Forward WE-ARMS
primer 5rcG12V_M:
GGCACTCTTGCCTACGCAAA
```

9.4. Target Sequence

Human gDNA extracted from the K562 cell line was used as template for in vitro amplification of the wild type gene and human gDNA extracted from the SW480 cell line was used for in vitro amplification of the point mutation G12V.

9.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 5 seconds and 64° C. for 20 seconds (minus 1° C. per cycle), 50 cycles of 95° C. for 5 seconds and 54° C. for 20 seconds (data collected at the 54° C. step). All reactions were run in duplicate and contained 40 nM forward primer and 100 nM partzyme A (combinations outlined in Table 15), 200 nM of reverse primer (3rcKRAS_2), 200 nM partzyme B (rcK- RAS_B/55-P), 200 nM substrate (Sub55-FIB), 8 mM MgCl$_2$, 200 µM of each dNTP, 10 units RiboSafe RNAase Inhibitor (Bioline), 1x ImmoBuffer (Bioline), 2 units of MyTaq™ HS DNA polymerase (Bioline) and either K562 or SW480 gDNA template (50 ng) or no target (NF H$_2$O).

difference in Ct between that of the wild type (K562) and that generated from mutant (SW480) DNA was 12 cycles (Table 16), demonstrating PASS primer and matching partzymes allow discrimination between mutant and wild type alleles. No cross reactivity was seen when the mis-

TABLE 15

Primer/partzyme combinations for wild type and variant

| System | Design | Oligo Format (Primer/Partzyme) | Forward Primer | Partzyme A |
|---|---|---|---|---|
| PASS | rcG12 Design 4 Variant wild type 2 bases from 3' end; mismatch 2 bases 5' of variant | Matched (G12/G12) Mismatched (G12/G12V) | 5rcG12_LM4i4Loop 5rcG12_LM4i4Loop | rcG12_LMi4A/55-P rcG12V_LMa4i1A/55-P |
|  | rcG12V Design 3 Variant mutant base at end; mismatch 2 bases 5' of variant | Matched (G12V/G12V) Mismatched (G12V/G12) | 5rcG12V_LM3a4i1Loop 5rcG12V_LM3a4i1Loop | rcG12V_LMa4i1A/55-P rcG12_LMi4A/55-P |
| WE-ARMS | rcG12 WE-ARMS Variant wild type base at end; mismatch 2 bases 5' of variant | Matched (G12/G12) Mismatched (G12/G12V) | 5rcG12_M 5rcG12_M | rcG12_MA/55-P rcG12V_MA/55-P |
|  | rcG12V WE-ARMS Variant mutant base at end; mismatch 2 bases 5' of variant | Matched (G12V/G12V) Mismatched (G12V/G12) | 5rcG12V_M 5rcG12V_M | rcG12V_MA/55-P rcG12_MA/55-P |

9.6. Results: Amplification of Target and Cleavage of Reporter Substrate

The results of amplification using PASS primers and WE-ARMS primers followed by detection using either primer-specific partzymes or mismatched partzymes are shown in Table 16.

TABLE 16

Ct values for G12 and G12V combinations

| System | Design | Oligo Format (Primer/Partzyme) | Reaction type | Ct (Ave) |
|---|---|---|---|---|
| rcG12 | PASS | Matched (G12/G12) | Test (K562) | 22.2 |
|  |  |  | Negative control (SW480) | 34.2 |
|  |  | Mismatched (G12/G12V) | Test (K562) | No Ct |
|  |  |  | Negative control (SW480) | No Ct |
|  | WE_ARMS | Matched (G12/G12) | Test (K562) | 22.0 |
|  |  |  | Negative control (SW480) | 44.5 |
|  |  | Mismatched (G12/G12V) | Test (K562) | 25.6 |
|  |  |  | Negative control (SW480) | 45.0^ |
| rcG12V | PASS | Matched (G12V/G12V) | Test (SW480) | 22.0 |
|  |  |  | Negative control (K562) | No Ct |
|  |  | Mismatched (G12V/G12) | Test (SW480) | No Ct |
|  |  |  | Negative control (K562) | No Ct |
|  | WE_ARMS | Matched (G12V/G12V) | Test (SW480) | 24.3 |
|  |  |  | Negative control (K562) | No Ct |
|  |  | Mismatched (G12V/G12) | Test (SW480) | 33.4 |
|  |  |  | Negative control (K562) | No Ct |

^only one replicate produced a signal, Ct not averaged

The PASS primer matched to the reverse complement strand of the wild type amplified the rcG12 allele in Test (K562) DNA and this was detected by the partzyme matched to wild type and US insert i4. The reverse complement wild type PASS primer/partzyme system preferentially amplified and detected the wild type allele and signal was generated later in the reaction when Negative Control template (SW480) was used under these experimental conditions. The matched partzymes specific for the variant mutant and US insert, i1, were used in conjunction with the wild type PASS primer (Table 16).

The WE-ARMS primer matched to the wild type amplified the rcG12 allele in Test (K562) DNA and this was detected by the partzyme matched to wild type. This wild type ARMS primer/partzyme system was specific for wild type allele and a late signal was generated when Negative Control template (SW480) was used. The difference in Ct between that of the wild type (K562) and that generated from mutant (SW480) DNA was greater than 22 cycles (Table 16). Cross reactivity was seen when the mismatched partzymes specific for the variant mutant were used in conjunction with the wild type WE-ARMS primer. The Ct for the mismatched reaction was similar to the matched indicating the partzyme, designed to be specific for the variant mutant, could not discriminate between wild type and mutant amplicons generated by WE-ARMS primers (Table 16) under the reaction conditions.

The PASS primer matched to the reverse complement strand of the mutant variant amplified the rcG12V allele in Test (SW480) DNA and this was detected by the partzyme matched to mutant and US insert i1. This mutant PASS primer/partzyme system specifically detected the mutant allele and no signal was generated when Negative Control template (K562) was used. No cross reactivity was seen when partzymes specific for the wild type and US insert i4, were used in conjunction with the mutant PASS primer (Table 16).

The WE-ARMS primer matched to the reverse complement of the mutant variant amplified the rcG12V allele in Test (SW480) DNA and this was detected by the partzyme matched to mutant. This mutant WE-ARMS primer/partzyme system specifically detected the mutant allele and no signal was generated when Negative Control template (K562) was analysed. Cross reactivity was seen when the mismatched partzymes specific for the wild type were used in conjunction with the wild type WE-ARMS primer. The Ct for the mismatched reaction was ~9 Ct later to the matched indicating the partzyme, designed to be specific for the variant mutant, had inferior ability to discriminate between wild type and mutant amplicons generated by WE-ARMS primers (Table 16) under the reaction conditions.

No amplification was detected using any primer/partzyme pair when no template (no DNA) was added.

The data in this example demonstrates the capacity of PASS primers to perform in a manner superior to an alternative technology for detection of single base changes, WE-ARMS, which is well known in the art. Further the introduction of the US by the PASS primer into the amplicon affords an added level of specificity when a partzyme is to discriminate between two closely related sequences, a scenario that may arise in a multiplex qPCR. The PASS primers allowed the introduction of additional, unique sequences into amplicons. Different unique sequences were introduced into the wild type and mutant variant amplicons. This additional sequence enhances the difference and prevents cross reactivity of partzymes on alternate amplicons, for example, wild type PASS amplicons are not detected by partzymes matching the mutant PASS amplicons and visa versa. This enables the assays to be combined in a multiplex reaction and the variant and the wild type identified. In contrast, the small difference of only two bases that existed between the wild type and mutant WE-ARMS amplicons and their fully matched partzymes was insufficient to prevent cross reactivity of partzymes on alternate amplicons, for example, wild type WE-ARMS amplicons were detected by partzymes matching the mutant WE-ARMS amplicons and visa versa, therefore they could not be combined in a multiplex reaction.

Example 10: Influence of the Length of the S2 Region of PASS Primers on Amplification of a Target Sequence There are multiple regions in a PASS primer, S1 which is 5' of the US is designed to anchor the PASS primer to the target sequence of interest, S2 which is 3' of the unique sequence provides the initiating portion of the PASS primer and the US which lies between S1 and S2. In this example the US inserts a region of unique sequence into the amplicon (FIG. 1). All regions can be tailored to a particular application by lengthening or shortening their sequences.

In this example, the influence of length of the S2 region of the PASS primer on amplification of the CCB gene was investigated when combined with MNAzyme detection for readout in qPCR. PASS primers and partzymes were designed to determine if various scenarios of length of the S2 domain of the PASS primer were compatible with amplification and detection of the CCB gene. The length of the S2 domain of the PASS primer (containing either a Loop or Planar US), was altered from the 3' end and was either 3, 4, 5, 6 or 7 bases long or the 5' end and was either 5, 6 or 7 bases long.

10.1. Partzyme Oligonucleotides

Partzymes were designed to specifically target the CCB gene and the cUS introduced via a PASS primer. In the following sequences the bases in bold hybridize with the target sequence of interest and bases underlined hybridise to the cUS. The "-P" indicates 3' phosphorylation of the oligonucleotide. All sequences are written 5' to 3'.

SEQ ID NO: 86 partzyme B CCBB/2-P:
TGCCCAGGGAGGCTAGCTGGTCCATGGCTTCTGGGTA

SEQ ID NO: 89 partzyme A CCB_2i2A/2-P:
AGACATACTACCAGAGCCCAACAACGAGAGGAAACCTT SEQ ID NO: 90 partzyme A CCB_2i2L5_6A/2-P:
CAGACATACTACAGAGCCCAACAACGAGAGGAAACCTT SEQ ID NO: 91 partzyme A CCB_2i2L5_5A/2-P:
CC<u>AGACATACTA</u>AGAGCCCAACAACGAGAGGAAACCTT SEQ ID NO: 92 partzyme A CCB_2i2P5_6A/2-P:
A<u>AGACATACTA</u>CAGAGCCCAACAACGAGAGGAAACCTT SEQ ID NO: 93 partzyme A CCB_2i2P5_5A/2-P:
AT<u>AGACATACTA</u>AGAGCCCAACAACGAGAGGAAACCTT 10.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by an "IB" in the name of the substrate below). Cleavage of the substrate was monitored at 530 nm (FAM emission wavelength) with excitation at 485 nm (FAM excitation wavelength). The reporter substrate for this example is shown below with the sequence, 5' to 3'. The lower case bases represent RNA and the upper case bases represent DNA.

SEQ ID NO: 94 Substrate Sub2-FIB:
AAGGTTTCCTCguCCCTGGGCA 10.3. Target Sequence and PCR Primers for Amplification of CCB DNA The target sequence for this example was the CCB gene in human gDNA extracted from the IM9 cell line (Promega). The oligonucleotide PASS primers are listed below. In the following sequences the bases underlined are the US insert i2. All sequences are written 5' to 3'.

SEQ ID NO: 7 Reverse primer 3CCB:
CTCAGGAATTTCCCAGCTAC

SEQ ID NO: 13 Forward PASS primer 5CCB_2i2Loop:
TTCTTCTTGGATGGTCATCT<u>AGACATACTA</u>CCAGAGC SEQ ID NO: 95 Forward PASS primer 5CCB_2i2Loop3_6:
TTCTTCTTGGATGGTCATCT<u>AGACATACTA</u>CCAGAG SEQ ID NO: 96 Forward PASS primer 5CCB_2i2Loop3_5:
TTCTTCTTGGATGGTCATCT<u>AGACATACTA</u>CCAGA SEQ ID NO: 97 Forward PASS primer 5CCB_2i2Loop3_4:
TTCTTCTTGGATGGTCATCT<u>AGACATACTA</u>CCAG SEQ ID NO: 98 Forward PASS primer 5CCB_2i2Loop3_3:
TTCTTCTTGGATGGTCATCT<u>AGACATACTA</u>CCA SEQ ID NO: 14 Forward PASS primer 5CCB_2i2Planar:
CTTGTCTCAGTTCTTCTTGG<u>AGACATACTA</u>CCAGAGC SEQ ID NO: 100 Forward PASS primer 5CCB_2i2Planar3_6:
CTTGTCTCAGTTCTTCTTGG<u>AGACATACTA</u>CCAGAG SEQ ID NO: 101 Forward PASS primer 5CCB_2i2Planar3_5:
CTTGTCTCAGTTCTTCTTGG<u>AGACATACTA</u>CCAGA

```
SEQ ID NO: 102 Forward PASS primer
5CCB_2i2Planar3_4:
CTTGTCTCAGTTCTTCTTGGAGACATACTACCAG SEQ ID NO: 103 Forward PASS primer
5CCB_2i2Planar3_3:
CTTGTCTCAGTTCTTCTTGGAGACATACTACCA SEQ ID NO: 104 Forward PASS primer
5CCB_2i2Loop5_6:
CTTCTTGGATGGTCATCTCAGACATACTACAGAGC SEQ ID NO: 105 Forward PASS primer
5CCB_2i2Loop5_5:
TTCTTGGATGGTCATCTCCAGACATACTAAGAGC SEQ ID NO: 106 Forward PASS primer
5CCB_2i2Planar5_6:
CTTGTCTCAGTTCTTCTTGGAAGACATACTACAGAGC SEQ ID NO: 107 Forward PASS primer
5CCB_2i2Planar5_5:
CTTGTCTCAGTTCTTCTTGGATAGACATACTAAGAGC
```

10.4. Reaction Components: Amplification and Detection of Target Sequence

Real-time amplification and detection of the target sequence was performed in a total reaction volume of 25 μL. The reactions were conducted in an Mx3005p (Stratagene). The cycling parameters were 95° C. for 2 minutes, 5 cycles of 95° C. for 15 seconds and 55° C. for 30 seconds, 40 cycles of 95° C. for 15 seconds and 52° C. for 60 seconds (data collected at the 52° C. step). All reactions were run in duplicate and contained 40 nM forward primer and 200 nM partzyme A (combinations listed in Table 17), 200 nM of reverse primer (3CCB), 200 nM partzyme B (CCBB/2-P), 200 nM substrate (Sub2-FIB), 8 mM MgCl$_2$, 200 μM of each dNTP, 10 units RiboSafe RNAase Inhibitor (Bioline), 1× ImmoBuffer (Bioline), 2 units of MyTaq™ HS DNA polymerase (Bioline) and either gDNA template (50 ng) or no target (NF H2O).

TABLE 17

Forward PASS primer and partzymeA combinations

| Design | Size (bp) S2 | PASS Primer | Partzyme A |
|---|---|---|---|
| Original Loop | 7 | 5CCB_2i2Loop | CCB_2i2A/2-P |
| Original Planar | 7 | 5CCB_2i2Planar | |
| Reducing S2 of the PASS primer from 3' end Matched partzyme A for all primers | 6 | 5CCB_2i2Loop3_6 | |
| | 5 | 5CCB_2i2Loop3_5 | |
| | 4 | 5CCB_2i2Loop3_4 | |
| | 3 | 5CCB_2i2Loop3_3 | |
| | 6 | 5CCB_2i2Planar3_6 | |
| | 5 | 5CCB_2i2Planar3_5 | |
| | 4 | 5CCB_2i2Planar3_4 | |
| | 3 | 5CCB_2i2Planar3_3 | |
| Reducing S2 of the PASS primer from 5' end Matched partzyme A for all primers | 6 | 5CCB_2i2Loop5_6 | CCB_2i2L5_6A/2-P |
| | 5 | 5CCB_2i2Loop5_5 | CCB_2i2L5_5A/2-P |
| | 6 | 5CCB_2i2Planar5_6 | CCB_2i2P5_6A/2-P |
| | 5 | 5CCB_2i2Planar5_5 | CCB_2i2P5_5A/2-P |
| Controls | | | |
| Original Loop, mismatched partzyme A | 7 | 5CCB_2i2Loop | CCB_2i2L5_6A/2-P CCB_2i2L5_5A/2-P |
| Original Planar, mismatched partzyme A | 7 | 5CCB_2i2Planar | CCB_2i2P5_6A/2-P CCB_2i2P5_5A/2-P |

TABLE 17-continued

Forward PASS primer and partzymeA combinations

| Design | Size (bp) S2 | PASS Primer | Partzyme A |
|---|---|---|---|
| Reducing S2 of the PASS primer from 5' end Mismatched partzyme A for all primers | 6 | 5CCB_2i2Loop5_6 | CCB_2i2A/2-P |
| | 5 | 5CCB_2i2Loop5_5 | |
| | 6 | 5CCB_2i2Loop5_6 | |
| | 5 | 5CCB_2i2Loop5_5 | |

10.6. Results: Amplification of Target and Cleavage of Reporter Substrate

The PASS primers were used to produce amplicons for the real-time detection and quantification of CCB and the partzymes bound to both the cUS and the amplified target specific sequence. This reaction showed an increase in fluorescence over time when the target sequence used was human gDNA amplified via qPCR. The fluorescence of the no-DNA target control was lower than that in the DNA target-containing reactions and did not increase during the reaction. This demonstrates that the increase in fluorescence produced in target-containing reactions is due to target dependent assembly of catalytically active MNAzyme that then cleaved the reporter substrate.

TABLE 18

Ct values for PASS primer and partzyme combinations

| Design | Partzyme A | PASS primer S2 size | Ct (ave) | ΔCt from original |
|---|---|---|---|---|
| Loop | Matched | Original - 7 bp | 21.5 | |
| | | 3' end - 6 bp | 26.7 | 5.2 |
| | | 3' end - 5 bp | 30.2 | 8.7 |
| | | 3' end - 4 bp | No Ct | — |
| | | 3' end - 3 bp | No Ct | — |
| | | 5' end - 6 bp | 24.0 | 2.5 |
| | | 5' end - 5 bp | No Ct | |
| | Loops out 1 base from amplicon (5_6) | Original - 7 bp | 22.6 | 1.1 |
| | Loops out 2 bases from amplicon (5_5) | Original - 7 bp | 26.8 | 5.3 |
| | Loops out 1 base from partzyme (7) | 5' end - 6 bp | 24.6 | 3.1 |
| | Loops out 2 bases from partzyme (7) | 5' end - 5 bp | No Ct | — |
| Planar | Matched | Original - 7 bp | 21.3 | |
| | | 3' end - 6 bp | 21.8 | 0.5 |
| | | 3' end - 5 bp | 22.5 | 1.3 |
| | | 3' end - 4 bp | 23.1 | 1.8 |
| | | 3' end - 3 bp | 25.6 | 4.3 |
| | | 5' end - 6 bp | 21.6 | 0.3 |
| | | 5' end - 5 bp | 22.7 | 1.4 |
| | Loops out 1 base from amplicon (5_6) | Original - 7 bp | 22.2 | 0.9 |
| | Loops out 2 bases from amplicon (5_5) | Original - 7 bp | 27.6 | 6.3 |
| | Loops out 1 base from partzyme (7) | 5' end - 6 bp | 22.4 | 1.1 |
| | Loops out 2 bases from partzyme (7) | 5' end - 5 bp | 27.7 | 6.4 |

When the S2 region of the forward PASS primer containing US that was looped was decreased in length from the 3' end from 7, to 6 and 5 bases the shorter primers still produced a detectable signal however the Ct was increased by 5.2 and 8.7 respectively (Table 18). Decreasing S2 any further from the 3' end did not produced a detectable signal under the reaction conditions tested. When the S2 region of the loop PASS primer was decreased from the 5' end from 7 bases to 6 bases the Ct was increased by 2.5 however decreasing the length further resulted in no detectable signal under the reaction conditions tested.

When the S2 region of the forward PASS primer that contained US that was planar was decreased in length from the 3' end from 7, to 6 and 5 bases all primers still produced a detectable signal with little impact on the Ct value (Table 18). Decreasing S2 further from the 3' end to 4 and 3 bases still produced a detectable signal however the Ct was increased by 1.8 and 4.3 respectively (Table 18). When the S2 region of the planar PASS primer was decreased from the 5' end from 7 bases to 6 and 5 bases, a detectable signal was still produced without significantly impacting on the Ct value (Table 18).

As a control, the partzymes specific for shortened PASS primers were combined with the longer PASS primer and vice versa. This resulted in either bases being looped out from the amplicon or from the partzyme. For both the loop and planar PASS primers when only one base is looped out from either the amplicon or the partzyme there is only a small increase in Ct by ~1, except for the loop PASS primer where the 1 base looped out partzyme had a Ct increased by 3.1 under these experimental conditions. Further when the partzyme or amplicon contained a looped out region of 2 bases the Ct was increased by 5 to 6 Cts, except for the loop PASS primer where the looped out partzyme had no detectable signal under these experimental conditions.

Overall, when the PASS primer contained a US in planar formation the S2 region could be decreased to 4 bases without overly affecting the efficiency of the reaction (Ct value). However, when the PASS primer contained a US in loop formation decreasing the S2 region even by 1 base this had a significant impact on the Ct value. Of note is that for the Loop PASS primers there is no gap between S1 and S2 under the loop region which could be increasing the stringency of the reaction.

The observations of this experiment demonstrate there is considerable flexibility in design of the regions of the PASS primers which follow either the Loop or Planar format. The optimal length for any region will depend on the target sequence, the specific application and experimental conditions including but not limited to the buffer, salt concentration, reaction temperature, cycling times and other factors.

Example 11: Investigation into Varying the Length of the US Insert Contained within a PASS Primer In this example, the length of the US insert in the PASS primer was investigated to determine the influence on amplification efficiency. In previous examples the USI was 10 bases long.

PASS Primers were designed that contained looped US that was either, 8, 9, 10, 12 or 13 bases long or planar US that was either, 10, 12, 13, 17, 22 or 29 bases long. Each PASS primer was combined with MNAzyme detection for a readout in qPCR to determine if various scenarios of length of the US inserts in the PASS primer were compatible with amplification and detection of the CCB gene.

11.1. Partzyme Oligonucleotides

Partzymes were designed to specifically target the CCB gene and the cUS introduced via a PASS primer. In the following sequences the bases in bold hybridize with the target sequence of interest and bases underlined hybridise to the cUS. The "-P" indicates 3' phosphorylation of the oligonucleotide. All sequences are written 5' to 3'.

SEQ ID NO: 86 partzyme B CCBB/2-P:
TGCCCAGGGAGGCTAGCTGGTCCATGGCTTCTGGGTA

SEQ ID NO: 89 partzyme A CCB_2i2A/2-P:
AGACATACTACCAGAGCCCAACAACGAGAGGAAACCTT 11.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by an "IB" in the name of the substrate below). Cleavage of the substrate was monitored at 530 nm (FAM emission wavelength) with excitation at 485 nm (FAM excitation wavelength). The reporter substrate for this example is shown below with the sequence, 5' to 3'. The lower case bases represent RNA and the upper case bases represent DNA.

SEQ ID NO: 94 Substrate Sub2-FIB:

AAGGTTTCCTCguCCCTGGGCA 11.3. Target Sequence and PCR Primers for Amplification of CCB DNA The target sequence for this example was the CCB gene in human gDNA extracted from the IM9 cell line (Promega). The oligonucleotide PASS primers listed below. In the following sequences the bases underlined are the US inserts. All sequences are written 5' to 3'.

SEQ ID NO: 7 Reverse primer 3CCB:
CTCAGGAATTTCCCAGCTAC

SEQ ID NO: 13 Forward PASS primer 5CCB_2i2Loop:
TTCTTCTTGGATGGTCATCTAGACATACTACCAGAGC SEQ ID NO: 108 Forward PASS primer 5CCB_2i2(-1)Loop_US9:
TTCTTCTTGGATGGTCATCTGACATACTACCAGAGC SEQ ID NO: 109 Forward PASS primer 5CCB_2i2(-2)Loop_US8:
TTCTTCTTGGATGGTCATCTACATACTACCAGAGC SEQ ID NO: 110 Forward PASS primer 5CCB_2i2(+2)Loop_US12:
TTCTTCTTGGATGGTCATCTAAAGACATACTACCAGAGC SEQ ID NO: 111 Forward PASS primer 5CCB_2i2(+3)Loop_US13:
TTCTTCTTGGATGGTCATCTCAAAGACATACTACCAGAGC SEQ ID NO: 14 Forward PASS primer 5CCB_2i2Planar:
CTTGTCTCAGTTCTTCTTGGAGACATACTACCAGAGC SEQ ID NO: 112 Forward PASS primer 5CCB_2i2(+2)Planar_US12:
TCTCTTGTCTCAGTTCTTCTTAAAGACATACTACCAGAGC SEQ ID NO: 113 Forward PASS primer 5CCB_2i2(+3)Planar_US13:
GTCTCTTGTCTCAGTTCTTCTCAAAGACATACTACCAGAGC SEQ ID NO: 114 Forward PASS primer 5CCB_2i2(+7)Planar_US17:
CTCAAGTCTCTTGTCTCAGTTCCCGACAAAGACATACTACCAGAGC -continued SEQ ID NO: 115 Forward PASS primer
5CCB_2i2(+12)Planar_US22:
GGCTCTCAAGTCTCTTGTCTC<u>CAAGTCCGACAAAGACATACTA</u>CCAGAGC SEQ ID NO: 116 Forward PASS primer
5CCB_2i2(+19)Planar_US29:
TCTGGGGGCTCTCAAGTCTC<u>CATGACACAAGTCCGACAAAGACATACTAC</u>
CAGAGC 11.4. Reaction Components: Amplification and Detection of Target Sequence Real-time amplification and detection of the target sequence was performed in a total reaction volume of 25 µL. The reactions were conducted in a Mx3005p (Stratagene). The cycling parameters were 95° C. for 2 minutes, 5 cycles of 95° C. for 15 seconds and 55° C. for 30 seconds, 40 cycles of 95° C. for 15 seconds and 52° C. for 60 seconds (data collected at the 52° C. step). Reactions were run in duplicate and contained 40 nM forward PASS primer, 200 nM partzyme A (CCB_2 i2A/2-P), 200 nM of reverse primer (3CCB), 200 nM partzyme B (CCBB/2-P), 200 nM substrate (Sub2-FIB), 8 mM MgCl$_2$, 200 µM of each dNTP, 10 units RiboSafe RNAase Inhibitor (Bioline), 1× ImmoBuffer (Bioline), 2 units of MyTaq™ HS DNA polymerase (Bioline) and either gDNA template (50 ng) or no target (NF H2O).

11.6. Results: Amplification of Target and Cleavage of Reporter Substrate

The PASS primers were used to produce amplicons for the real-time detection of CCB with detection via partzymes complementary to both the cUS's and amplified target specific sequence. This reaction showed an increase in fluorescence over time when the target sequence used was human gDNA amplified via qPCR. The fluorescence of the no-DNA target control was lower than that in the DNA target-containing reactions and did not increase during the reaction. This demonstrates that the increase in fluorescence produced in target-containing reactions is due to target dependent assembly of catalytically active MNAzyme that then cleaved the reporter substrate.

TABLE 19

Ct values for different PASS primers

| Design | Reaction type | Size US bp | Ct (Ave) | ΔCt from original |
|---|---|---|---|---|
| Loop | Original | 10 | 21.5 | |
|  | US − 2 bp | 8 | 21.5 | 0 |
|  | US − 1 bp | 9 | 21.5 | 0 |
|  | US + 2 bp | 12 | 21.8 | 0.3 |
|  | US + 3 bp | 13 | 23.0 | 1.5 |
| Planar | Original | 10 | 21.4 | |
|  | US + 2 bp | 12 | 21.2 | −0.2 |
|  | US + 3 bp | 13 | 21.4 | 0 |
|  | US + 7 bp | 17 | 22.0 | 0.6 |
|  | US + 12 bp | 22 | 22.1 | 0.7 |
|  | US + 19 bp | 30 | 22.6 | 1.2 |

When the forward PASS primer contained US that was looped, decreasing the length of the US to 9 and 8 bases did not affect the Ct value and the detectable signal was similar to that observed for the original PASS primer containing a US insert of 10 bases (Table 19). Likewise, increasing the US to 12 bases did not affect the Ct value, however there was a slight increase in the Ct value when the US was increased to 13 bases (Table 19) under the current experimental conditions.

When the forward PASS primer contained US that was planar, increasing the length of the US up to 22 bases had minimal impact on the Ct value (Table 19). Increasing the US to 29 bases increased the Ct value by 1.2 showing a slight impact on the amplification of the target sequence (Table 19) under the current experimental conditions.

Of note, in this example the same MNAzyme was used to test all US sizes whether the US was in a loop or planar formation. This removes any variability that might be encountered with different MNAzymes and results in the outcome being purely reflective of the amplification efficiency of the PASS primer.

The observations of this experiment demonstrate there is considerable flexibility in design of the length of US inserts within PASS primers which follow either the Loop or Planar format.

Example 12: Use of a PASS Partzyme to Skip Variant Sequence in Related Amplicons PASS partzymes are combined with variant-specific primers in an MNAzyme qPCR reaction. In a manner analagous to PASS primers, PASS partzymes can also be designed to contain regions that are mismatched with regard to the starting template target sequence (FIG. 10). In this example, primers are designed to specifically amplify the deletion variant sequences, but not wild type sequence, and the MNAzyme comprises a first PASS partzyme and a second fully matched "standard" partzyme that bind adjacently on the amplified target sequence of interest. The PASS partzyme contains a region of sequence not complementary to the target sequence, the unique sequence (US), which is designed to align where the variant sequence is contained in the amplicon so that one MNAzyme can be used to detect all variants. The US present in the PASS partzyme can be in planar formation where the number of non-complementary bases in the PASS partzyme matches the number of unbound bases in the target sequence (FIG. 10, panel ii (a)). Alternatively, the US present in the PASS partzyme can be looped, when the number of non-complementary bases in the partzyme is greater or smaller than the target sequence and the sequence bulges or loops out (FIG. 10, panel ii (b)). Formation of active MNAzymes from partzyme components results in the cleavage of the universal probe labeled with fluorophore and quencher dye pair, producing a signal that can be monitored in real-time.

In this example, a specific primer was designed to amplify each of four EGFR exon 19 deletion variants, c.2236-2250del15 (v4), c.2239-2248>C (v13), c.2239-2253del15 (v15) or c.2240-2257del18 (v20). Each variant sequence contains different lengths of deleted sequence creating variable targets each requiring specific 5' primers, which were designed such that they spanned the various deletion junctions. A PASS partzyme A was designed to detect all four variant amplicons since the US region of the PASS partzyme was designed to align with the variable regions of the deletion amplicons. The PASS partzyme A formed a planar formation with v13 and a loop formation with variants v4, v15 and v20. The amplified variants were either assayed with an MNAzyme containing a PASS partzyme A and a "standard" partzyme B or with an MNAzyme containing fully matched standard partzymes A and B, which are complementary to a fully conserved region central to all variant amplicons or any amplicons resulting from mispriming from wild type template if this occurred. This is used as a control to demonstrate the effect of the US in the PASS partzyme on the specificity of the MNAzyme to detect the variant sequences.

12.1. Partzyme Oligonucleotides

Partzymes were designed that were either fully matched "standard" partzymes where the sensor arm was fully complementary to the target sequence or "PASS" partzymes where a region of sequence not complementary to the amplicon (US) has been inserted into the sensor arm between two regions that are complementary to the amplicon. In the following sequences, the bases in bold hybridize with the target sequence of interest and bases underlined are the unique sequence (US) which is mismatched with respect to all four target sequences. The "-P" indicates 3' phosphorylation of the oligonucleotide. All sequences are written 5' to 3'.

SEQ ID NO: 117 partzyme B EGFR _1B/56-P:
TGGCGTGGAGAGGCTAGCTCGATGTGAGTTTCTGCTTTGCTG

SEQ ID NO: 118 partzyme A EGFR_1A/56-P:
GAAAGCCAACAAGGAAATCCTACAACGAGGGGTCGAG SEQ ID NO: 119 partzyme B EGFR_2B/56-P:
TGGCGTGGAGAGGCTAGCTAACAAGGAAATCCTCGATGTGA

SEQ ID NO: 120 PASS partzyme A EGFR_2US15A/56-P:
AAGTTAAAATTCCCGTCGCTATCAACTCTAGCTGTAGCATG**AAAGCA
CAACGAGGGGTCGAG**

12.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 121 Substrate Sub56-FIB:
CTCGACCCCguCTCCACGCCA

12.3. PCR Primers for Amplification of EGFR DNA

In vitro amplification of plasmid DNA was performed using the oligonucleotide PCR primers listed below. In the following sequences the bases underlined are the variant bases with respect to the wild type. The forward primers are deletion specific and the reverse primer is constant for all. All sequences are written 5' to 3'.

SEQ ID NO: 122 Reverse primer 3EGFR:
GCCTGAGGTTCAGAGCCATGG

SEQ ID NO: 123 Forward primer 5EGFRv4:
TTAAAATTCCCGTCGCTATCAAG<u>AC</u>

SEQ ID NO: 124 Forward primer 5EGFRv13:
ATTCCCGTCGCTATCAAGGAA<u>CC</u>

SEQ ID NO: 125 Forward primer 5EGFRv15:
TCCCGTCGCTATCAAGGAA<u>TCTC</u>

SEQ ID NO: 126 Forward primer 5EGFRv20:
TCCCGTCGCTATCAAGGAAT<u>CGA</u>

12.4. Target Sequence

DNA Plasmids containing sequence corresponding to a region of exon 19 of the EGFR gene were used as template (IDT). Plasmid contained either wild type sequence or sequence corresponding to EGFR exon 19 deletion variants, c.2236-2250del15 (v4), c.2239-2248>C (v13), c.2239-2253del15 (v15) or c.2240-2257del18 (v20). Plasmids were linearised before use by digesting with the restriction enzyme EcoR1 (Thermo Scientific), following the manufacturer's instructions.

Genomic DNA extracted from the IM9 cell line was used as a control DNA sample representing human wild type EGFR DNA.

12.5. Reaction Components: Amplification of Target Sequence

Real-time amplification and detection of the target sequence was performed in a total reaction volume of 25 µL. The reactions were conducted in a CFX96™ Real-Time PCR detection System (BioRad). The cycling parameters were, 95° C. for 2 minutes, 10 cycles of 95° C. for 15 seconds and 61° C. for 60 seconds (minus 1° C. per cycle), 40 cycles of 95° C. for 15 seconds and 52° C. for 60 seconds (data collected at the 52° C. step). Each set of reaction conditions was tested in duplicate and contained 40 nM deletion-specific forward primer, 100 nM of partzyme A and 200 nM of partzyme B, as outlined in Table 20. All reactions also contained 200 nM of reverse primer (3EGFR), 200 nM substrate (Sub56-FIB), 8 mM MgCl$_2$, 200 µM of each dNTP, 10 units RiboSafe RNase inhibitor (Bioline), 1× ImmoBuffer (Bioline), 2 units of MyTaq™ HS DNA polymerase (Bioline) and either Plasmid DNA template for v4 ($10^4$ copies) or v13 ($10^4$ copies) or v15 ($10^4$ copies) or v20 ($10^4$ copies); or wild type (WT) ($10^4$ copies), or IM9 gDNA (35 ng) or either v4, v13, v15 or v20 plasmid template diluted ~1 in 100 in a constant background of IM9 gDNA template (100 ng) or no target (NF H$_2$O).

TABLE 20

Forward primer, partzymes and template combinations for the variant assays

| Design | Forward Primer | Partzymes | Template | Reaction type |
|---|---|---|---|---|
| EGFR v4 2236-2250del15 | 5EGFRv4 | PASS EGFR_2B/56-P & EGFR_2US15A/56-P | v4 plasmid v4 plasmid (1/100) WT plasmid IM9 NF H$_2$0 | Test Test Negative control Negative control No template |
| | | Standard EGFR_1B/56-P & EGFR_1A/56-P | v4 plasmid v4 plasmid (1/100) WT plasmid IM9 NF H$_2$0 | Test Test Negative control Negative control No template |
| EGFR v13 2239-2248 > C | 5EGFRv13 | PASS EGFR_2B/56-P & EGFR_2US15A/56-P | v13 plasmid v13 plasmid (1/100) WT plasmid IM9 NF H$_2$0 | Test Test Negative control Negative control No template |
| | | Standard EGFR_1B/56-P & EGFR_1A/56-P | v13 plasmid v13 plasmid (1/100) WT plasmid IM9 NF H$_2$0 | Test Test Negative control Negative control No template |

TABLE 20-continued

Forward primer, partzymes and template combinations for the variant assays

| Design | Forward Primer | Partzymes | Template | Reaction type |
|---|---|---|---|---|
| EGFR v15 2239-2253del15 | 5EGFRv15 | PASS EGFR_2B/56-P & EGFR_2 US15A/56-P | v15 plasmid v15 plasmid (1/100) WT plasmid IM9 NF H₂0 | Test Test Negative control Negative control No template |
| | | Standard EGFR_1B/56-P & EGFR_ 1A/56-P | v15 plasmid v15 plasmid (1/100) WT plasmid IM9 NF H₂0 | Test Test Negative control Negative control No template |
| EGFR v20 2240-2257del18 | 5EGFRv20 | PASS EGFR_2B/56-P & EGFR_ 2US15A/56-P | v20 plasmid v20 plasmid (1/100) WT plasmid IM9 NF H₂0 | Test Test Negative control Negative control No template |
| | | Standard EGFR_1B/56-P & EGFR_ 1A/56-P | v20 plasmid v20 plasmid (1/100) WT plasmid IM9 NF H₂0 | Test Test Negative control Negative control No template |

12.6. Results: Amplification of Target and Cleavage of Reporter Substrate

For all reactions, the fluorescence of the no template control was lower than that in the DNA target-containing reactions. This demonstrates that the increase in fluorescence produced in target-containing reactions is due to target dependent assembly of catalytically active MNAzymes that then cleaved universal reporter substrates.

The deletion-specific forward primers were used to produce amplicons for the real-time detection of the EGFR deletion variants. The ΔCt was used as a measure of the specificity of the the primer/partzyme A combinations and is calculated as the difference in Ct between that for the deletion amplicons to that from background amplification of wild type template. The primers designed to amplify deletions v4 and v15 exhibited high specificity for the deletions with ΔCts at 9.6 or greater in all reactions. In contrast the primer designed to be specific for the v20 deletion behaved non-specifically, amplifying both v20 and wild type sequence. The primer designed to be specific for v13 produced ΔCts of 6.6 and 4.8 for the wild type plasmid and IM9 gDNA respectively when using the standard partzyme.

For v4 and v15 PASS partzyme assays, a signal was not produced when gDNA (IM9) template alone was used and the WT plasmid, produced ΔCts>15 Cts after the variant template. For v20, WT plasmid and IM9 gDNA produced ΔCts of 4.6 and 5.5 respectively and for v13, WT plasmid and IM9 gDNA produced ΔCts of 10.3 and 10.2 respectively (Table 21).

TABLE 21

Ct values for MNAzyme qPCR performed using deletion-specific primers and a universal MNAzyme

| Design | Type of partzyme A | Template | Reaction type | Ct (Ave) | ΔCt |
|---|---|---|---|---|---|
| EGFR v4 | PASS | v4 plasmid | Test | 22.6 | |
| | | v4 plasmid (1/100) | Test | 31.8 | — |
| | | WT plasmid | Negative control | 38.4 | 15.8 |
| | | IM9 | Negative control | No Ct | >17.4 |
| | | NF H₂0 | No template | No Ct | |
| | Standard | V4 | Test | 17.2 | |
| | | V4 plasmid (1/100) | Test | 23.9 | — |
| | | WT | Negative control | 26.8 | 9.6 |
| | | IM9 | Negative control | 27.6 | 10.4 |
| | | NF H₂0 | No template | No Ct | |
| EGFR v13 | PASS | v13 plasmid | Test | 20.1 | |
| | | v13 plasmid (1/100) | Test | 26.9 | — |
| | | WT plasmid | Negative control | 30.3 | 10.3 |
| | | IM9 | Negative control | 30.4 | 10.2 |
| | | NF H₂0 | No template | No Ct | |
| | Standard | v13 plasmid | Test | 18.2 | |
| | | v13 plasmid (1/100) | Test | 22.4 | — |
| | | WT plasmid | Negative control | 24.6 | 6.6 |
| | | IM9 | Negative control | 23.0 | 4.8 |
| | | NF H₂0 | No template | No Ct | |
| EGFR v15 | PASS | v15 plasmid | Test | 20.6 | |
| | | v15 plasmid (1/100) | Test | 28.2 | — |
| | | WT plasmid | Negative control | 35.6 | 15 |
| | | IM9 | Negative control | No Ct | >19.4 |
| | | NF H₂0 | No template | No Ct | |
| | Standard | v15 plasmid | Test | 18.0 | |
| | | v15 plasmid (1/100) | Test | 24.4 | — |
| | | WT plasmid | Negative control | 32.1 | 14.1 |
| | | IM9 | Negative control | 36.2 | 18.3 |
| | | NF H₂0 | No template | No Ct | |
| EGFR v20 | PASS | v20 plasmid | Test | 20.1 | |
| | | v20 plasmid (1/100) | Test | 25.1 | — |
| | | WT plasmid | Negative control | 24.7 | 4.6 |
| | | IM9 | Negative control | 25.7 | 5.5 |
| | | NF H₂0 | No template | No Ct | |
| | Standard | v20 plasmid | Test | 18.7 | |
| | | v20 plasmid (1/100) | Test | 19.5 | — |
| | | WT plasmid | Negative control | 18.5 | −0.2 |
| | | IM9 | Negative control | 19.3 | 1.0 |
| | | NF H₂0 | No template | No Ct | |

N.B. When no Ct was produced for a negative control sample the final Ct of 50 was used to produce the ΔCt and a greater than symbol (>) placed in front to indicate that the ΔCt would be expected to be higher than this value.

When variant template was diluted 1 in 100 the v4, v13 and v15 assays could detect and discriminate the deletion amplicons from the non-specific wild type background signal for both the PASS and to some degree the standard partzyme assays.

Overall, the reactions using standard partzymes for the detection of amplicons produced ΔCts, which were less than that produce by the PASS partzyme assay (Table 21). This demonstrates the use of a PASS partzyme greatly improves the specificity of the reaction over using a standard partzyme. Furthermore, the same PASS partzyme whether it bound to the amplicons in a loop (V4, v15 and v20) or planar formation (v13) was able to detect all four variants irrespective of the sequence deleted. The MNAzyme in this assay used one partzyme with a sensor arm which had two regions which were complementary to all four deletion variants and one region (the US insert) which was mismatched to all four in the regions which were variant between the amplicons. As such this parztyme would be anticipated to bind to all four amplicons with similar efficiency thus allowing detection of all four variants simultaneously with one MNAzyme.

Example 13: Combining a PASS Partzyme with a PASS Primer to Skip Variant Sequence in an Amplicon and Improve Discrimination Between Variant and Wild Type Sequence Another PASS PCR strategy involves the combination of a PASS partzyme with a PASS primer to further improve the reaction efficiency and specificity when analyzing related amplicons. This strategy involves a PASS primer designed with (i) S2 specific for a deletion variant in EGFR exon 19, (ii) S1 region common to all EGFR sequence and (iii) a first US insert (US1) located between S1 and S2 which is not complementary to the target sequence (FIG. 11, panel (i)). The strategy also has an MNAzyme comprising a PASS partzyme A. The target sensor arm of the PASS partzyme A contains several domains comprising (i) US1 (matched to all amplicons generated from PASS primers), (ii) a second US insert US2 (mismatched to all amplicons generated from PASS primers) and (iii) regions which are complementary to the starting sequence of the target. The US2 region of the PASS partzyme is not complementary to the amplified target sequence and is designed such that the US2 aligns on the amplicon where the sequence varies due to the presence of different deletions. The PASS partzyme may form a planar or looped out conformation when it binds to the target amplicon (FIG. 11, panel (ii)).

In this example, fully matched "standard" deletion-specific primers and deletion-specific PASS primers were designed to amplify EGFR exon 19 deletion c.2235-2249del15 (v2). The amplified deletion variants were either assayed in real time with (i) an MNAzyme containing a PASS partzyme which formed either a planar or looped out US2 but lacking US1 (for use with standard primers) or (ii) an MNAzyme containing a PASS partzyme incorporating both US1 and US2, in a planar or loop formation (for use with PASS primer).

13.1. Partzyme Oligonucleotides

Partzymes were designed that were either (i) standard partzymes where the sensor arm was fully complementary to the amplicon, (ii) PASS partzymes containing only alternate US2 inserts (designated either US15 or US9; i.e. regions of sequence not complementary to the target amplicon) or (iii) PASS partzymes containing US2 (either US15 or US9) and US1 (i4) (which binds to the cUS1 inserted into the amplicon by the PASS primer). In addition, standard partzymes were designed to bind all amplicons is outside of the variable region (variant and wild type) in a region which did not overlap with the primer region of the amplicon. PASS partzymes were designed to bind all deletion variant amplicons across the variable region in the EGFR exon 19, when amplified with variant deletion-specific primers. In the following sequences, the bases in bold hybridize with the target sequence of interest and bases underlined are the second unique sequence insert (US2) which is mismatched with respect to the template. The region underlined and italic represents US1 (i4), incorporated into the amplicon by the PASS primer. The "-P" indicates 3' phosphorylation of the oligonucleotide. All sequences are written 5' to 3'.

SEQ ID NO: 118 partzyme B EGFR_1A/56-P:
GAAAGCCAACAAGGAAATCCTACAACGAGGGGTCGAG

SEQ ID NO: 117 partzyme B EGFR_1B/56-P:
TGGCGTGGAGAGGCTAGCTCGATGTGAGTTTCTGCTTTGCTG

SEQ ID NO: 119 partzyme B EGFR_2B/56-P:
TGGCGTGGAGAGGCTAGCTCAACAAGGAAATCCTCGATGTGA

SEQ ID NO: 120 PASS partzyme A EGFR_2US15A/56-P:
AAGTTAAAATTCCCGTCGCTATCAACTCTAGCTGTAGCATGAAAGCACA

ACGAGGGGTCGAG

SEQ ID NO: 127 PASS partzyme A EGFR_2US9A/56-P:
AAGTTAAAATTCCCGTCGCTATCAACTGTAGCATGAAAGCACAACGAGG

GGTCGAG

SEQ ID NO: 128 PASS partzyme A EGFR_2i4US9A/56-P:
CCGTC*TCAATACCAT*GCTATCAACTGTAGCATGAAAGCACAACGAGGGG

TCGAG

SEQ ID NO: 129 PASS partzyme A
EGFR_2i4US15A/56-P:
CCGTC*TCAATACCAT*GCTATCAACTCTAGCTGTAGCATGAAAGCACAAC

GAGGGGTCGAG 13.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 121 Substrate Sub56-FIB:
CTCGACCCCguCTCCACGCCA 13.3. PCR Primers for Amplification of EGFR DNA In vitro amplification of plasmid DNA was performed using the deletion-specific oligonucleotide PCR primers listed below. In the following sequences the bases underlined are the variant bases and bases underlined and in italics represent the US1 (i4). All sequences are written 5' to 3'.

SEQ ID NO: 122 Reverse primer 3EGFR:
GCCTGAGGTTCAGAGCCATGG

SEQ ID NO: 130 Forward primer 5EGFRv2:
AGTTAAAATTCCCGTCGCTATCAAAA

SEQ ID NO: 131 Forward PASS
primer 5EGFRv2_i4:
GAAAGTTAAAATTCCCGTC*TCAATACCAT*GCTATCAAAA 13.4. Target Sequence DNA Plasmids containing sequence corresponding to a region of exon 19 of the EGFR gene were used as template (IDT). Plasmid contained either wild type sequence or sequence corresponding to EGFR deletion variant v2. Plasmids were linearised before use by digesting with the restriction enzyme EcoR1 (Thermo Scientific), following the manufacturer's instructions. Genomic DNA extracted from the IM9 cell line was used as a control DNA sample representing human wild type EGFR DNA.

13.5. Reaction Components: Amplification of Target Sequence

Real-time amplification and detection of the target sequence was performed in a total reaction volume of 25 µL. The reactions were conducted in a CFX96™ Real-Time PCR detection System (BioRad). The cycling parameters were, 95° C. for 2 minutes, 10 cycles of 95° C. for 15 seconds and 61° C. for 60 seconds (minus 1° C. per cycle), 40 cycles of 95° C. for 15 seconds and 52° C. for 60 seconds (data collected at the 52° C. step). Each set of reaction conditions was tested in duplicate and contained 40 nM forward deletion-specific primer, 100 nM of partzyme A and 200 nM of partzyme B as outlined in Table 22. All reactions contained 200 nM of reverse primer (3EGFR), 200 nM substrate (Sub56-FIB), 8 mM $MgCl_2$, 200 µM of each dNTP, 10 units RiboSafe RNase inhibitor (Bioline), 1× ImmoBuffer (Bioline), 2 units of MyTaq™ HS DNA polymerase (Bioline) and either plasmid DNA template for v2 ($10^4$ copies), v2 plasmid ($10^2$ copies) template diluted ~1 in 100 in a constant background of IM9 gDNA template (35 ng) or wild type plasmid (WT) ($10^4$ copies), or IM9 gDNA (35 ng) or no template (NF $H_2O$).

TABLE 22

Primer, partzyme and template combinations for the variant assays

| Reaction | Forward Primer | Partzymes | Template | Reaction type |
|---|---|---|---|---|
| Standard Primer/ Standard MNAzyme No US | 5EGFRv2 | EGFR_1A/56-P EGFR_1B/56-P | v2 plasmid v2 plasmid (1/100) WT plasmid IM9 NF $H_2O$ | Test Test Negative control Negative control No template |
| Standard primer/ Looped PASS partzyme A US2 only | | EGFR_2US15A/ 56-P EGFR_2B/56-P | v2 plasmid v2 plasmid (1/100) WT plasmid IM9 NF $H_2O$ | Test Test Negative control Negative control No template |
| Standard primer/ Planar PASS partzyme A US2 only | | EGFR_2US9A/ 56-P EGFR_2B/56-P | v2 plasmid v2 plasmid (1/100) WT plasmid IM9 NF $H_2O$ | Test Test Negative control Negative control No template |
| PASS primer/ Looped PASS partzyme A US1 & US2 | 5EGFRv2_i4 | EGFR_2i4US15A/56-P EGFR_2B/56-P | v2 plasmid v2 plasmid (1/100) WT plasmid IM9 NF H20 | Test Test Negative control Negative control No template |
| PASS primer/Planar PASS partzyme A US1 & US2 | | EGFR_2i4US9A/ 56-P EGFR_2B/56-P | v2 plasmid v2 plasmid (1/100) WT plasmid IM9 NF H20 | Test Test Negative control Negative control No template |

13.6. Results: Amplification of Target and Cleavage of Reporter Substrate

For all reactions, the fluorescence of the no template control was lower than that in the DNA target-containing reactions. This demonstrates that the increase in fluorescence produced in target-containing reactions is due to target dependent assembly of catalytically active MNAzymes that then cleaved the universal reporter substrate.

All combinations of primers and MNAzymes containing a PASS partzyme resulted in greater specificity when compared to the assays containing standard primers and standard MNAzyme (Table 23). The ΔCt of for the fully matched "standard" detection of v2 ranged from 6 to 7 Cts with the wild type signal only ~1 to 2 Ct's behind the sample diluted 1 in 100.

TABLE 23

Ct values for MNAzyme qPCR performed using variant specific primers and a universal MNAzyme

| Forward primer | Partzyme A | Template | Reaction type | Ct (Ave) | ΔCt |
|---|---|---|---|---|---|
| Standard | Standard | v2 plasmid | Test | 16.6 | |
| | | v2 plasmid (1/100) | Test | 21.9 | — |
| | | WT plasmid | Negative control | 23.7 | 7.1 |
| | | IM9 | Negative control | 22.7 | 6.1 |
| | | NF $H_2O$ | No template | No Ct | |
| | Looped PASS (US2) | v2 plasmid | Test | 25.3 | |
| | | v2 plasmid (1/100) | Test | 35.0 | — |
| | | WT plasmid | Negative control | No Ct | >14.7 |
| | | IM9 | Negative control | No Ct | >14.7 |
| | | NF $H_2O$ | No template | No Ct | |
| | Planar PASS (US2) | v2 plasmid | Test | 23.3 | |
| | | v2 plasmid (1/100) | Test | 31.8 | — |
| | | WT plasmid | Negative control | 37.9 | 14.6 |
| | | IM9 | Negative control | 37.6 | 14.3 |
| | | NF $H_2O$ | No template | No Ct | |
| PASS (US1) | Looped PASS (US2 & US1) | v2 plasmid | Test | 19.0 | |
| | | v2 plasmid | Test | 26.3 | — |
| | | (1/100) | | | |
| | | WT plasmid | Negative control | 36.4 | 17.4 |
| | | IM9 | Negative control | 35.8 | 16.8 |
| | | NF $H_2O$ | No template | No Ct | |
| | Planar PASS (US2 & US1) | v2 plasmid | Test | 18.2 | |
| | | v2 plasmid (1/100) | Test | 25.2 | — |

TABLE 23-continued

Ct values for MNAzyme qPCR performed using variant
specific primers and a universal MNAzyme

| Forward primer | Partzyme A | Template | Reaction type | Ct (Ave) | ΔCt |
|---|---|---|---|---|---|
| & US1) | | WT plasmid | Negative control | 36.0 | 17.8 |
| | | IM9 | Negative control | 35.9 | 17.7 |
| | | NF H$_2$0 | No template | No Ct | |

N.B. When no Ct was produced for a negative control sample the final Ct of 50 was used to produce the ΔCt and a greater than symbol (>) placed in front to indicate that the ΔCt would be expected to be higher than this value.

The combination of a Standard primer and an MNAzyme comprised of a PASS partzyme containing only US2 that forms a planar alignment with the target sequence detected the target v2 earlier (Ct 23.3) compared to the PASS partzyme that forms a looped alignment with the target sequence (Ct 25.3). Both loop and planar PASS partzymes displayed similar high specificity when assayed with the wild type template (plasmid and gDNA), ΔCt of ~14.5 (Table 23). When variant template was diluted 1 in 100 the v2 assays containing a standard primer and a PASS partzyme containing only US2 could detect it and discriminate the signal from the non-specific amplification of the wild type with a ΔCt of ~5 to 6 (Table 23).

The combination of a PASS primer and an MNAzyme comprised of a PASS partzyme containing US2 and US1 that forms a planar alignment with the target sequence detected the target v2 slightly earlier (Ct 18.2) compared to the PASS partzyme that forms a looped alignment with the target sequence (Ct 19.0). The assay containing the planar PASS partzymes displayed slightly more specificity compared to the looped PASS partzyme when assayed with the wild type template (plasmid and gDNA). When variant template was diluted 1 in 100 the v2 assays containing a PASS primer and a PASS partzyme containing US2 and US1 detected and discriminated the signal from the non-specific amplification of the wild type with a ΔCt of ~10.

The addition of the PASS primer to the PASS PCR strategy containing a PASS partzyme improved the efficiency of the reaction with earlier Cts and the specificity of the reaction with greater ΔCts. The experiment demonstrates the capacity to combine PASS primers with PASS partzymes for analysis of related sequences in assays which are highly specific and efficient. In this example the use of deletion-specific PASS primers together with a single PASS partzyme with incomplete, but equal, complementarity with the variant sequences allowed detection of deletion amplicons simultaneously in real time.

Example 14: Testing the Sensitivity of the PASS qPCR Strategy Containing a PASS Primer and an MNAzme Comprising a PASS Partzyme In this example, the EGFR deletion variant in exon 19 referred to as v2 is assayed using serial dilutions of the v2 template in a background of wild type template. Dilutions of 1 in 10, 100 and 1000 of v2 in a background of wild type template were tested.

The PASS primer in a planar formation containing US1 (i4) is used for the specific amplification of v2 sequence. The PASS primers are combined with MNAzyme qPCR whereby MNAzymes comprise a first PASS partzyme that binds to the complement of the unique sequence (cUS1), as well as amplified target sequence and also contains a region of sequence not complementary to the amplified target sequence (US2) which is designed such that the US2 aligns on the amplicon where the variant sequence lies. The second partzyme binds adjacently to the first partzyme within amplified target sequence of interest.

PASS qPCR was tested for the efficiency, linearity and sensitivity of the strategy.

14.1. Partzyme Oligonucleotides

Partzymes were designed to be either standard partzymes where the sensor arm was fully complementary to the amplicon, or PASS partzymes containing US2 (designated US9) and US1 insert i4 (which binds to the cUS1 inserted into the amplicon by the PASS primer). In the following sequences, the bases in bold hybridize with the target sequence of interest and bases underlined are the unique sequence (US2) which is mismatched with respect to the template. The region underlined and in italics represents US1 (i4). The "-P" indicates 3' phosphorylation of the oligonucleotide. All sequences are written 5' to 3'.

SEQ ID NO: 119 partzyme B EGFR_2B/56-P:
TGGCGTGGAGAGGCTAGCTCAACAAGGAAATCCTCGATGTGA

SEQ ID NO: 128 PASS partzyme A EGFR_2i4US9A/56-P:
CCGTC*TCAATACCAT*GCTATCAACTGTAGCATGAAAGCACAA

CGAGGGGTCGAG 14.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 121 Substrate Sub56-FIB:
CTCGACCCCguCTCCACGCCA 14.3. PCR Primers for Amplification of EGFR DNA In vitro amplification of plasmid DNA was performed using the deletion-specific oligonucleotide PCR primers listed below. In the following sequences the bases underlined are the variant bases (with respect to wild type sequence) and bases underlined and in italics represent the US1 (i4). All sequences are written 5' to 3'.

SEQ ID NO: 122 Reverse primer 3EGFR:
GCCTGAGGTTCAGAGCCATGG

SEQ ID NO: 131 Forward PASS primer 5EGFRv2_i4:
GAAAGTTAAAATTCCCGTC*TCAATACCAT*GCTATCA_AA_

14.4. Target Sequence

DNA Plasmids containing sequence corresponding to a region of exon 19 of the EGFR gene were used as template (IDT). Plasmid contained either wild type sequence or sequence corresponding to EGFR deletion variants v2. Plasmids were linearised before use by digesting with the restriction enzyme EcoR1 (Thermo Scientific), following the manufacturer's instructions. Genomic DNA extracted from the IM9 cell line was used as a control DNA sample representing human wild type EGFR gDNA.

14.5. Reaction Components: Amplification of Target Sequence

Real-time amplification and detection of the target sequence was performed in a total reaction volume of 25 µL. The reactions were conducted in a CFX96™ Real-Time PCR detection System (BioRad). The cycling parameters were, 95° C. for 2 minutes, 10 cycles of 95° C. for 15 seconds and 61° C. for 60 seconds (minus 1° C. per cycle), 40 cycles of 95° C. for 15 seconds and 52° C. for 60 seconds (data collected at the 52° C. step). Each set of reaction conditions was tested in duplicate and contained 40 nM forward primer (5EGFRv2_i4), 100 nM of partzyme A (EGFR 2i4US9A/56-P), 200 nM of partzyme B (EGFR 2B/56-P), 200 nM of reverse primer (3EGFR), 200 nM substrate (Sub56-FIB), 8 mM MgCl$_2$, 200 µM of each dNTP, 10 units RiboSafe RNase inhibitor (Bioline), 1x ImmoBuffer (Bioline), 2 units of MyTaq™ HS DNA polymerase (Bioline) and either plasmid DNA template for v2 ($10^4$ copies), plasmid DNA template for WT ($10^4$ copies), IM9 gDNA template (35 ng), plasmid DNA template for v2 ($10^4$ copies) diluted 1 in 10, 1 in 100 or 1 in 1000 in a constant background of IM9 gDNA template (35 ng) or no target (NF H$_2$O).

14.6. Results: Amplification of Target and Cleavage of Reporter Substrate

The PASS strategy was used to produce amplicons for the real-time detection and quantification of the EGFR deletion variant (v2). This reaction showed an increase in fluorescence over time when the reaction contained target sequence specific for v2 (Table 23).

TABLE 23

Ct values for EGFR v2 serial dilutions

|  | Template | Result |
|---|---|---|
| Ct (Ave) | $10^4$ copies v2 (deletion plasmid) | 18.4 |
|  | 1 in 10 | 21.9 |
|  | 1 in 100 | 25.5 |
|  | 1 in 1000 | 29.0 |
|  | 35 ng IM9 (wild type gDNA) | 34.1 |
|  | $10^4$ copies WT (plasmid) | 34.4 |
|  | No template | No Ct |
| ΔCt | $10^4$ copies v2 to IM9 | 15.7 |
|  | $10^1$ copies v2 to IM9 | 5.1 |
|  | $10^4$ copies v2 to WT | 16.0 |
|  | $10^1$ copies v2 to WT | 5.4 |
| Standard | Efficiency | 92% |
| curve | Linearity ($R^2$) | 0.994 |

The plasmid DNA template, specific for v2 deletion, was serially diluted 10-fold in a background of wild type (IM9) template. A standard curve, generated by plotting the log of the DNA concentration against the threshold cycle (Ct), resulted in a linear plot with an efficiency of 92% and an $R^2$ of 0.994. The Ct of each dilution is shown in Table 23. The Ct values shown in the table are an average of the results for duplicate reactions.

The PASS assay was able to detect the v2 sequence when diluted 1 in 1000 in a background of wild type. The signal from the negative control wild type templates was 15.7 Ct behind the signal from an equal number of copies of variant template.

The fluorescence of the no template control did not increase during the reaction. This demonstrates that the increase in fluorescence produced in target-containing reactions is due to target dependent assembly of catalytically active MNAzyme that then cleaved the reporter substrate.

This demonstrates that the PASS strategy as illustrated in FIG. 11, which combines PASS primers with PASS partzymes is highly efficient, specific and sensitive for the detection of variant sequences.

Example 15: PASS Primers and Pinch PASS Primers that can Loop Out Different Lengths of Target Sequence In this example, the size of the target specific region located between the target sequence complementary to the S1 and S2 regions of the PASS primer was increased in size from 2 (original Loop PASS primer) (FIG. 12 (*iii*)), to 20, 40, 60, 100 and 200 target bases (Target Loop PASS primers) (FIG. 12 (*i*)). To do this the S1 region of the PASS primer was moved further 5' such that the target sequence between the sequence complementary to the 3' and 5' target specific regions of the PASS primer had increasing sizes of non-complementary intervening sequence looped out.

The US in the Pinch PASS oligonucleotide is not an insert of non-complementary sequence per sec but rather comprises a Unique Sequence Junction (USJ) created by juxtaposing two non-contiguous sequences of the target. In the Pinch PASS oligonucleotide the sequences S1 and S2 are complementary to target and bind to two regions separated by intervening sequence. When the Pinch PASS oligonucleotide hybridises to the target the intervening target sequence loops out bringing the complementary target regions into close proximity creating amplicons which contain a USJ. In this example, Pinch PASS primers were tested with varying sizes of intervening target region located between the target sequence complementary to the S1 and S2 regions. The non-complementary intervening sequence looped out ranged in size from 10, 20, 60 and 100 target bases (FIG. 12 (*ii*)).

In this example, the Loop PASS primer, Target Loop PASS primers and Pinch PASS primers were used to amplify a region of the CCB gene and each one was combined with MNAzyme detection for a readout in qPCR to determine if the various scenarios of target looping by the different PASS primer types were compatible with amplification and detection of a gene.

15.1. Partzyme Oligonucleotides

Partzymes were designed to specifically target the CCB gene and/or any cUS introduced via a PASS primer. In the following sequences the bases in bold hybridize with the target sequence of interest, the bases in bold and underlined represent two bases either side of the USJ and bases underlined hybridise to the cUS insert. The "-P" indicates 3' phosphorylation of the oligonucleotide. All sequences are written 5' to 3'.

SEQ ID NO: 86 partzyme B CCBB/2-P:
TGCCCAGGGAGGCTAGCTGGTCCATGGCTTCTGGGTA

SEQ ID NO: 89 partzyme A CCB_2i2A/2-P:
<u>AGACATACTA</u>CCAGAGCCCAACAACGAGAGGAAACCTT SEQ ID NO: 132 partzyme A CCB_2LT1(10)A/2-P:
TTCTTCTTGG<u>CC</u>AGAGCCCAACAACGAGAGGAAACCTT SEQ ID NO: 133 partzyme A:
CCB_2LT1(20)A4/2-P
CTTGTCTCAG<u>CC</u>AGAGCCCAACAACGAGAGGAAACCTT SEQ ID NO: 134 partzyme A CCB_2LT1(60)A/2-P:
GATGTGCTAT<u>CC</u>AGAGCCCAACAACGAGAGGAAACCTT SEQ ID NO: 135 partzyme A:
CCB_2LT1(100)A/2-P
GTGAGTTGATCCAGAGCCCAACAACGAGAGGAAACCTT

15.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by an "IB" in the name of the substrate below). Cleavage of the substrate was monitored at 530 nm (FAM emission wavelength) with excitation at 485 nm (FAM excitation wavelength). The reporter substrate for this example is shown below with the sequence, 5' to 3'. The lower case bases represent RNA and the upper case bases represent DNA.

SEQ ID NO: 94 Substrate Sub2-FIB:
AAGGTTTCCTCguCCCTGGGCA

15.3. Target Sequence and PCR Primers for Amplification of CCB DNA

The target sequence for this example was the CCB gene in human gDNA, extracted from the IM9 cell line (Promega). The oligonucleotide PASS primers are listed below. In the following sequences the bases in bold hybridize with the target sequence of interest, the bases in bold and underlined represent two bases either side of the USJ and bases underlined are the USI. All sequences are written 5' to 3'.

SEQ ID NO: 7 Reverse primer 3CCB:
CTCAGGAATTTCCCAGCTAC

SEQ ID NO: 13 Forward PASS primer 5CCB_2i2Loop:
TTCTTCTTGGATGGTCATCTAGACATACTACCAGAGC

SEQ ID NO: 136 Forward PASS primer 5CCB_LTi2(20):
CTCTGGGGGCTCTCAAGTCTAGACATACTACCAGAGC

SEQ ID NO: 137 Forward PASS primer 5CCB_LTi2(40):
GGGTAGAAGTCTCTGGGGGCAGACATACTACCAGAGC

SEQ ID NO: 138 Forward PASS primer 5CCB_LTi2(60):
TGACGGTGTTGGGATGTGCTATAGACATACTACCAGAGC

SEQ ID NO: 139 Forward PASS primer 5CCB_LTi2(100):
GGTTTAACTGCAGGTGAGTTGATAGACATACTACCAGAGC

SEQ ID NO: 140 Forward PASS primer 5CCB_LTi2(200):
AGCATCGTATTTGGAAGAAGAGGAGACATACTACCAGAGC

SEQ ID NO: 141 Forward Pinch PASS primer 5CCB_LT1(10):
CTTGTCTCAGTTCTTCTTGGCCCAGAGC

SEQ ID NO: 142 Forward Pinch PASS primer 5CCB_LT1(20):
GCTCTCAAGTCTCTTGTCTCAGCCCAGAGC

SEQ ID NO: 143 Forward Pinch PASS primer 5CCB_LT1(60):
TGACGGTGTTGGGATGTGCTATCCAGAGC

SEQ ID NO: 144 Forward Pinch PASS primer 5CCB_LT1(100):
GGTTTAACTGCAGGTGAGTTGATCCAGAGC

15.4. Reaction Components: Amplification and Detection of Target Sequence

Real-time amplification and detection of the target sequence was performed in a total reaction volume of 25 µL. The reactions were conducted in a CFX96™ Real-Time PCR detection System (BioRad). The cycling parameters were 95° C. for 2 minutes, 5 cycles of 95° C. for 15 seconds and 55° C. for 30 seconds, 50 cycles of 95° C. for 15 seconds and 52° C. for 50 seconds (data collected at the 52° C. step). All reactions were run in duplicate and contained 40 nM forward PASS primer, 200 nM partzyme A (the combinations are listed in Table 24), 200 nM of reverse primer (3CCB), 200 nM partzyme B (CCBB/2-P), 200 nM substrate (Sub2-FIB), 8 mM MgCl$_2$, 200 µM of each dNTP, 10 units RiboSafe RNAase Inhibitor (Bioline), 1× ImmoBuffer (Bioline), 2 units of MyTaq™ HS DNA polymerase (Bioline) and either gDNA template (50 ng) or no target (NF H2O).

TABLE 24

PASS primer and partzyme A combinations

| Primer Design | Partzyme A | PASS Primer | # of bases in target not hybribized to primer regions S1 & S2 | US type | Design Name (& # with reference to FIG. 12) |
|---|---|---|---|---|---|
| Loop PASS primer USI | CCB_2i2A/2-P | 5CCB_2i2Loop | 2 | USI | Loop/2 (iii) |
| Target Loop PASS primers with USI | | 5CCB_LTi2(20) | 20 | USI | Loop/20 (i) |
| | | 5CCB_LTi2(40) | 40 | USI | Loop/40 (i) |
| | | 5CCB_LTi2(60) | 60 | USI | Loop/60 (i) |
| | | 5CCB_LTi2(100) | 100 | USI | Loop/100 (i) |
| | | 5CCB_LTi2(200) | 200 | USI | Loop/200 (i) |
| Pinch PASS primers with USJ | CCB_2LT1(10)A/2-P | 5CCB_LT1(10) | 10 | USJ | Pinch/10 (ii) |
| | CCB_2LT1(20)A/2-P | 5CCB_LT1(20) | 20 | USJ | Pinch/20 (ii) |
| | CCB_2LT1(60)A/2-P | 5CCB_LT1(60) | 60 | USJ | Pinch/60 (ii) |
| | CCB_2LT1(100)A/2-P | 5CCB_LT1(100) | 100 | USJ | Pinch/100 (ii) |

15.5. Results: Amplification of Target and Cleavage of Reporter Substrate

The results of amplification and detection are summarised in the following Table 25.

TABLE 25

Ct values for PASS primer and partzyme A combinations

| Design | Design Name | 50 ng Ct (Ave) | ΔCt from Loop/2 |
|---|---|---|---|
| Loop PASS primer with USI (primer looped out) | Loop/2 | 15.6 | — |
| Target Loop PASS Primers with USI (target looped out) | Loop/20 | 17.0 | 1.4 |
| | Loop/40 | 18.1 | 2.5 |
| | Loop/60 | 20.0 | 4.4 |
| | Loop/100 | 22.9 | 7.3 |
| | Loop/200 | 26.2 | 10.6 |
| Pinch PASS Primer with a USJ (target looped out) | Pinch/10 | 16.1 | 0.5 |
| | Pinch/20 | 16.3 | 0.7 |
| | Pinch/60 | 20.3 | 4.7 |
| | Pinch/100 | 26.7 | 11.1 |

The Ct values indicate that PASS primers which have either Loop or Pinch Designs can all efficiently amplify the target gene (Table 25). When the Loop/2 design was compared to Target Loop designs with the lengths of the sequence of target which did not bind to the Target Loop PASS primer ranging from 20 (Loop/20) to 40 (Loop/40) to 60 (Loop/60) to 100 (Loop/100) and then 200 (Loop/200) the Ct values were increased by 1.4, 2.5, 4.4, 7.3 and 10.6 respectively (Table 25). This indicates that primers can bind to and extend from the target despite the presence of long sequence stretches of targets which do not hybridize to the primer.

When the Loop/2 design was compared to the Pinch PASS primer designs with unbound sequence between S1 and S2 of 10 (Pinch/10), 20 (Pinch/40), 60 (Pinch/60) or 100 (Pinch/100) bases the Ct was increased by 0.5, 0.7, 4.7 and 11.1 respectively (Table 25). This demonstrates that Pinch primers can bind to and extend from the target despite the presence of long sequence stretches of target which does not hybridize to the primer. The Ct values for the Pinch/60 (vi) and the Loop/60 (iv) were very comparable, indicating that Target Loop and Pinch PASS primers with up at least 60 bases of unhybridized target between cS1 and cS2 can function similarly and efficiently.

This example demonstrates that it will be feasible to use PASS primers which can "jump" over sequence in the target. This has application when, for example, it is desired to amplify two targets which have regions of homology and regions of variability. PASS primers (Pinch or Loop) can be designed to bind to homologous regions of the targets but not bind to variable regions. This can result in one primer that can amplify two targets with equal efficiency since the number of bases bound by the primer will be the same for the two targets.

Example 16: Investigation into PASS Partzymes and Pinch PASS Partzymes to Loop Out Different Lengths of Target Sequence In a manner analogous to PASS primers or Pinch PASS primers, PASS partzymes or Pinch PASS partzymes can also be designed to loop out regions of sequence whether it is the partzyme sensor arm or the target sequence or both.

In this example, primers are designed to specifically amplify the TFRC gene and the MNAzyme comprises a first PASS or Pinch PASS partzyme and a second fully matched "standard" partzyme that binds adjacently on the amplified target sequence of interest. The PASS partzyme contains a USI region not complementary to the target sequence, which is located between two regions (S1 and S2) of sequence that are complementary to the target sequence (cS1 and cS2) of interest. The USI present in the PASS partzyme can be in planar formation where the number of non-complementary bases in the PASS partzyme match the number of unbound bases in the target sequence, which in this example was 5, 10 or 15 bp (FIG. 13 (*i*)) or looped where the number of non-complementary bases in the partzyme are greater or less than the number in the target sequence and the sequence (partzyme or target) bulges or loops out, which in this example the partzyme was looped out by 5, 10 or 15 bp (FIG. 13 (*ii*)). Alternatively, a Pinch PASS partzyme can be used which does not contain a USI but rather contains a USJ created when it binds to that target such that it loops out a region of target sequence in between two regions (S1 and S2) of sequence that are complementary to the target sequence (cS1 and cS2). The region looped out in this example by the Pinch PASS partzyme was 5, 10, 15, 20 or 40 bp long (FIG. 13 (*iii*)). The partzymes are designed such that formation of active MNAzymes from partzyme components could result in the cleavage of the universal probe labeled with fluorophore and quencher dye pair, producing a signal that can be monitored in real-time.

Each Planar, Loop and Pinch PASS partzyme was combined with PCR amplification for a readout in qPCR to determine if various scenarios of unbound target between cS1 and cS2 created by binding of the Loop or Planar PASS partzymes or Pinch PASS partzyme were compatible with detection of the TFRC gene and formation of an active MNAzyme producing a detectable signal in real-time.

16.1. Partzyme Oligonucleotides

Partzymes were designed that were either a) fully matched "standard" partzymes where the sensor arms were fully and consecutively complementary to the target sequence, b) "PASS" partzymes where a region of sequence not complementary to the amplicon (USI) has been inserted into the sensor arm between two regions that are complementary to the amplicon or c) Pinch PASS partzymes where a region of target sequence has been looped out between two regions that are complementary to the amplicon resulting the presence of a USJ in the sensor arm of the partzyme. In the following sequences, the bases in bold hybridize with the target sequence of interest, the bases in bold and underlined represent the two bases either side of the USJ and bases underlined are the USI which is mismatched with respect to all three target sequences. The "-P" indicates 3' phosphorylation of the oligonucleotide. All sequences are written 5' to 3'.

SEQ ID NO: 145 partzyme B TFRC_2B/84-P:
TGGACGAGGGAGGCTAGCTTCTGACTGGAAAACAGACTCTA

SEQ ID NO: 146 partzyme A TFRC_2A/84-P:
CTGATTCTAGGAATATGGAAGGAGACTGTCCCACAACGAGAGGGTCGAG SEQ ID NO: 147 PASS partzyme A planar TFRC_2P2i15A/84-P:
AGAACTTACGCCTGCTTTCTGATTCTAATTCACGTCTCATCAACTGTCCC
ACAACGAGAGGGTCGAG SEQ ID NO: 148 PASS partzyme A planar
TFRC_2P2i10A/84-P:
TTACGCCTGCTTTCTGATTCTAGGAATCGTCTCATCAACTGTCCCACAAC
GAGAGGGTCGAG SEQ ID NO: 149 PASS partzyme A planar
TFRC_2P2i5A/84-P:
CCTGCTTTCTGATTCTAGGAATATGGACATCAACTGTCCCACAACGAGAG
GGTCGAG SEQ ID NO: 150 PASS partzyme A loop
TFRC_2L2i15A/84-P:
TTTCTGATTCTAGGAATATGGAAGGATTCACGTCTCATCAACTGTCCCAC
AACGAGAGGGTCGAG SEQ ID NO: 151 PASS partzyme A loop
TFRC_2L2i10A/84-P:
TTTCTGATTCTAGGAATATGGAAGGCGTCTCATCAACTGTCCCACAACGA
GAGGGTCGAG SEQ ID NO: 152 PASS partzyme A loop
TFRC_2L2i5A/84-P:
TTTCTGATTCTAGGAATATGGAAGGCATCAACTGTCCCACAACGAGAGGG
TCGAG SEQ ID NO: 153 Pinch PASS partzyme A
TFRC_2pp40A/84-P:
CCCTGGGCAAGGAACAATAACTCAGACTGTCCCACAACGAGAGGGTCGAG SEQ ID NO: 154 Pinch PASS partzyme A
TFRC_2pp20A/84-P:
ACTCAGAACTTACGCCTGCTTTCTGAACTGTCCCACAACGAGAGGGTCGA
G SEQ ID NO: 155 Pinch PASS partzyme A
TFRC_2pp15A/84-P:
AGAACTTACGCCTGCTTTCTGATTCTAACTGTCCCACAACGAGAGGGTCG
AG SEQ ID NO: 156 Pinch PASS partzyme A
TFRC_2pp10A/84-P:
TTACGCCTGCTTTCTGATTCTAGGAATACTGTCCCACAACGAGAGGGTCG
AG SEQ ID NO: 157 Pinch PASS partzyme A
TFRC_2pp5A/84-P:
CCTGCTTTCTGATTCTAGGAATATGGAACTGTCCCACAACGAGAGGGTCG
AG

16.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 158 Substrate Sub84-FIB:
CTCGACCCTCguCCCTCGTCCA

16.3. Target Sequence and PCR Primers for Amplification of TFRC

The target sequence for this example was the TFRC gene in human genomic DNA extracted from the IM9 cell line (Promega). The oligonucleotide PCR primers are listed below. The sequence in bold at the 5' termini of the primer sequences corresponds to a tag (T1 or T2) that increases the Tm of the primer without affecting the specificity of the primer to the gene target. These tags improve amplification efficiency in later rounds of the PCR reactions. Primer sequences are listed 5' to 3'.

SEQ ID NO: 159 Reverse primer 3TFRC_T2:
CAGCTCTTTCAGCACATTGCTCACA

SEQ ID NO: 160 Forward primer 5TFRC_T1:
CTAACTGGGCAAGGAACAATAACTC

16.4. Reaction Components: Amplification of Target Sequence

Real-time amplification and detection of the target sequence was performed in a total reaction volume of 25 µL. The reactions were conducted in a CFX96™ Real-Time PCR detection System (BioRad). The cycling parameters were, 95° C. for 2 minutes, 10 cycles of 95° C. for 15 seconds and 59° C. for 60 seconds (minus 1° C. per cycle), 50 cycles of 95° C. for 15 seconds and 50° C. for 50 seconds (data collected at the 50° C. step). Each set of reaction conditions was tested in duplicate and contained 100 nM of partzyme A, as outlined in Table 26. All reactions contained 40 nM forward primer (5TFRC_T1), 200 nM of partzyme B (TFRC_2B/84-P), 200 nM of reverse primer (3TFRC_T2), 200 nM substrate (Sub84-FIB), 8 mM MgCl$_2$, 200 µM of each dNTP, 10 units RiboSafe RNase inhibitor (Bioline), 1× ImmoBuffer (Bioline), 2 units of MyTaq™ HS DNA polymerase (Bioline) and either IM9 gDNA (50 ng or 50 pg) or no target (NF H$_2$O).

TABLE 26

| Design | Unique sequence (US) type (number of bases in the target amplicon that do not bind to the partzyme) | Partzyme A |
|---|---|---|
| Standard | None | TFRC_2A/84-P |
| PASS Partzyme | Planar USI (15) | TFRC_2P2i15A/84-P |
| | Planar USI (10) | TFRC_2P2i10A/84-P |
| | Planar USI (5) | TFRC_2P2i5A/84-P |
| | Loop USI (15) | TFRC_2L2i15A/84-P |
| | Loop USI (10) | TFRC_2L2i10A/84-P |
| | Loop USI (5) | TFR_2L2i5A/84-P |
| Pinch PASS partzyme | USJ (40) | TFRC_2pp40A/84-P |
| | USJ (20) | TFRC_2pp20A/84-P |
| | USJ (15) | TFRC_2pp15A/84-P |
| | USJ (10) | TFRC_2pp10A/84-P |
| | USJ (5) | TFRC_2pp5A/84-P |

16.5. Results: Amplification of Target and Cleavage of Reporter Substrate

For all reactions, the fluorescence of the no template control was lower than that in the DNA target-containing reactions. This demonstrates that the increase in fluorescence produced in target-containing reactions is due to target dependent assembly of catalytically active MNAzymes that then cleaved universal reporter substrate.

The PASS partzymes, whether loop or planar with 5, 10 or 15 bp of unique sequence all performed similarly with the maximum difference of 0.6 Ct for 50 ng of template and 0.7

Ct for 50 pg of template, when compared to the standard MNAzyme containing no PASS partzymes (Table 27).

TABLE 27

Ct values for MNAzyme qPCR performed using PASS partzymes and Pinch PASS partzymes

| Design | Unique sequence (US) type (number of bases in the target amplicon that do not bind to the partzyme) | Ct (Ave) 50 ng | Ct (Ave) 50 pg |
|---|---|---|---|
| Standard | None | 15.1 | 26.1 |
| PASS Partzyme | Planar USI (5) | 15.7 | 26.8 |
| | Loop USI (5) | 15.4 | 26.7 |
| | Planar USI (10) | 15.7 | 27.1 |
| | Loop USI (10) | 15.5 | 26.1 |
| | Planar USI (15) | 15.7 | 26.2 |
| | Loop USI (15) | 15.6 | 25.7 |
| Pinch PASS partzyme | USJ (5) | 14.7 | 24.7 |
| | USJ (10) | 15.1 | 25.2 |
| | USJ (15) | 15.3 | 25.9 |
| | USJ (20) | 15.7 | 26.5 |
| | USJ (40) | 24.2 | 38.9 |

A Pinch PASS partzyme, looping out 5 bp of amplicon, performed marginally better than the standard MNAzyme reaction. Increasing the size of the amplicon sequence looped out to 10, 15 and 20 bp, resulted in only a minimal shift in Ct with the maximum increase of 0.6 Ct for 50 ng of template and 0.4 Ct for 50 pg, when compared to the standard MNAzyme containing no PASS partzymes (Table 27). When a Pinch PASS partzyme looping out 40 bp of amplicon was compared to the standard MNAzyme the Ct increased by 9.1 and 21.8 (50 ng and 50 pg respectively). This indicates that larger regions up to 40 bp can be looped out of the amplicon if required, however it may impact on the Ct value under these experimental conditions.

Overall, detection of a target sequence using an MNAzyme that contains a PASS partzyme or a Pinch PASS partzyme that does not fully bind the amplicon sequence had minimal impact on the Ct value and sensitivity of the assays with all PASS varieties strongly detecting 50 pg of template, in a similar fashion to the standard MNAzyme assay. This demonstrates that an active MNAzyme can still form when one of the partzyme sensor arms is not fully matched to consecutive target sequence and in this experiment the looped out target sequence can be at least up to 40 bp.

Example 17: PASS Primers and Pinch PASS Primers Both Combined with MNAzymes to Detect Single Base Changes in Sequence The specificity of the PASS primers containing either a USI or a USJ was demonstrated in assays targeting the point mutations in codon 12 of KRAS referred to as G12V and G12S. The example investigated the ability to detect the variants G12V and G12S and to discriminate these from wild type and other KRAS G12/G13 variants.

In this example, the size of the target specific region located between the target sequence complementary to the S1 and S2 regions of the Target Loop PASS primer was varied in size from 1 (FIG. 12 (iii)), to 20, 40, 60, 100 and 200 target bases for G12V and from 10, to 20, 40 and 60 target bases for G12S (FIG. 12 (i)). To achieve this the S1 region of the PASS primer was moved further 5' such that the target sequence between the sequence complementary to the 3' and 5' target specific regions of the PASS primer had increasing sizes of non-complementary intervening target sequence looped out. The US in the Pinch PASS oligonucleotide is not an insert of non-complementary sequence per se but rather comprises a Unique Sequence Junction (USJ) created by juxtaposing two non-contiguous sequences of the target. In the Pinch PASS oligonucleotide the sequences S1 and S2 are complementary to the target and bind to two regions separated by intervening sequence. When the Pinch PASS oligonucleotide hybridises to the target the intervening target sequence loops out bringing the complementary target regions into close proximity creating amplicons which contain a USJ. In this example, Pinch PASS primers were tested with the size of the intervening target sequence located between the target sequence complementary to the S1 and S2 regions being 10 or 100 target bases for G12V and 10 target bases for G12S (FIG. 12 (ii)).

Each Target Loop PASS primer or Pinch PASS primer was combined with MNAzyme detection in qPCR with a fluorescent readout to determine if various scenarios of target looping by the Target Loop PASS primer or Pinch PASS primer influenced the specificity of the reaction with respect to the ability to discriminate the variant sequence from the wild type and/or other variants.

17.1. Partzyme Oligonucleotides

Partzymes were designed to specifically target the KRAS gene for the variant G12S or G12V and/or any cUS insert introduced via a PASS primer. In the following sequences the bases in bold hybridize with the target sequence of interest, the bases in bold and underlined represent two bases either side of the USJ, bases underlined hybridise to the cUS insert and bases in bold and italicised represent the variant bases (G12S or G12V) and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 161 partzyme A: G12S_gi2A/55-P:
<u>ACATACTA</u>GTTGGAG<u>GT</u>***A*GT**GACAACGAGAGGTGCGGT SEQ ID NO: 162 partzyme A: G12S_LT10A/55-P:
TGAATATA<u>A</u>GTTGGAG<u>GT</u>***A*GT**GACAACGAGAGGTGCGGT SEQ ID NO: 63 partzyme B rcKRAS_B/55-P:
GAGCTGGGGAGGCTAGCTGCTCCAACTACCACAAGTTT

SEQ ID NO: 64 partzyme A rcG12V_LMi1A/55-P:
<u>ACAATCAGT</u>CCTACGC<u>GA</u>***A*CA**ACAACGAGAGGTGCGGT SEQ ID NO: 164 partzyme A: rcG12V_LT10A/55-P:
ATCGTCA<u>A</u>CCTACGC<u>GA</u>***A*CA**ACAACGAGAGGTGCGGT SEQ ID NO: 165 partzyme A: rcG12V_LT100A/55-P:
TGGTCCT<u>G</u>CCTACGC<u>GA</u>***A*CA**ACAACGAGAGGTGCGGT 17.2. Reporter Substrate In the current example, the substrate were end labelled with a 6-FAM moiety at the 5' end (indicated by a "F" in the name of the substrates below) and an Iowa Black® FQ quencher moiety at the 3' end (indicated by a "TB" in the name of the substrates below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 25 Substrate Sub55-FIB:
ACCGCACCTCguCCCCAGCTC

17.3. PCR Primers for Amplification of KRAS DNA

In vitro amplification of human gDNA was performed using the oligonucleotide PCR primers listed below. In the following sequences the bases in bold hybridize with the target sequence, bases underlined are the USI (G12S insert i2 and rcG12V insert i1) which are mismatched with respect to the starting template, bases bold and italicised are the variant base, bases in bold and underlined are the USJ and bases underlined and italicised represent an additional base mismatched to both targets. All sequences are written 5' to 3'.

SEQ ID NO: 26 Reverse primer 3KRAS:
GGTCCTGCACCAGTAATATGC

SEQ ID NO: 166 Forward PASS primer
5G12S_gi2Planar:
CCTGCTGAAAATGACTGAATATAAAGACATACTAGTTGGAGGTA SEQ ID NO: 167 Forward PASS primer
5G12S_LTi2(20):
TATTATAAGGCCTGCTGAAAATGAAGACATACTAGTTGGAGGTA SEQ ID NO: 168 Forward PASS primer
5G12S_LTi2(40):
ATATAGTCACATTTTCATTATTTTTATTAGACATACTAGTTGGAGGTA SEQ ID NO: 169 Forward PASS primer
5G12S_LTi2(60):
GTGTGACATGTTCTAATATAGTCAGACATACTAGTTGGAGGTA SEQ ID NO: 170 Forward Pinch PASS primer
5G12S_LT10:
CCTGCTGAAAATGACTGAATATAAGTTGGAGGTA SEQ ID NO: 65 Reverse primer 3rcKRAS:
TATTAAAAGGTACTGGTGGAGTA SEQ ID NO: 66 Forward PASS primer
5rcG12V_LM3i1Loop:
CTGTATCGTCAAGGCACTCTTCACAATCAGTCCTACGCGAA SEQ ID NO: 172 Forward PASS primer
5rcG12V_LTi1(20):
CACAAAATGATTCTGAATTAGCTCACAATCAGTCCTACGCGAA SEQ ID NO: 173 Forward PASS primer
5rcG12V_LTi1(40):
TTGTTGGATCATATTCGTCCACCACAATCAGTCCTACGCGAA SEQ ID NO: 174 Forward PASS primer
5rcG12V_LTi1(60):
ATATTAAAACAAGATTTACCTCTATTCACAATCAGTCCTACGCGAA SEQ ID NO: 175 Forward PASS primer
5rcG12V_LTi1(100):
TATCTGTATCAAAGAATGGTCCTGCACAATCAGTCCTACGCGAA SEQ ID NO: 176 Forward PASS primer
5rcG12V_LTi1(200):
TGGTTACATATAACTTGAAACCCAACACAATCAGTCCTACGCGAA SEQ ID NO: 177 Forward Pinch PASS primer
5rcG12V_LT10:
TTCTGAATTAGCTGTATCGTCAACCTACGCGAA SEQ ID NO: 178 Forward Pinch PASS primer
5rcG12V_LT100:
TATCTGTATCAAAGAATGGTCCTGCCTACGCGAA

17.4. Target Sequence

Human gDNA extracted from the A549 cell line was used as template for in vitro amplification of the point mutation G12S and human gDNA extracted from the SW480 cell line was used as template for in vitro amplification of the point mutation G12V. Human gDNA extracted from the cell lines IM9 (wild type), Calu1 (G12C), MDA-MB231 (G13D) and SW480 (G12V) were used as negative control template for KRAS variant G12S and human gDNA extracted from the cell lines IM9 and Calu1 were used as negative control template for the KRAS variant G12V.

17.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds, 50 cycles of 95° C. for 15 seconds and 54° C. for 50 seconds (data collected at the 54° C. step). Reactions were run in duplicate and contained 40 nM forward PASS primer, 100 nM partzyme A, 200 nM of reverse primer and 200 nM partzyme B (the combinations are listed in Table 28). All reactions contained 200 nM substrate (Sub55-FIB), 8 mM MgCl$_2$, 200 μM of each dNTP, 10 units RiboSafe RNAase Inhibitor (Bioline), 1× ImmoBuffer (Bioline), 2 units of MyTaq™ HS DNA polymerase (Bioline). Either 35 ng of A549 gDNA template was used as a positive control for KRAS G12S target and 35 ng of SW480 (G12V), IM9 (WT), Calu1 (G12C) and MDA-MB231 (MDA) (G13D) was used as negative controls, 35 ng of SW480 gDNA template was used as a positive control for KRAS G12V target and 35 ng of IM9 (WT) was used as negative control and additional controls contained no target (NF H$_2$O).

TABLE 28

Primer/partzyme combinations for the variant assays

| Primer Design | Partzyme A | Forward PASS Primer | Partzyme B & Reverse primer | # of target bases between S1 & S2 | US type | Design Name |
|---|---|---|---|---|---|---|
| KRAS variant G12S | | | | | | |
| PASS Primers with USI | G12S_gi2A/ 55-P | 5G12S_gi2Planar | KRAS_B/ 55-P & 3KRAS | 10 | USI | Planar/10 |
| | | 5G12S_LTi2(20) | | 20 | USI | Loop/20 |
| | | 5G12S_LTi2(40) | | 40 | USI | Loop/40 |
| | | 5G12S_LTi2(60) | | 60 | USI | Loop/60 |
| Pinch PASS Primer with USJ | G12S_LT10A/ 55-P | 5G12S_LT10 | | 10 | USJ | Pinch/10 |

TABLE 28-continued

Primer/partzyme combinations for the variant assays

| Primer Design | Partzyme A | Forward PASS Primer | Partzyme B & Reverse primer | # of target bases between S1 & S2 | US type | Design Name |
|---|---|---|---|---|---|---|
| KRAS variant G12V | | | | | | |
| PASS Primers with USI | rcG12V_LMi1A/ 55-P | 5rcG12V_LM3ilLooP 5rcG12V_LTi1(20) 5rcG12V_LTi1(40) 5rcG12V_LTi1(60) 5rcG12V_LTi1(100) 5rcG12V_LTi1(200) | rcKRAS_B/ 55-P & 3rcKRAS | 1 20 40 60 100 200 | USI USI USI USI USI USI | Loop/1 Loop/20 Loop/40 Loop/60 Loop/100 Loop/200 |
| Pinch PASS Primer with USJ | rcG12V_LT10A/ 55-P rcG12V_LT100A/ 55-P | 5rcG12V_LT10 5rcG12V_LT100 | | 10 100 | USJ USJ | Pinch/10 Pinch/100 |

17.6. Results: Amplification of Target and Cleavage of Reporter Substrate

The results of amplification and detection are summarised in the following Table 29.

TABLE 29

Ct values for PASS primer and partzyme combinations

| Design | Design Name | Test | Template | Ct (Ave) | ΔCt from positive |
|---|---|---|---|---|---|
| KRAS variant G12S | | | | | |
| Planar PASS primer with USI (no target loop) | Planar/10 | Positive Negative Negative Negative Negative | G12S (A549) WT (IM9) G12C (Calu1) G12V (SW480) G13D (MDA) | 20.2 33.7 39.5 31.9 34.0 | 13.4 19.3 11.7 13.7 |
| Target Loop PASS Primers with USI (target looped out) | Loop/20 | Positive Negative Negative Negative Negative | G12S (A549) WT (IM9) G12C (Calu1) G12V (SW480) G13D (MDA) | 23.2 35.2 39.8 35.9 40.3 | 12.0 16.6 12.7 17.0 |
| | Loop/40 | Positive Negative Negative Negative Negative | G12S (A549) WT (IM9) G12C (Calu1) G12V (SW480) G13D (MDA) | 26.4 40.5 40.4* 39.8 41.4 | 14.1 14.1 13.4 15.0 |
| | Loop/60 | Positive Negative Negative Negative Negative | G12S (A549) WT (IM9) G12C (Calu1) G12V (SW480) G13D (MDA) | 27.3 39.9 41.2* 36.7 38.8 | 11.6 13.9 9.4 11.5 |
| Pinch PASS Primer with a USJ (target looped out) | Pinch/10 | Positive Negative Negative Negative Negative | G12S (A549) WT (IM9) G12C (Calu1) G12V (SW480) G13D (MDA) | 20.9 No Ct No Ct No Ct No Ct | >29.1 >29.1 >29.1 >29.1 |
| KRAS variant G12SV | | | | | |
| Loop PASS primer with USI (primer looped out) | Loop/1 | Positive Negative | G12V (SW480) WT (IM9) | 18.5 38.1 | 19.6 |
| Target Loop PASS primer with USI (target looped out) | Loop/20 | Positive Negative | G12V (SW480) WT (IM9) | 21.5 47.3 | 25.8 |
| | Loop/40 | Positive Negative | G12V (SW480) WT (IM9) | 25.0 46.6* | 21.6 |
| | Loop/60 | Positive Negative | G12V (SW480) WT (IM9) | 31.5 No Ct | >18.5 |
| | Loop/100 | Positive Negative | G12V (SW480) WT (IM9) | 32.9 No Ct | >17.1 |
| | Loop/200 | Positive Negative | G12V (SW480) WT (IM9) | 36.7 No Ct | >13.3 |
| Pinch PASS Primer with a USJ (target looped out) | Pinch/10 | Positive Negative | G12V (SW480) WT (IM9) | 19.3 37.0 | 17.7 |
| | Pinch/ 100 | Positive Negative | G12V (SW480) WT (IM9) | 32.6 No Ct | >17.4 |

*Ct value for single replicate, other replicate did not produced signal, Ct not averaged
N.B. When no Ct was produced for a negative control sample the final Ct of 50 was used to produce the ΔCt and a greater than symbol (>) placed in front to indicate that the ΔCt would be expected to be higher than this value.

The Ct values (Table 29) indicate that the PASS primers which have either Target Loop or Pinch Designs can all amplify the target genes. When the G12S Planar/10 design was compared to the Target Loop designs where the length of the sequence of target which did not bind to the PASS primer was increased from 20 (Loop/20) to 40 (Loop/40) and then 60 (Loop/60) the Ct values were increased by 3.0, 6.2 and 7.1 respectively. The specificity was also influenced by the size of the target loop with Planar/10, containing no target loop, the most specific with regards to off target signal from the wild type but Loop/20 and Loop/40 displaying greater specificity with regards to off target signal from for the other variant sequences. This indicates that primers can bind to and extend from the target despite the presence of long sequence stretches of targets which do not hybridize to the primer, and that this can further improve the specificity of the assay.

When a Pinch PASS primer was used with unbound non-complementary sequence in the target between S1 and S2 of 10 bases for G12S (Pinch/10), the Ct was increased by 0.7 when compared to the original Planar PASS primer indicting efficient priming by Pinch/10 (Table 29). However the specificity was superior for the Pinch PASS primers with no signal evident for any of the negative controls. This demonstrates that Pinch PASS primers can bind to and extend from the target despite the presence of long sequence stretches of targets which do not hybridize to the primer and that this may improve the specificity of the reaction.

When the G12V Loop/1 PASS primer design was compared to Loop Target designs where the length of the sequence of target which did not bind to the Target Loop PASS primer between S1 and S2 was increased from 20 (Loop/20) to 40 (Loop/40), 60 (Loop/60), 100 (Loop/100) and then 200 (Loop/200) the Ct values were increased by 3.0, 7.5, 13, 14.4 and 18.2 respectively (Table 29). The specificity was also influenced by the size of the target loop with the most specific reactions coming from Loop/20, Loop/40 and Loop/60. However compared to Loop/20 the Ct of the positive reactions was increased for Loop/40 and Loop/60. When the loop was 100 or 200 bp (Loop/100 or Loop/200) the specificity advantage was lost as the Ct was greatly increased. This indicates that primers can bind to and extend from the target despite the presence of long sequence stretches of targets which do not hybridize to the primer, and that this can further improve the specificity of the assay.

When a Pinch PASS primer G12V (Pinch/10) (which had unbound sequence between S1 and S2 of 10 bases) was used, the Ct was increased by 0.8 when compared to the original Loop PASS primer (Loop/1) indicting efficient priming by Pinch/10 (Table 29). The specificity was also comparable. When a Pinch PASS primer with unbound sequence between S1 and S2 of 100 bp was used the Ct was increased by 14.1 when compared to the Loop/1 while maintaining a good level of specificity (Table 29). This demonstrates that Pinch PASS primers can bind to and extend from the target despite the presence of long sequence stretches of targets which do not hybridize to the primer and that this may improve the specificity of the reaction.

This example demonstrates that it will be feasible to use PASS primers which can "jump" over sequence in the target. Further the type of PASS primer whether it contains a USJ or USI can be screened to determine the most specific assay when variant sequences are to be discriminated.

Example 18: Comparing the Sensitivity of PASS Primers to Wobble-Enhanced ARMS (WE-ARMS) Primers Both Combined with Either Allele Specific MNAzyme, Generic MNAzyme or TagMan® to Detect Single Bases Changes in a Sequence In this example, the KRAS point mutation in codon 12 referred to as G12V is assayed using serial dilutions of the G12V template in a background of wild type KRAS template. Dilutions of 1 in 10, 100 and 1000 of G12V in a background of wild type were tested.

The design 3 (FIG. 7) planar PASS primers are used for the amplification of G12V sequence. This was compared to the G12V WE-ARMS primers. The PASS primers were combined with an allele specific MNAzyme qPCR readout, a generic MNAzyme qPCR readout or a TagMan® probe readout. In allele specific systems the MNAzyme binding region overlaps with the primer binding regions (PASS or WE-ARMS primers); whereas in the generic systems the MNAzyme or TagMan® probes were located internal to the amplicon with no overlap to sequence related to the PASS or WE-ARMS primers. In the PASS assays the allele specific MNAzymes comprise a first partzyme that binds to the complement of the unique sequence (cUS) as well as amplified target sequence containing the complement of the variant (mutant) base and the mismatch base introduced by the PASS primer. The second partzyme binds adjacently to the first partzyme within amplified target sequence of interest. The generic MNAzyme and TagMan® probe both bind to sequence downstream of the variant (mutant) base and these assays rely on the primer only to confer specificity for the mutation since they do not provide any inherent mechanism for discrimination between wild type and mutant sequence. The WE-ARMS primers were combined with MNAzymes with either an allele specific MNAzyme qPCR readout, generic MNAzyme qPCR readout or a TagMan® probe. In these WE-ARMS primer assays the allele specific MNAzymes comprise a first partzyme that binds to amplified target sequence containing the complement of the variant (mutant) base and the mismatch base introduced by the WE-ARMS primer. The second partzyme binds adjacently to the first partzyme within the amplified target sequence of interest. The generic MNAzyme and TaqMan® probe both bind to sequence downstream of the variant (mutant) base and as before do not provide any additional mechanism for discrimination between wild type and mutant sequence.

PASS primers were compared to WE-ARMS primers to investigate the efficiency, linearity and sensitivity of each amplification and detection strategy.

18.1. Partzyme Oligonucleotides

The allele specific MNAzymes were designed with partzymes that specifically target the G12V sequence and any mismatch introduced via a primer as well as cUS insert in the case of the PASS primer. The generic MNAzyme was designed with partzymes that do not bind to the variant base or to any additional mismatches introduced via a primer ie in the case of the PASS primer they do not bind to the cUS. In the following sequences the bases in bold hybridize with the target sequence of interest and bases underlined are the US insert (i2) which is mismatched with respect to the starting template. Bases in bold and italicised represent the variant (mutant) bases and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 24 PASS partzyme A G12V_LMi2A/55-P:
<u>AGACATACTA</u>**TGGAGCCG*T*TG**ACAACGAGAGGTGCGGT SEQ ID NO: 44 partzyme A G12V_MA/55-P:
**TGTGGTAGTTGGAGCCG*T*TG**ACAACGAGAGGTGCGGT SEQ ID NO: 179 partzyme A KRAS_5A/55-P:
GCTAATTCAGAATCATTTTGTGACAACGAGAGGTGCGGT SEQ ID NO: 180 partzyme B KRAS_5B/55-P:
GAGCTGGGGAGGCTAGCTGACGAATATGATCCAACAATAG

18.2. Reporter Substrate

In the current example, the substrate was end labelled with a 6-FAM moiety at the 5' end (indicated by a "F" in the name of the substrates below) and an Iowa Black® FQ quencher moiety at the 3' end (indicated by a "IB" in the name of the substrates below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 25 Sub55-FIB:
ACCGCACCTCguCCCCAGCTC

18.3. TaqMan® Probe

The TaqMan® probe was designed such that it did not bind to the variant base or to any mismatch introduced via a primer, nor with the cUS in the case of the PASS primer. The TaqMan® probe was end labelled with a 6-FAM moiety at the 5' end (indicated by a "F" in the name of the probe below) and a minor groove binding moiety at the 3' end (indicated by a "MGB" in the name of the probe below). Cleavage of the TaqMan® probe was monitored between 510-530 nm (FAM emission wavelength range on the CFX96 (BioRad)) with excitation between 450-490 nm (FAM excitation wavelength range on the CFX96 (BioRad)). In the following sequence the bases in bold hybridize with the target sequence of interest. The sequence is are written 5' to 3'.

```
SEQ ID NO: 181 TaqMan probe KRAS_5-FMGB:
CAAGAGTGCCTTGACGATAC
```

18.4. PCR Primers for Amplification of KRAS DNA

In vitro amplification of human gDNA was performed using the oligonucleotide PCR primers listed below. In the following sequences the bases in bold hybridize with the target sequence, bases underlined are the US insert i2 which are mismatched with respect to the starting template, bases bold and underlined are the variant base and bases italicised represent an additional base mismatched (M) to both targets. All sequences are written 5' to 3'.

```
SEQ ID NO: 26 Reverse primer 3KRAS:
GGTCCTGCACCAGTAATATGC

SEQ ID NO: 87 Forward PASS primer
5G12V_LM4i2Planar:
CTGCTGAAAATGACTGAATATAAACAGACATACTATGGAGCCGT SEQ ID NO: 46 Forward WE-ARMS primer 5G12V_M:
CTTGTGGTAGTTGGAGCCGT
```

18.5. Target Sequence

Human gDNA extracted from the SW480 cell line was used as template for in vitro amplification of the the KRAS gene containing the variant point mutation G12V. A calibration curve was made by serially diluting SW480 in a constant background of the KRAS wild type gDNA, extracted from the cell line K562.

18.6. Reaction Components: Amplification and Quantitation of Target Sequence Real-time amplification and quantitation of the target sequence was performed in a total reaction volume of 25 μL. The reactions were run in duplicate and conducted in a CFX96™ Real-Time PCR detection System (BioRad). The cycling parameters were 95° C. for 2 minutes, 60 cycles of 95° C. for 5 seconds and 54° C. for 20 seconds (data collected at the 54° C. step). MNAzyme reactions contained 40 nM forward primer, 100 nM partzyme A, and 200 nM partzyme B (the combinations are listed in Table 30) as well as 400 nM of reverse primer (3KRAS), 200 nM substrate (Sub55-FIB) and 8 mM $MgCl_2$. TaqMan reactions contained 300 nM forward primer, 900 nM of reverse primer (3KRAS), 250 nM TaqMan® probe (KRAS_5-FMGB) and 4 mM $MgCl_2$. All reactions contained 200 μM of each dNTP, 10 units RiboSafe RNAase Inhibitor (Bioline), 1× ImmoBuffer (Bioline), 2 units of MyTaq™ HS DNA polymerase (Bioline) and either SW480 gDNA template (35 ng), SW480 gDNA template diluted 1 in 10, 1 in 100 or 1 in 1000 in a constant background of K562 gDNA template (35 ng), K562 gDNA template (35 ng) or no target (NF $H_2O$).

TABLE 30

| | | | | | |
|---|---|---|---|---|---|
| Oligonucleotide combinations for the variant assays | | | | | |
| Primer Design | qPCR readout | Forward Primer | Partzyme A & B | TaqMan ® Probe | Reverse primer |
| PASS | Allele specific MNAzyme | 5G12V_LM4i 2Planar | G12V_LMi2A/55-P & KRAS_B/55-P | — | 3KRAS |
| | Generic MNAzyme | | KRAS_5A/55-P & KRAS_5B/55-P | — | |
| | TaqMan ® probe | | — | KRAS_5-FMGB | |
| WE_ARMS | Allele specific MNAzyme | 5G12V_M | G12V_MA/55-P & KRAS_B/55-P | — | |
| | Generic MNAzyme | | KRAS_5A/55-P & KRAS_5B/55-P | — | |
| | TaqMan ® probe | | — | KRAS_5-FMGB | |

18.7. Results: Amplification of Target and Cleavage of Reporter Substrate

The PASS and WE-ARMS forward primers were used to produce amplicons for the real-time detection and quantification of the KRAS point mutation (G12V). MNAzymes were designed to be either allele specific and hence tailored for detection of the complement of either the specific PASS or WE-ARMS primers used to amplify the mutant sequence; or MNAzymes were generic whereby the sequence hybridized to the MNAzyme was present in all amplicons produced from amplification of the target KRAS variant or from the off-target wild type. Similarly a TaqMan® probe was also designed that would bind sequence present in all KRAS variants and wild type amplicons. These reactions showed an increase in fluorescence over time when the reaction contained target sequence specific for G12V (Table 31).

The SW480 DNA template, specific for G12V, was serially diluted 10-fold in a background of K562 template which contains G12. The serial dilutions of DNA were amplified with either a PASS or WE-ARMS forward primer and detected in real-time with either an allele specific MNAzyme, a generic MNAzyme or a TaqMan® probe, the Ct of each dilution is shown in Table 31. The Ct values shown in the table are an average of the results for duplicate reactions. The ΔCt values indicate the difference in the number of cycles observed for detection of KRAS mutant amplicons compared to off-target wild type control amplicons when equal amounts of DNA were present.

The Ct values for detection with the allele specific MNAzyme are slightly increased compared to the generic MNAzyme and the TaqMan® probe (Table 31); however this novel design provided greater specificity to the reaction. The use of the PASS primer with the allele specific MNAzyme resulted in a very specific reaction with no signal being generated from the wild type negative control. Combining the allele specific MNAzyme with the WE-ARMS primer also improved the specificity of the reaction increasing the ΔCt between mutant and wildtype to 16.9 opposed to 8.7 and 7.0 for the generic MNAzyme and the TaqMan® probe respectively.

Applying a PASS primer instead of a WE-ARMS primer with a generic MNAzyme or TaqMan® probe readout showed greater specificity, with an increased ΔCt, when compared to a WE-ARMS primer (Table 31). Further the use of a PASS primer increased the limit of detection of G12V sequence from the wild type. Using a WE-ARMS primer the generic MNAzyme could not clearly discriminate between 1 in 100 mutant dilution and the negative control (K562—wild type) with Ct difference of 1.2. In contrast, the PASS primer easily allowed detection of 1 in 100 and had a Ct difference of 1.6 between the 1 in 1000 dilution and the negative control. A similar advantage was also seen when using PASS primers compared with the WE-ARMS with a TaqMan® readout. Using a WE-ARMS primer the TaqMan® readout could not clearly discriminate between 1 in 100 and the negative control (K562—wild type) with a Ct difference of 0.2; whereas the PASS primer easily detected 1 in 100 and had a Ct difference of 0.6 between the 1 in 1000 sample and the negative control. This demonstrates that the advantages of PASS primers are inherent to the design of the PASS primer and superior results are not just associated with the method used for a readout (allele specific MNAzymes versus generic MNAzyme versus TaMan® probes). As demonstrated in this experiment, the PASS primers also have advantages when coupled to other qPCR chemistries such as TaqMan®. Further, PASS primers could be combined with additional qPCR chemistries such as Molecular Beacons or Scorpion probes.

TABLE 31

Ct values for G12V PASS vs. WE-ARMS primer after amplification of mutant DNA (SW480) or wild type DNA (K562) or dilutions of SW480 in K562 DNA. The lowest dilution which could be discriminated from wild type with a ΔCt of at least 2 cycles is underlined for each technology combination.

|  | Template | PASS primer Ct (Ave) | WE-ARMS primer Ct (Ave) |
|---|---|---|---|
| Allele specific MNAzyme | 35 ng SW480 | 33.0 | 32.2 |
|  | 1 in 10 | 37.7 | 37.6 |
|  | 1 in 100 | 40.9 | 42.0 |
|  | 1 in 1000 | 43.6 | 50.2 |
|  | 35 ng K562 | No Ct | 49.1 |
|  | ΔCt 35 ng SW480 to K562 | — | 16.9 |
| Generic MNAzyme | 35 ng SW480 | 29.1 | 28.1 |
|  | 1 in 10 | 33.7 | 32.8 |
|  | 1 in 100 | 37.1 | 35.6 |
|  | 1 in 1000 | 39.8 | 36.4 |
|  | 35 ng K562 | 41.4 | 36.8 |
|  | ΔCt 35 ng SW480 to K562 | 12.3 | 8.7 |
| TaqMan® probe | 35 ng SW480 | 26.4 | 25.7 |
|  | 1 in 10 | 31.2 | 30.1 |
|  | 1 in 100 | 34.8 | 32.3 |
|  | 1 in 1000 | 38.1 | 32.9 |
|  | 35 ng K562 | 38.7 | 32.7 |
|  | ΔCt 35 ng SW480 to K562 | 12.3 | 7.0 |

Example 19: Comparing Different Unique Sequences (US) in PASS Primers Combined with an MNAzyme Readout In this example, fifteen different unique sequences (US) were inserted into the PASS primer specific for the CCB gene. PASS primers containing the US insert in either a loop or planar formation contained the US i1, i1a, i2, i2a, i2b, i3, i4, i5, i5a, i6, i7, i8, i9, i10 or i11 (Table 32).

The PASS primers are combined with MNAzyme qPCR whereby MNAzymes comprise a first partzyme that binds to the complement of the unique sequence (cUS) as well as amplified target sequence that is tailored for CCB. The second partzyme binds adjacently to the first partzyme on the amplified target sequence of interest.

PASS primers and partzymes were designed for each US to determine if the various unique sequences were compatible with amplification and detection of a gene.

TABLE 32

Number and sequence for each US insert

| Insert number | Sequence (5' to 3') |
|---|---|
| i1 (SEQ ID NO: 182) | CACAATCAGT |
| i1a (SEQ ID NO: 183) | CACAATGATG |
| i2 (SEQ ID NO: 184) | AGACATACTA |
| i2a (SEQ ID NO: 185) | AGACAGTTAC |
| i2b (SEQ ID NO: 186) | AGAGTCATTC |
| i3 (SEQ ID NO: 187) | CGTTGGCTAC |
| i4 (SEQ ID NO: 188) | TCAATACCAT |
| i5 (SEQ ID NO: 189) | GATTCGAGAA |
| i5a (SEQ ID NO: 190) | GATTCGAGTT |
| i6 (SEQ ID NO: 191) | GTTACCTGAA |
| i7 (SEQ ID NO: 192) | CATTAGTGCC |
| i8 (SEQ ID NO: 193) | CATTGACAGA |
| i9 (SEQ ID NO: 194) | CGAAAGCGAC |

TABLE 32-continued

Number and sequence for each US insert

| Insert number | Sequence (5' to 3') |
|---|---|
| i10 (SEQ ID NO: 195) | CGTCTCATCA |
| i11 (SEQ ID NO: 196) | GGATTAGATC |

19.1. Partzyme Oligonucleotides

Partzymes were designed to specifically target the CCB gene plus any cUS introduced via a PASS primer. In the following sequences the bases in bold hybridize with the target sequence of interest and bases underlined are the unique sequence inserts (i1, i1a, i2, i2a, i2b, i3, i4, i5, i5a, i6, i7, i8, i9, i10 or i11) which are mismatched with respect to the starting template. The "-P" indicates 3' phosphorylation of the oligonucleotide. All sequences are written 5' to 3'.

SEQ ID NO: 86 partzyme B CCBB/2-P:
TGCCCAGGGAGGCTAGCTGGTCCATGGCTTCTGGGTA

SEQ ID NO: 197 partzyme A CCB_2i1A/2-P:
CACAATCAGTCCAGAGCCCAACAACGAGAGGAAACCTT SEQ ID NO: 198 partzyme A CCB_2i1aA/2-P:
CACAATGATGCCAGAGCCCAACAACGAGAGGAAACCTT SEQ ID NO: 89 partzyme A CCB_2i2A/2-P:
AGACATACTACCAGAGCCCAACAACGAGAGGAAACCTT SEQ ID NO: 199 partzyme A CCB_2i2aA/2-P:
AGACAGTTACCCAGAGCCCAACAACGAGAGGAAACCTT SEQ ID NO: 200 partzyme A CCB_2ibA/2-P:
AGAGTCATTCCCAGAGCCCAACAACGAGAGGAAACCTT SEQ ID NO: 201 partzyme A CCB_2i3A/2-P:
GTTGGCTACCCAGAGCCCAACAACGAGAGGAAACCTT SEQ ID NO: 202 partzyme A CCB_2i4A/2-P:
TCAATACCATCCAGAGCCCAACAACGAGAGGAAACCTT SEQ ID NO: 203 partzyme A CCB_2i5A/2-P:
GATTCGAGAACCAGAGCCCAACAACGAGAGGAAACCTT SEQ ID NO: 204 partzyme A CCB_2i5aA/2-P:
GATTCGAGTTCCAGAGCCCAACAACGAGAGGAAACCTT SEQ ID NO: 205 partzyme A CCB_2i6A/2-P:
GTTACCTGAACCAGAGCCCAACAACGAGAGGAAACCTT SEQ ID NO: 206 partzyme A CCB_2i7A/2-P:
CATTAGTGCCCCAGAGCCCAACAACGAGAGGAAACCTT SEQ ID NO: 207 partzyme A CCB_2i8A/2-P:
CATTGACAGACCAGAGCCCAACAACGAGAGGAAACCTT SEQ ID NO: 208 partzyme A CCB_2i9A/2-P:
GAAAGCGACCCAGAGCCCAACAACGAGAGGAAACCTT SEQ ID NO: 209 partzyme A CCB_2i10A/2-P:
CGTCTCATCACCAGAGCCCAACAACGAGAGGAAACCTT SEQ ID NO: 210 partzyme A CCB_2i11A/2-P:
GGATTAGATCCCAGAGCCCAACAACGAGAGGAAACCTT 19.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 94 Substrate Sub2-FIB:
AAGGTTTCCTCguCCCTGGGCA 19.3. PCR Primers for Amplification of CCB DNA In vitro amplification of the CCB gene in human gDNA was performed using the oligonucleotide PCR primers listed below. PASS primers are designed so that the forward primer was specific for CCB and contained US insert (i1, i1a, i2, i2a, i2b, i3, i4, i5, i5a, i6, i7, i8, i9, i10 or i11). In the following sequences bases underlined are the unique sequence inserts which are mismatched with respect to the starting template. The L represents the US in loop formation and the P represents the US in planar formation. All sequences are written 5' to 3'.

SEQ ID NO: 7 Reverse primer 3CCB:
CTCAGGAATTTCCCAGCTAC

SEQ ID NO: 211 Forward PASS primer 5CCB_Pi1:
CTCTTGTCTCAGTTCTTCTTGG<u>CACAATCAGT</u>CCAGAGC SEQ ID NO: 212 Forward PASS primer 5CCB_Li1:
TCAGTTCTTCTTGGATGGTCAT<u>CACAATCAGT</u>CCAGAGC SEQ ID NO: 213 Forward PASS primer 5CCB_Pi1a:
CTCTTGTCTCAGTTCTTCTTGG<u>CACAATGATG</u>CCAGAGC SEQ ID NO: 214 Forward PASS primer 5CCB_Li1a:
TCAGTTCTTCTTGGATGGTCAT<u>CACAATGATG</u>CCAGAGC SEQ ID NO: 215 Forward PASS primer 5CCB_Li2:
TCAGTTCTTCTTGGATGGTCAT<u>AGACATACTA</u>CCAGAGC SEQ ID NO: 216 Forward PASS primer 5CCB_Pi2:
CTCTTGTCTCAGTTCTTCTTGG<u>AGACATACTA</u>CCAGAGC SEQ ID NO: 217 Forward PASS primer 5CCB_Pi2a:
CTCTTGTCTCAGTTCTTCTTGG<u>AGACAGTTAC</u>CCAGAGC SEQ ID NO: 218 Forward PASS primer 5CCB_Li2a:
TCAGTTCTTCTTGGATGGTCAT<u>AGACAGTTAC</u>CCAGAGC SEQ ID NO: 219 Forward PASS primer 5CCB_Pi2b:
CTCTTGTCTCAGTTCTTCTTGG<u>AGAGTCATTC</u>CCAGAGC SEQ ID NO: 220 Forward PASS primer 5CCB_Li2b:
TCAGTTCTTCTTGGATGGTCAT<u>AGAGTCATTC</u>CCAGAGC SEQ ID NO: 221 Forward PASS primer 5CCB_Pi3:
CTCTTGTCTCAGTTCTTCTTGG<u>CGTTGGCTAC</u>CCAGAGC SEQ ID NO: 222 Forward PASS primer 5CCB_Li3:
TCAGTTCTTCTTGGATGGTCAT<u>CGTTGGCTAC</u>CCAGAGC SEQ ID NO: 223 Forward PASS primer 5CCB_Pi4:
CTCTTGTCTCAGTTCTTCTTGG<u>TCAATACCAT</u>CCAGAGC Forward PASS primer 5CCB_Li4
SEQ ID NO: 224
TCAGTTCTTCTTGGATGGTCAT<u>TCAATACCAT</u>CCAGAGC Forward PASS primer 5CCB_Pi5
SEQ ID NO: 225
CTCTTGTCTCAGTTCTTCTTGG<u>GATTCGAGAA</u>CCAGAGC Forward PASS primer 5CCB_Li5
SEQ ID NO: 226
TCAGTTCTTCTTGGATGGTCAT<u>GATTCGAGAA</u>CCAGAGC -continued SEQ ID NO: 227 Forward PASS primer 5CCB_Pi5a:
CTCTTGTCTCAGTTCTTCTTGGGATTCGAGTTCCAGAGC SEQ ID NO: 228 Forward PASS primer 5CCB_Li5a:
TCAGTTCTTCTTGGATGGTCATGATTCGAGTTCCAGAGC SEQ ID NO: 229 Forward PASS primer 5CCB_Pi6:
CTCTTGTCTCAGTTCTTCTTGGGTTACCTGAACCAGAGC SEQ ID NO: 230 Forward PASS primer 5CCB_Li6:
TCAGTTCTTCTTGGATGGTCATGTTACCTGAACCAGAGC SEQ ID NO: 231 Forward PASS primer 5CCB_Pi7:
CTCTTGTCTCAGTTCTTCTTGGCATTAGTGCCCCAGAGC SEQ ID NO: 232 Forward PASS primer 5CCB_Li7:
TCAGTTCTTCTTGGATGGTCATCATTAGTGCCCCAGAGC SEQ ID NO: 233 Forward PASS primer 5CCB_Pi8:
CTCTTGTCTCAGTTCTTCTTGGCATTGACAGACCAGAGC SEQ ID NO: 234 Forward PASS primer 5CCB_Li8:
TCAGTTCTTCTTGGATGGTCATCATTGACAGACCAGAGC SEQ ID NO: 235 Forward PASS primer 5CCB_Pi9:
CTTGTCTCAGTTCTTCTTGGCGAAAGCGACCCAGAGC SEQ ID NO: 236 Forward PASS primer 5CCB_Li9:
TTCTTCTTGGATGGTCATCTCGAAAGCGACCCAGAGC SEQ ID NO: 237 Forward PASS primer 5CCB_Pi10:
CTCTTGTCTCAGTTCTTCTTGGCGTCTCATCACCAGAGC SEQ ID NO: 238 Forward PASS primer 5CCB_Li10:
TCAGTTCTTCTTGGATGGTCATCGTCTCATCACCAGAGC SEQ ID NO: 239 Forward PASS primer 5CCB_Pi11:
CTCTTGTCTCAGTTCTTCTTGGGGATTAGATCCCAGAGC SEQ ID NO: 240 Forward PASS primer 5CCB_Li11:
TCAGTTCTTCTTGGATGGTCATGGATTAGATCCCAGAGC

19.4. Target Sequence

Human gDNA extracted from the IM9 cell line was used as template for in vitro amplification of the CCB gene.

19.5. Reaction Components: Amplification and Detection of Target Sequence

Real-time amplification and detection of the target sequence was performed in a total reaction volume of 25 µL The reactions were conducted in a CFX96™ Real-Time PCR detection System (BioRad). The cycling parameters were 95° C. for 2 minutes, 5 cycles of 95° C. for 15 seconds and 55° C. for 30 seconds, 40 cycles of 95° C. for 15 seconds and 52° C. for 50 seconds (data collected at the 52° C.). All reactions were run in duplicate and contained 40 nM forward primer and 200 nM partzyme A (as outlined in Table 33), 200 nM of reverse primer (3CCB), 200 nM partzyme B (CCBB/2-P), 200 nM substrate (Sub2-FIB), 8 mM $MgCl_2$, 200 µM of each dNTP, 10 units RiboSafe RNAase Inhibitor (Bioline), 1× ImmoBuffer (Bioline), 2 units of MyTaq™ HS DNA polymerase (Bioline) and either IM9 gDNA template (50 ng) or no target (NF $H_2O$).

TABLE 33

Forward PASS Primer and partzyme A combinations.

| Unique sequence | Partzyme A | Forward PASS Primer | PASS type |
|---|---|---|---|
| Insert 1 | CCB_2i1A/2-P | 5CCB_Li1 | Loop |
| | | 5CCB_Pi1 | Planar |
| Insert 1a | CCB_2i1aA/2-P | 5CCB_Li1a | Loop |
| | | 5CCB_Pi1a | Planar |
| Insert 2 | CCB_2i2A/2-P | 5CCB_Li2 | Loop |
| | | 5CCB_Pi2 | Planar |

TABLE 33-continued

Forward PASS Primer and partzyme A combinations.

| Unique sequence | Partzyme A | Forward PASS Primer | PASS type |
|---|---|---|---|
| Insert 2a | CCB_2i2aA/2-P | 5CCB_Li2a | Loop |
| | | 5CCB_Pi2a | Planar |
| Insert 2b | CCB_2i2bA/2-P | 5CCB_Li2b | Loop |
| | | 5CCB_Pi2b | Planar |
| Insert 3 | CCB_2i3A/2-P | 5CCB_Li3 | Loop |
| | | 5CCB_Pi3 | Planar |
| Insert 4 | CCB_2i4A/2-P | 5CCB_Li4 | Loop |
| | | 5CCB_Pi4 | Planar |
| Insert 5 | CCB_2i5A/2-P | 5CCB_Li5 | Loop |
| | | 5CCB_Pi5 | Planar |
| Insert 5a | CCB_2i5aA/2-P | 5CCB_Li5a | Loop |
| | | 5CCB_Pi5a | Planar |
| Insert 6 | CCB_2i6A/2-P | 5CCB_Li6 | Loop |
| | | 5CCB_Pi6 | Planar |
| Insert 7 | CCB_2i7A/2-P | 5CCB_Li7 | Loop |
| | | 5CCB_Pi7 | Planar |
| Insert 8 | CCB_2i8A/2-P | 5CCB_Li8 | Loop |
| | | 5CCB_Pi8 | Planar |
| Insert 9 | CCB_2i9A/2-P | 5CCB_Li9 | Loop |
| | | 5CCB_Pi9 | Planar |
| Insert 10 | CCB_2i10A/2-P | 5CCB_Li10 | Loop |
| | | 5CCB_Pi10 | Planar |
| Insert 11 | CCB_2i11A/2-P | 5CCB_Li11 | Loop |
| | | 5CCB_Pi11 | Planar |

19.6. Results: Amplification of Target and Cleavage of Reporter Substrate

In reactions containing the CCB PASS primer (Planar and Loop) comprising US, i1, i1a, i2, i2a, i2b, i3, i4, i5, i5a, i6, i7, i8, i9, i10 or i11, the Ct values for 50 ng gDNA (IM9) indicated successful amplification and detection (Table 34).

The Cts of the Loop PASS primer assays showed very little variation for the insert sequences i1, i1a, i2, i2b, i5, i5a, i6, i7, i8, i10 and i11, with Cts ranging from 21.3 to 22.9 (Table 34). The other Loop PASS primers i2a, i3, i4, and i9 had Cts ranging from 26.0 to 30.9 (Table 34 (underlined)) indicating that the unique sequence impacted on the efficiency of amplification when coupled with this target under theses reaction conditions. Analysis of secondary structure of the amplicon generated from the Loop PASS primers containing the unique sequences for inserts i2a, i3, or i4 showed potential formation of a strong hairpin which may impact amplification efficiency.

The Cts of the Planar PASS primer assays showed very little variation for the insert sequences i1, i1a, i2, i2b, i4, i5, i5a, i6, i7, i8, i10 and i11, with Cts ranging from 21.2 to 22.5 (Table 34). The other Planar PASS primers i2a, i3, and i9 had Cts ranging from 25.0 to 29.0 (Table 34 (underlined)) indicating the unique sequence impacted on the efficiency of amplification when coupled with this target under theses reaction conditions. Analysis of secondary structure of the amplicon generated from the Planar PASS primers containing the unique sequences for inserts i2a and i3 showed potential formation of a strong hairpin which may impact amplification efficiency.

Overall, eleven (Loop) and twelve (Planar) of the fifteen US inserts were suitable for analysis of CCB sequence. However, the experiment demonstrated that a variety of different unique insert sequences can be used for amplification and detection of the same target and if amplification efficiency appears to be affected then testing another insert sequence may improve the signal. Those US inserts which did not perform well within the context of this CCB amplicon may be useful in PASS systems targeting other genes.

TABLE 34

Ct values for PASS primer and partzyme combinations for CCB assays

| PASS Design | Insert # | IM9 50 ng Ct (Ave) | PASS Design | Insert # | IM9 50 ng Ct (Ave) |
|---|---|---|---|---|---|
| Loop | 1 | 21.3 | Planar | 1 | 21.3 |
| | 1a | 22.0 | | 1a | 22.0 |
| | 2 | 21.9 | | 2 | 21.9 |
| | 2a | 26.5 | | 2a | 27.4 |
| | 2b | 22.4 | | 2b | 22.5 |
| | 3 | 30.9 | | 3 | 29.0 |
| | 4 | 26.0 | | 4 | 21.6 |
| | 5 | 21.6 | | 5 | 21.6 |
| | 5a | 21.4 | | 5a | 21.2 |
| | 6 | 21.4 | | 6 | 21.7 |
| | 7 | 22.0 | | 7 | 22.2 |
| | 8 | 22.9 | | 8 | 21.7 |
| | 9 | 27.2 | | 9 | 25.0 |
| | 10 | 21.3 | | 10 | 21.2 |
| | 11 | 22.0 | | 11 | 22.5 |

Example 20: Comparing Different Unique Sequence Inserts in PASS Primers and Combined with MNAzymes to Detect Single Base Changes in Sequence PASS primers can be designed to discriminate between two sequences that vary by a single base, such that the target-specific 3' end (S2) contains the variant base and a mismatched base (FIG. 2 (i) and (ii) bottom). Further the US can be different for each variant adding another level of selectivity and specificity (FIG. 3).

In this example, fifteen different unique sequences were inserted into the PASS primer for the reverse complement KRAS wild type sequence in codon 12 referred to as rcG12. PASS primers containing the US in either a loop or planar formation were designed to be specific for the G12 sequence and contained the US inserts i1, i1a, i2, i2a, i2b, i3, i4, i5, i5a, i6, i7, i8, i9, i10 or i11 (Table 32).

The PASS primers are combined with MNAzyme qPCR whereby MNAzymes comprise a first partzyme that binds to the complement of the unique sequence (cUS) as well as amplified target sequence containing the complement of the wild type sequence and mismatched base. The second partzyme binds adjacently to the first partzyme on the amplified target sequence of interest.

PASS primers and partzymes were designed for each US to determine if the various scenarios improved reaction efficiency and specificity for the KRAS wild type G12 over the mutation variant G12S.

20.1. Partzyme Oligonucleotides

Partzymes were designed to specifically target the wild type rcG12 of the KRAS gene plus any cUS insert and mismatch introduced via a PASS primer. In the following sequences the bases in bold hybridize with the target sequence of interest, bases bold and underlined represent the wild type variant base that is different when compared to the G12S template, bases underlined and in italics represent a mismatched base and bases underlined are the unique sequences inserts (i1, i1a, i2, i2a, i2b, i3, i4, i5, i5a, i6, i7, i8, i9, i10 or i11) which are mismatched with respect to the starting template. The "-P" indicates 3' phosphorylation of the oligonucleotide. All sequences are written 5' to 3'.

SEQ ID NO: 241 partzyme B: rcG12_2B/55-P
GAGCTGGGGAGGCTAGCTCTCCAACTACCACAAGTTTATA SEQ ID NO: 242 partzyme A: rcG12_2i1A/55-P
CACAATCAGTACGCCTCCAGACAACGAGAGGTGCGG SEQ ID NO: 243 partzyme A: rcG12_2i1aA/55-P
CACAATGATGACGCCTCCAGACAACGAGAGGTGCGG SEQ ID NO: 244 partzyme A: rcG12_2i2A/55-P
AGACATACTAACGCCTCCAGACAACGAGAGGTGCGG SEQ ID NO: 245 partzyme A: rcG12_2i2aA/55-P
AGACAGTTACACGCCTCCAGACAACGAGAGGTGCGG SEQ ID NO: 246 partzyme A: rcG12_2i2bA/55-P
AGAGTCATTCACGCCTCCAGACAACGAGAGGTGCGG SEQ ID NO: 247 partzyme A: rcG12_2i3A/55-P
GTTGGCTACACGCCTCCAGACAACGAGAGGTGCGG SEQ ID NO: 248 partzyme A: rcG12_2i4A/55-P
CAATACCATACGCCTCCAGACAACGAGAGGTGCGGT SEQ ID NO: 249 partzyme A: rcG12_2i5A/55-P
GATTCGAGAAACGCCTCCAGACAACGAGAGGTGCGG SEQ ID NO: 250 partzyme A: rcG12_2i5aA/55-P
GATTCGAGTTACGCCTCCAGACAACGAGAGGTGCGG SEQ ID NO: 251 partzyme A: rcG12_2i6A/55-P
GTTACCTGAAACGCCTCCAGACAACGAGAGGTGCGG SEQ ID NO: 252 partzyme A: rcG12_2i7A/55-P
CATTAGTGCCACGCCTCCAGACAACGAGAGGTGCGG SEQ ID NO: 253 partzyme A: rcG12_2i8A/55-P
CATTGACAGAACGCCTCCAGACAACGAGAGGTGCGG SEQ ID NO: 254 partzyme A: rcG12_2i9A/55-P
GAAAGCGACACGCCTCCAGACAACGAGAGGTGCGG SEQ ID NO: 255 partzyme A: rcG12_2i10A/55-P
CGTCTCATCAACGCCTCCAGACAACGAGAGGTGCGG SEQ ID NO: 256 partzyme A: rcG12_2i11A/55-P
GGATTAGATCACGCCTCCAGACAACGAGAGGTGCGG 20.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 25 Substrate Sub55-FIB:
ACCGCACCTCguCCCCAGCTC 20.3. PCR Primers for Amplification of KRAS DNA In vitro amplification of the KRAS gene in human gDNA was performed using the oligonucleotide PCR primers listed below. PASS primers are designed so that the forward primer was specific for the wild type and contained US insert (i1, i1a, i2, i2a, i2b, i3, i4, i5, i5a, i6, i7, i8, i9, i10 or i11). In the following sequences bases underlined are the unique sequence inserts which are mismatched with respect to the starting template, bases in bold hybridize with the target sequence, bases bold and underlined represent the wild type variant base that is different when compared to the G12S template, and bases italicised represent a base mismatched to the target. The L represents the US in loop formation and the P represents the US in planar formation. All sequences are written 5' to 3'.

SEQ ID NO: 65 Reverse primer: 3rcKRAS
TATTAAAAGGTACTGGTGGAGTA

SEQ ID NO: 257 Forward PASS primer: 5rcG12_i1L
TGTATCGTCAAGGCACTCTTGC<u>CACAATCAGT</u>ACGCC<u>TCC</u>

SEQ ID NO: 258 Forward PASS primer: 5rcG12_i1P
TGAATTAGCTGTATCGTCAAGGC<u>CACAATCAGT</u>ACGCC<u>TCC</u>

SEQ ID NO: 259 Forward PASS primer: 5rcG12_i1aL
TGTATCGTCAAGGCACTCTTGC<u>CACAATGATG</u>ACGCC<u>TCC</u>

SEQ ID NO: 260 Forward PASS primer: 5rcG12_i1aP
TGAATTAGCTGTATCGTCAAGGC<u>CACAATGATG</u>ACGCC<u>TCC</u>

SEQ ID NO: 261 Forward PASS primer: 5rcG12_i2L
TGTATCGTCAAGGCACTCTTGC<u>AGACATACTA</u>ACGCC<u>TCC</u>

SEQ ID NO: 262 Forward PASS primer: 5rcG12_i2P
TGAATTAGCTGTATCGTCAAGGC<u>AGACATACTA</u>ACGCC<u>TCC</u>

SEQ ID NO: 263 Forward PASS primer: 5rcG12_i2aL
TGTATCGTCAAGGCACTCTTGC<u>AGACAGTTAC</u>ACGCC<u>TCC</u>

SEQ ID NO: 264 Forward PASS primer: 5rcG12_i2aP
TGAATTAGCTGTATCGTCAAGGC<u>AGACAGTTAC</u>ACGCC<u>TCC</u>

SEQ ID NO: 265 Forward PASS primer: 5rcG12_i2bL
TGTATCGTCAAGGCACTCTTGC<u>AGAGTCATT</u>CACGCC<u>TCC</u>

SEQ ID NO: 266 Forward PASS primer: 5rcG12_i2bP
TGAATTAGCTGTATCGTCAAGGC<u>AGAGTCATT</u>CACGCC<u>TCC</u>

SEQ ID NO: 267 Forward PASS primer: 5rcG12_i3L
TGTATCGTCAAGGCACTCTTGC<u>CGTTGGCTAC</u>ACGCC<u>TCC</u>

SEQ ID NO: 268 Forward PASS primer: 5rcG12_i3P
TGAATTAGCTGTATCGTCAAGGC<u>CGTTGGCTAC</u>ACGCC<u>TCC</u>

SEQ ID NO: 269 Forward PASS primer: 5rcG12_i4L
TGTATCGTCAAGGCACTCTTGC<u>TCAATACCAT</u>ACGCC<u>TCC</u>

SEQ ID NO: 270 Forward PASS primer: 5rcG12_i4P
TGAATTAGCTGTATCGTCAAGGC<u>TCAATACCAT</u>ACGCC<u>TCC</u>

SEQ ID NO: 271 Forward PASS primer: 5rcG12_i5L
TGTATCGTCAAGGCACTCTTGC<u>GATTCGAGAA</u>ACGCC<u>TCC</u>

SEQ ID NO: 272 Forward PASS primer: 5rcG12_i5P
TGAATTAGCTGTATCGTCAAGGC<u>GATTCGAGAA</u>ACGCC<u>TCC</u>

SEQ ID NO: 273 Forward PASS primer: 5rcG12_i5aL
TGTATCGTCAAGGCACTCTTGC<u>GATTCGAGTT</u>ACGCC<u>TCC</u>

SEQ ID NO: 274 Forward PASS primer: 5rcG12_i5aP
TGAATTAGCTGTATCGTCAAGGC<u>GATTCGAGTT</u>ACGCC<u>TCC</u>

SEQ ID NO: 275 Forward PASS primer: 5rcG12_i6L
TGTATCGTCAAGGCACTCTTGC<u>GTTACCTGAA</u>ACGCC<u>TCC</u>

SEQ ID NO: 276 Forward PASS primer: 5rcG12_i6P
TGAATTAGCTGTATCGTCAAGGC<u>GTTACCTGAA</u>ACGCC<u>TCC</u>

SEQ ID NO: 277 Forward PASS primer: 5rcG12_i7L
TGTATCGTCAAGGCACTCTTGC<u>CATTAGTGCC</u>ACGCC<u>TCC</u>

SEQ ID NO: 278 Forward PASS primer: 5rcG12_i7P
TGAATTAGCTGTATCGTCAAGGC<u>CATTAGTGCC</u>ACGCC<u>TCC</u>

SEQ ID NO: 279 Forward PASS primer: 5rcG12_i8L
TGTATCGTCAAGGCACTCTTGC<u>CATTGACAGA</u>ACGCC<u>TCC</u>

SEQ ID NO: 280 Forward PASS primer: 5rcG12_i8P
TGAATTAGCTGTATCGTCAAGGC<u>CATTGACAGA</u>ACGCC<u>TCC</u>

SEQ ID NO: 281 Forward PASS primer: 5rcG12_i9L
TGTATCGTCAAGGCACTCTTGC<u>CGAAAGCGAC</u>ACGCC<u>TCC</u>

SEQ ID NO: 282 Forward PASS primer: 5rcG12_i9P
TGAATTAGCTGTATCGTCAAGGC<u>CGAAAGCGAC</u>ACGCC<u>TCC</u>

SEQ ID NO: 283 Forward PASS primer: 5rcG12_i10L
TGTATCGTCAAGGCACTCTTGC<u>CGTCTCATCA</u>ACGCC<u>TCC</u>

SEQ ID NO: 284 Forward PASS primer: 5rcG12_i10P
TGAATTAGCTGTATCGTCAAGGC<u>CGTCTCATCA</u>ACGCC<u>TCC</u>

SEQ ID NO: 285 Forward PASS primer: 5rcG12_i11L
TGTATCGTCAAGGCACTCTTGC<u>GGATTAGATC</u>ACGCC<u>TCC</u>

SEQ ID NO: 286 Forward PASS primer: 5rcG12_i11P
TGAATTAGCTGTATCGTCAAGGC<u>GGATTAGATC</u>ACGCC<u>TCC</u>

20.4. Target Sequence

Human gDNA extracted from the IM9 cell line was used as template for in vitro amplification of the wild type KRAS gene and human gDNA extracted from the A549 cell line as a negative control containing the homozygous point mutation G12S.

20.5. Reaction Components: Amplification and Detection of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 40 cycles of 95° C. for 15 seconds and 54° C. for 50 seconds (data collected at the 54° C.). All reactions were run in duplicate and contained 40 nM forward primer and 100 nM partzyme A (as outlined in Table 35), 200 nM of reverse primer (3rcKRAS), 200 nM partzyme B (rcG12_2B/55-P), 200 nM substrate (Sub55-FIB), 8 mM MgCl$_2$, 200 μM of each dNTP, 10 units RiboSafe RNAase Inhibitor (Bioline), 1× ImmoBuffer (Bioline), 2 units of MyTaq™ HS DNA polymerase (Bioline) and either IM9 gDNA template (35 ng) as a Test, A549 gDNA template (35 ng) as a negative control or no target (NF H$_2$O).

TABLE 35

Forward PASS Primer and partzyme A combinations.

| Unique sequence | Partzyme A | Forward Primer | PASS type |
| --- | --- | --- | --- |
| Insert 1 | rcG12_2i1A/55-P | 5rcG12_i1L | Loop |
| | | 5rcG12_i1P | Planar |
| Insert 1a | rcG12_2i1aA/55-P | 5rcG12_i1aL | Loop |
| | | 5rcG12_i1aP | Planar |
| Insert 2 | rcG12_2i2A/55-P | 5rcG12_i2L | Loop |
| | | 5rcG12_i2P | Planar |
| Insert 2a | rcG12_2i2aA/55-P | 5rcG12_i2aL | Loop |
| | | 5rcG12_i2aP | Planar |
| Insert 2b | rcG12_2i2bA/55-P | 5rcG12_i2bL | Loop |
| | | 5rcG12_i2bP | Planar |
| Insert 3 | rcG12_2i3A/55-P | 5rcG12_i3L | Loop |
| | | 5rcG12_i3P | Planar |
| Insert 4 | rcG12_2i4A/55-P | 5rcG12_i4L | Loop |
| | | 5rcG12_i4P | Planar |
| Insert 5 | rcG12_2i5A/55-P | 5rcG12_i5L | Loop |
| | | 5rcG12_i5P | Planar |
| Insert 5a | rcG12_2i5aA/55-P | 5rcG12_i5aL | Loop |
| | | 5rcG12_i5aP | Planar |
| Insert 6 | rcG12_2i6A/55-P | 5rcG12_i6L | Loop |
| | | 5rcG12_i6P | Planar |
| Insert 7 | rcG12_2i7A/55-P | 5rcG12_i7L | Loop |
| | | 5rcG12_i7P | Planar |
| Insert 8 | rcG12_2i8A/55-P | 5rcG12_i8L | Loop |
| | | 5rcG12_i8P | Planar |

TABLE 35-continued

Forward PASS Primer and partzyme A combinations.

| Unique sequence | Partzyme A | Forward Primer | PASS type |
|---|---|---|---|
| Insert 9 | rcG12_2i9A/55-P | 5rcG12_i9L | Loop |
| | | 5rcG12_i9P | Planar |
| Insert 10 | rcG12_2i10A/55-P | 5rcG12_i10L | Loop |
| | | 5rcG12_i10P | Planar |
| Insert 11 | rcG12_2i11A/55-P | 5rcG12_i11L | Loop |
| | | 5rcG12_i11P | Planar |

20.6. Results: Amplification of Target and Cleavage of Reporter Substrate

PASS primers containing different US inserts were used to produce amplicons for the real-time detection of the KRAS wild type (G12). This reaction showed an increase in fluorescence over time when the target sequence used was Test human gDNA (K562) amplified via PCR. The fluorescence of the no template control was lower than that in the DNA target-containing reactions. This demonstrates that the increase in fluorescence produced in target-containing reactions is due to target dependent assembly of catalytically active MNAzyme that then cleaved the reporter substrate.

In reactions containing wild type G12 PASS primer (Planar and Loop) comprising US, i1, i1a, i2, i2a, i2b, i3, i4, i5, i5a, i6, i7, i8, i9, i10 or i11, the Ct values for the "Test" DNA (K562) indicated successful amplification and detection of the wild type KRAS allele in K562. The signal for the "Negative control" (G12S) reached threshold Ct values as shown in Table 36 indicating that some background signal was produced when variant allele was used, and that the ΔCt values between wild type and variant G12S could be influenced by the composition of the unique sequence inserted into the PASS primer.

The Cts of the Loop PASS primer assays for the Test sample showed very little variation with Cts ranging from 18.6 to 21.3 however the negative controls had Cts ranging from 29.7 to 37.3 indicating the US could impact on the specificity of the reaction (Table 36). For the Loop PASS primer the greatest ΔCt calculated between the Test and the negative control was 18.5 when US i7 was used this was followed by US i3 and i9 both with ΔCts>15. The ΔCts for the other US inserts were all very similar.

The Cts of the Planar PASS primer assays for the Test sample showed very little variation with Cts ranging from 17.9 to 20.9 however the negative controls had Cts ranging from 26.1 to 33.9 indicating the US could impact on the specificity for the reaction (Table 36). For the Planar PASS primer the greatest ΔCt calculated between the Test and the negative control was 11.8 when US i6 was used. All of the other ΔCts for the other US inserts were very similar falling within 2.3 Cts of each other.

TABLE 36

Ct values for PASS primer and partzyme A combinations for the wild type and mutant assays

| Design | US inserted | Reaction type | Ct | ΔCt from Test |
|---|---|---|---|---|
| Insert 1 | Loop | Test | 18.6 | 14.0 |
| | | Negative control | 32.6 | |
| | Planar | Test | 18.5 | 8.4 |
| | | Negative control | 26.9 | |
| Insert 1a | Loop | Test | 19.0 | 11.2 |
| | | Negative control | 30.2 | |
| | Planar | Test | 18.4 | 8.4 |
| | | Negative control | 26.8 | |
| Insert 2 | Loop | Test | 19.3 | 11.1 |
| | | Negative control | 30.4 | |
| | Planar | Test | 18.8 | 9.0 |
| | | Negative control | 27.8 | |
| Insert 2a | Loop | Test | 19.1 | 11.3 |
| | | Negative control | 30.4 | |
| | Planar | Test | 18.8 | 9.1 |
| | | Negative control | 27.9 | |
| Insert 2b | Loop | Test | 18.8 | 12.3 |
| | | Negative control | 31.1 | |
| | Planar | Test | 19.0 | 8.8 |
| | | Negative control | 27.8 | |
| Insert 3 | Loop | Test | 19.5 | 15.3 |
| | | Negative control | 34.8 | |
| | Planar | Test | 19.5 | 8.0 |
| | | Negative control | 27.5^ | |
| Insert 4 | Loop | Test | 19.0 | 12.4 |
| | | Negative control | 31.4 | |
| | Planar | Test | 18.9 | 11.1 |
| | | Negative control | 30^ | |
| Insert 5 | Loop | Test | 18.6 | 11.4 |
| | | Negative control | 30.0 | |
| | Planar | Test | 19.8 | 10.5 |
| | | Negative control | 30.2 | |
| Insert 5a | Loop | Test | 18.6 | 12.6 |
| | | Negative control | 30.5 | |
| | Planar | Test | 18.8 | 9.9 |
| | | Negative control | 28.7 | |
| Insert 6 | Loop | Test | 18.6 | 11.5 |
| | | Negative control | 30.1 | |
| | Planar | Test | 22.1 | 11.8 |
| | | Negative control | 33.9 | |

TABLE 36-continued

Ct values for PASS primer and partzyme A combinations for the wild type and mutant assays

| Design | US inserted | Reaction type | Ct | ΔCt from Test |
|---|---|---|---|---|
| Insert 7 | Loop | Test | 18.9 | 18.5 |
| | | Negative control | 37.4 | |
| | Planar | Test | 17.9 | 8.2 |
| | | Negative control | 26.1 | |
| Insert 8 | Loop | Test | 21.0 | 14.1 |
| | | Negative control | 35.1 | |
| | Planar | Test | 18.7 | 9.4 |
| | | Negative control | 28.1 | |
| Insert 9 | Loop | Test | 21.3 | 16.0 |
| | | Negative control | 37.3 | |
| | Planar | Test | 18.4 | 8.6 |
| | | Negative control | 27.0 | |
| Insert 10 | Loop | Test | 19.4 | 12.8 |
| | | Negative control | 32.3 | |
| | Planar | Test | 18.7 | 8.9 |
| | | Negative control | 27.6 | |
| Insert 11 | Loop | Test | 19.0 | 10.7 |
| | | Negative control | 29.7 | |
| | Planar | Test | 20.9 | 10.1 |
| | | Negative control | 31.0 | |

^only one replicate worked due to experimental error

Overall, all fifteen US's were suitable for analysis of wild type target sequence. There were differences in the results with slightly more variability observed in the Loop PASS primer assays than for the Planar PASS primer assays evident by the greater range of Ct values obtained. However, the experiment demonstrated that a variety of different unique insert sequences can be used for amplification and detection of the same target and screening to find the best PASS primer/US insert combination can help to improve the specificity of the reaction.

Example 21: Comparing the Specificity of a PASS Primer Reaction to One that Combines a Forward PASS Primer with a Reverse Pinch PASS Primer Both Combined with MNAzymes to Detect Single Base Changes in Sequence The specificity of the PASS primers containing either a USI or a USJ was investigated in assays targeting the point mutations in codon 12 of KRAS referred to as G12V and G12S. This example investigates the ability to detect the variant strains G12V and G12S and to discriminate these from wild type and other KRAS G12/G13 variants.

In this example, a reverse standard primer was compared to using a reverse Pinch PASS primer both in combination with a forward PASS primer or forward Pinch PASS primer (G12S only) and an MNAzyme readout. The 3' S2 region of the reverse Pinch PASS primer bound closer to the partzyme sensing region than the standard reverse primer and looped out 43 bases from the target sequence resulting in an amplicon size of 100 bp compared to 160 bp with the standard reverse primer.

The assays containing a standard reverse primer were compared to those containing a reverse Pinch PASS primer both of which were combined with a forward PASS primer and MNAzyme detection in qPCR with a fluorescent readout to determine if a forward PASS primer can be combined with a reverse Pinch PASS primer and whether the additional PASS primer could influence the specificity of the reaction with respect to the ability to discriminate the variant sequence from the wild type and/or other variants.

21.1. Partzyme Oligonucleotides

Partzymes were designed to specifically target the KRAS gene for the variant G12S or G12V and/or any cUS introduced via a PASS primer. In the following sequences the bases in bold hybridize with the target sequence of interest, the bases in bold and underlined represent the two bases either side of the USJ, bases underlined hybridise to the cUS insert and bases in bold and italicised represent the variant bases (G12S or G12V) and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 161 partzyme A: G12S_gi2A/55-P
ACATACTAGTTGGAGGTAGTGACAACGAGAGGTGCGGT SEQ ID NO: 162 partzyme A: G12S_LT10A/55-P
TGAATATAAGTTGGAGGTAGTGACAACGAGAGGTGCGGT SEQ ID NO: 24 partzyme A G12V_LMi2A/55-P:
AGACATACTATGGAGCCG*T*TGACAACGAGAGGTGCGGT 21.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission u) wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 25 Substrate Sub55-FIB:
ACCGCACCTCguCCCCAGCTC 21.3. PCR Primers for Amplification of KRAS DNA In vitro amplification of human gDNA was performed using the oligonucleotide PCR primers listed below. In the following sequences the bases in bold hybridize with the target sequence, bases underlined are the USI which are mismatched with respect to the starting template, bases bold and italicised are the variant base, bases in bold and underlined are the USJ and bases italicised and underlined represent an additional base mismatched to both targets. All sequences are written 5' to 3'.

```
SEQ ID NO: 26 Reverse primer 3KRAS:
GGTCCTGCACCAGTAATATGC

SEQ ID NO: 166 Forward PASS primer
5G12S_gi2Planar:
CCTGCTGAAAATGACTGAATATAAAGACATACTAGTTGGAGGTA SEQ ID NO: 170 Forward Pinch PASS
primer 5G12S_LT10:
CCTGCTGAAAATGACTGAATATAAGTTGGAGGTA SEQ ID NO: 87 Forward PASS primer
5G12V_LM4i2Planar:
CTGCTGAAAATGACTGAATATAAACAGACATACTATGGAGCCGT SEQ ID NO: 171 Reverse Pinch PASS primer3
3Kras_LT4
TGCATATTAAAACAAGATTTACCTCTGTATCGTC
```

21.4. Target Sequence

Human gDNA extracted from the A549 cell line was used as template for in vitro amplification of the point mutation G12S and human gDNA extracted from the SW480 cell line was used as template for in vitro amplification of the point mutation G12V. Human gDNA extracted from the cell lines IM9 (wild type), and SW480 (G12V) were used as negative control template for KRAS variant G12S and human gDNA extracted from the cell lines IM9 (wild type) and A549 (G12S) were used as negative control template for the KRAS variant G12V.

21.5. Reaction Components: Amplification and Detection of Target Sequence

Real-time amplification and detection of the target sequence was performed in a total reaction volume of 25 µL. The reactions were conducted in a CFX96™ Real-Time PCR detection System (BioRad). The cycling parameters were 95° C. for 2 minutes, 10 cycles of 95° C. for 15 seconds and 64° C. for 60 seconds (minus 1° C. per cycle), 50 cycles of 95° C. for 15 seconds and 54° C. for 50 seconds (data collected at the 54° C. step). All reactions were run in duplicate and contained 40 nM forward primer, 100 nM partzyme A and 200 nM of reverse primer (the combinations are listed in Table 37). All reactions also contained 200 nM partzyme B (KRAS_B/55-P), 200 nM substrate (Sub55-FIB), 8 mM MgCl$_2$, 200 µM of each dNTP, 10 units RiboSafe RNAase Inhibitor (Bioline), 1x ImmoBuffer (Bioline), 2 units of MyTaq™ HS DNA polymerase (Bioline) and either 35 ng of A549 gDNA template used as a positive control for KRAS G12S target and 35 ng of SW480 (G12V) and IM9 (WT) used as negative controls, 35 ng of SW480 gDNA template was used as a positive control for KRAS G12V target and 35 ng of IM9 (WT) and A549 (G12S) was used as negative control and additional controls contained no target (NF H$_2$O).

TABLE 37

Forward primer, reverse primer and partzyme A combinations for the variant assays

| Target | Partzyme A | Forward Primer | Reverse primer |
|---|---|---|---|
| G12S | G12S_gi2A4/55-P | PASS (USI) 5G12S_gi2Planar | Standard 3KRAS |
|  |  |  | Pinch PASS 3KRAS_LT43 |
|  | G12S_LT10A4/55-P | PASS (USJ) 5G12S_LT10 | Standard 3KRAS |
|  |  |  | Pinch PASS 3KRAS_LT43 |
| G12V | G12V_LMi2A/55-P | PASS (USI) 5G12V_LM4i2Planar | Standard 3KRAS |
|  |  |  | Pinch PASS 3KRAS_LT43 |

21.6. Results: Amplification of Target and Cleavage of Reporter Substrate

The results of amplification and detection are summarised in the following Table 38.

TABLE 38

Ct values for PASS primer and partzyme combinations

| Target | Design | Reverse primer | Test | Template | Ct (Ave) | ΔCt from positive |
|---|---|---|---|---|---|---|
| G12S | PASS primer with USI | Standard | Positive | G12S (A549) | 21.6 |  |
|  |  |  | Negative | WT (IM9) | 34.5 | 12.9 |
|  |  |  | Negative | G12V (SW480) | 35.5 | 13.9 |
|  |  | Pinch PASS | Positive | G12S (A549) | 22.1 |  |
|  |  |  | Negative | WT (IM9) | 40.2 | 18.1 |
|  |  |  | Negative | G12V (SW480) | 40.6 | 18.5 |
|  | Pinch PASS primer with USJ | Standard | Positive | G12S (A549) | 22.3 |  |
|  |  |  | Negative | WT (IM9) | No Ct | >27.7 |
|  |  |  | Negative | G12V (SW480) | No Ct | >27.7 |
|  |  | Pinch PASS | Positive | G12S (A549) | 22.8 |  |
|  |  |  | Negative | WT (IM9) | No Ct | >27.2 |
|  |  |  | Negative | G12V (SW480) | No Ct | >27.2 |
| G12V | PASS primer with USI | Standard | Positive | G12V (SW480) | 21.3 |  |
|  |  |  | Negative | WT (IM9) | 37.1 | 15.8 |
|  |  |  | Negative | G12S (A549) | 37.5 | 16.2 |

TABLE 38-continued

Ct values for PASS primer and partzyme combinations

| Target | Design | Reverse primer | Test | Template | Ct (Ave) | ΔCt from positive |
|---|---|---|---|---|---|---|
| | | Pinch PASS | Positive | G12V (SW480) | 22.2 | |
| | | | Negative | WT (IM9) | No Ct | >27.8 |
| | | | Negative | G12S (A549) | No Ct | >27.8 |

N.B. When no Ct was produced for a negative control sample the final Ct of 50 was used to produce the ΔCt and a greater than symbol (>) placed in front to indicate that the ΔCt would be expected to be higher than this value.

The Ct values (Table 38) indicate that all combination of primers can efficiently amplify the target genes. When the G12S forward PASS primer combined with a standard reverse primer was compared to being combined with a reverse Pinch PASS primer the Ct of the positive sample was similar for both however when the negative control samples were tested the reverse Pinch PASS primer demonstrated greater specificity with the ΔCt increased by ~5 (Table 38). The G12S assay that employs a forward Pinch PASS primer demonstrated good amplification and specificity when used with a standard reverse primer. Combining it with the reverse Pinch PASS primer demonstrated efficient amplification and high specificity giving similar Ct's and ΔCt's (Table 38).

When the G12V forward PASS primer combined with a standard reverse primer was compared to results when combined with a reverse Pinch PASS primer the Ct of the positive sample was similar for both, however when the negative control samples were tested the reverse Pinch PASS primer demonstrated greater specificity with the ΔCt increased by greater than 11 (Table 38).

This example demonstrates that it will be feasible to combine forward PASS primers with reverse PASS primers without impacting amplification efficiency. Further combining forward PASS primers with reverse PASS primers may also improve the specificity of the reaction.

Example 22: Comparing the Sensitivity of PASS Primers with the Mismatch Base in Different Positions Combined with MNAzymes to Detect Single Base Changes in a Sequence The specificity of the PASS primers containing various types of mismatch bases at different positions was investigated in assays targeting the point mutation in codon 12 of KRAS referred to as G12V. The example investigated the ability to detect the variant strain G12V and to discriminate it from the wild type.

The design 3 (FIG. 7) planar and loop PASS primers were used for the amplification of G12V sequence. The mismatch base was located at position 2, 3 or 4 from the 3' end of S2 and was either a C:C, A:C, A:G, G:A, A:A or C:A mismatch. The PASS primers were combined with MNAzyme qPCR whereby MNAzymes comprise a first partzyme that binds to the complement of the unique sequence (cUS) as well as amplified target sequence containing the complement of the variant (mutant) base and mismatched base. The second partzyme binds adjacently to the first partzyme within amplified target sequence of interest.

PASS primers with different mismatch combinations were compared to investigate the effect on specificity.

22.1. Partzyme Oligonucleotides

Partzymes were designed to specifically target the G12V sequence and any mismatch and cUS introduced via the PASS primer. In the following sequences the bases in bold hybridize with the target sequence of interest and bases underlined are the unique sequence insert (i2) which is mismatched with respect to the starting template. Bases in bold and italicised represent the variant (mutant) base and bases underlined and in italics represent an additional mismatched base. The "-P" indicates 3' phosphorylation of the oligonucleotide. All sequences are written 5' to 3'.

SEQ ID NO: 18 partzyme B KRAS_B/55-P:
GAGCTGGGGAGGCTAGCTGCGTAGGCAAGAGTGCCTT

SEQ ID NO: 24 partzyme A G12V_LMi2A/55-P:
AGACATACTATGGAGC*C*GTTGACAACGAGAGGTGCGGT SEQ ID NO: 287 partzyme A G12V_g3i2A/55-P
AGACATACTATGGAGC*G*GTTGACAACGAGAGGTGCGGT SEQ ID NO: 288 partzyme A G12V_a3i2A/55-P
AGACATACTATGGAGC*A*GTTGACAACGAGAGGTGCGGT SEQ ID NO: 289 partzyme A G12V_c2i2A/55-P
AGACATACTATGGAGCT*C*TTGACAACGAGAGGTGCGGT SEQ ID NO: 290 partzyme A G12V_a2i2A/55-P
AGACATACTATGGAGCT*A*TTGACAACGAGAGGTGCGGT SEQ ID NO: 291 partzyme A G12V_a4i2A/55-P
AGACATACTATGGAG*A*TGTTGACAACGAGAGGTGCGGT 22.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

SEQ ID NO: 25 Substrate Sub55-FIB:
ACCGCACCTCguCCCCAGCTC 22.3. PCR Primers for Amplification of KRAS DNA In vitro amplification of human gDNA was performed using the oligonucleotide PCR primers listed below. In the following sequences the bases in bold hybridize with the target sequence, bases underlined are the unique sequences which are mismatched with respect to the starting template, bases bold and italicised are the variant base and bases italicised and underlined represent an additional base mismatched to both targets. All sequences are written 5' to 3'.

```
SEQ ID NO: 26 Reverse primer 3KRAS:
GGTCCTGCACCAGTAATATGC

SEQ ID NO: 50 Forward PASS primer
5G12V_LM3i2LLoop
GACTGAATATAAACTTGTGGTAGTAGACATACTATGGAGCCGT SEQ ID NO: 292 Forward PASS primer
5G12V_g3i2Loop
GACTGAATATAAACTTGTGGTAGTAGACATACTATGGAGCGGT SEQ ID NO: 293 Forward PASS primer
5G12V_a3i2Loop
GACTGAATATAAACTTGTGGTAGTAGACATACTATGGAGCAGT SEQ ID NO: 294 Forward PASS primer
5G12V_c2i2Loop
GACTGAATATAAACTTGTGGTAGTAGACATACTATGGAGCTCT SEQ ID NO: 295 Forward PASS primer
5G12V_a2i2Loop
GACTGAATATAAACTTGTGGTAGTAGACATACTATGGAGCTAT SEQ ID NO: 296 Forward PASS primer
5G12V_a4i2Loop
GACTGAATATAAACTTGTGGTAGTAGACATACTATGGAGATGT SEQ ID NO: 87 Forward PASS primer
5G12V_LM4i2Planar:
CTGCTGAAAATGACTGAATATAAACAGACATACTATGGAGCCGT SEQ ID NO: 297 Forward PASS primer
5G12V_g3i2Planar
CTGCTGAAAATGACTGAATATAAACAGACATACTATGGAGCGGT SEQ ID NO: 298 Forward PASS primer
5G12V_a3i2Planar
CTGCTGAAAATGACTGAATATAAACAGACATACTATGGAGCAGT SEQ ID NO: 299 Forward PASS primer
5G12V_c2i2Planar
CTGCTGAAAATGACTGAATATAAACAGACATACTATGGAGCTCT SEQ ID NO: 300 Forward PASS primer
5G12V_a2i2Planar
CTGCTGAAAATGACTGAATATAAACAGACATACTATGGAGCTAT SEQ ID NO: 301 Forward PASS primer
5G12V_a4i2Planar
CTGCTGAAAATGACTGAATATAAACAGACATACTATGGAGATGT
```

22.4. Target Sequence

Human gDNA extracted from the SW480 cell line was used as template for in vitro amplification of the point mutation G12V. Human gDNA extracted from the cell line IM9 (wild type) was used as negative control template for KRAS variant G12V.

22.5. Reaction Components: Amplification and Quantitation of Target Sequence

Real-time amplification and quantitation of the target sequence was performed in a total reaction volume of 25 µL. The reactions were conducted in a CFX96™ Real-Time PCR detection System (BioRad). The cycling parameters were 95° C. for 2 minutes, 10 cycles of 95° C. for 5 seconds and 60° C. for 20 seconds (minus 0.6° C. per cycle), 50 cycles of 95° C. for 5 seconds and 54° C. for 20 seconds (data collected at the 54° C. step). All reactions were run in duplicate and contained 40 nM forward primer and 100 nM partzyme A (outlined in Table 39), 200 nM of reverse primer (3KRAS), 200 nM partzyme B (KRAS_B/55-P), 200 nM substrate (Sub55-FIB), 8 mM MgCl$_2$, 200 µM of each dNTP, 10 units RiboSafe RNAase Inhibitor (Bioline), 1× ImmoBuffer (Bioline), 2 units of MyTaq™ HS DNA polymerase (Bioline) and either SW480 gDNA as the Test template (35 ng), K562 gDNA as the negative control template (35 ng) or no target (NF H$_2$O).

TABLE 39

Forward primer and partzyme A combinations for the variant assay

| Mismatch position (bases from 3' end) | Mismatch type | Partzyme A | Forward Primer |
|---|---|---|---|
| 3 | C:A | G12V_LMi2A/55-P | 5G12V_LM3i2LLoop<br>5G12V_LM4i2Planar |
| 3 | G:A | G12V_g3i2A/55-P | 5G12V_g3i2Loop<br>5G12V_g3i2Planar |
| 3 | A:A | G12V_a3i2A/55-P | 5G12V_a3i2Loop<br>5G12V_a3i2Planar |
| 2 | C:C | G12V_c2i2A/55-P | 5G12V_c2i2Loop<br>5G12V_c2i2Planar |
| 2 | A:C | G12V_a2i2A/55-P | 5G12V_a2i2Loop<br>5G12V_a2i2Planar |
| 4 | A:G | G12V_a4i2A/55-P | 5G12V_a4i2Loop<br>5G12V_a4i2Planar |

22.6. Results: Amplification of Target and Cleavage of Reporter Substrate

PASS primers containing different mismatch bases at different locations were used to produce amplicons for the real-time detection of the KRAS variant G12V. This reaction showed an increase in fluorescence over time when the target sequence used was Test human gDNA (SW480) amplified via PCR. The fluorescence of the no template control was lower than that in the DNA target-containing reactions. This demonstrates that the increase in fluorescence produced in target-containing reactions is due to target dependent assembly of catalytically active MNAzyme that then cleaved the reporter substrate.

In reactions containing a PASS primer with the mismatch base at position 3, the C:A mismatch produce an earlier Ct of 22.7/22.5 (Loop/Planar) for the Test reaction compared to the A:A mismatch with a Ct of 24.2/23.9 (Loop/Planar) (Table 40). The C:A mismatch was also more specific than the A:A mismatch with a ΔCt between the test and negative control of 15.4/14.2 (Loop/Planar) versus 12.6/14.0 (Loop/Planar) for the A:A mismatch (Table 40).

The PASS primer with a G:A mismatch at position 3 could not distinguish between the Test and negative control template, with negative ΔCt's for both loop and planar designs (Table 40). Further analysis of the PASS primer sequence created by having a "G" inserted at position 3, opposed to a "C" or "A" showed that the first 3 bases at the 3' end of S2 could bind to the wild type template 1 base 3' of where the S2 region would bind in the variant template, this binding was sufficiently strong that the PASS primer was no longer specific for the variant. This is an important feature that should be investigated each time a PASS primer is designed, and that is to check for any possible mis-priming that might arise due to the mismatch base selected, on any Test and negative control template.

The PASS primers that contained the mismatch base at position 2 from the 3' end of S2, demonstrated increased specificity with ΔCt's ranging from 15.0 to >24.0 (Table 40). However placing the mismatch at position 2 is more destabilising than at position 3 as the Ct values of the Test reactions were also increased. The C:C mismatch at position 2 was more destabilising than C:A increasing the Ct to 32.1/31.7 (loop/planar), and was also increased by almost 10 Ct more than the position 3 mismatches (Table 40). The A:C mismatch was seen to be less destabilising only increasing the Ct to −25 for both loop and planar PASS primers which is only 3 Ct more than the best mismatch at position 3. Of note with the PASS primers containing an A:C mismatch at position 2 was the only design where the US in loop formation displayed an advantage over the US in planar formation with a ΔCt of >24.3 compared to 15.0 for the planar (Table 40).

PASS primers with a mismatch at position 4 also demonstrated good specificity compared to having a mismatch at position 3 with ΔCt's of 13.1/14.4 (loop/planar) (Table 40).

This example demonstrates that the mismatch base can be located at various positions in the S2 region of the PASS primer and still maintain effectiveness and that the type of mismatch can be tailored to avoid any possible mis-priming or secondary structure.

TABLE 40

Ct values for G12V PASS vs. WE-ARMS primer

| Mismatch position & mismatch | US inserted | Reaction type | Ct | ΔCt from Test |
|---|---|---|---|---|
| 3 & C:A | Loop | Test | 22.7 | 15.4 |
|  |  | Negative control | 38.0 |  |
|  | Planar | Test | 22.5 | 14.2 |
|  |  | Negative control | 36.6 |  |
| 3 & G:A | Loop | Test | 27.8 | −1.0 |
|  |  | Negative control | 26.8 |  |
|  | Planar | Test | 27.0 | −0.5 |
|  |  | Negative control | 26.5 |  |
| 3 & A:A | Loop | Test | 24.2 | 12.6 |
|  |  | Negative control | 36.8 |  |
|  | Planar | Test | 23.9 | 14.0 |
|  |  | Negative control | 37.8 |  |
| 2 & C:C | Loop | Test | 32.1 | >17.9 |
|  |  | Negative control | No Ct |  |
|  | Planar | Test | 31.7 | >18.3 |
|  |  | Negative control | No Ct |  |
| 2 & A:C | Loop | Test | 25.8 | >24.3 |
|  |  | Negative control | No Ct |  |
|  | Planar | Test | 25.3 | 15.0 |
|  |  | Negative control | 40.3 |  |
| 4 & A:G | Loop | Test | 23.7 | 13.1 |
|  |  | Negative control | 36.8 |  |
|  | Planar | Test | 23.0 | 14.4 |
|  |  | Negative control | 37.4 |  |

N.B. When no Ct was produced for a negative control sample the final Ct of 50 was used to produce the ΔCt and a greater than symbol (>) placed in front to indicate that the ΔCt would be expected to be higher than this value.

Example 23: Investigating the Use of Different Primer and Partzyme a Design Combinations in a Model System In this example, the TFRC genome was used as a model system for testing different combinations of primer and partzyme A designs as described in FIG. 14.

More specifically, the following scenarios were tested, (i) a standard forward primer was combined with either a standard MNAzyme binding downstream of the forward primer (FIG. 14 (*i* A)) or an MNAzyme containing a Pinch Pass partzyme A binding downstream of the forward primer (FIG. 14 (*i* B)), (ii) a standard forward primer was combined with either a standard MNAzyme binding in a region overlapping with the forward primer (FIG. 14 (*ii* A)) or an MNAzyme containing a Pinch Pass partzyme A binding in a region overlapping with the forward primer (FIG. 14 (*ii* B)) or (iii) a forward primer containing a tag combined with either a standard MNAzyme binding in a region overlapping with the forward primer (FIG. 14 (*iii* A)) or an MNAzyme containing a tagged Pinch Pass partzyme A binding in a region overlapping with the tagged portion of the forward primer (FIG. 14 (*iii* C)).

The different combination of forward primers and partzyme A's, were combined with PCR amplification for a readout in real-time to determine if they were compatible with amplification and detection of the TFRC gene.

23.1. Partzyme Oligonucleotides

Partzymes were designed that were either a) fully matched "standard" partzymes where the sensor arm was fully and consecutively complementary to the target sequence or b) Pinch PASS partzymes in which, the partzyme A is complementary to non-consecutive stretches of sequence in the target amplicon, such that a portion of the amplicon is looped out at the USJ in the sensor arm of the partzyme. In the following sequences, the bases in bold hybridize with the target sequence of interest, the lowercase bases represent the first bases either side of the USJ and bases underlined bind to the complementary tag sequence inserted into the amplicon by the tagged forward primer. The "-P" indicates 3' phosphorylation of the oligonucleotide. All sequences are written 5' to 3'.

SEQ ID NO: 145 partzyme
B TFRC_2B/84-P:
TGGACGAGGGAGGCTAGCTTCTGACTGGAAAACAGACTCTA

SEQ ID NO: 146 partzyme
A TFRC_2A/84-P:
CTGATTCTAGGAATATGGAAGGAGACTGTCCCACAACGAGA

GGGTCGAG

SEQ ID NO: 302 Pinch PASS
partzyme A TFRC_2(54)pp10A/84-P:
TGCTTTCTGATTCTAGGAAtaCTGTCCCACAACGAGAGGGTCGAG SEQ ID NO: 303 Pinch PASS
partzyme A TFRC_2tagppA/84-P:
<u>TCGTTACCTAGTCTAAGc</u>aCTGTCCCACAACGAGAGGGTCGAG 23.2. Reporter Substrate In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored in real time by excitation at 450-490 nm (FAM excitation wavelength range on the CFX96 (BioRad)) and emission at 510-530 nm (FAM emission wavelength range on the CFX96 (BioRad)). The reporter substrate used in this this example is shown below with the sequence, 5' to 3'. The lower case bases represent RNA and the upper case bases represent DNA.

SEQ ID NO: 158 Substrate Sub84-FIB:
CTCGACCCTCguCCCTCGTCCA 23.3. Target Sequence and PCR Primers for Amplification of TFRC The target sequence for this example was the TFRC gene in human genomic DNA extracted from the IM9 cell line (Promega). The oligonucleotide PCR primers are listed below. The sequence in bold at the 5' termini of the primer sequences corresponds to a tag (T1, T2 or T3) not found in the target gene sequence. T1 and T2 are used to increase the Tm of the primer without affecting the specificity of the primer to the gene target. T3 is a longer tag that is used to introduce a stretch of tag sequence into the 5' end of the amplicon. Primer sequences are listed 5' to 3'.

SEQ ID NO: 304 Reverse primer 3TFRC_2T2:
CAGCTTTCTGAGGTTACCATCCTA

SEQ ID NO: 160 Forward primer 5TFRC_T1:
CTAACTGGGCAAGGAACAATAACTC

SEQ ID NO: 305 Forward primer 5TFRC_3
AGAACTTACGCCTGCTTTCTGATTCTAGGAATATGGAAGGAG SEQ ID NO: 306 Forward primer 5TFRC_3T3
TCGTTACCTAGTCTAAGCCTGATTCTAGGAATATGGAAGGAG

23.4. Reaction Components: Amplification of Target Sequence

Real-time amplification and detection of the target sequence was performed in a total reaction volume of 25 μL. The reactions were conducted in a CFX96™ Real-Time PCR detection System (BioRad). The cycling parameters were 95° C. for 2 minutes, 5 cycles of 95° C. for 15 seconds and 55° C. for 30 seconds, 50 cycles of 95° C. for 15 seconds and 52° C. for 60 seconds (data collected at the 52° C. step). Each set of reaction conditions was tested in duplicate and contained 40 nM forward primer and 100 nM of partzyme A, as outlined in Table 41, 200 nM of partzyme B (TFRC_2B/84-P), 200 nM of reverse primer (3TFRC_2T2), 200 nM substrate (Sub84-FIB), 8 mM MgCl$_2$, 200 μM of each dNTP, 10 units RiboSafe RNase inhibitor (Bioline), 1× ImmoBuffer (Bioline), 2 units of MyTaq™ HS DNA polymerase (Bioline) and either IM9 gDNA (50 ng or 50 pg) or no target (NF H$_2$O).

TABLE 41

Partzyme A and forward primer combinations

| Forward primer design | Primer name | Partzyme A design | Partzyme A name | Reaction |
|---|---|---|---|---|
| Standard; upstream of partzyme A | 5TFRC_T1 | Standard Pinch PASS; loops out 10 bases of target sequence | TFRC_2A/84-P TFRC_2(54) pp10A/84-P | (i A) (i B) |
| Standard; overlaps with partzyme A | 5TFRC_3 | Standard Pinch PASS; loops out 10 bases of target sequence | TFRC_2A/84-P TFRC_2(54) pp10A/84-P | (ii A) (ii B) |
| Standard with tag; overlaps with partzyme A | 5TFRC_3T3 | Standard tagged Pinch PASS; loops out 24 bases of target | TFRC_2A/84-P TFRC_2tagppA/84-P | (iii A) (iii C) |

23.5. Results: Amplification of Target and Cleavage of Reporter Substrate

The final fluorescence of the no template control reactions was lower than that in the DNA target-containing reactions. This demonstrates that the increase in fluorescence produced in target-containing reactions is due to target dependent assembly of catalytically active MNAzymes and subsequent cleavage of the reporter substrate.

Using a standard primer upstream of a standard partzyme A (reaction i A) resulted in detection of the TFRC gene with Ct values of 15.2 & 26 for 50 ng and 50 pg respectively (Table 42).

TABLE 42

Ct values for MNAzyme qPCR

| Forward primer design | Partzyme A design | Reaction | Ct 50 ng IM9 gDNA | Ct 50 pg IM9 gDNA |
|---|---|---|---|---|
| Standard; upstream of partzyme A | Standard | (i A) | 15.2 | 26.0 |
| | Pinch PASS; loops out 10 bases of target sequence | (i B) | 16.5 | 27.1 |
| Standard; overlaps with partzyme A | Standard | (ii A) | 26.5 | no Ct |
| | Pinch PASS; loops out 10 bases of target sequence | (ii B) | 23.6 | 43.4 |
| Standard with tag; overlaps with partzyme A | Standard | (iii A) | 16.4 | 33.7 |
| | tagged Pinch PASS; loops out 24 bases of target | (iii C) | 16.5 | 27.1 |

Use of a Pinch PASS partzyme A (reaction i B) similarly detected the TFRC gene (Table 42), with efficient detection of 50 pg of target.

Use of a standard forward primer overlapping with the standard partzyme A (reaction ii A) resulted in a much later Ct value (26.5) for the 50 ng of template and failed to detect 50 pg of template when compared to using an upstream primer (Table 42) which has reduced the efficiency of the reaction due to the competition for binding when the 5' end of the partzyme overlaps with the 3' end of the primer. However, by comparison, detection using the Pinch PASS partzyme A (reaction ii B) following amplification with this same primer resulted in an earlier Ct value than for reaction ii A indicating the reaction ii B design is advantageous due to a reduction in binding competition.

Use of a tagged standard forward primer overlapping with a standard partzyme A (reaction iii A) improved the Ct values compared to the overlapping standard forward primer (reaction ii A) (Table 42). When used in combination with the tagged Pinch PASS partzyme A the reaction (iii C), performed similarly to when using an upstream primer with a standard partzyme A (reaction i A) and the same as using an upstream primer with a Pinch PASS partzyme A (reaction i B) (Table 42).

Overall, detection of a target sequence using an MNAzyme that contains a Pinch PASS partzyme and an overlapping forward primer can be improved by the addition of a tag sequence to the forward primer and partzyme A. This has application when, for example, it is desired to amplify two targets which have regions of homology and regions of variability. Pinch PASS partzymes with tag primers can be designed to bind to homologous regions of the targets and the tag is used so that the Pinch PASS partzyme "jumps" the variable regions. The example demonstrates the feasibility of using all or any of the designs illustrated in FIG. 14 and the specific application of an assay may influence choice of design.

Example 24: Investigating the Use of PASS Primers Containing a US Insert Composed of an Antisense DNAzyme PASS primers have been shown that contain a US that is non-complementary to the target sequence and hence provide a unique sequence for the partzyme to bind when inserted into the amplicon during PCR. It is also possible to use the US to insert a functional sequence into an amplicon, such as a DNAzyme, aptamer or assembly facilitator.

In this example, the US of a PASS primer was designed to be composed of sequence that is the inactive, antisense form of a DNAzyme while still being non-complementary to the target sequence. Upon amplification during PCR an active, sense DNAzyme is inserted into the amplicon and can cleave a substrate to produce a signal in real-time (FIG. 15 panel (ii)). This was compared to a standard PASS primer whereby the US had no function and was non-complementary to the target sequence (FIG. 15 panel (i)). Both PASS primers were combined with MNAzyme qPCR whereby MNAzymes comprise a first partzyme that binds to the complement of the unique sequence (cUS) as well as amplified target sequence. The second partzyme binds adjacently to the first partzyme on the amplified target sequence of interest. The active MNAzyme then cleaves substrate 1 (Sub 1) producing a signal that can be monitored in real-time. A second substrate 2 (Sub 2) was added to both reactions such that when a standard PASS partzyme is used the substrate 2 remains uncleaved and does not produce a signal (FIG. 15 panel (i)). However when the PASS primers are used that contain the antisense of the DNAzyme, upon amplification the active DNAzyme is formed and can cleave substrate 2 producing a signal that can be monitored in real-time (FIG. 15 panel (ii)). Substrate 2 can be labeled with a different fluorophore to substrate 1 so the two signals can be distinguished or substrate 2 can be labeled with the same flurophore as substrate 1 boosting the signal produced and possibly decreasing the Ct value.

The Standard PASS primer and the Functional PASS primer were compared and combined with PCR amplification for a readout in real-time to determine if they were compatible with amplification and detection of the ROCK1 gene. Further, an additional substrate was added to the qPCR mix to determine if an active DNAzyme could be inserted into the amplicon and its affect on signal strength.

24.1. Partzyme Oligonucleotides

Partzymes were designed to specifically target the ROCK1 gene plus any cUS introduced via a PASS primer. In the following sequences the bases in bold hybridize with the target sequence of interest and bases underlined bind to the complement of the unique sequence. The "-P" indicates 3' phosphorylation of the oligonucleotide. All sequences are written 5' to 3'.

```
partzyme B ROCK1_B/2-P
                                  SEQ ID NO: 307
TGCCCAGGGAGGCTAGCTCAGCTGTGTCCGATTCTGTC partzyme A ROCK1_i13A/2-P
                                  SEQ ID NO: 308
CCACTCTTCCTCAATCTTAACAACGAGAGGAAACCTT
```

24.2. Reporter Substrates

In the current example, the Sub2 and Sub84 substrates were end labelled with a 6-FAM moiety at the 5' end (indicated by a "F" in the name of the substrates below) and an Iowa Black® FQ quencher moiety at the 3' end (indicated by a "IB" in the name of the substrates below). Cleavage of the substrates was monitored between 510-530 nm (FAM emission wavelength range on the CFX96 (BioRad)) with excitation between 450-490 nm (FAM excitation wavelength range on the CFX96 (BioRad)). The Sub84 substrate was end labelled with a Quasar 670 moiety at the 5' end (indicated by a "Q6" in the name of the substrate below) and a Black Hole Quencher® 2 moiety at the 3' end (indicated by a "B2" in the name of the substrate below). Cleavage of the substrate was monitored between 675-690 nm (Quasar 670 emission wavelength range on the CFX96 (BioRad)) with excitation between 620-650 nm (Quasar 670 excitation wavelength range on the CFX96 (BioRad)). The lower case bases represent RNA and the upper case bases represent DNA. The reporter substrates for this example are shown below with the sequence, 5' to 3'.

```
SEQ ID NO: 94 Substrate Sub2-FIB:
AAGGTTTCCTCguCCCTGGGCA

SEQ ID NO: 158 Substrate Sub84-FIB:
CTCGACCCTCguCCCTCGTCCA

SEQ ID NO: 158 Substrate Sub84-Q6B2:
CTCGACCCTCguCCCTCGTCCA
```

24.3. Target Sequence and PCR Primers for Amplification of TFRC

The target sequence for this example was the ROCK1 gene in human genomic DNA extracted from the IM9 cell line (Promega). In the following sequences the bases in bold hybridize with the target sequence of interest, bases underlined are the unique sequence and bases underlined and in italics are the unique sequence composed of an antisense DNAzyme. The oligonucleotide PCR primers are listed below. Primer sequences are listed 5' to 3'.

```
SEQ ID NO: 309 Reverse primer 3ROCK1:
GCCAATGACTTACTTAGGAC

SEQ ID NO: 310 Forward PASS primer
5ROCK1_i13Planar:
AACTGACTAATTGACTTGCTCATCCATAGTGCCACTCTTCCTCAA SEQ ID NO: 311 Forward PASS primer
5ROCK1_i13asDz84P:
TGCAACTCTCTGTTCAGGGACTCTCGACCCTCTCGTTGTAGC

TAGCCTCCCTCGTCCACTCTTCCTCAA
```

24.4. Reaction Components: Amplification of Target Sequence

Real-time amplification and detection of the target sequence was performed in a total reaction volume of 25 μL. The reactions were conducted in a CFX96™ Real-Time PCR detection System (BioRad). The cycling parameters were, 95° C. for 2 minutes, 10 cycles of 95° C. for 15 seconds and 61° C. for 60 seconds (−1° C./cycle), 40 cycles of 95° C. for 15 seconds and 52° C. for 50 seconds (data collected at the 52° C. step). Each set of reaction conditions was tested in duplicate and contained 40 nM forward primer and 200 nM of additional substrate, as outlined in Table 43. All reactions contained 100 nM of partzyme A (ROCK1_i13A/2-P), 200 nM of partzyme B (ROCK1_B/2-P), and 200 nM of is reverse primer (3ROCK1), 200 nM substrate (Sub2-FIB), 8 mM MgCl$_2$, 200 μM of each dNTP, 10 units RiboSafe RNase inhibitor (Bioline), 1× ImmoBuffer (Bioline), 2 units of MyTaq™ HS DNA polymerase (Bioline) and either IM9 gDNA (50 pg) or no target (NF H$_2$O).

TABLE 43

| PASS primer and substrate combinations | | |
|---|---|---|
| PASS primer Design | PASS primer | Additional Substrate |
| Incorporates cUS for partzyme A to bind into amplicon | 5ROCK1_i13Planar | Sub84-Q6B2 Sub84-FIB |
| Incorporates cUS for partzyme A to bind and an active DNAzyme into amplicon | 5ROCK1_i13asDz84L | Sub84-Q6B2 Sub84-FIB |

24.5. Results: Amplification of Target and Cleavage of Reporter Substrate

In reactions containing the ROCK1 PASS primer comprising either a standard or functional US the Ct values for 50 pg gDNA (IM9) indicated successful amplification and detection (Table 44).

The assay containing the Standard PASS primer, with the MNAzyme cleaving Sub2-FIB, performed comparably whether the additional substrate, Sub84 was labelled with FAM or Quasar 670 (Q670) with a Ct of ~24 for 50 pg (Table 44). When the functional PASS primer was used, which incorporates an active DNAzyme into the amplicon, MNAzyme cleavage of Sub2-FIB and DNAzyme cleavage of Sub84-Q670 both produced Ct's of ~25 (Table 44). The use of Sub2 and Sub84 both labelled with FAM, producing a single curve for both MNAzyme and DNAzyme cleavage of the substrates, resulted in a Ct of ~23.

This demonstrates that a DNAzyme can be inserted into an amplicon without affecting the efficiency of the MNAzyme reaction and that combining the MNAzyme and DNAzyme signal can improve the Ct value obtained.

While this example uses a PASS primer to incorporate a DNAzyme into the amplicon, it is obvious to one in the art that the PASS primer could also be used to incorporate other functional sequences into an amplicon such as an aptamer, a partzyme or an additional MNAzyme assembly facilitator.

TABLE 44

Ct values for MNAzyme qPCR

| PASS primer Design | Substrate Design | Substrates | FAM 50 pg (Ave Ct) | Q670 50 pg (Ave Ct) |
| --- | --- | --- | --- | --- |
| Incorporates cUS for partzyme A to bind into amplicon | MNAzyme FAM signal no DNAzyme | Sub2-FIB Sub84-Q6B2 | 24.1 | No Ct |
| | MNAzyme FAM signal no DNAzyme | Sub2-FIB Sub84-FIB | 24.7 | n/a |
| Incorporates cUS for partzyme A to bind and an active DNAzyme into amplicon | MNAzyme FAM signal DNAzyme Q670 signal | Sub2-FIB Sub84-Q6B2 | 25.9 | 25.3 |
| | MNAzyme FAM signal DNAzyme FAM signal | Sub2-FIB Sub84-FIB | 23.2 | n/a |

Example 25: Detection of Multiple Enterovirus RNAs Using a Single PASS Primer and Single MNAzyme The genus Enterovirus is a group of over 60 closely related but unique viruses. Detecting the presence of any enterovirus is a critical step in the treatment plan for meningitis. As such, a simple inexpensive test which can efficiently detect as many enteroviruses as possible is highly sought after. Here we describe the use of a PASS primer which is designed to bind at its 5' end (S1) and 3'end (S2) to common sequence found in all enteroviruses, but skips a 68 bp variable region in each enterovirus through the addition of a unique sequence (US) in between S1 and S2 (as described in FIG. 6 and FIG. 12 (ii)). The PASS primer is designed to amplify all known enterovirus RNA and will introduce the complement of the US into the amplicon in place of the variable sequence. A single MNAzyme is then used to detect any amplified enterovirus sequence by targeting the complement of the US and common (conserved) enterovirus sequence (as described in FIG. 6 and FIG. 12 (ii)).

In this example we demonstrate the use of a PASS primer designed to amplify both Enterovirus 71 and Poliovirus 3 and combined with MNAzyme detection in qPCR whereby both viruses can be detected with the same MNAzyme that comprises a first partzyme that binds to the complement of the US insert (cUS) and the amplified common target sequence for both Enterovirus 71 and Poliovirus 3. The second partzyme binds adjacently to the first partzyme, hybridizing to the amplified target sequence of interest. This was compared to the use of a standard primer designed to amplify both Enterovirus 71 and Poliovirus 3 and combined with MNAzyme detection in qPCR whereby each virus requires a unique MNAzyme that comprises a first partzyme that specifically targets each virus and a second partzyme that can be used for both and binds adjacently to the first partzyme, hybridizing to the amplified target sequence of interest.

25.1. Partzyme Oligonucleotides

Partzymes were designed to detect either the (i) Enterovirus 71 RNA (ii) Polio Virus 3 RNA or (iii) all Enterovirus RNA (by switching variable sequence to a US in the amplicon, through use of a PASS primer). Bases in bold indicate sequence specific for the two viral targets, bases in italics indicate common enterovirus sequence, underlined bases represent US. The "-P" indicates 3' phosphorylation of the oligonucleotide. All sequences are written 5' to 3'.

Partzyme A (i) Ent71_A/55-P
SEQ ID NO: 312
AACTCTGCA*GCGGAACCGACTAACAACGAGAGGTGCGGT*

Partzyme A (ii) Polio3_A/55-P
SEQ ID NO: 313
AAGTCTGTG*GCGGAACCGACTAACAACGAGAGGTGCGGT*

Partzyme A (iii) Ent_i14A/55-P
SEQ ID NO: 314
<u>CTCCATTACT</u>*GCGGAACCGACTAACAACGAGAGGTGCGGT*

Partzyme B Ent_B/55-P
SEQ ID NO: 315
GAGCTGGGGAGGCTAGCT*CTTTGGGTGTCCGTGTTTCCT*

25.2. Reporter Substrate

In the current example, the substrate was end labelled with a 6-FAM moiety at the 5' end (indicated by a "F" in the name of the substrate below) and an Iowa Black® FQ quencher moiety at the 3' end (indicated by a "IB" in the name of the substrate below). Cleavage of the substrate was monitored between 510-530 nm (FAM emission wavelength range on the CFX96 (BioRad)) with excitation between 450-490 nm (FAM excitation wavelength range on the CFX96 (BioRad)). The reporter substrate for this example is shown below with the sequence, 5' to 3'. The lower case bases represent RNA and the upper case bases represent DNA.

Substrate Sub55-FIB
SEQ ID NO: 25
ACCGCACCTCguCCCCAGCTC 25.3. PCR Primers for Enterovirus RNA.

Standard and PASS primers were designed to bind to common sequence in all Enterovirus RNA species. In the following sequences, the bases in bold hybridize with the sequence common to both enterovirus species while underlined bases represent the unique sequence which is mismatched to the variable region of the Enterovirus RNA. Italicised bases indicate a short tag sequence (T1 or T2) not part of the target sequence added to increase the Tm of the primer. All sequences are written 5' to 3'.

Forward primer 5Ent_T1
SEQ ID NO: 316
CTAACCCTGAATGCGGCTAATCC

Forward PASS primer 5Ent_i14
SEQ ID NO: 317
TCCGGCCCCTGAATGCGGCTCCATTACTGCGGAACC Reverse primer 3Ent_T2
SEQ ID NO: 318
CAGATTGTCACCATAAGCAGCCA 25.4. Template Extracted Enterovirus 71 RNA was obtained from Viricell. Poliovirus 3 RNA was obtained from Asuragen as bacteriophage coated RNA (Armored RNA). The Poliovirus 3 RNA was released from the bacteriophage by heating at 75° C. for 3 minutes.

25.5. Reaction Components

Reverse transcription and real-time amplification and detection of the target sequences was performed in a total reaction volume of 25 μL. The reactions were conducted in a CFX96™ Real-Time PCR detection System (BioRad). The cycling parameters were 48° C. for 20 minutes, 95° C. for 2 minutes, 5 cycles of 95° C. for 15 seconds and 55° C. for 30 seconds, 40 cycles of 95° C. for 15 seconds and 54° C. for 60 seconds (data collected at the 54° C. step). Each set of reaction conditions was tested in duplicate and contained 40 nM forward primer and 200 nM Partzyme A (i) or (ii) or 100 nM Partzyme A (iii) as outlined in Table 45. All reactions contained 200 nM of substrate (Sub55-FIB), reverse primer (3Ent_T2) and partzyme B (Ent_B/55-P), 8 mM MgCl$_2$, 200 μM of each dNTP and 1× SensiFAST™ Probe No-ROX One-Step Kit (Bioline) containing SensiFAST™ Probe No-ROX One-Step Mix, RiboSafe RNAse Inhibitor, Reverse transcriptase (used as per manufacturers instructions). The template used was either Enterovirus 71 (1000 and 100 copies) or Poliovirus 3 RNA template (1000 and 100 copies) or no target control (NF H$_2$O).

TABLE 45

Forward primer and partzyme A combinations

| Partzyme A target | Partzyme A | Forward primer type | Forward primer | Template | Reaction |
|---|---|---|---|---|---|
| Enterovirus 71 | (i) Ent71_A/55-P | standard | 5Ent_T1 | Enterovirus 71 | (1) |
| Poliovirus 3 | (ii) Polio3_A/55-P | standard | 5Ent_T1 | Poliovirus 3 | (2) |
| All Enterovirus | (iii) Ent_i14A/55-P | PASS | 5Ent_i14 | Enterovirus 71 | (3a) |
| | | | | Poliovirus 3 | (3b) |

25.6. Results: Amplification of Target and Cleavage of Reporter Substrate

The PASS primer detected the Enterovirus 71 template (reaction (3a)) and Poliovirus 3 template (reaction (3b)) with signal produced at very similar Ct values, indicating that the PASS primer is capable of detecting multiple enterovirus sequences with similar efficiency (Table 46). Furthermore the PASS system detected the respective viruses with similar efficiency to their equivalent standard primer and matched partzyme combination (reactions (1) & (2)), even in the presence of low copy number (100 copies) (Table 46), indicating that the PASS primer system had similar sensitivity to the species specific fully matched systems.

TABLE 46

Ct values for MNAzyme qPCR

| Partzyme A target | Forward primer type | Template | Reaction | Ct (ave) 1000 copies | Ct (ave) 100 copies |
|---|---|---|---|---|---|
| Enterovirus 71 | standard | Enterovirus 71 | (1) | 28.6 | 31.5 |
| Poliovirus 3 | standard | Poliovirus 3 | (2) | 28.8 | 31.5 |
| All Enterovirus | PASS | Enterovirus 71 | (3a) | 29.2 | 31.9 |
| | | Poliovirus 3 | (3b) | 29.5 | 31.7 |

The experiment demonstrates that PASS primers can be used to specifically and sensitively amplify variant but related sequences with similar efficiency to fully matched standard primers. Further this PASS primer allowed the looping out of a large region of sequence variable between the different species of a viral family. In this example the region, which was skipped by the PASS primer, was almost 70 bases long and was highly variable between Enterovirus 71 RNA and Polio Virus 3 RNA.

Additional Note Regarding Partzymes/MNAzymes Used in Examples of Present Specification The MNAzymes referred to in the Examples above comprise first and second partzyme components that hybridise adjacent to one another on a target sequence by complementary base pairing. When such MNAzymes are used in applications that involve producing copies of a target polynucleotide sequence where DNA polymerase is used in conjunction with primers to generate amplicons (e.g. PCR), it is preferable to modify the 3' end of the partzymes to prevent the DNA polymerase extending the partzyme if hybridised to a target polynucleotide or an amplicon thereof. Such extension could produce amplification products that sequester reaction components away from (i) amplification from the PCR primers and (ii) detection using MNAzyme partzymes.

Oligonucleotides may be modified in a number of ways to prevent extension by DNA polymerases. In the Examples above the partzymes have been 3' phosphorylated for use in qPCR. However, the skilled person will recognise that other modifications could be used. For example, the following modifications have been used in the art to prevent extension of oligonucleotides by DNA polymerases: 3' phosphorylation (phosphorylation of the 3' carbon of the ribose or 2-deoxyribose sugar of the nucleotide) of the 3' terminal nucleotide of the oligonucleotide; use of a "dideoxy" nucleotide (2',3' dideoxynucleotide) as the 3' terminal nucleotide of the oligonucleotide; addition of a C3-spacer (3' propyl group) to the 3' terminal nucleotide of an oligonucleotide; use of a 3'3' linkage between the terminal and penultimate nucleotides in the oligonucleotide ("inverted" terminal nucleotide). One skilled in the art would appreciate that any of these methods could be used to prevent extension of the partzymes during amplification methods such as PCR. Further one skilled in the art would also acknowledge that when the target sequence is not to be amplified but directly detected by the MNAzyme then any of the partzymes used in the Examples above could be used without 3' modification as there would be no risk of extension of the partzymes.

The invention claimed is:

1. A double-stranded nucleic acid duplex comprising:
an oligonucleotide comprising:
a first component terminating at the 5' end of the oligonucleotide,
a second component terminating at the 3' end of the oligonucleotide and capable of hybridising to a second portion of a polynucleotide by complementary base pairing, and
a third component located between the first and second components; and
(ii) the polynucleotide, wherein:
the first component is hybridised to a first portion of the polynucleotide by complementary base pairing;
the second component is hybridised to a second portion of the polynucleotide by complementary base pairing, and
the third component comprises a sequence of at least two nucleotides that do not share base pair complementarity with an opposing sequence of nucleotides in the polynucleotide.

2. The double-stranded nucleic acid duplex of claim 1, wherein the third component is located partially or completely in the 3' half of the oligonucleotide.

3. The double-stranded nucleic acid duplex of claim 1, wherein the third component comprises a sequence of at least four nucleotides, at least five, at least six, at least seven, or at least eight nucleotides that do not share base pair complementarity with an opposing sequence of nucleotides in the polynucleotide.

4. The double-stranded nucleic acid duplex according to claim 1, wherein the polynucleotide comprises unhybridized nucleotides located between its first and second portions.

5. The double-stranded nucleic acid duplex according to claim 4, wherein the number of said unhybridized nucleotides is equal to the number of nucleotides in said third component that do not share base pair complementarity with the opposing sequence.

6. The double-stranded nucleic acid duplex according to claim 4, wherein the number of said unhybridized nucleotides exceeds the number of nucleotides in said third component that do not share base pair complementarity with the opposing sequence.

7. The double-stranded nucleic acid duplex according to claim 4, wherein the number of said unhybridized nucleotides is less than the number of nucleotides in said third component that do not share base pair complementarity with the opposing sequence.

8. The double-stranded nucleic acid duplex according to claim 1, wherein the number of nucleotides in said third component is between 1 and 200 nucleotides, 1 and 150 nucleotides, 1 and 100 nucleotides, 1 and 75 nucleotides, 1 and 50 nucleotides 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides, less than the number of unhybridized nucleotides in the polynucleotide located between portions of the polynucleotide hybridised to said first and second components.

9. The double-stranded nucleic acid duplex according to claim 1, wherein the oligonucleotide and/or the polynucleotide is genomic DNA, complementary DNA (cDNA), or RNA.

10. The double-stranded nucleic acid duplex according to claim 1, wherein the melting temperature of the first component is greater than the melting temperature of the second component when hybridised to the polynucleotide strand by complementary base pairing.

11. The double-stranded nucleic acid duplex according to claim 1, wherein the polynucleotide comprises an intermediate portion between said first and second portions, and the intermediate portion comprises nucleotides that do not share base pair complementarity with an opposing sequence of nucleotides in said third component.

12. The double-stranded nucleic acid duplex according to claim 11, wherein the first component and the second component each hybridise by complementary base pairing to distinct non-contiguous components of the polynucleotide, thereby juxtaposing the non-contiguous components and creating a loop portion comprising said unhybridized nucleotides of the intermediate portion of the polynucleotide.

13. The double-stranded nucleic acid duplex according to claim 11, wherein all nucleotides of the first oligonucleotide are hybridised to the polynucleotide by complementary base pairing.

14. The double-stranded nucleic acid duplex according to claim 12, wherein the loop portion of the polynucleotide comprises between 1 and 200 nucleotides, 1 and 150 nucleotides, 1 and 100 nucleotides, 1 and 75 nucleotides, 1 and 50 nucleotides 1 and 25 nucleotides, 5 and 200 nucleotides, 5 and 150 nucleotides, 5 and 100 nucleotides, 5 and 100 nucleotides, 5 and 75 nucleotides, 5 and 50 nucleotides 5 and 25 nucleotides, 10 and 200 nucleotides, 10 and 150 nucleotides, 10 and 100 nucleotides, 10 and 100 nucleotides, 10 and 75 nucleotides, 10 and 50 nucleotides, or 10 and 25 nucleotides.

15. The double-stranded nucleic acid duplex according to claim 1, wherein the duplex is isolated.

16. The double-stranded nucleic acid duplex according to claim 1, wherein the oligonucleotide or, the polynucleotide, or both of the oligonucleotide and the polynucleotide, is/are synthetic or recombinantly made.

17. The double-stranded nucleic acid duplex according to claim 1, wherein the oligonucleotide or the polynucleotide, or both the oligonucleotide and the polynucleotide, are labelled with a detectable moiety.

* * * * *

UNITED STATES PATENT AND TRADEMARK OFFICE
CERTIFICATE OF CORRECTION

PATENT NO. : 11,802,308 B2
APPLICATION NO. : 16/912622
DATED : October 31, 2023
INVENTOR(S) : Alison Velyian Todd et al.

It is certified that error appears in the above-identified patent and that said Letters Patent is hereby corrected as shown below:

In the Claims

In Column 273, Line 54, Claim 1, delete "an" and insert -- (i) an --, therefor.

In Column 275, Line 20, Claim 8, delete "50 nucleotides 1" and insert -- 50 nucleotides, 1 --, therefor.

In Column 275, Lines 22-23, Claim 8, delete "50 nucleotides 5" and insert -- 50 nucleotides, 5 --, therefor.

In Column 276, Lines 21-22, Claim 14, delete "50 nucleotides 1" and insert -- 50 nucleotides, 1 --, therefor.

In Column 276, Line 24, Claim 14, delete "50 nucleotides 5" and insert -- 50 nucleotides, 5 --, therefor.

Signed and Sealed this
Seventh Day of May, 2024

Katherine Kelly Vidal
*Director of the United States Patent and Trademark Office*

SEQUENCE LISTING

<160> NUMBER OF SEQ ID NOS: 318

<210> SEQ ID NO 1
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 1
atggtcatct ccagagccca acaacgagag gcgtgat                          37

<210> SEQ ID NO 2
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 2
ctgggaggag aggctagctg gtccatggct tctgggta                         38

<210> SEQ ID NO 3
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 3
agacatacta ctccagagcc caacaacgag aggcgtgat                        39

<210> SEQ ID NO 4
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 4
agacatacta ccagagccca acaacgagag gcgtgat                          37

<210> SEQ ID NO 5
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 5
atgagacata ctagagccca acaacgagag gcgtgat                          37

<210> SEQ ID NO 6

```
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: ribonucleotides

<400> SEQUENCE: 6
atcacgcctc guctcctccc ag                                              22

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
ctcaggaatt tcccagctac                                                 20

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
gtctcagttc ttcttggatg                                                 20

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
cttggatggt catctccaga                                                 20

<210> SEQ ID NO 10
<211> LENGTH: 37
<212> TYPE: DNA
<213> ORGANISM: Artificial sequence
<220> FEATURE:
<223> OTHER INFORMATION: Synthetic

<400> SEQUENCE: 10
agttcttctt ggatggtcat agacatacta ctccaga                              37

<210> SEQ ID NO 11
<211> LENGTH: 37
<212> TYPE: DNA
<213> ORGANISM: Artificial sequence
<220> FEATURE:
<223> OTHER INFORMATION: Synthetic

<400> SEQUENCE: 11
ctcttgtctc agttcttctt agacatacta ctccaga                              37

<210> SEQ ID NO 12
<211> LENGTH: 19
<212> TYPE: DNA
<213> ORGANISM: Artificial sequence
```

```
<220> FEATURE:
<223> OTHER INFORMATION: Synthetic

<400> SEQUENCE: 12
ggatggtcat ctccagagc                                          19

<210> SEQ ID NO 13
<211> LENGTH: 37
<212> TYPE: DNA
<213> ORGANISM: Artificial sequence
<220> FEATURE:
<223> OTHER INFORMATION: Synthetic

<400> SEQUENCE: 13
ttcttcttgg atggtcatct agacatacta ccagagc                      37

<210> SEQ ID NO 14
<211> LENGTH: 37
<212> TYPE: DNA
<213> ORGANISM: Artificial sequence
<220> FEATURE:
<223> OTHER INFORMATION: Synthetic

<400> SEQUENCE: 14
cttgtctcag ttcttcttgg agacatacta ccagagc                      37

<210> SEQ ID NO 15
<211> LENGTH: 19
<212> TYPE: DNA
<213> ORGANISM: Artificial sequence
<220> FEATURE:
<223> OTHER INFORMATION: Synthetic

<400> SEQUENCE: 15
tggtcatctc cagagccca                                          19

<210> SEQ ID NO 16
<211> LENGTH: 38
<212> TYPE: DNA
<213> ORGANISM: Artificial sequence
<220> FEATURE:
<223> OTHER INFORMATION: Synthetic

<400> SEQUENCE: 16
cttcttggat ggtcatctcc aagacatact agagccca                     38

<210> SEQ ID NO 17
<211> LENGTH: 37
<212> TYPE: DNA
<213> ORGANISM: Artificial sequence
<220> FEATURE:
<223> OTHER INFORMATION: Synthetic

<400> SEQUENCE: 17
gtctcagttc ttcttggatg agacatacta gagccca                      37

<210> SEQ ID NO 18
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 18
```
gagctgggga ggctagctgc gtaggcaaga gtgcctt 37

<210> SEQ ID NO 19
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 19
cacaatcagt gagctggtga caacgagagg tgcggt 36

<210> SEQ ID NO 20
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 20
cacaatcagt gagcaggtga caacgagagg tgcggt 36

<210> SEQ ID NO 21
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 21
cacaatcagt tggagcaggt gacaacgaga ggtgcggt 38

<210> SEQ ID NO 22
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 22
agacatacta gagctgttga caacgagagg tgcggt 36

<210> SEQ ID NO 23
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 23
agacatacta gagccgttga caacgagagg tgcggt 36

```
<210> SEQ ID NO 24
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 24
agacatacta tggagccgtt gacaacgaga ggtgcggt                              38

<210> SEQ ID NO 25
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: ribonucleotides

<400> SEQUENCE: 25
accgcacctc gucccccagct c                                              21

<210> SEQ ID NO 26
<211> LENGTH: 21
<212> TYPE: DNA
<213> ORGANISM: Artificial sequence
<220> FEATURE:
<223> OTHER INFORMATION: Synthetic

<400> SEQUENCE: 26
ggtcctgcac cagtaatatg c                                               21

<210> SEQ ID NO 27
<211> LENGTH: 37
<212> TYPE: DNA
<213> ORGANISM: Artificial sequence
<220> FEATURE:
<223> OTHER INFORMATION: Synthetic

<400> SEQUENCE: 27
atataaactt gtggtagttg cacaatcagt gagctgg                              37

<210> SEQ ID NO 28
<211> LENGTH: 39
<212> TYPE: DNA
<213> ORGANISM: Artificial sequence
<220> FEATURE:
<223> OTHER INFORMATION: Synthetic

<400> SEQUENCE: 28
gaaaatgact gaatataaac ttcacaatca gtgagctgg                            39

<210> SEQ ID NO 29
<211> LENGTH: 39
<212> TYPE: DNA
<213> ORGANISM: Artificial sequence
<220> FEATURE:
<223> OTHER INFORMATION: Synthetic

<400> SEQUENCE: 29
atataaactt gtggtagttg cacaatcagt gagctggtg                            39
```

```
<210> SEQ ID NO 30
<211> LENGTH: 41
<212> TYPE: DNA
<213> ORGANISM: Artificial sequence
<220> FEATURE:
<223> OTHER INFORMATION: Synthetic

<400> SEQUENCE: 30
gaaaatgact gaatataaac ttcacaatca gtgagctggt g                    41

<210> SEQ ID NO 31
<211> LENGTH: 39
<212> TYPE: DNA
<213> ORGANISM: Artificial sequence
<220> FEATURE:
<223> OTHER INFORMATION: Synthetic

<400> SEQUENCE: 31
tgatataaac ttgtggtagt cacaatcagt tggagcagg                       39

<210> SEQ ID NO 32
<211> LENGTH: 41
<212> TYPE: DNA
<213> ORGANISM: Artificial sequence
<220> FEATURE:
<223> OTHER INFORMATION: Synthetic

<400> SEQUENCE: 32
ctgaaaatga ctgaatataa accacaatca gttggagcag g                    41

<210> SEQ ID NO 33
<211> LENGTH: 39
<212> TYPE: DNA
<213> ORGANISM: Artificial sequence
<220> FEATURE:
<223> OTHER INFORMATION: Synthetic

<400> SEQUENCE: 33
atataaactt gtggtagttg cacaatcagt gagcaggtg                       39

<210> SEQ ID NO 34
<211> LENGTH: 41
<212> TYPE: DNA
<213> ORGANISM: Artificial sequence
<220> FEATURE:
<223> OTHER INFORMATION: Synthetic

<400> SEQUENCE: 34
gaaaatgact gaatataaac ttcacaatca gtgagcaggt g                    41

<210> SEQ ID NO 35
<211> LENGTH: 37
<212> TYPE: DNA
<213> ORGANISM: Artificial sequence
<220> FEATURE:
<223> OTHER INFORMATION: Synthetic

<400> SEQUENCE: 35
atataaactt gtggtagttg agacatacta gagctgt                         37

<210> SEQ ID NO 36
<211> LENGTH: 39
<212> TYPE: DNA
<213> ORGANISM: Artificial sequence
<220> FEATURE:
<223> OTHER INFORMATION: Synthetic
```

<400> SEQUENCE: 36
gaaaatgact gaatataaac ttagacatac tagagctgt             39

<210> SEQ ID NO 37
<211> LENGTH: 39
<212> TYPE: DNA
<213> ORGANISM: Artificial sequence
<220> FEATURE:
<223> OTHER INFORMATION: Synthetic

<400> SEQUENCE: 37
atataaactt gtggtagttg agacatacta gagctgttg             39

<210> SEQ ID NO 38
<211> LENGTH: 41
<212> TYPE: DNA
<213> ORGANISM: Artificial sequence
<220> FEATURE:
<223> OTHER INFORMATION: Synthetic

<400> SEQUENCE: 38
gaaaatgact gaatataaac ttagacatac tagagctgtt g          41

<210> SEQ ID NO 39
<211> LENGTH: 39
<212> TYPE: DNA
<213> ORGANISM: Artificial sequence
<220> FEATURE:
<223> OTHER INFORMATION: Synthetic

<400> SEQUENCE: 39
tgatataaac ttgtggtagt agacatacta tggagccgt             39

<210> SEQ ID NO 40
<211> LENGTH: 41
<212> TYPE: DNA
<213> ORGANISM: Artificial sequence
<220> FEATURE:
<223> OTHER INFORMATION: Synthetic

<400> SEQUENCE: 40
ctgaaaatga ctgaatataa acagacatac tatggagccg t          41

<210> SEQ ID NO 41
<211> LENGTH: 39
<212> TYPE: DNA
<213> ORGANISM: Artificial sequence
<220> FEATURE:
<223> OTHER INFORMATION: Synthetic

<400> SEQUENCE: 41
atataaactt gtggtagttg agacatacta gagccgttg             39

<210> SEQ ID NO 42
<211> LENGTH: 41
<212> TYPE: DNA
<213> ORGANISM: Artificial sequence
<220> FEATURE:
<223> OTHER INFORMATION: Synthetic

<400> SEQUENCE: 42
gaaaatgact gaatataaac ttagacatac tagagccgtt g          41

<210> SEQ ID NO 43
<211> LENGTH: 35

```
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (43)..(43)

<400> SEQUENCE: 43
tggtagttgg agcaggtgac aacgagaggt gcggt                                35

<210> SEQ ID NO 44
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 44
tgtggtagtt ggagccgttg acaacgagag gtgcggt                              37

<210> SEQ ID NO 45
<211> LENGTH: 19
<212> TYPE: DNA
<213> ORGANISM: Artificial sequence
<220> FEATURE:
<223> OTHER INFORMATION: Synthetic

<400> SEQUENCE: 45
ttgtggtagt tggagcagg                                                  19

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
cttgtggtag ttggagccgt                                                 20

<210> SEQ ID NO 47
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 47
agacatacta tggagccgtt gacaacgaga ggcgtgat                             38

<210> SEQ ID NO 48
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: ribonucleotides

<400> SEQUENCE: 48
```

```
atcacgcctc gtcccccagct c                                              21
```

<210> SEQ ID NO 49
<211> LENGTH: 44
<212> TYPE: DNA
<213> ORGANISM: Artificial sequence
<220> FEATURE:
<223> OTHER INFORMATION: Synthetic

<400> SEQUENCE: 49

```
ctgctgaaaa tgactgaata taaaccacaa tcagttggag cagg                      44
```

<210> SEQ ID NO 50
<211> LENGTH: 43
<212> TYPE: DNA
<213> ORGANISM: Artificial sequence
<220> FEATURE:
<223> OTHER INFORMATION: Synthetic

<400> SEQUENCE: 50

```
gactgaatat aaacttgtgg tagtagacat actatggagc cgt                       43
```

<210> SEQ ID NO 51
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 51

```
agacatacta gagctggtga caacgagagg tgcggt                               36
```

<210> SEQ ID NO 52
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 52

```
cgttggctac gagctggtga caacgagagg tgcggt                               36
```

<210> SEQ ID NO 53
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 53

```
cacaatcagt gagctgttga caacgagagg tgcggt                               36
```

<210> SEQ ID NO 54
<211> LENGTH: 36
<212> TYPE: DNA
<213> ORGANISM: Artificial sequence
<220> FEATURE:
<223> OTHER INFORMATION: Synthetic

```
<220> FEATURE:
<221> NAME/KEY: Phosphorylation
<222> LOCATION: (36)..(36)

<400> SEQUENCE: 54
cgttggctac gagctgttga caacgagagg tgcggt                    36

<210> SEQ ID NO 55
<211> LENGTH: 37
<212> TYPE: DNA
<213> ORGANISM: Artificial sequence
<220> FEATURE:
<223> OTHER INFORMATION: Synthetic

<400> SEQUENCE: 55
atataaactt gtggtagttg agacatacta gagctgg                   37

<210> SEQ ID NO 56
<211> LENGTH: 39
<212> TYPE: DNA
<213> ORGANISM: Artificial sequence
<220> FEATURE:
<223> OTHER INFORMATION: Synthetic

<400> SEQUENCE: 56
gaaaatgact gaatataaac ttagacatac tagagctgg                 39

<210> SEQ ID NO 57
<211> LENGTH: 37
<212> TYPE: DNA
<213> ORGANISM: Artificial sequence
<220> FEATURE:
<223> OTHER INFORMATION: Synthetic

<400> SEQUENCE: 57
atataaactt gtggtagttg cgttggctac gagctgg                   37

<210> SEQ ID NO 58
<211> LENGTH: 40
<212> TYPE: DNA
<213> ORGANISM: Artificial sequence
<220> FEATURE:
<223> OTHER INFORMATION: Synthetic

<400> SEQUENCE: 58
gaaaatgact gaatataaac ttacgttggc tacgagctgg                40

<210> SEQ ID NO 59
<211> LENGTH: 37
<212> TYPE: DNA
<213> ORGANISM: Artificial sequence
<220> FEATURE:
<223> OTHER INFORMATION: Synthetic

<400> SEQUENCE: 59
atataaactt gtggtagttg cacaatcagt gagctgt                   37

<210> SEQ ID NO 60
<211> LENGTH: 39
<212> TYPE: DNA
<213> ORGANISM: Artificial sequence
<220> FEATURE:
<223> OTHER INFORMATION: Synthetic

<400> SEQUENCE: 60
gaaaatgact gaatataaac ttcacaatca gtgagctgt                 39
```

<210> SEQ ID NO 61
<211> LENGTH: 37
<212> TYPE: DNA
<213> ORGANISM: Artificial sequence
<220> FEATURE:
<223> OTHER INFORMATION: Synthetic

<400> SEQUENCE: 61
atataaactt gtggtagttg cgttggctac gagctgt                              37

<210> SEQ ID NO 62
<211> LENGTH: 39
<212> TYPE: DNA
<213> ORGANISM: Artificial sequence
<220> FEATURE:
<223> OTHER INFORMATION: Synthetic

<400> SEQUENCE: 62
gaaaatgact gaatataaac ttcgttggct acgagctgt                            39

<210> SEQ ID NO 63
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 63
gagctgggga ggctagctgc tccaactacc acaagttt                             38

<210> SEQ ID NO 64
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 64
acaatcagtc ctacgcgaac aacaacgaga ggtgcggt                             38

<210> SEQ ID NO 65
<211> LENGTH: 23
<212> TYPE: DNA
<213> ORGANISM: Artificial sequence
<220> FEATURE:
<223> OTHER INFORMATION: Synthetic

<400> SEQUENCE: 65
tattaaaagg tactggtgga gta                                             23

<210> SEQ ID NO 66
<211> LENGTH: 41
<212> TYPE: DNA
<213> ORGANISM: Artificial sequence
<220> FEATURE:
<223> OTHER INFORMATION: Synthetic

<400> SEQUENCE: 66
ctgtatcgtc aaggcactct tcacaatcag tcctacgcga a                         41

<210> SEQ ID NO 67
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 67
agacatacta ctacgacaac aacaacgaga ggtgcggt                             38

<210> SEQ ID NO 68
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (34)..(34)

<400> SEQUENCE: 68
agacatacta gcaaacaaca acgagaggtg cggt                                 34

<210> SEQ ID NO 69
<211> LENGTH: 21
<212> TYPE: DNA
<213> ORGANISM: Artificial sequence
<220> FEATURE:
<223> OTHER INFORMATION: Synthetic

<400> SEQUENCE: 69
tacgatacac gtctgcagtc a                                               21

<210> SEQ ID NO 70
<211> LENGTH: 40
<212> TYPE: DNA
<213> ORGANISM: Artificial sequence
<220> FEATURE:
<223> OTHER INFORMATION: Synthetic

<400> SEQUENCE: 70
tgtatcgtca aggcactctt gagacatact actacgacaa                           40

<210> SEQ ID NO 71
<211> LENGTH: 40
<212> TYPE: DNA
<213> ORGANISM: Artificial sequence
<220> FEATURE:
<223> OTHER INFORMATION: Synthetic

<400> SEQUENCE: 71
ctgtatcgtc aaggcactct tagacatact actacgacaa                           40

<210> SEQ ID NO 72
<211> LENGTH: 40
<212> TYPE: DNA
<213> ORGANISM: Artificial sequence
<220> FEATURE:
<223> OTHER INFORMATION: Synthetic

<400> SEQUENCE: 72
gctgtatcgt caaggcactc tagacatact actacgacaa                           40

```
<210> SEQ ID NO 73
<211> LENGTH: 39
<212> TYPE: DNA
<213> ORGANISM: Artificial sequence
<220> FEATURE:
<223> OTHER INFORMATION: Synthetic

<400> SEQUENCE: 73
gctgtatcgt caaggcactc agacatacta ctacgacaa                    39

<210> SEQ ID NO 74
<211> LENGTH: 37
<212> TYPE: DNA
<213> ORGANISM: Artificial sequence
<220> FEATURE:
<223> OTHER INFORMATION: Synthetic

<400> SEQUENCE: 74
gtcaaggcac tcttgcctac agacatacta gcaaaca                      37

<210> SEQ ID NO 75
<211> LENGTH: 37
<212> TYPE: DNA
<213> ORGANISM: Artificial sequence
<220> FEATURE:
<223> OTHER INFORMATION: Synthetic

<400> SEQUENCE: 75
cgtcaaggca ctcttgccta agacatacta gcaaaca                      37

<210> SEQ ID NO 76
<211> LENGTH: 37
<212> TYPE: DNA
<213> ORGANISM: Artificial sequence
<220> FEATURE:
<223> OTHER INFORMATION: Synthetic

<400> SEQUENCE: 76
tcgtcaaggc actcttgcct agacatacta gcaaaca                      37

<210> SEQ ID NO 77
<211> LENGTH: 37
<212> TYPE: DNA
<213> ORGANISM: Artificial sequence
<220> FEATURE:
<223> OTHER INFORMATION: Synthetic

<400> SEQUENCE: 77
atcgtcaagg cactcttgcc agacatacta gcaaaca                      37

<210> SEQ ID NO 78
<211> LENGTH: 38
<212> TYPE: DNA
<213> ORGANISM: Artificial sequence
<220> FEATURE:
<223> OTHER INFORMATION: Synthetic

<400> SEQUENCE: 78
gtatcgtcaa ggcactcttg cagacatact agcaaaca                     38

<210> SEQ ID NO 79
<211> LENGTH: 38
<212> TYPE: DNA
<213> ORGANISM: Artificial sequence
<220> FEATURE:
<223> OTHER INFORMATION: Synthetic
```

```
<400> SEQUENCE: 79
tgtatcgtca aggcactctt gagacatact agcaaaca                                38

<210> SEQ ID NO 80
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 80
tcaataccat tacgcgacca acaacgagag gtgcggt                                 37

<210> SEQ ID NO 81
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (34)..(34)

<400> SEQUENCE: 81
tcttgcctac gcgaccaaca acgagaggtg cggt                                    34

<210> SEQ ID NO 82
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (35)..(35)

<400> SEQUENCE: 82
ctcttgccta cgcaaacaac aacgagaggt gcggt                                   35

<210> SEQ ID NO 83
<211> LENGTH: 41
<212> TYPE: DNA
<213> ORGANISM: Artificial sequence
<220> FEATURE:
<223> OTHER INFORMATION: Synthetic

<400> SEQUENCE: 83
tgtatcgtca aggcactctt gtcaatacca ttacgcgacc a                            41

<210> SEQ ID NO 84
<211> LENGTH: 19
<212> TYPE: DNA
<213> ORGANISM: Artificial sequence
<220> FEATURE:
<223> OTHER INFORMATION: Synthetic

<400> SEQUENCE: 84
gcactcttgc ctacgcgac                                                     19

<210> SEQ ID NO 85
<211> LENGTH: 20
<212> TYPE: DNA
<213> ORGANISM: Artificial sequence
<220> FEATURE:
```

```
<223> OTHER INFORMATION: Synthetic

<400> SEQUENCE: 85
ggcactcttg cctacgcaaa                                                    20

<210> SEQ ID NO 86
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 86
tgcccaggga ggctagctgg tccatggctt ctgggta                                 37

<210> SEQ ID NO 87
<211> LENGTH: 44
<212> TYPE: DNA
<213> ORGANISM: Artificial sequence
<220> FEATURE:
<223> OTHER INFORMATION: Synthetic

<400> SEQUENCE: 87
ctgctgaaaa tgactgaata taaacagaca tactatggag ccgt                         44

<210> SEQ ID NO 88
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 88
acaatcagtc ctacgacaac aacaacgaga ggtgcggt                                38

<210> SEQ ID NO 89
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 89
agacatacta ccagagccca acaacgagag gaaacctt                                38

<210> SEQ ID NO 90
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 90
cagacatact acagagccca acaacgagag gaaacctt                                38
```

<210> SEQ ID NO 91
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 91
ccagacatac taagagccca acaacgagag gaaacctt                                38

<210> SEQ ID NO 92
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 92
aagacatact acagagccca acaacgagag gaaacctt                                38

<210> SEQ ID NO 93
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 93
atagacatac taagagccca acaacgagag gaaacctt                                38

<210> SEQ ID NO 94
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (12)..(13)
<223> OTHER INFORMATION: ribonucleotides

<400> SEQUENCE: 94
aaggtttcct cguccctggg ca                                                 22

<210> SEQ ID NO 95
<211> LENGTH: 36
<212> TYPE: DNA
<213> ORGANISM: Artificial sequence
<220> FEATURE:
<223> OTHER INFORMATION: Synthetic

<400> SEQUENCE: 95
ttcttcttgg atggtcatct agacatacta ccagag                                  36

<210> SEQ ID NO 96
<211> LENGTH: 35
<212> TYPE: DNA
<213> ORGANISM: Artificial sequence
<220> FEATURE:
<223> OTHER INFORMATION: Synthetic

```
<400> SEQUENCE: 96
ttcttcttgg atggtcatct agacatacta ccaga                                35

<210> SEQ ID NO 97
<211> LENGTH: 34
<212> TYPE: DNA
<213> ORGANISM: Artificial sequence
<220> FEATURE:
<223> OTHER INFORMATION: Synthetic

<400> SEQUENCE: 97
ttcttcttgg atggtcatct agacatacta ccag                                 34

<210> SEQ ID NO 98
<211> LENGTH: 33
<212> TYPE: DNA
<213> ORGANISM: Artificial sequence
<220> FEATURE:
<223> OTHER INFORMATION: Synthetic

<400> SEQUENCE: 98
ttcttcttgg atggtcatct agacatacta cca                                  33

<210> SEQ ID NO 99
<211> LENGTH: 41
<212> TYPE: DNA
<213> ORGANISM: Artificial sequence
<220> FEATURE:
<223> OTHER INFORMATION: Synthetic

<400> SEQUENCE: 99
ctgtatcgtc aaggcactct tcacaatcag tcctacgaca a                         41

<210> SEQ ID NO 100
<211> LENGTH: 36
<212> TYPE: DNA
<213> ORGANISM: Artificial sequence
<220> FEATURE:
<223> OTHER INFORMATION: Synthetic

<400> SEQUENCE: 100
cttgtctcag ttcttcttgg agacatacta ccagag                               36

<210> SEQ ID NO 101
<211> LENGTH: 35
<212> TYPE: DNA
<213> ORGANISM: Artificial sequence
<220> FEATURE:
<223> OTHER INFORMATION: Synthetic

<400> SEQUENCE: 101
cttgtctcag ttcttcttgg agacatacta ccaga                                35

<210> SEQ ID NO 102
<211> LENGTH: 34
<212> TYPE: DNA
<213> ORGANISM: Artificial sequence
<220> FEATURE:
<223> OTHER INFORMATION: Synthetic

<400> SEQUENCE: 102
cttgtctcag ttcttcttgg agacatacta ccag                                 34

<210> SEQ ID NO 103
```

<211> LENGTH: 33
<212> TYPE: DNA
<213> ORGANISM: Artificial sequence
<220> FEATURE:
<223> OTHER INFORMATION: Synthetic

<400> SEQUENCE: 103
cttgtctcag ttcttcttgg agacatacta cca                           33

<210> SEQ ID NO 104
<211> LENGTH: 35
<212> TYPE: DNA
<213> ORGANISM: Artificial sequence
<220> FEATURE:
<223> OTHER INFORMATION: Synthetic

<400> SEQUENCE: 104
cttcttggat ggtcatctca gacatactac agagc                         35

<210> SEQ ID NO 105
<211> LENGTH: 34
<212> TYPE: DNA
<213> ORGANISM: Artificial sequence
<220> FEATURE:
<223> OTHER INFORMATION: Synthetic

<400> SEQUENCE: 105
ttcttggatg gtcatctcca gacatactaa gagc                          34

<210> SEQ ID NO 106
<211> LENGTH: 37
<212> TYPE: DNA
<213> ORGANISM: Artificial sequence
<220> FEATURE:
<223> OTHER INFORMATION: Synthetic

<400> SEQUENCE: 106
cttgtctcag ttcttcttgg aagacatact acagagc                       37

<210> SEQ ID NO 107
<211> LENGTH: 37
<212> TYPE: DNA
<213> ORGANISM: Artificial sequence
<220> FEATURE:
<223> OTHER INFORMATION: Synthetic

<400> SEQUENCE: 107
cttgtctcag ttcttcttgg atagacatac taagagc                       37

<210> SEQ ID NO 108
<211> LENGTH: 36
<212> TYPE: DNA
<213> ORGANISM: Artificial sequence
<220> FEATURE:
<223> OTHER INFORMATION: Synthetic

<400> SEQUENCE: 108
ttcttcttgg atggtcatct gacatactac cagagc                        36

<210> SEQ ID NO 109
<211> LENGTH: 35
<212> TYPE: DNA
<213> ORGANISM: Artificial sequence
<220> FEATURE:
<223> OTHER INFORMATION: Synthetic

<400> SEQUENCE: 109
ttcttcttgg atggtcatct acatactacc agagc                    35

<210> SEQ ID NO 110
<211> LENGTH: 39
<212> TYPE: DNA
<213> ORGANISM: Artificial sequence
<220> FEATURE:
<223> OTHER INFORMATION: Synthetic

<400> SEQUENCE: 110
ttcttcttgg atggtcatct aaagacatac taccagagc                39

<210> SEQ ID NO 111
<211> LENGTH: 40
<212> TYPE: DNA
<213> ORGANISM: Artificial sequence
<220> FEATURE:
<223> OTHER INFORMATION: Synthetic

<400> SEQUENCE: 111
ttcttcttgg atggtcatct caaagacata ctaccagagc               40

<210> SEQ ID NO 112
<211> LENGTH: 40
<212> TYPE: DNA
<213> ORGANISM: Artificial sequence
<220> FEATURE:
<223> OTHER INFORMATION: Synthetic

<400> SEQUENCE: 112
tctcttgtct cagttcttct taaagacata ctaccagagc               40

<210> SEQ ID NO 113
<211> LENGTH: 41
<212> TYPE: DNA
<213> ORGANISM: Artificial sequence
<220> FEATURE:
<223> OTHER INFORMATION: Synthetic

<400> SEQUENCE: 113
gtctcttgtc tcagttcttc tcaaagacat actaccagag c             41

<210> SEQ ID NO 114
<211> LENGTH: 46
<212> TYPE: DNA
<213> ORGANISM: Artificial sequence
<220> FEATURE:
<223> OTHER INFORMATION: Synthetic

<400> SEQUENCE: 114
ctcaagtctc ttgtctcagt tcccgacaaa gacatactac cagagc        46

<210> SEQ ID NO 115
<211> LENGTH: 50
<212> TYPE: DNA
<213> ORGANISM: Artificial sequence
<220> FEATURE:
<223> OTHER INFORMATION: Synthetic

<400> SEQUENCE: 115
ggctctcaag tctcttgtct ccaagtccga caaagacata ctaccagagc    50

<210> SEQ ID NO 116
<211> LENGTH: 56
<212> TYPE: DNA

```
<213> ORGANISM: Artificial sequence
<220> FEATURE:
<223> OTHER INFORMATION: Synthetic

<400> SEQUENCE: 116
tctgggggct ctcaagtctc catgacacaa gtccgacaaa gacatactac cagagc      56

<210> SEQ ID NO 117
<211> LENGTH: 42
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (42)..(42)

<400> SEQUENCE: 117
tggcgtggag aggctagctc gatgtgagtt tctgctttgc tg                     42

<210> SEQ ID NO 118
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 118
gaaagccaac aaggaaatcc tacaacgagg ggtcgag                           37

<210> SEQ ID NO 119
<211> LENGTH: 42
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (42)..(42)

<400> SEQUENCE: 119
tggcgtggag aggctagctc aacaaggaaa tcctcgatgt ga                     42

<210> SEQ ID NO 120
<211> LENGTH: 62
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (62)..(62)

<400> SEQUENCE: 120
aagttaaaat tcccgtcgct atcaactcta gctgtagcat gaaagcacaa cgagggtcg ag  62

<210> SEQ ID NO 121
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: ribonucleotides
```

<400> SEQUENCE: 121
ctcgaccccg uctccacgcc a                                         21

<210> SEQ ID NO 122
<211> LENGTH: 21
<212> TYPE: DNA
<213> ORGANISM: Artificial sequence
<220> FEATURE:
<223> OTHER INFORMATION: Synthetic

<400> SEQUENCE: 122
gcctgaggtt cagagccatg g                                         21

<210> SEQ ID NO 123
<211> LENGTH: 25
<212> TYPE: DNA
<213> ORGANISM: Artificial sequence
<220> FEATURE:
<223> OTHER INFORMATION: Synthetic

<400> SEQUENCE: 123
ttaaaattcc cgtcgctatc aagac                                     25

<210> SEQ ID NO 124
<211> LENGTH: 23
<212> TYPE: DNA
<213> ORGANISM: Artificial sequence
<220> FEATURE:
<223> OTHER INFORMATION: Synthetic

<400> SEQUENCE: 124
attcccgtcg ctatcaagga acc                                       23

<210> SEQ ID NO 125
<211> LENGTH: 23
<212> TYPE: DNA
<213> ORGANISM: Artificial sequence
<220> FEATURE:
<223> OTHER INFORMATION: Synthetic

<400> SEQUENCE: 125
tcccgtcgct atcaaggaat ctc                                       23

<210> SEQ ID NO 126
<211> LENGTH: 23
<212> TYPE: DNA
<213> ORGANISM: Artificial sequence
<220> FEATURE:
<223> OTHER INFORMATION: Synthetic

<400> SEQUENCE: 126
tcccgtcgct atcaaggaat cga                                       23

<210> SEQ ID NO 127
<211> LENGTH: 56
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (56)..(56)

<400> SEQUENCE: 127
aagttaaaat tcccgtcgct atcaactgta gcatgaaagc acaacgaggg gtcgag    56

<210> SEQ ID NO 128
<211> LENGTH: 54
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (54)..(54)

<400> SEQUENCE: 128
ccgtctcaat accatgctat caactgtagc atgaaagcac aacgagggggt cgag      54

<210> SEQ ID NO 129
<211> LENGTH: 60
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (60)..(60)

<400> SEQUENCE: 129
ccgtctcaat accatgctat caactctagc tgtagcatga aagcacaacg agggggtcgag      60

<210> SEQ ID NO 130
<211> LENGTH: 26
<212> TYPE: DNA
<213> ORGANISM: Artificial sequence
<220> FEATURE:
<223> OTHER INFORMATION: Synthetic

<400> SEQUENCE: 130
agttaaaatt cccgtcgcta tcaaaa      26

<210> SEQ ID NO 131
<211> LENGTH: 39
<212> TYPE: DNA
<213> ORGANISM: Artificial sequence
<220> FEATURE:
<223> OTHER INFORMATION: Synthetic

<400> SEQUENCE: 131
gaaagttaaa attcccgtct caataccatg ctatcaaaa      39

<210> SEQ ID NO 132
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 132
ttcttcttgg ccagagccca acaacgagag gaaacctt      38

<210> SEQ ID NO 133
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation

<222> LOCATION: (38)..(38)

<400> SEQUENCE: 133
cttgtctcag ccagagccca acaacgagag gaaacctt    38

<210> SEQ ID NO 134
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 134
gatgtgctat ccagagccca acaacgagag gaaacctt    38

<210> SEQ ID NO 135
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 135
gtgagttgat ccagagccca acaacgagag gaaacctt    38

<210> SEQ ID NO 136
<211> LENGTH: 37
<212> TYPE: DNA
<213> ORGANISM: Artificial sequence
<220> FEATURE:
<223> OTHER INFORMATION: Synthetic

<400> SEQUENCE: 136 ctctggggc tctcaagtct agacatacta ccagagc    37

<210> SEQ ID NO 137
<211> LENGTH: 37
<212> TYPE: DNA
<213> ORGANISM: Artificial sequence
<220> FEATURE:
<223> OTHER INFORMATION: Synthetic

<400> SEQUENCE: 137
gggtagaagt ctctggggc agacatacta ccagagc    37

<210> SEQ ID NO 138
<211> LENGTH: 39
<212> TYPE: DNA
<213> ORGANISM: Artificial sequence
<220> FEATURE:
<223> OTHER INFORMATION: Synthetic

<400> SEQUENCE: 138
tgacggtgtt gggatgtgct atagacatac taccagagc    39

<210> SEQ ID NO 139
<211> LENGTH: 40
<212> TYPE: DNA
<213> ORGANISM: Artificial sequence
<220> FEATURE:
<223> OTHER INFORMATION: Synthetic

<400> SEQUENCE: 139
ggtttaactg caggtgagtt gatagacata ctaccagagc        40

<210> SEQ ID NO 140
<211> LENGTH: 40
<212> TYPE: DNA
<213> ORGANISM: Artificial sequence
<220> FEATURE:
<223> OTHER INFORMATION: Synthetic

<400> SEQUENCE: 140
agcatcgtat ttggaagaag aggagacata ctaccagagc        40

<210> SEQ ID NO 141
<211> LENGTH: 27
<212> TYPE: DNA
<213> ORGANISM: Artificial sequence
<220> FEATURE:
<223> OTHER INFORMATION: Synthetic

<400> SEQUENCE: 141
cttgtctcag ttcttcttgg ccagagc        27

<210> SEQ ID NO 142
<211> LENGTH: 29
<212> TYPE: DNA
<213> ORGANISM: Artificial sequence
<220> FEATURE:
<223> OTHER INFORMATION: Synthetic

<400> SEQUENCE: 142
gctctcaagt ctcttgtctc agccagagc        29

<210> SEQ ID NO 143
<211> LENGTH: 29
<212> TYPE: DNA
<213> ORGANISM: Artificial sequence
<220> FEATURE:
<223> OTHER INFORMATION: Synthetic

<400> SEQUENCE: 143
tgacggtgtt gggatgtgct atccagagc        29

<210> SEQ ID NO 144
<211> LENGTH: 30
<212> TYPE: DNA
<213> ORGANISM: Artificial sequence
<220> FEATURE:
<223> OTHER INFORMATION: Synthetic

<400> SEQUENCE: 144
ggtttaactg caggtgagtt gatccagagc        30

<210> SEQ ID NO 145
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (41)..(41)

<400> SEQUENCE: 145
tggacgaggg aggctagctt ctgactggaa aacagactct a        41

```
<210> SEQ ID NO 146
<211> LENGTH: 49
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (49)..(49)

<400> SEQUENCE: 146
ctgattctag gaatatggaa ggagactgtc ccacaacgag agggtcgag           49

<210> SEQ ID NO 147
<211> LENGTH: 67
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (67)..(67)

<400> SEQUENCE: 147
agaacttacg cctgctttct gattctaatt cacgtctcat caactgtccc acaacgagag    60
ggtcgag                                                              67

<210> SEQ ID NO 148
<211> LENGTH: 62
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (62)..(62)

<400> SEQUENCE: 148
ttacgcctgc tttctgattc taggaatcgt ctcatcaact gtcccacaac gagagggtcg ag   62

<210> SEQ ID NO 149
<211> LENGTH: 57
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (57)..(57)

<400> SEQUENCE: 149
cctgctttct gattctagga atatggacat caactgtccc acaacgagag ggtcgag       57

<210> SEQ ID NO 150
<211> LENGTH: 65
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (65)..(65)

<400> SEQUENCE: 150
tttctgattc taggaatatg gaaggattca cgtctcatca actgtccacaacgagaggg    60 tcgag                                                              65
```

<210> SEQ ID NO 151
<211> LENGTH: 60
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (60)..(60)

<400> SEQUENCE: 151
tttctgattc taggaatatg aaggcgtct catcaactgt cccacaacga gagggtcgag     60

<210> SEQ ID NO 152
<211> LENGTH: 55
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (55)..(55)

<400> SEQUENCE: 152
tttctgattc taggaatatg aaggcatca actgtcccac aacgagaggg tcgag          55

<210> SEQ ID NO 153
<211> LENGTH: 50
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (50)..(50)

<400> SEQUENCE: 153
ccctgggcaa ggaacaataa ctcagactgt cccacaacga gagggtcgag               50

<210> SEQ ID NO 154
<211> LENGTH: 51
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (51)..(51)

<400> SEQUENCE: 154
actcagaact tacgcctgct ttctgaactg tcccacaacg agagggtcga g             51

<210> SEQ ID NO 155
<211> LENGTH: 52
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (52)..(52)

<400> SEQUENCE: 155
agaacttacg cctgctttct gattctaact gtcccacaac gagagggtcg ag            52

<210> SEQ ID NO 156
<211> LENGTH: 52

```
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (52)..(52)

<400> SEQUENCE: 156
ttacgcctgc tttctgattc taggaatact gtcccacaac gagagggtcg ag          52

<210> SEQ ID NO 157
<211> LENGTH: 52
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (52)..(52)

<400> SEQUENCE: 157
cctgctttct gattctagga atatggaact gtcccacaac gagagggtcg ag          52

<210> SEQ ID NO 158
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: ribonucleotides

<400> SEQUENCE: 158
ctcgaccctc guccctcgtc ca                                          22

<210> SEQ ID NO 159
<211> LENGTH: 25
<212> TYPE: DNA
<213> ORGANISM: Artificial sequence
<220> FEATURE:
<223> OTHER INFORMATION: Synthetic

<400> SEQUENCE: 159
cagctctttc agcacattgc tcaca                                       25

<210> SEQ ID NO 160
<211> LENGTH: 25
<212> TYPE: DNA
<213> ORGANISM: Artificial sequence
<220> FEATURE:
<223> OTHER INFORMATION: Synthetic

<400> SEQUENCE: 160
ctaactgggc aaggaacaat aactc                                       25

<210> SEQ ID NO 161
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 161
```
acatactagt tggaggtagt gacaacgaga ggtgcggt                                    38

<210> SEQ ID NO 162
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 162
tgaatataag ttggaggtag tgacaacgag aggtgcggt                                   39

<210> SEQ ID NO 163

<400> SEQUENCE: 163

000

<210> SEQ ID NO 164
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 164
atcgtcaacc tacgcgaaca acaacgagag gtgcggt                                     37

<210> SEQ ID NO 165
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 165
tggtcctgcc tacgcgaaca acaacgagag gtgcggt                                     37

<210> SEQ ID NO 166
<211> LENGTH: 44
<212> TYPE: DNA
<213> ORGANISM: Artificial sequence
<220> FEATURE:
<223> OTHER INFORMATION: Synthetic

<400> SEQUENCE: 166
cctgctgaaa atgactgaat ataaagacat actagttgga ggta                             44

<210> SEQ ID NO 167
<211> LENGTH: 44
<212> TYPE: DNA
<213> ORGANISM: Artificial sequence
<220> FEATURE:
<223> OTHER INFORMATION: Synthetic

<400> SEQUENCE: 167
tattataagg cctgctgaaa atgaagacat actagttgga ggta                             44

```
<210> SEQ ID NO 168
<211> LENGTH: 48
<212> TYPE: DNA
<213> ORGANISM: Artificial sequence
<220> FEATURE:
<223> OTHER INFORMATION: Synthetic

<400> SEQUENCE: 168
atatagtcac attttcatta tttttattag acatactagt tggaggta                    48

<210> SEQ ID NO 169
<211> LENGTH: 43
<212> TYPE: DNA
<213> ORGANISM: Artificial sequence
<220> FEATURE:
<223> OTHER INFORMATION: Synthetic

<400> SEQUENCE: 169
gtgtgacatg ttctaatata gtcagacata ctagttggag gta                         43

<210> SEQ ID NO 170
<211> LENGTH: 34
<212> TYPE: DNA
<213> ORGANISM: Artificial sequence
<220> FEATURE:
<223> OTHER INFORMATION: Synthetic

<400> SEQUENCE: 170
cctgctgaaa atgactgaat ataagttgga ggta                                   34

<210> SEQ ID NO 171
<211> LENGTH: 34
<212> TYPE: DNA
<213> ORGANISM: Artificial sequence
<220> FEATURE:
<223> OTHER INFORMATION: Synthetic

<400> SEQUENCE: 171
tgcatattaa aacaagattt acctctgtat cgtc                                   34

<210> SEQ ID NO 172
<211> LENGTH: 43
<212> TYPE: DNA
<213> ORGANISM: Artificial sequence
<220> FEATURE:
<223> OTHER INFORMATION: Synthetic

<400> SEQUENCE: 172
cacaaaatga ttctgaatta gctcacaatc agtcctacgc gaa                         43

<210> SEQ ID NO 173
<211> LENGTH: 42
<212> TYPE: DNA
<213> ORGANISM: Artificial sequence
<220> FEATURE:
<223> OTHER INFORMATION: Synthetic

<400> SEQUENCE: 173
ttgttggatc atattcgtcc accacaatca gtcctacgcg aa                          42

<210> SEQ ID NO 174
<211> LENGTH: 46
<212> TYPE: DNA
<213> ORGANISM: Artificial sequence
<220> FEATURE:
<223> OTHER INFORMATION: Synthetic
```

```
<400> SEQUENCE: 174
atattaaaac aagatttacc tctattcaca atcagtccta cgcgaa          46

<210> SEQ ID NO 175
<211> LENGTH: 44
<212> TYPE: DNA
<213> ORGANISM: Artificial sequence
<220> FEATURE:
<223> OTHER INFORMATION: Synthetic

<400> SEQUENCE: 175
tatctgtatc aaagaatggt cctgcacaat cagtcctacg cgaa            44

<210> SEQ ID NO 176
<211> LENGTH: 45
<212> TYPE: DNA
<213> ORGANISM: Artificial sequence
<220> FEATURE:
<223> OTHER INFORMATION: Synthetic

<400> SEQUENCE: 176
tggttacata taacttgaaa cccaacacaa tcagtcctac gcgaa           45

<210> SEQ ID NO 177
<211> LENGTH: 33
<212> TYPE: DNA
<213> ORGANISM: Artificial sequence
<220> FEATURE:
<223> OTHER INFORMATION: Synthetic

<400> SEQUENCE: 177
ttctgaatta gctgtatcgt caacctacgc gaa                        33

<210> SEQ ID NO 178
<211> LENGTH: 34
<212> TYPE: DNA
<213> ORGANISM: Artificial sequence
<220> FEATURE:
<223> OTHER INFORMATION: Synthetic

<400> SEQUENCE: 178
tatctgtatc aaagaatggt cctgcctacg cgaa                       34

<210> SEQ ID NO 179
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 179
gctaattcag aatcattttg tgacaacgag aggtgcggt                  39

<210> SEQ ID NO 180
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (40)..(40)
```

```
<400> SEQUENCE: 180 gagctggggga ggctagctga cgaatatgat ccaacaatag                          40

<210> SEQ ID NO 181
<211> LENGTH: 20
<212> TYPE: DNA
<213> ORGANISM: Artificial sequence
<220> FEATURE:
<223> OTHER INFORMATION: Synthetic

<400> SEQUENCE: 181
caagagtgcc ttgacgatac                                                 20

<210> SEQ ID NO 182
<211> LENGTH: 10
<212> TYPE: DNA
<213> ORGANISM: Artificial sequence
<220> FEATURE:
<223> OTHER INFORMATION: Synthetic

<400> SEQUENCE: 182
cacaatcagt                                                            10

<210> SEQ ID NO 183
<211> LENGTH: 10
<212> TYPE: DNA
<213> ORGANISM: Artificial sequence
<220> FEATURE:
<223> OTHER INFORMATION: Synthetic

<400> SEQUENCE: 183
cacaatgatg                                                            10

<210> SEQ ID NO 184
<211> LENGTH: 10
<212> TYPE: DNA
<213> ORGANISM: Artificial sequence
<220> FEATURE:
<223> OTHER INFORMATION: Synthetic

<400> SEQUENCE: 184
agacatacta                                                            10

<210> SEQ ID NO 185
<211> LENGTH: 10
<212> TYPE: DNA
<213> ORGANISM: Artificial sequence
<220> FEATURE:
<223> OTHER INFORMATION: Synthetic

<400> SEQUENCE: 185
agacagttac                                                            10

<210> SEQ ID NO 186
<211> LENGTH: 10
<212> TYPE: DNA
<213> ORGANISM: Artificial sequence
<220> FEATURE:
<223> OTHER INFORMATION: Synthetic

<400> SEQUENCE: 186
agagtcattc                                                            10

<210> SEQ ID NO 187
<211> LENGTH: 10
```

```
<212> TYPE: DNA
<213> ORGANISM: Artificial sequence
<220> FEATURE:
<223> OTHER INFORMATION: Synthetic

<400> SEQUENCE: 187
cgttggctac                                                              10

<210> SEQ ID NO 188
<211> LENGTH: 10
<212> TYPE: DNA
<213> ORGANISM: Artificial sequence
<220> FEATURE:
<223> OTHER INFORMATION: Synthetic

<400> SEQUENCE: 188
tcaataccat                                                              10

<210> SEQ ID NO 189
<211> LENGTH: 10
<212> TYPE: DNA
<213> ORGANISM: Artificial sequence
<220> FEATURE:
<223> OTHER INFORMATION: Synthetic

<400> SEQUENCE: 189
gattcgagaa                                                              10

<210> SEQ ID NO 190
<211> LENGTH: 10
<212> TYPE: DNA
<213> ORGANISM: Artificial sequence
<220> FEATURE:
<223> OTHER INFORMATION: Synthetic

<400> SEQUENCE: 190
gattcgagtt                                                              10

<210> SEQ ID NO 191
<211> LENGTH: 10
<212> TYPE: DNA
<213> ORGANISM: Artificial sequence
<220> FEATURE:
<223> OTHER INFORMATION: Synthetic

<400> SEQUENCE: 191
gttacctgaa                                                              10

<210> SEQ ID NO 192
<211> LENGTH: 10
<212> TYPE: DNA
<213> ORGANISM: Artificial sequence
<220> FEATURE:
<223> OTHER INFORMATION: Synthetic

<400> SEQUENCE: 192
cattagtgcc                                                              10

<210> SEQ ID NO 193
<211> LENGTH: 10
<212> TYPE: DNA
<213> ORGANISM: Artificial sequence
<220> FEATURE:
<223> OTHER INFORMATION: Synthetic

<400> SEQUENCE: 193
```
cattgacaga                                                        10

<210> SEQ ID NO 194
<211> LENGTH: 10
<212> TYPE: DNA
<213> ORGANISM: Artificial sequence
<220> FEATURE:
<223> OTHER INFORMATION: Synthetic

<400> SEQUENCE: 194
cgaaagcgac                                                        10

<210> SEQ ID NO 195
<211> LENGTH: 10
<212> TYPE: DNA
<213> ORGANISM: Artificial sequence
<220> FEATURE:
<223> OTHER INFORMATION: Synthetic

<400> SEQUENCE: 195
cgtctcatca                                                        10

<210> SEQ ID NO 196
<211> LENGTH: 10
<212> TYPE: DNA
<213> ORGANISM: Artificial sequence
<220> FEATURE:
<223> OTHER INFORMATION: Synthetic

<400> SEQUENCE: 196
ggattagatc                                                        10

<210> SEQ ID NO 197
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 197
cacaatcagt ccagagccca acaacgagag gaaacctt                         38

<210> SEQ ID NO 198
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 198
cacaatgatg ccagagccca acaacgagag gaaacctt                         38

<210> SEQ ID NO 199
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 199
agacagttac ccagagccca acaacgagag gaaacctt					38

<210> SEQ ID NO 200
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 200
agagtcattc ccagagccca acaacgagag gaaacctt					38

<210> SEQ ID NO 201
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 201
gttggctacc cagagcccaa caacgagagg aaacctt					37

<210> SEQ ID NO 202
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 202
tcaataccat ccagagccca acaacgagag gaaacctt					38

<210> SEQ ID NO 203
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 203
gattcgagaa ccagagccca acaacgagag gaaacctt					38

<210> SEQ ID NO 204
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 204
gattcgagtt ccagagccca acaacgagag gaaacctt					38

```
<210> SEQ ID NO 205
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 205
gttacctgaa ccagagccca acaacgagag gaaaccctt                              38

<210> SEQ ID NO 206
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 206
cattagtgcc ccagagccca acaacgagag gaaaccctt                              38

<210> SEQ ID NO 207
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 207
cattgacaga ccagagccca acaacgagag gaaaccctt                              38

<210> SEQ ID NO 208
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 208
gaaagcgacc cagagcccaa caacgagagg aaaccctt                               37

<210> SEQ ID NO 209
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 209
cgtctcatca ccagagccca acaacgagag gaaaccctt                              38

<210> SEQ ID NO 210
<211> LENGTH: 38
<212> TYPE: DNA
```

```
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 210
ggattagatc ccagagccca acaacgagag gaaaccctt                              38

<210> SEQ ID NO 211
<211> LENGTH: 39
<212> TYPE: DNA
<213> ORGANISM: Artificial sequence
<220> FEATURE:
<223> OTHER INFORMATION: Synthetic

<400> SEQUENCE: 211
ctcttgtctc agttcttctt ggcacaatca gtccagagc                              39

<210> SEQ ID NO 212
<211> LENGTH: 39
<212> TYPE: DNA
<213> ORGANISM: Artificial sequence
<220> FEATURE:
<223> OTHER INFORMATION: Synthetic

<400> SEQUENCE: 212
tcagttcttc ttggatggtc atcacaatca gtccagagc                              39

<210> SEQ ID NO 213
<211> LENGTH: 39
<212> TYPE: DNA
<213> ORGANISM: Artificial sequence
<220> FEATURE:
<223> OTHER INFORMATION: Synthetic

<400> SEQUENCE: 213
ctcttgtctc agttcttctt ggcacaatga tgccagagc                              39

<210> SEQ ID NO 214
<211> LENGTH: 39
<212> TYPE: DNA
<213> ORGANISM: Artificial sequence
<220> FEATURE:
<223> OTHER INFORMATION: Synthetic

<400> SEQUENCE: 214
tcagttcttc ttggatggtc atcacaatga tgccagagc                              39

<210> SEQ ID NO 215
<211> LENGTH: 39
<212> TYPE: DNA
<213> ORGANISM: Artificial sequence
<220> FEATURE:
<223> OTHER INFORMATION: Synthetic

<400> SEQUENCE: 215
tcagttcttc ttggatggtc atagacatac taccagagc                              39

<210> SEQ ID NO 216
<211> LENGTH: 39
<212> TYPE: DNA
<213> ORGANISM: Artificial sequence
<220> FEATURE:
<223> OTHER INFORMATION: Synthetic
```

```
<400> SEQUENCE: 216
ctcttgtctc agttcttctt ggagacatac taccagagc                                      39

<210> SEQ ID NO 217
<211> LENGTH: 39
<212> TYPE: DNA
<213> ORGANISM: Artificial sequence
<220> FEATURE:
<223> OTHER INFORMATION: Synthetic

<400> SEQUENCE: 217
ctcttgtctc agttcttctt ggagacagtt acccagagc                                      39

<210> SEQ ID NO 218
<211> LENGTH: 39
<212> TYPE: DNA
<213> ORGANISM: Artificial sequence
<220> FEATURE:
<223> OTHER INFORMATION: Synthetic

<400> SEQUENCE: 218
tcagttcttc ttggatggtc atagacagtt acccagagc                                      39

<210> SEQ ID NO 219
<211> LENGTH: 39
<212> TYPE: DNA
<213> ORGANISM: Artificial sequence
<220> FEATURE:
<223> OTHER INFORMATION: Synthetic

<400> SEQUENCE: 219
ctcttgtctc agttcttctt ggagagtcat tcccagagc                                      39

<210> SEQ ID NO 220
<211> LENGTH: 39
<212> TYPE: DNA
<213> ORGANISM: Artificial sequence
<220> FEATURE:
<223> OTHER INFORMATION: Synthetic

<400> SEQUENCE: 220
tcagttcttc ttggatggtc atagagtcat tcccagagc                                      39

<210> SEQ ID NO 221
<211> LENGTH: 39
<212> TYPE: DNA
<213> ORGANISM: Artificial sequence
<220> FEATURE:
<223> OTHER INFORMATION: Synthetic

<400> SEQUENCE: 221
ctcttgtctc agttcttctt ggcgttggct acccagagc                                      39

<210> SEQ ID NO 222
<211> LENGTH: 39
<212> TYPE: DNA
<213> ORGANISM: Artificial sequence
<220> FEATURE:
<223> OTHER INFORMATION: Synthetic

<400> SEQUENCE: 222
tcagttcttc ttggatggtc atcgttggct acccagagc                                      39

<210> SEQ ID NO 223
<211> LENGTH: 39
```

```
<212> TYPE: DNA
<213> ORGANISM: Artificial sequence
<220> FEATURE:
<223> OTHER INFORMATION: Synthetic

<400> SEQUENCE: 223
ctcttgtctc agttcttctt ggtcaatacc atccagagc                              39

<210> SEQ ID NO 224
<211> LENGTH: 39
<212> TYPE: DNA
<213> ORGANISM: Artificial sequence
<220> FEATURE:
<223> OTHER INFORMATION: Synthetic

<400> SEQUENCE: 224
tcagttcttc ttggatggtc attcaatacc atccagagc                              39

<210> SEQ ID NO 225
<211> LENGTH: 39
<212> TYPE: DNA
<213> ORGANISM: Artificial sequence
<220> FEATURE:
<223> OTHER INFORMATION: Synthetic

<400> SEQUENCE: 225
ctcttgtctc agttcttctt gggattcgag aaccagagc                              39

<210> SEQ ID NO 226
<211> LENGTH: 39
<212> TYPE: DNA
<213> ORGANISM: Artificial sequence
<220> FEATURE:
<223> OTHER INFORMATION: Synthetic

<400> SEQUENCE: 226
tcagttcttc ttggatggtc atgattcgag aaccagagc                              39

<210> SEQ ID NO 227
<211> LENGTH: 39
<212> TYPE: DNA
<213> ORGANISM: Artificial sequence
<220> FEATURE:
<223> OTHER INFORMATION: Synthetic

<400> SEQUENCE: 227
ctcttgtctc agttcttctt gggattcgag ttccagagc                              39

<210> SEQ ID NO 228
<211> LENGTH: 39
<212> TYPE: DNA
<213> ORGANISM: Artificial sequence
<220> FEATURE:
<223> OTHER INFORMATION: Synthetic

<400> SEQUENCE: 228
tcagttcttc ttggatggtc atgattcgag ttccagagc                              39

<210> SEQ ID NO 229
<211> LENGTH: 39
<212> TYPE: DNA
<213> ORGANISM: Artificial sequence
<220> FEATURE:
<223> OTHER INFORMATION: Synthetic

<400> SEQUENCE: 229
```
ctcttgtctc agttcttctt gggttacctg aaccagagc    39

<210> SEQ ID NO 230
<211> LENGTH: 39
<212> TYPE: DNA
<213> ORGANISM: Artificial sequence
<220> FEATURE:
<223> OTHER INFORMATION: Synthetic

<400> SEQUENCE: 230
tcagttcttc ttggatggtc atgttacctg aaccagagc    39

<210> SEQ ID NO 231
<211> LENGTH: 39
<212> TYPE: DNA
<213> ORGANISM: Artificial sequence
<220> FEATURE:
<223> OTHER INFORMATION: Synthetic

<400> SEQUENCE: 231
ctcttgtctc agttcttctt ggcattagtg ccccagagc    39

<210> SEQ ID NO 232
<211> LENGTH: 39
<212> TYPE: DNA
<213> ORGANISM: Artificial sequence
<220> FEATURE:
<223> OTHER INFORMATION: Synthetic

<400> SEQUENCE: 232
tcagttcttc ttggatggtc atcattagtg ccccagagc    39

<210> SEQ ID NO 233
<211> LENGTH: 39
<212> TYPE: DNA
<213> ORGANISM: Artificial sequence
<220> FEATURE:
<223> OTHER INFORMATION: Synthetic

<400> SEQUENCE: 233
ctcttgtctc agttcttctt ggcattgaca gaccagagc    39

<210> SEQ ID NO 234
<211> LENGTH: 39
<212> TYPE: DNA
<213> ORGANISM: Artificial sequence
<220> FEATURE:
<223> OTHER INFORMATION: Synthetic

<400> SEQUENCE: 234
tcagttcttc ttggatggtc atcattgaca gaccagagc    39

<210> SEQ ID NO 235
<211> LENGTH: 37
<212> TYPE: DNA
<213> ORGANISM: Artificial sequence
<220> FEATURE:
<223> OTHER INFORMATION: Synthetic

<400> SEQUENCE: 235
cttgtctcag ttcttcttgg cgaaagcgac ccagagc    37

<210> SEQ ID NO 236
<211> LENGTH: 37
<212> TYPE: DNA
<213> ORGANISM: Artificial sequence

```
<220> FEATURE:
<223> OTHER INFORMATION: Synthetic

<400> SEQUENCE: 236
ttcttcttgg atggtcatct cgaaagcgac ccagagc                              37

<210> SEQ ID NO 237
<211> LENGTH: 39
<212> TYPE: DNA
<213> ORGANISM: Artificial sequence
<220> FEATURE:
<223> OTHER INFORMATION: Synthetic

<400> SEQUENCE: 237
ctcttgtctc agttcttctt ggcgtctcat caccagagc                            39

<210> SEQ ID NO 238
<211> LENGTH: 39
<212> TYPE: DNA
<213> ORGANISM: Artificial sequence
<220> FEATURE:
<223> OTHER INFORMATION: Synthetic

<400> SEQUENCE: 238
tcagttcttc ttggatggtc atcgtctcat caccagagc                            39

<210> SEQ ID NO 239
<211> LENGTH: 39
<212> TYPE: DNA
<213> ORGANISM: Artificial sequence
<220> FEATURE:
<223> OTHER INFORMATION: Synthetic

<400> SEQUENCE: 239
ctcttgtctc agttcttctt ggggattaga tcccagagc                            39

<210> SEQ ID NO 240
<211> LENGTH: 39
<212> TYPE: DNA
<213> ORGANISM: Artificial sequence
<220> FEATURE:
<223> OTHER INFORMATION: Synthetic

<400> SEQUENCE: 240
tcagttcttc ttggatggtc atggattaga tcccagagc                            39

<210> SEQ ID NO 241
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (40)..(40)

<400> SEQUENCE: 241
gagctgggga ggctagctct ccaactacca caagtttata                           40

<210> SEQ ID NO 242
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
```

<222> LOCATION: (36)..(36)

<400> SEQUENCE: 242
cacaatcagt acgcctccag acaacgagag gtgcgg 36

<210> SEQ ID NO 243
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 243
cacaatgatg acgcctccag acaacgagag gtgcgg 36

<210> SEQ ID NO 244
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 244
agacatacta acgcctccag acaacgagag gtgcgg 36

<210> SEQ ID NO 245
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 245
agacagttac acgcctccag acaacgagag gtgcgg 36

<210> SEQ ID NO 246
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 246
agagtcattc acgcctccag acaacgagag gtgcgg 36

<210> SEQ ID NO 247
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (35)..(35)

<400> SEQUENCE: 247
gttggctaca cgcctccaga caacgagagg tgcgg                          35

<210> SEQ ID NO 248
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 248
caataccata cgcctccaga caacgagagg tgcggt                         36

<210> SEQ ID NO 249
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 249
gattcgagaa acgcctccag acaacgagag gtgcgg                         36

<210> SEQ ID NO 250
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 250
gattcgagtt acgcctccag acaacgagag gtgcgg                         36

<210> SEQ ID NO 251
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 251
gttacctgaa acgcctccag acaacgagag gtgcgg                         36

<210> SEQ ID NO 252
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 252
cattagtgcc acgcctccag acaacgagag gtgcgg                         36

<210> SEQ ID NO 253

```
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 253
cattgacaga acgcctccag acaacgagag gtgcgg                                   36

<210> SEQ ID NO 254
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (35)..(35)

<400> SEQUENCE: 254
gaaagcgaca cgcctccaga caacgagagg tgcgg                                    35

<210> SEQ ID NO 255
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 255
cgtctcatca acgcctccag acaacgagag gtgcgg                                   36

<210> SEQ ID NO 256
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (36)..(36)

<400> SEQUENCE: 256
ggattagatc acgcctccag acaacgagag gtgcgg                                   36

<210> SEQ ID NO 257
<211> LENGTH: 40
<212> TYPE: DNA
<213> ORGANISM: Artificial sequence
<220> FEATURE:
<223> OTHER INFORMATION: Synthetic

<400> SEQUENCE: 257
tgtatcgtca aggcactctt gccacaatca gtacgcctcc                               40

<210> SEQ ID NO 258
<211> LENGTH: 41
<212> TYPE: DNA
<213> ORGANISM: Artificial sequence
<220> FEATURE:
<223> OTHER INFORMATION: Synthetic

<400> SEQUENCE: 258
```
tgaattagct gtatcgtcaa ggccacaatc agtacgcctc c    41

<210> SEQ ID NO 259
<211> LENGTH: 40
<212> TYPE: DNA
<213> ORGANISM: Artificial sequence
<220> FEATURE:
<223> OTHER INFORMATION: Synthetic

<400> SEQUENCE: 259
tgtatcgtca aggcactctt gccacaatga tgacgcctcc    40

<210> SEQ ID NO 260
<211> LENGTH: 41
<212> TYPE: DNA
<213> ORGANISM: Artificial sequence
<220> FEATURE:
<223> OTHER INFORMATION: Synthetic

<400> SEQUENCE: 260
tgaattagct gtatcgtcaa ggccacaatg atgacgcctc c    41

<210> SEQ ID NO 261
<211> LENGTH: 40
<212> TYPE: DNA
<213> ORGANISM: Artificial sequence
<220> FEATURE:
<223> OTHER INFORMATION: Synthetic

<400> SEQUENCE: 261
tgtatcgtca aggcactctt gcagacatac taacgcctcc    40

<210> SEQ ID NO 262
<211> LENGTH: 41
<212> TYPE: DNA
<213> ORGANISM: Artificial sequence
<220> FEATURE:
<223> OTHER INFORMATION: Synthetic

<400> SEQUENCE: 262
tgaattagct gtatcgtcaa ggcagacata ctaacgcctc c    41

<210> SEQ ID NO 263
<211> LENGTH: 40
<212> TYPE: DNA
<213> ORGANISM: Artificial sequence
<220> FEATURE:
<223> OTHER INFORMATION: Synthetic

<400> SEQUENCE: 263
tgtatcgtca aggcactctt gcagacagtt acacgcctcc    40

<210> SEQ ID NO 264
<211> LENGTH: 41
<212> TYPE: DNA
<213> ORGANISM: Artificial sequence
<220> FEATURE:
<223> OTHER INFORMATION: Synthetic

<400> SEQUENCE: 264
tgaattagct gtatcgtcaa ggcagacagt tacacgcctc c    41

<210> SEQ ID NO 265
<211> LENGTH: 40
<212> TYPE: DNA

<213> ORGANISM: Artificial sequence
<220> FEATURE:
<223> OTHER INFORMATION: Synthetic

<400> SEQUENCE: 265
tgtatcgtca aggcactctt gcagagtcat tcacgcctcc            40

<210> SEQ ID NO 266
<211> LENGTH: 41
<212> TYPE: DNA
<213> ORGANISM: Artificial sequence
<220> FEATURE:
<223> OTHER INFORMATION: Synthetic

<400> SEQUENCE: 266
tgaattagct gtatcgtcaa ggcagagtca ttcacgcctc c            41

<210> SEQ ID NO 267
<211> LENGTH: 40
<212> TYPE: DNA
<213> ORGANISM: Artificial sequence
<220> FEATURE:
<223> OTHER INFORMATION: Synthetic

<400> SEQUENCE: 267
tgtatcgtca aggcactctt gccgttggct acacgcctcc            40

<210> SEQ ID NO 268
<211> LENGTH: 41
<212> TYPE: DNA
<213> ORGANISM: Artificial sequence
<220> FEATURE:
<223> OTHER INFORMATION: Synthetic

<400> SEQUENCE: 268
tgaattagct gtatcgtcaa ggccgttggc tacacgcctc c            41

<210> SEQ ID NO 269
<211> LENGTH: 40
<212> TYPE: DNA
<213> ORGANISM: Artificial sequence
<220> FEATURE:
<223> OTHER INFORMATION: Synthetic

<400> SEQUENCE: 269
tgtatcgtca aggcactctt gctcaatacc atacgcctcc            40

<210> SEQ ID NO 270
<211> LENGTH: 41
<212> TYPE: DNA
<213> ORGANISM: Artificial sequence
<220> FEATURE:
<223> OTHER INFORMATION: Synthetic

<400> SEQUENCE: 270
tgaattagct gtatcgtcaa ggctcaatac catacgcctc c            41

<210> SEQ ID NO 271
<211> LENGTH: 40
<212> TYPE: DNA
<213> ORGANISM: Artificial sequence
<220> FEATURE:
<223> OTHER INFORMATION: Synthetic

<400> SEQUENCE: 271
tgtatcgtca aggcactctt gcgattcgag aaacgcctcc            40

<210> SEQ ID NO 272
<211> LENGTH: 41
<212> TYPE: DNA
<213> ORGANISM: Artificial sequence
<220> FEATURE:
<223> OTHER INFORMATION: Synthetic

<400> SEQUENCE: 272
tgaattagct gtatcgtcaa ggcgattcga gaaacgcctc c            41

<210> SEQ ID NO 273
<211> LENGTH: 40
<212> TYPE: DNA
<213> ORGANISM: Artificial sequence
<220> FEATURE:
<223> OTHER INFORMATION: Synthetic

<400> SEQUENCE: 273
tgtatcgtca aggcactctt gcgattcgag ttacgcctcc            40

<210> SEQ ID NO 274
<211> LENGTH: 41
<212> TYPE: DNA
<213> ORGANISM: Artificial sequence
<220> FEATURE:
<223> OTHER INFORMATION: Synthetic

<400> SEQUENCE: 274
tgaattagct gtatcgtcaa ggcgattcga gttacgcctc c            41

<210> SEQ ID NO 275
<211> LENGTH: 40
<212> TYPE: DNA
<213> ORGANISM: Artificial sequence
<220> FEATURE:
<223> OTHER INFORMATION: Synthetic

<400> SEQUENCE: 275
tgtatcgtca aggcactctt gcgttacctg aaacgcctcc            40

<210> SEQ ID NO 276
<211> LENGTH: 41
<212> TYPE: DNA
<213> ORGANISM: Artificial sequence
<220> FEATURE:
<223> OTHER INFORMATION: Synthetic

<400> SEQUENCE: 276
tgaattagct gtatcgtcaa ggcgttacct gaaacgcctc c            41

<210> SEQ ID NO 277
<211> LENGTH: 40
<212> TYPE: DNA
<213> ORGANISM: Artificial sequence
<220> FEATURE:
<223> OTHER INFORMATION: Synthetic

<400> SEQUENCE: 277
tgtatcgtca aggcactctt gccattagtg ccacgcctcc            40

<210> SEQ ID NO 278
<211> LENGTH: 41
<212> TYPE: DNA
<213> ORGANISM: Artificial sequence
<220> FEATURE:

<223> OTHER INFORMATION: Synthetic

<400> SEQUENCE: 278
tgaattagct gtatcgtcaa ggccattagt gccacgcctc c                              41

<210> SEQ ID NO 279
<211> LENGTH: 40
<212> TYPE: DNA
<213> ORGANISM: Artificial sequence
<220> FEATURE:
<223> OTHER INFORMATION: Synthetic

<400> SEQUENCE: 279
tgtatcgtca aggcactctt gccattgaca gaacgcctcc                                40

<210> SEQ ID NO 280
<211> LENGTH: 41
<212> TYPE: DNA
<213> ORGANISM: Artificial sequence
<220> FEATURE:
<223> OTHER INFORMATION: Synthetic

<400> SEQUENCE: 280
tgaattagct gtatcgtcaa ggccattgac agaacgcctc c                              41

<210> SEQ ID NO 281
<211> LENGTH: 40
<212> TYPE: DNA
<213> ORGANISM: Artificial sequence
<220> FEATURE:
<223> OTHER INFORMATION: Synthetic

<400> SEQUENCE: 281
tgtatcgtca aggcactctt gccgaaagcg acacgcctcc                                40

<210> SEQ ID NO 282
<211> LENGTH: 41
<212> TYPE: DNA
<213> ORGANISM: Artificial sequence
<220> FEATURE:
<223> OTHER INFORMATION: Synthetic

<400> SEQUENCE: 282
tgaattagct gtatcgtcaa ggccgaaagc gacacgcctc c                              41

<210> SEQ ID NO 283
<211> LENGTH: 40
<212> TYPE: DNA
<213> ORGANISM: Artificial sequence
<220> FEATURE:
<223> OTHER INFORMATION: Synthetic

<400> SEQUENCE: 283
tgtatcgtca aggcactctt gccgtctcat caacgcctcc                                40

<210> SEQ ID NO 284
<211> LENGTH: 41
<212> TYPE: DNA
<213> ORGANISM: Artificial sequence
<220> FEATURE:
<223> OTHER INFORMATION: Synthetic

<400> SEQUENCE: 284
tgaattagct gtatcgtcaa ggccgtctca tcaacgcctc c                              41

```
<210> SEQ ID NO 285
<211> LENGTH: 40
<212> TYPE: DNA
<213> ORGANISM: Artificial sequence
<220> FEATURE:
<223> OTHER INFORMATION: Synthetic

<400> SEQUENCE: 285
tgtatcgtca aggcactctt gcggattaga tcacgcctcc                                 40

<210> SEQ ID NO 286
<211> LENGTH: 41
<212> TYPE: DNA
<213> ORGANISM: Artificial sequence
<220> FEATURE:
<223> OTHER INFORMATION: Synthetic

<400> SEQUENCE: 286
tgaattagct gtatcgtcaa ggcggattag atcacgcctc c                               41

<210> SEQ ID NO 287
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 287
agacatacta tggagcggtt gacaacgaga ggtgcggt                                   38

<210> SEQ ID NO 288
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 288
agacatacta tggagcagtt gacaacgaga ggtgcggt                                   38

<210> SEQ ID NO 289
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 289
agacatacta tggagctctt gacaacgaga ggtgcggt                                   38

<210> SEQ ID NO 290
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)
```

```
<400> SEQUENCE: 290
agacatacta tggagctatt gacaacgaga ggtgcggt                              38

<210> SEQ ID NO 291
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 291
agacatacta tggagatgtt gacaacgaga ggtgcggt                              38

<210> SEQ ID NO 292
<211> LENGTH: 43
<212> TYPE: DNA
<213> ORGANISM: Artificial sequence
<220> FEATURE:
<223> OTHER INFORMATION: Synthetic

<400> SEQUENCE: 292
gactgaatat aaacttgtgg tagtagacat actatggagc ggt                        43

<210> SEQ ID NO 293
<211> LENGTH: 43
<212> TYPE: DNA
<213> ORGANISM: Artificial sequence
<220> FEATURE:
<223> OTHER INFORMATION: Synthetic

<400> SEQUENCE: 293
gactgaatat aaacttgtgg tagtagacat actatggagc agt                        43

<210> SEQ ID NO 294
<211> LENGTH: 43
<212> TYPE: DNA
<213> ORGANISM: Artificial sequence
<220> FEATURE:
<223> OTHER INFORMATION: Synthetic

<400> SEQUENCE: 294
gactgaatat aaacttgtgg tagtagacat actatggagc tct                        43

<210> SEQ ID NO 295
<211> LENGTH: 43
<212> TYPE: DNA
<213> ORGANISM: Artificial sequence
<220> FEATURE:
<223> OTHER INFORMATION: Synthetic

<400> SEQUENCE: 295
gactgaatat aaacttgtgg tagtagacat actatggagc tat                        43

<210> SEQ ID NO 296
<211> LENGTH: 43
<212> TYPE: DNA
<213> ORGANISM: Artificial sequence
<220> FEATURE:
<223> OTHER INFORMATION: Synthetic

<400> SEQUENCE: 296
gactgaatat aaacttgtgg tagtagacat actatggaga tgt                        43
```

```
<210> SEQ ID NO 297
<211> LENGTH: 44
<212> TYPE: DNA
<213> ORGANISM: Artificial sequence
<220> FEATURE:
<223> OTHER INFORMATION: Synthetic

<400> SEQUENCE: 297
ctgctgaaaa tgactgaata taaacagaca tactatggag cggt           44

<210> SEQ ID NO 298
<211> LENGTH: 44
<212> TYPE: DNA
<213> ORGANISM: Artificial sequence
<220> FEATURE:
<223> OTHER INFORMATION: Synthetic

<400> SEQUENCE: 298
ctgctgaaaa tgactgaata taaacagaca tactatggag cagt           44

<210> SEQ ID NO 299
<211> LENGTH: 44
<212> TYPE: DNA
<213> ORGANISM: Artificial sequence
<220> FEATURE:
<223> OTHER INFORMATION: Synthetic

<400> SEQUENCE: 299
ctgctgaaaa tgactgaata taaacagaca tactatggag ctct           44

<210> SEQ ID NO 300
<211> LENGTH: 44
<212> TYPE: DNA
<213> ORGANISM: Artificial sequence
<220> FEATURE:
<223> OTHER INFORMATION: Synthetic

<400> SEQUENCE: 300
ctgctgaaaa tgactgaata taaacagaca tactatggag ctat           44

<210> SEQ ID NO 301
<211> LENGTH: 44
<212> TYPE: DNA
<213> ORGANISM: Artificial sequence
<220> FEATURE:
<223> OTHER INFORMATION: Synthetic

<400> SEQUENCE: 301
ctgctgaaaa tgactgaata taaacagaca tactatggag atgt           44

<210> SEQ ID NO 302
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (45)..(45)

<400> SEQUENCE: 302
tgctttctga ttctaggaat actgtcccac aacgagaggg tcgag          45

<210> SEQ ID NO 303
<211> LENGTH: 43
<212> TYPE: DNA
```

<213> ORGANISM: Artificial sequence
<220> FEATURE:
<223> OTHER INFORMATION: Synthetic
<220> FEATURE:
<221> NAME/KEY: Phosphorylation
<222> LOCATION: (43)..(43)

<400> SEQUENCE: 303
tcgttaccta gtctaagcac tgtcccacaa cgagagggtc gag               43

<210> SEQ ID NO 304
<211> LENGTH: 24
<212> TYPE: DNA
<213> ORGANISM: Artificial sequence
<220> FEATURE:
<223> OTHER INFORMATION: Synthetic

<400> SEQUENCE: 304
cagctttctg aggttaccat ccta                                    24

<210> SEQ ID NO 305
<211> LENGTH: 42
<212> TYPE: DNA
<213> ORGANISM: Artificial sequence
<220> FEATURE:
<223> OTHER INFORMATION: Synthetic

<400> SEQUENCE: 305
agaacttacg cctgctttct gattctagga atatggaagg ag                42

<210> SEQ ID NO 306
<211> LENGTH: 42
<212> TYPE: DNA
<213> ORGANISM: Artificial sequence
<220> FEATURE:
<223> OTHER INFORMATION: Synthetic

<400> SEQUENCE: 306
tcgttaccta gtctaagcct gattctagga atatggaagg ag                42

<210> SEQ ID NO 307
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (38)..(38)

<400> SEQUENCE: 307
tgcccaggga ggctagctca gctgtgtccg attctgtc                     38

<210> SEQ ID NO 308
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (37)..(37)

<400> SEQUENCE: 308
ccactcttcc tcaatcttaa caacgagagg aaacctt                      37

<210> SEQ ID NO 309

<211> LENGTH: 20
<212> TYPE: DNA
<213> ORGANISM: Artificial sequence
<220> FEATURE:
<223> OTHER INFORMATION: Synthetic

<400> SEQUENCE: 309
gccaatgact tacttaggac                                          20

<210> SEQ ID NO 310
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (45)..(45)

<400> SEQUENCE: 310
aactgactaa ttgacttgct catccatagt gccactcttc ctcaa              45

<210> SEQ ID NO 311
<211> LENGTH: 69
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (69)..(69)

<400> SEQUENCE: 311
tgcaactctc tgttcaggga ctctcgaccc tctcgttgta gctagcctcc ctcgtccact    60
cttcctcaa                                                      69

<210> SEQ ID NO 312
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 312
aactctgcag cggaaccgac taacaacgag aggtgcggt                     39

<210> SEQ ID NO 313
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 313
aagtctgtgg cggaaccgac taacaacgag aggtgcggt                     39

<210> SEQ ID NO 314
<211> LENGTH: 40
<212> TYPE: DNA
<213> ORGANISM: Artificial sequence
<220> FEATURE:
<223> OTHER INFORMATION: Synthetic

```
<220> FEATURE:
<221> NAME/KEY: Phosphorylation
<222> LOCATION: (40)..(40)

<400> SEQUENCE: 314
ctccattact gcggaaccga ctaacaacga gaggtgcggt                              40

<210> SEQ ID NO 315
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: Phosphorylation
<222> LOCATION: (39)..(39)

<400> SEQUENCE: 315
gagctgggga ggctagctct ttgggtgtcc gtgtttcct                               39

<210> SEQ ID NO 316
<211> LENGTH: 23
<212> TYPE: DNA
<213> ORGANISM: Artificial sequence
<220> FEATURE:
<223> OTHER INFORMATION: Synthetic

<400> SEQUENCE: 316
ctaaccctga atgcggctaa tcc                                               23

<210> SEQ ID NO 317
<211> LENGTH: 36
<212> TYPE: DNA
<213> ORGANISM: Artificial sequence
<220> FEATURE:
<223> OTHER INFORMATION: Synthetic

<400> SEQUENCE: 317
tccggcccct gaatgcggct ccattactgc ggaacc                                 36

<210> SEQ ID NO 318
<211> LENGTH: 23
<212> TYPE: DNA
<213> ORGANISM: Artificial sequence
<220> FEATURE:
<223> OTHER INFORMATION: Synthetic

<400> SEQUENCE: 318
cagattgtca ccataagcag cca                                               23
```